US009926271B2

(12) United States Patent
Petrukhin et al.

(10) Patent No.: US 9,926,271 B2
(45) Date of Patent: *Mar. 27, 2018

(54) OCTAHYDROCYCLOPENTAPYRROLES, THEIR PREPARATION AND USE

(71) Applicant: The Trustees of Columbia University in the City of New York, New York, NY (US)

(72) Inventors: Konstantin Petrukhin, New Windsor, NY (US); Christopher Cioffi, Albany, NY (US); Graham Johnson, Sanbornton, NH (US); Nicoleta Dobri, New York, NY (US); Emily Freeman, Albany, NY (US); Ping Chen, Albany, NY (US); Michael Conlon, Albany, NY (US); Lei Zhu, Albany, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/457,821

(22) Filed: Mar. 13, 2017

(65) Prior Publication Data
US 2017/0247327 A1    Aug. 31, 2017

Related U.S. Application Data

(63) Continuation of application No. 14/775,540, filed as application No. PCT/US2014/026818 on Mar. 13, 2014, now Pat. No. 9,637,450.

(60) Provisional application No. 61/785,288, filed on Mar. 14, 2013.

(51) Int. Cl.
| | | |
|---|---|---|
| C07D 209/52 | (2006.01) |
| C07D 403/06 | (2006.01) |
| C07D 471/04 | (2006.01) |
| C07D 498/04 | (2006.01) |
| C07D 487/04 | (2006.01) |
| C07D 401/12 | (2006.01) |
| C07D 403/04 | (2006.01) |
| C07D 403/12 | (2006.01) |
| C07D 401/04 | (2006.01) |

(52) U.S. Cl.
CPC ......... *C07D 209/52* (2013.01); *C07D 401/04* (2013.01); *C07D 401/12* (2013.01); *C07D 403/04* (2013.01); *C07D 403/06* (2013.01); *C07D 403/12* (2013.01); *C07D 471/04* (2013.01); *C07D 487/04* (2013.01); *C07D 498/04* (2013.01)

(58) Field of Classification Search
CPC .................................................. C07D 209/52
See application file for complete search history.

(56) References Cited

U.S. PATENT DOCUMENTS

| | | |
|---|---|---|
| 5,231,083 A | 7/1993 | Linz et al. |
| 5,312,814 A | 5/1994 | Biller et al. |
| 5,523,430 A | 6/1996 | Patel et al. |
| 5,532,243 A | 7/1996 | Gilligan et al. |
| 5,703,091 A | 12/1997 | Steiner et al. |
| 6,372,793 B1 | 4/2002 | Lamango et al. |
| 6,638,980 B1 | 10/2003 | Su et al. |
| 7,157,451 B2 | 1/2007 | Atwal et al. |
| 7,501,405 B2 | 3/2009 | Kampen et al. |
| 7,718,669 B2 | 5/2010 | Petry et al. |
| 7,781,436 B2 | 8/2010 | Bissantz et al. |
| 7,947,692 B2 | 5/2011 | Brinkman et al. |
| 8,168,783 B2 | 5/2012 | Kokubo et al. |
| 8,586,571 B2 | 11/2013 | Kasai et al. |
| 8,980,924 B2 | 3/2015 | Petrukhin et al. |
| 9,333,202 B2 | 5/2016 | Petrukhin et al. |
| 9,434,727 B2 | 9/2016 | Petrukhin et al. |
| 9,637,450 B2 | 5/2017 | Petrukhin et al. |
| 2003/0195195 A1 | 10/2003 | Haviv et al. |
| 2004/0097575 A1 | 5/2004 | Doherty et al. |
| 2004/0180877 A1 | 9/2004 | Peters et al. |
| 2004/0220171 A1 | 11/2004 | Pauls et al. |

(Continued)

FOREIGN PATENT DOCUMENTS

| | | |
|---|---|---|
| DE | 4130514 | 3/1993 |
| EP | 1190710 A1 | 3/2002 |
| JP | 59-036670 A | 2/1984 |
| JP | 2006-0770063 | 3/2006 |
| JP | 2006-176503 | 7/2006 |
| JP | 2012/184205 A | 9/2012 |
| WO | WO 1997/17954 | 5/1997 |
| WO | WO 97/38665 | 10/1997 |
| WO | WO 98/39000 | 9/1998 |
| WO | WO 99/37304 | 7/1999 |

(Continued)

OTHER PUBLICATIONS

International Search Report in connection with PCT/US2011/061763 dated May 29, 2012.

(Continued)

*Primary Examiner* — Rebecca L Anderson
*Assistant Examiner* — Karen Cheng
(74) *Attorney, Agent, or Firm* — John P. White; Cooper & Dunham LLP

(57) ABSTRACT

The present invention provides Octahydrocyclopentapyrrole compounds having the structure: (structurally represented) wherein psi is absent or present, and when present is a bond; R1, R2, R3, R4, and R5 are each independently H, halogen, CF, or C1-C4 alkyl; R6 is absent or present, and when present is H, OH, or halogen; A is absent or present, and when present is C(O) or C(O)NH; B is substituted or unsubstituted monocycle, bicycle, heteromonocycle, heterobicycle, benzyl, CO2H or (C1-C4 alkyl)-CO2H, wherein when B is CO2H, then A is present and is C(O); and when psi is present, then R6 is absent and when psi is absent, then R6 is present, or a pharmaceutically acceptable salt thereof, for treatment of diseases characterized by excessive lipofuscin accumulation in the retina.

28 Claims, 9 Drawing Sheets

(56) References Cited

U.S. PATENT DOCUMENTS

| | | |
|---|---|---|
| 2005/0043354 A1 | 2/2005 | Wager et al. |
| 2006/0074121 A1 | 4/2006 | Chen et al. |
| 2006/0089378 A1 | 4/2006 | Xia et al. |
| 2006/0111366 A1 | 5/2006 | Anderson et al. |
| 2006/0135460 A1 | 6/2006 | Widder et al. |
| 2006/0199837 A1 | 9/2006 | Thompson et al. |
| 2006/0270688 A1 | 11/2006 | Chong et al. |
| 2007/0015827 A1 | 1/2007 | Widder et al. |
| 2007/0027163 A1 | 2/2007 | Bissantzet et al. |
| 2007/0254911 A1 | 11/2007 | Xia et al. |
| 2008/0039442 A1 | 2/2008 | Blom et al. |
| 2008/0051409 A1 | 2/2008 | Gmeiner et al. |
| 2008/0139552 A1 | 6/2008 | Bissantz et al. |
| 2008/0254140 A1 | 10/2008 | Widder et al. |
| 2009/0054532 A1 | 2/2009 | Mata et al. |
| 2009/0088435 A1 | 4/2009 | Mata et al. |
| 2009/0143376 A1 | 6/2009 | Milburn et al. |
| 2010/0022530 A1 | 1/2010 | Schiemann et al. |
| 2010/0063047 A1 | 3/2010 | Borchardt et al. |
| 2010/0222357 A1 | 9/2010 | Bizzantz et al. |
| 2010/0292206 A1 | 11/2010 | Kasai et al. |
| 2011/0003820 A1 | 1/2011 | Henrich et al. |
| 2011/0201657 A1 | 8/2011 | Boueres et al. |
| 2011/0251182 A1 | 10/2011 | Sun et al. |
| 2011/0251187 A1 | 10/2011 | Kasai et al. |
| 2011/0257196 A1 | 10/2011 | Lu et al. |
| 2011/0294854 A1 | 12/2011 | Searle et al. |
| 2011/0319393 A1 | 12/2011 | Chassaing et al. |
| 2011/0319412 A1 | 12/2011 | Sakagami et al. |
| 2012/0010186 A1 | 1/2012 | Lachance et al. |
| 2012/0065189 A1 | 3/2012 | Takahashi et al. |
| 2012/0071489 A1 | 3/2012 | Kasai et al. |
| 2012/0071503 A1 | 3/2012 | Cosford et al. |
| 2012/0077844 A1 | 3/2012 | Cavezza et al. |
| 2012/0077854 A1 | 3/2012 | Petrassi et al. |
| 2014/0031392 A1 | 1/2014 | Petrukhin et al. |
| 2015/0057320 A1 | 2/2015 | Petrukhin et al. |
| 2015/0315197 A1 | 11/2015 | Petrukhin et al. |
| 2016/0030422 A1 | 2/2016 | Petrukhin et al. |
| 2016/0046632 A1 | 2/2016 | Petrukhin et al. |
| 2016/0046648 A1 | 2/2016 | Petrukhin et al. |
| 2016/0046649 A1 | 2/2016 | Petrukhin et al. |
| 2016/0287607 A1 | 10/2016 | Petrukhin et al. |
| 2016/0368925 A1 | 12/2016 | Petrukhin et al. |

FOREIGN PATENT DOCUMENTS

| | | |
|---|---|---|
| WO | WO 1999/65867 | 12/1999 |
| WO | WO 00/021557 | 4/2000 |
| WO | WO 2000/42852 | 7/2000 |
| WO | WO 00/061606 | 10/2000 |
| WO | WO 2001/07436 | 2/2001 |
| WO | WO 2001/66114 A1 | 9/2001 |
| WO | WO 01/87921 A2 | 11/2001 |
| WO | WO 2002/05819 A1 | 1/2002 |
| WO | WO 2002/088097 A1 | 11/2002 |
| WO | WO 2003/024450 A1 | 3/2003 |
| WO | WO 2003/024456 A1 | 3/2003 |
| WO | WO 2003/032914 A2 | 4/2003 |
| WO | WO 2003/066581 A1 | 6/2003 |
| WO | WO 2003/076400 A1 | 9/2003 |
| WO | WO 2003/092606 A2 | 11/2003 |
| WO | WO 2004/002531 A1 | 1/2004 |
| WO | WO 2004/010942 A2 | 2/2004 |
| WO | WO 2004/014374 A1 | 2/2004 |
| WO | WO 2004/017950 A2 | 3/2004 |
| WO | WO 2004/034963 A2 | 4/2004 |
| WO | WO 2004/089416 A1 | 10/2004 |
| WO | WO 2005/074535 A3 | 8/2005 |
| WO | WO 2005/087226 A1 | 9/2005 |
| WO | WO 2005/116009 | 12/2005 |
| WO | WO 2006/003030 A1 | 1/2006 |
| WO | WO 2006/004201 A1 | 1/2006 |
| WO | WO 2006/034441 A1 | 3/2006 |
| WO | WO 2006/034446 A1 | 3/2006 |
| WO | WO 2006/049880 A1 | 5/2006 |
| WO | WO 2006/065479 A2 | 6/2006 |
| WO | WO 2006/085108 A1 | 8/2006 |
| WO | WO 2006/138657 A1 | 12/2006 |
| WO | WO 2007/020888 A1 | 2/2007 |
| WO | WO 2007/027532 A2 | 3/2007 |
| WO | WO 2007/037187 A1 | 4/2007 |
| WO | WO 2007/073432 A2 | 6/2007 |
| WO | WO 2007/086584 A1 | 8/2007 |
| WO | WO 2008/045393 A2 | 4/2008 |
| WO | WO 2008080455 A1 | 7/2008 |
| WO | WO 2008/157791 A2 | 12/2008 |
| WO | WO 2009/023179 A2 | 2/2009 |
| WO | WO 2009/042444 A2 | 4/2009 |
| WO | WO 2009/051244 A1 | 4/2009 |
| WO | WO 2010/077915 A1 | 7/2010 |
| WO | WO 2010/088050 A2 | 8/2010 |
| WO | WO 2010/091409 A1 | 8/2010 |
| WO | WO 2010/108268 A1 | 9/2010 |
| WO | WO 2010/119992 A1 | 10/2010 |
| WO | WO 2010/120741 A1 | 10/2010 |
| WO | WO 2010/138487 A1 | 12/2010 |
| WO | WO 2011/033255 | 3/2011 |
| WO | WO 2011/059881 A1 | 5/2011 |
| WO | WO 2011/116123 A1 | 9/2011 |
| WO | WO 2011/156632 A2 | 12/2011 |
| WO | WO 2012/025164 A1 | 3/2012 |
| WO | WO 2012/071369 A2 | 5/2012 |
| WO | WO 2012/125904 A1 | 9/2012 |
| WO | WO 2012/158844 A1 | 11/2012 |
| WO | WO 2007/044804 A2 | 11/2013 |
| WO | WO 2013/166037 | 11/2013 |
| WO | WO 2013/166040 | 11/2013 |
| WO | WO 2013/166041 | 11/2013 |
| WO | WO 2014/133182 A1 | 9/2014 |
| WO | WO 2014/151936 A1 | 9/2014 |
| WO | WO 2014/151959 A1 | 9/2014 |
| WO | WO 2014/152013 A1 | 9/2014 |
| WO | WO 2014/152018 A1 | 9/2014 |
| WO | WO 2014/160409 A1 | 10/2014 |
| WO | WO 2004/108135 A1 | 12/2014 |
| WO | WO 2015/168286 A1 | 11/2015 |

OTHER PUBLICATIONS

International Preliminary Report on Patentability in connection with PCT/US2011/061763 dated May 29, 2012.

Written Opinion dated May 29, 2012 in connection with PCT/US2011/061763.

Notification of Transmittal of the International Search Report and the Written Opinion of the International Searching Authority, or the Declaration dated May 29, 2012 in connection with PCT/US2011/061763.

Office Action dated Apr. 10, 2014 in connection with U.S. Appl. No. 13/988,754.

Notice of Allowance dated Feb. 10, 2015 in connection with U.S. Appl. No. 13/988,754.

Extended European Search Report dated Aug. 19, 2014 in connection with European Patent Application No. 11842785.5.

Office Action (including English Language summary thereof prepared by Japanese agent) dated Sep. 29, 2015 in connection with Japanese Patent application No. 2013-541006.

International Search Report in connection with PCT/US2013/038908 dated Sep. 20, 2013.

International Preliminary Report on Patentability in connection with PCT/US2013/038908 dated Nov. 4, 2014.

Written Opinion dated Sep. 20, 2013 in connection with PCT/US2013/038908.

Notification of Transmittal of the International Search Report and the Written Opinion of the International Searching Authority, or the Declaration dated Sep. 20, 2013 in connection with PCT/US2013/038908.

International Search Report in connection with PCT/US2013/038905 dated Sep. 27, 2013.

International Preliminary Report on Patentability in connection with PCT/US2013/038905 dated Nov. 4, 2014.

(56) References Cited

OTHER PUBLICATIONS

Written Opinion dated Sep. 24, 2013 in connection with PCT/US2013/038905.
Notification of Transmittal of the International Search Report and the Written Opinion of the International Searching Authority, or the Declaration dated Sep. 27, 2013 in connection with PCT/US2013/038905.
Office Action dated Oct. 31, 2016 in connection with U.S. Appl. No. 15/093,179.
International Search Report in connection with PCT/US2013/038910 dated Sep. 24, 2013.
International Preliminary Report on Patentability in connection with PCT/US2013/038910 dated Nov. 4, 2014.
Written Opinion dated Sep. 24, 2013 in connection with PCT/US2013/038910.
Notification of Transmittal of the International Search Report and the Written Opinion of the International Searching Authority, or the Declaration dated Sep. 24, 2013 in connection with PCT/US2013/038910.
Office Action dated Dec. 10, 2015 in connection with U.S. Appl. No. 14/530,516.
Office Action dated Jul. 5, 2016 in connection with U.S. Appl. No. 14/530,516.
International Search Report in connection with PCT/US2014/026813 dated Jul. 18, 2014.
International Preliminary Report on Patentability in connection with PCT/US2014/026813 dated Sep. 15, 2015.
Written Opinion of the International Searching Authority dated Jul. 18, 2014 in connection with PCT/US2014/026813.
Notification of Transmittal of the International Search Report and the Written Opinion of the International Searching Authority, or the Declaration dated Jul. 18, 2014 in connection with PCT/US2013/026813.
Office Action dated Jun. 27, 2016 in connection with U.S. Appl. No. 14/775,532.
Office Action dated Sep. 23, 2016 in connection with U.S. Appl. No. 14/775,532.
International Search Report in connection with PCT/US2014/026523 dated Aug. 22, 2014.
International Preliminary Report on Patentability in connection with PCT/US2014/026523 dated Sep. 15, 2015.
Written Opinion dated Aug. 22, 2014 in connection with PCT/US2014/026523.
Notification of Transmittal of the International Search Report and the Written Opinion of the International Searching Authority, or the Declaration dated Aug. 22, 2014 in connection with PCT/US2013/026523.
Office Action dated Mar. 23, 2016 in connection with U.S. Appl. No. 14/775,552.
Office Action dated Sep. 28, 2016 in connection with U.S. Appl. No. 14/775,552.
International Search Report in connection with PCT/US2014/026818 dated Jul. 18, 2014.
International Preliminary Report on Patentability in connection with PCT/US2014/026818 dated Sep. 15, 2015.
Written Opinion dated Jul. 18, 2014 in connection with PCT/US2014/026818.
Notification of Transmittal of the International Search Report and the Written Opinion of the International Searching Authority, or the Declaration dated Jul. 18, 2014 in connection with PCT/US2014/026818.
European Search Report dated Sep. 23, 2016 in connection with European Patent Application No. 14769383.2.
International Search Report in connection with PCT/US2014/026730 dated Jul. 21, 2014.
International Preliminary Report on Patentability in connection with PCT/US2014/026730 dated Sep. 15, 2015.
Written Opinion dated Jul. 21, 2014 in connection with PCT/US2014/026730.
Notification of Transmittal of the International Search Report and the Written Opinion of the International Searching Authority, or the Declaration dated Jul. 21, 2014 in connection with PCT/US2014/026730.
Office Action dated Mar. 18, 2016 in connection with U.S. Appl. No. 14/775,546.
Office Action dated Aug. 9, 2016 in connection with U.S. Appl. No. 14/775,546.
International Search Report in connection with PCT/US2014/026699 dated Jul. 18, 2014.
International Preliminary Report on Patentability in connection with PCT/US2014/026699 dated Sep. 15, 2015.
Written Opinion dated Jul. 18, 2014 in connection with PCT/US2014/026699.
Notification of Transmittal of the International Search Report and the Written Opinion of the International Searching Authority, or the Declaration dated Jul. 18, 2014 in connection with PCT/US2014/026699.
International Search Report in connection with PCT/US2015/028293 dated Jul. 10, 2015.
International Preliminary Report on Patentability in connection with PCT/US2015/028293 dated Nov. 1, 2016.
Written Opinion dated Jul. 10, 2015 in connection with PCT/US2015/028293.
Notification of Transmittal of the International Search Report and the Written Opinion of the International Searching Authority, or the Declaration dated May 11, 2015 in connection with PCT/US2015/028293.
Office Action dated Nov. 25, 2015 in connection with U.S. Appl. No. 14/699,672.
Notice of Allowance dated May 12, 2016 in connection with U.S. Appl. No. 14/699,672.
Motani, et al. (2009) Identification and Characterization of a Non-retinoid Ligand for Retinal-binding Protein 4 Which Lowers Serum Retinol-binding Protein 4 Levels in Vivo. Journal of Biological Chemistry, 284(12):7673-7690.
Petrukhin (2007) New therapeutic targets in atrophic age-related macular degeneration. Expert Opin Ther Targets. 2007, 11(5):625-639; p. 629.
Sparrow, et al. (2010) Phospholipid meets all-trans-retinal: the making of RPE bisretinoids. Lipid Res 51(2): 247-261.
Elenewski, et al (2010) Free energy landscape of the retinol/serum retinal binding protein complex: a biological host-guest system. J Phys Chem B 02, 114(34):11315-11322.
Sharif, et al (2009) Time-resolved fluorescence resonance energy transfer and surface plasmon resonance-based assays for retinoid and transthyretin binding to retinol-binding protein 4. Anal Biochem, 392(2):162-168.
Bourgault, S. et al. (2011) Mechanisms of transthyretin cardiomyocyte toxicity inhibition by resveratrol analogs.Biochem. Biophys Res Commun.410(4):707-13.
Wu et al (2009) Novel Lipofuscin bisretinoids prominent in human retina and in a model of recessive Stragardt disease. J. Biol. Chem 284(30) 20155-20166.
Sparrow, et al. (2010) Interpretations of Fundus Autofluorescence from Studies of the Bisretinoids of the Retina. Invest. Ophthalmol. Vis. Sci. vol. 51 No. 9 4351-4357.
Dobri et al (2013) A1120, a Nonretinoid RBP4 Antagonist, Inhibits Formation of Cytotoxic Bisretinoids in the Animal Model of Enhanced Retinal Lipofuscinogenesis. Investigative Ophthalmology & Visual Science, vol. 54, No. 1, 85-95.
Nov. 8, 2010 CAS Search Report.
Feb. 24, 2013 CAS Search Report.
Mar. 5, 2013 CAS Search Report.
Dec. 9, 2014 CAS Search Report.
Petrukhin, K. et al. (1998) Identification of the gene responsible for Best macular dystrophy. Nature Genetics, 19, 241-247.
Cioffi, C. et al. (2014) Design, Synthesis, and Evaluation of Nonretinoid Retinol Binding Protein 4 Antagonists for the Potential Treatment of Atrophic Age-Related Macular Degeneration and Stargardt Disease. J. Med. Chem. 57, 18, 7731-7757.

(56) References Cited

OTHER PUBLICATIONS

Cioffi, C. et al. (2015) Bicyclic [3.3.0]-Octahydrocyclopenta [c]pyrrolo Antagonists of Retinol Binding Protein 4: Potential Treatment of Atrophic Age-Related Macular Degeneration and Stargardt Disease. J. Med. Chem. 58, 15, 5863-5888.

STN—Chemical database registry # 1179485-09 for Methanone, [4-(4-chlorophenyl)-4-hydroxy-1-piperidinyl] (5, 6, 7 ,8-tetrahydro-4H-cyclohept[d]isoxazol-3-yl). Sep. 2, 2009.

Wakefield, B.1 "Fluorinated Pharmaceuticals" Innovations in Pharmaceutical Technology 2003, 74, 76-78.

Princeton Biomolecular Research Inc.: "http://web.archive.org/web/20100930184751/http://www.princetonbio.com/pages4.html", accessed Apr. 30, 2015.

Bonilha, V.Age and disease-related structural changes in the retinal pigment epithelium. Clinical Opthalmoiogy 2008:2(2) 413-424.

Communication Pursuant to Article 94(3) dated Apr. 11, 2017 in connection with European Patent Application No. 11842785.5.

Office Action dated Dec. 2, 2016 in connection with U.S. Appl. No. 14/530,516.

Final Office Action dated Apr. 13, 2017 in connection with U.S. Appl. No. 14/775,532.

European Search Report dated Jul. 11, 2016 in connection with European Patent Application No. 14769462.4.

Communication Pursuant to Article 94(3) dated Mar. 29, 2017 in connection with European Patent Application No. 14769462.4.

Office Action dated Sep. 8, 2016 in connection with U.S. Appl. No. 14/775,540.

Amendment filed Apr. 19, 2017 in connection with European Patent Application No. 14769383.2.

Office Action dated Dec. 2, 2016 in connection with U.S. Appl. No. 14/775,565.

Office Action dated Mar. 22, 2017 in connection with U.S. Appl. No. 14/775,565.

Office Action dated Feb. 13, 2017 in connection with U.S. Appl. No. 15/254,966.

Wang, Y. et al. (2014) Structure-assisted discovery of the first non-retinoid ligands for Retinol-Binding Protein 4. Bioorganic & Medicinal Chemistry Letters. 24, 2885-2891.

Yingcai Wang et al. (2011) Structure-Assisted Discovery of Non-Retinoid Ligands for Retinol-Binding Protein 4. Poster presented at 2011 conference.

Jones, N. (1997) Organic Chemistry. p. 84-99.

Lachance et al (2012) Bioorganic & Medicinal Chemistry Letters. 22(2), 980-984.

**all-*trans*-retinal dimer-phosphatidylethanolamine**

**all-*trans*-retinal dimer**

| Compound | RBP4 SPA Binding IC$_{50}$ (μM) | HTRF assay for antagonists of RBP4-TTR interaction IC$_{50}$ (uM) | Solubility | Metabolic Stability (% remaining @ 30 minutes) | | | | CYP Inhibition IC$_{50}$ (μM) | | | | %PPB | | hERG |
|---|---|---|---|---|---|---|---|---|---|---|---|---|---|---|
| | | | | H | R | M | D | 2C9 | 2C19 | 2D6 | 3A4 | H | R | |
| 17 | 0.0697 | 0.255 | 55 | 100 | 75 | 50 | 100 | 0.34 | 29 | > 100.0 | 28 | 99.97 ± 0.04 | 99.8 ± 0.1 | 26.3 |
| 18 | 0.0329 | 0.895 | | | | | | | | | | | | |
| 19 | 0.00419 | 0.0676 | 9.3 | 53 | 1.6 | 44 | 43 | 5.9 | 2.9 | > 100.0 | 16 | | | |
| 20 | 0.0113 | 0.246 | 85 | 82 | 29 | 73 | 94 | 22 | 48 | > 100.0 | 37 | 98.0 ± 0.6 | 96.0 ± 2.3 | |
| 21 | 0.00608 | 0.0618 | 4.5 | 47 | 7.8 | 7.2 | 70 | 2 | 4.9 | > 100.0 | 1.1 | | | |
| 22 | 0.0045 | 0.0494 | < 1.6 | 61 | 2.3 | 38 | 58 | 13 | 16 | > 100.0 | 6.2 | | | |
| 23 | 0.00349 | 0.0607 | < 1.6 | 76 | 69 | 61 | 81 | 6 | 1.3 | > 100.0 | 1.2 | | | |
| 24 | 0.00271 | 0.0715 | < 1.6 | 57 | 39 | 8.2 | 68 | 2.7 | 4.2 | > 100.0 | 1.3 | | | |
| 25 | | | 55 | 1.1 | 0.6 | 0.6 | 69 | > 100.0 | 17 | > 100.0 | 75 | | | |
| 27 | 0.0062 | 0.119 | | | | | | | | | | | | |
| 28 | 0.002 | 0.156 | | | | | | | | | | | | |
| 29 | 0.012 | 0.211 | | | | | | | | | | | | |
| 30 | 0.0146 | 0.241 | | | | | | | | | | | | |
| 31 | 0.01 | 0.211 | | | | | | | | | | | | |
| 32 | 0.006 | 0.09 | | | | | | | | | | | | |
| 33 | 0.0189 | 0.81 | | | | | | | | | | | | |
| 34 | 0.018 | 0.512 | 1.2 | 88 | 79 | 75 | 100 | 41 | 2.7 | > 100.0 | 26 | | | |
| 35a | 0.00877 | 0.144 | 6.4 | 64 | 24 | 34 | 33 | 9.2 | 3.3 | > 100.0 | 4.4 | | | |
| 35b | 0.00168 | 0.0208 | 47 | 0.6 | 0.5 | 0.3 | 2 | 3.4 | 1.4 | > 100.0 | 1.1 | | | |
| 36 | 0.0572 | 1.9 | | | | | | | | | | | | |
| 37 | 0.0206 | 0.451 | | | | | | | | | | | | |
| 38 | 0.00976 | 0.394 | 83 | 32 | 0.9 | 0 | 41 | | | | | | | |
| 39 | 0.0059 | 0.348 | 9.2 | 26 | 28 | 6.4 | 16 | 11 | 4.4 | 90 | 3.6 | | | |

Figure 8

| Compound | RBP4 SPA Binding IC$_{50}$ (μM) | HTRF assay for antagonists of RBP4-TTR interaction IC$_{50}$ (uM) | Solubility | Metabolic Stability (% remaining @ 30 minutes) | | | | CYP Inhibition IC$_{50}$ (μM) | | | |
|---|---|---|---|---|---|---|---|---|---|---|---|
| | | | | H | R | M | D | 2C9 | 2C19 | 2D6 | 3A4 |
| 41 | 0.0089 | 0.0759 | < 1.6 | 71 | 2.8 | 4.9 | 70 | > 100.0 | 98 | > 100.0 | > 100.0 |
| 42 | 0.0896 | 0.512 | 61 | 25 | 25 | 27 | 73 | 15 | 4.9 | > 100.0 | 1.7 |
| 43 | 0.0841 | 0.318 | 2.6 | 24 | 13 | 20 | 83 | > 100.0 | 14 | > 100.0 | 10 |
| 44 | 0.0438 | 0.464 | 43 | 100 | 54 | 90 | 93 | > 100.0 | 10 | > 100.0 | 10 |
| 45 | 0.0811 | 0.315 | 14 | 23 | 11 | 21 | 76 | > 100.0 | 13 | > 100.0 | 17 |
| 46 | 0.0419 | 0.599 | 92 | 35 | 37 | 37 | 88 | 13 | 5.7 | > 100.0 | 1.3 |
| 47 | | | > 100.0 | 66 | 38 | 9.2 | 66 | 13 | 0.16 | > 100.0 | 11 |
| 48 | 0.0484 | 0.66 | 12 | 45 | 31 | 4.4 | 73 | > 100.0 | 6.7 | > 100.0 | > 100.0 |
| 49 | 0.0112 | 0.142 | 62 | 47 | 49 | 9.5 | 90 | 27 | 14 | > 100.0 | 90 |
| 50 | 0.0188 | 0.18 | 29 | 81 | 82 | 89 | 99 | 5.6 | 2.1 | > 100.0 | < 0.046 |
| 51 | | | 34 | 89 | 72 | 70 | 95 | 13 | 75 | > 100.0 | 8 |
| 52 | 0.0888 | 0.285 | 55 | 57 | 100 | 69 | 100 | 0.33 | 31 | > 100.0 | 53 |
| 53 | 0.329 | 0.368 | 60 | 89 | 87 | 100 | 99 | 0.58 | 16 | > 100.0 | 50 |
| 54 | 0.163 | 1.56 | > 100.0 | 100 | 100 | 82 | 93 | 8.7 | 32 | > 100.0 | 42 |
| 55 | >3 | ND | | | | | | | | | |
| 56 | 0.149 | 0.481 | | | | | | | | | |
| 57 | 0.0602 | 0.279 | > 100.0 | 100 | 96 | 96 | 97 | 1.4 | 3.4 | > 100.0 | 1.9 |
| 59 | 0.0118 | 0.0556 | | | | | | | | | |

OCTAHYDROCYCLOPENTAPYRROLES, THEIR PREPARATION AND USE

This application is a continuation of U.S. Ser. No. 14/775,540, filed Sep. 11, 2015, now allowed, which is a § 371 national stage of PCT International Application No. PCT/US2014/026818, filed Mar. 13, 2014, claiming the benefit of U.S. Provisional Application No. 61/785,228, filed Mar. 14, 2013, the contents of each of which are hereby incorporated by reference in their entirety.

The invention was made with government support under Grant numbers NS067594 and NS074476 awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Age-related macular degeneration (AMD) is the leading cause of blindness in developed countries. It is estimated that 62.9 million individuals worldwide have the most prevalent atrophic (dry) form of AMD; 8 million of them are Americans. Due to increasing life expectancy and current demographics this number is expected to triple by 2020. There is currently no FDA-approved treatment for dry AMD. Given the lack of treatment and high prevalence, development of drugs for dry AMD is of upmost importance. Clinically, atrophic AMD represents a slowly progressing neurodegenerative disorder in which specialized neurons (rod and cone photoreceptors) die in the central part of the retina called macula (1). Histopathological and clinical imaging studies indicate that photoreceptor degeneration in dry AMD is triggered by abnormalities in the retinal pigment epithelium (RPE) that lies beneath photoreceptors and provides critical metabolic support to these light-sensing neuronal cells. Experimental and clinical data indicate that excessive accumulation of cytotoxic autofluorescent lipid-protein-retinoid aggregates (lipofuscin) in the RPE is a major trigger of dry AMD (2-9). In addition to AMD, dramatic accumulation of lipofuscin is the hallmark of Stargardt Disease (STGD), an inherited form of juvenile-onset macular degeneration. The major cytotoxic component of RPE lipofuscin is pyridinium bisretinoid A2E (FIG. 1). Additional cytotoxic bisretinoids are isoA2E, atRAL di-PE, and A2-DHP-PE (40, 41). Formation of A2E and other lipofuscin bisretinoids, such as A2-DHP-PE (A2-dihydropyridine-phosphatidylethanolamine) and atRALdi-PE (all-trans-retinal dimer-phosphatidylethanolamine), begins in photoreceptor cells in a non-enzymatic manner and can be considered as a by-product of the properly functioning visual cycle.

A2E is a product of condensation of all-trans retinaldehyde with phosphatidyl-ethanolamine which occurs in the retina in a non-enzymatic manner and, as illustrated in FIG. 4, can be considered a by-product of a properly functioning visual cycle (10). Light-induced isomerization of 11-cis retinaldehyde to its all-trans form is the first step in a signaling cascade that mediates light perception. The visual cycle is a chain of biochemical reactions that regenerate visual pigment (11-cis retinaldehyde conjugated to opsin) following exposure to light.

As cytotoxic bisretinoids are formed during the course of a normally functioning visual cycle, partial pharmacological inhibition of the visual cycle may represent a treatment strategy for dry AMD and other disorders characterized by excessive accumulation of lipofuscin (25-27, 40, 41).

SUMMARY OF THE INVENTION

The present invention provides a compound having the structure:

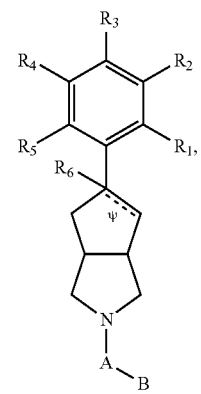

wherein
ψ is absent or present, and when present is a bond;
$R_1$, $R_2$, $R_3$, $R_4$, and $R_5$ are each independently H, halogen, $CF_3$ or $C_1$-$C_4$ alkyl;
$R_6$ is absent or present, and when present is H, OH, or halogen;
A is absent or present, and when present is

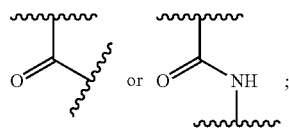

B is substituted or unsubstituted monocycle, bicycle, heteromonocycle, heterobicycle, benzyl, $CO_2H$ or ($C_1$-$C_4$ alkyl)-$CO_2H$,
wherein when B is $CO_2H$, then A is present and is

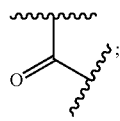

and
wherein when ψ is present, then $R_6$ is absent and when ψ is absent, then $R_6$ is present,
or a pharmaceutically acceptable salt thereof.

BRIEF DESCRIPTION OF THE FIGURES

FIG. 8. RBP4 Binding, RBP4-TTR Interaction and/or Pharmacokinetic Data of compounds 17-24 and 27-39. PPB: Plasma protein binding, H: Human, M: Mouse, R: Rat, D: Dog.

FIG. 9. RBP4 Binding, RBP4-TTR Interaction and/or Pharmacokinetic Data of compounds 41-59.

DETAILED DESCRIPTION OF THE INVENTION

Figure 1:
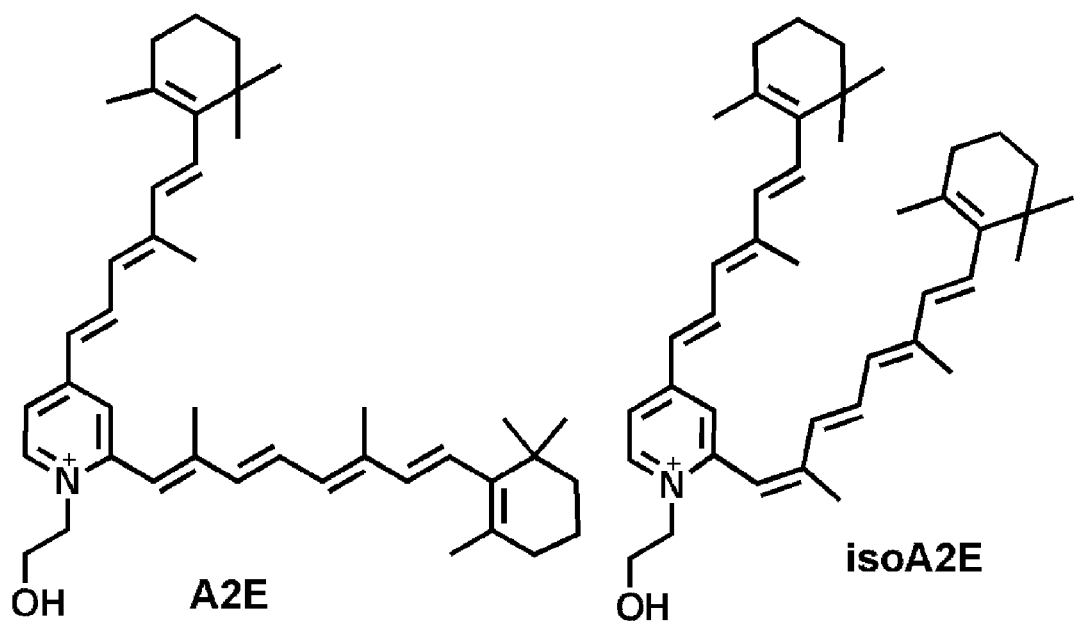
FIG. 1. Structure of bisretinoid A2E, a cytotoxic component of retinal lipofuscin.

The present invention provides a compound having the structure:

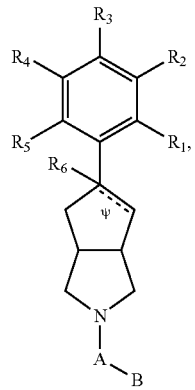

wherein
$\psi$ is absent or present, and when present is a bond;
$R_1$, $R_2$, $R_3$, $R_4$, and $R_5$ are each independently H, halogen, $CF_3$ or $C_1$-$C_4$ alkyl;
$R_6$ is absent or present, and when present is H, OH, or halogen;
A is absent or present, and when present is

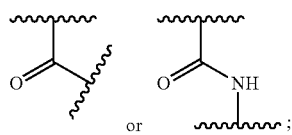

B is substituted or unsubstituted monocycle, bicycle, heteromonocycle, heterobicycle, benzyl, $CO_2H$ or ($C_1$-$C_4$ alkyl)-$CO_2H$, wherein when B is $CO_2H$, then A is present and is

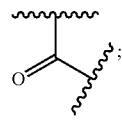

and
wherein when $\psi$ is present, then $R_6$ is absent and when $\psi$ is absent, then $R_6$ is present,
or a pharmaceutically acceptable salt thereof.

In some embodiments, the compound having the structure:

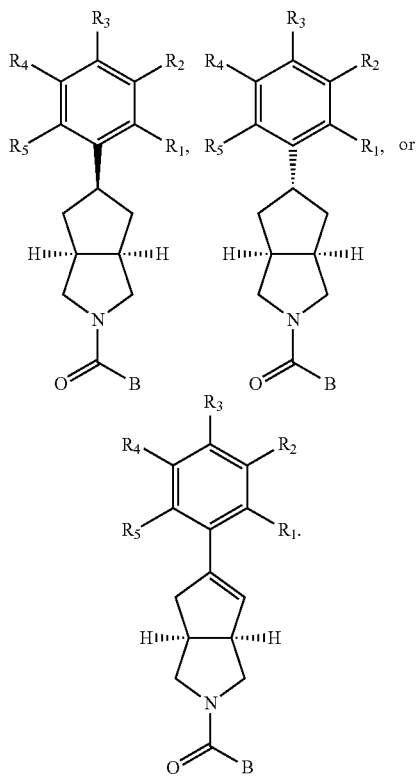

In some embodiments, the compound having the structure:

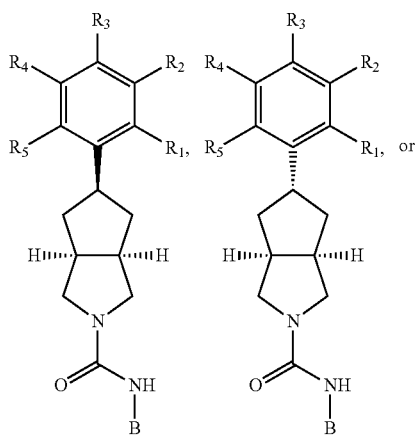

-continued

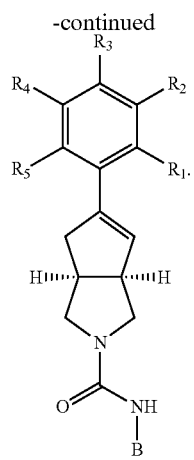

In some embodiments, the compound having the structure:

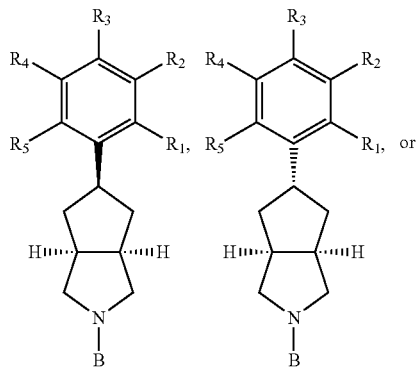

In some embodiments, the compound wherein B is a substituted or unsubstituted heterobicycle.

In some embodiments, the compound wherein B has the structure:

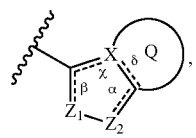

wherein

α, β, χ, and δ are each independently absent or present, and when present each is a bond;

X is C or N;

$Z_1$ is S, O, or N;

$Z_2$ is S, O, N or $NR_7$, wherein $R_7$ is H, $C_1$-$C_4$ alkyl, or oxetane;

Q is a substituted or unsubstituted 5, 6, or 7 membered ring structure.

In some embodiments of the above compound, the compound wherein B has the structure:

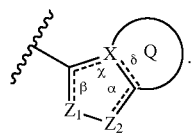

wherein when α is present, then $Z_1$ and $Z_2$ are N, X is N, β is present, and χ and δ are absent, or when α is present, then $Z_1$ is O or S, $Z_2$ is N, X is C, χ is present, and β and δ are absent;

when α is absent, then $Z_1$ is N, $Z_2$ is N—$R_7$, X is C, β and δ are present, and χ is absent, or when α is absent, then $Z_1$ is N, $Z_2$ is O or S, X is C, β and δ are present, and χ is absent.

In some embodiments, the compound wherein B has the structure:

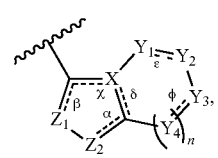

wherein n is an integer from 0-2;

α, β, χ, δ, ε, and φ are each independently absent or present, and when present each is a bond;

$Z_1$ is S, O or N;

$Z_2$ is S, O, N or N—$R_7$, wherein $R_7$ is H, $C_1$-$C_{10}$ alkyl, or oxetane;

X is C or N;

$Y_1$, $Y_2$, $Y_3$, and each occurrence of $Y_4$ are each independently $CR_8$, $C(R_9)_2$, N—$R_{10}$, O, N, $SO_2$, or C=O, wherein $R_8$ is H, halogen, $C_1$-$C_{10}$ alkyl, $C_3$-$C_6$ cycloalkyl, O—($C_1$-$C_{10}$ alkyl), C(O)OH, C(O)O($C_1$-$C_{10}$ alkyl), C(O)—$NH_2$, C(O)—NH($C_1$-$C_4$ alkyl), C(O)—NH($C_1$-$C_4$ alkyl)$_2$, NHC(O)—NH($C_1$-$C_{10}$ alkyl), NHC(O)—N($C_1$-$C_4$ alkyl)$_2$, $SO_2$—NH($C_1$-$C_{10}$ alkyl), $SO_2$—N($C_1$-$C_{10}$ alkyl)$_2$, CN, or $CF_3$;

$R_9$ is H or $C_1$-$C_{16}$ alkyl;

$R_{10}$ is H, $C_1$-$C_{10}$ alkyl, $C_3$-$C_6$ cycloalkyl, ($C_1$-$C_{10}$ alkyl)-$CF_3$, ($C_1$-$C_{10}$ alkyl)-$OCH_3$, ($C_1$-$C_{10}$ alkyl)-halogen, $SO_2$—($C_1$-$C_{10}$ alkyl), $SO_2$—($C_1$-$C_{10}$ alkyl)-$CF_3$, $SO_2$—($C_1$-$C_{10}$ alkyl)-$OCH_3$, $SO_2$—($C_1$-$C_{10}$ alkyl)-halogen, C(O)—($C_1$-$C_{10}$ alkyl), C(O)—($C_1$-$C_{10}$ alkyl)-$CF_3$, C(O)—($C_1$-$C_{10}$ alkyl)-$OCH_3$, C(O)—($C_1$-$C_{10}$ alkyl)-halogen, C(O)—NH—($C_1$-$C_{10}$ alkyl), C(O)—N($C_1$-$C_4$ alkyl)$_2$, ($C_1$-$C_{10}$ alkyl)-C(O)OH, C(O)—$NH_2$ or oxetane.

In some embodiments of the above compound, the compound wherein B has the structure:

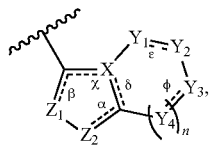

wherein when α is present, then $Z_1$ and $Z_2$ are N, X is N, β is present, and χ and δ are absent, or when α is present, then $Z_1$ is O or S, $Z_2$ is N, X is C, χ is present, and β and δ are absent;

when α is absent, then $Z_1$ is N, $Z_2$ is N—$R_7$, X is C, β and δ are present, and χ is absent, or when α is absent, then $Z_1$ is N, $Z_2$ is O or S, X is C, β and δ are present, and χ is absent.

when ε and φ are each present, then n=1, and each of $Y_1$, $Y_2$, $Y_3$, and $Y_4$ are independently C—$R_8$ or N;

when ε and φ are each absent, then n=0, 1 or 2, each of $Y_1$, $Y_2$, $Y_3$, and each occurrence of $Y_4$ are independently $C(R_9)_2$, N—$R_{10}$, O, or $SO_2$.

In some embodiments, the compound wherein

β and δ are present;

α, χ, ε, and φ are absent;

$Z_1$ is N;

$Z_2$ is O, S, or N—$R_7$, wherein $R_7$ is H, $C_1$-$C_4$ alkyl, or oxetane; and X is C.

In some embodiments, the compound wherein B has the structure:

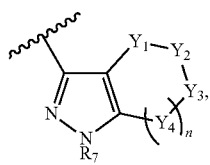

wherein n is 0;

$R_7$ is H, $C_1$-$C_4$ alkyl, or oxetane;

$Y_1$ and $Y_3$ are each $CH_2$ or $C(CH_3)_2$; and $Y_2$ is O, $SO_2$, or N—$R_{10}$, wherein $R_{10}$ is H, $C_1$-$C_4$ alkyl, $C_1$-$C_4$ cycloalkyl, ($C_1$-$C_4$ alkyl)-$CF_3$, ($C_1$-$C_4$ alkyl)-$OCH_3$, ($C_1$-$C_4$ alkyl)-halogen, $SO_2$—($C_1$-$C_4$ alkyl), $SO_2$—($C_1$-$C_4$ alkyl)-$CF_3$, $SO_2$—($C_1$-$C_4$ alkyl)-$OCH_3$, $SO_2$—($C_1$-$C_4$ alkyl)-halogen, C(O)—($C_1$-$C_4$ alkyl), C(O)—($C_1$-$C_4$ alkyl)-$CF_3$, C(O)—($C_1$-$C_4$ alkyl)-$OCH_3$, C(O)—($C_1$-$C_4$ alkyl)-halogen, C(O)—NH—($C_1$-$C_4$ alkyl), C(O)—N($C_1$-$C_4$ alkyl)$_2$, ($C_1$-$C_4$ alkyl)-C(O)OH, C(O)—$NH_2$ or oxetane.

In some embodiments, the compound wherein B has the structure:

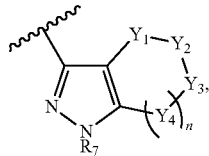

wherein n is 1;

$R_7$ is H, $C_1$-$C_4$ alkyl, or oxetane;

$Y_1$, $Y_2$ and $Y_4$ are each $CH_2$ or $C(CH_3)_2$; and $Y_3$ is O, $SO_2$, or N—$R_{10}$, wherein $R_{10}$ is H, $C_1$-$C_4$ alkyl, $C_1$-$C_4$ cycloalkyl, ($C_1$-$C_4$ alkyl)-$CF_3$, ($C_1$-$C_4$ alkyl)-$OCH_3$, ($C_1$-$C_4$ alkyl)-halogen, $SO_2$—($C_1$-$C_4$ alkyl), $SO_2$—($C_1$-$C_4$ alkyl)-$CF_3$, $SO_2$—($C_1$-$C_4$ alkyl)-$OCH_3$, $SO_2$—($C_1$-$C_4$ alkyl)-halogen, C(O)—($C_1$-$C_4$ alkyl), C(O)—($C_1$-$C_4$ alkyl)-$CF_3$, C(O)—($C_1$-$C_4$ alkyl)-$OCH_3$, C(O)—($C_1$-$C_4$ alkyl)-halogen, C(O)—NH—($C_1$-$C_4$ alkyl), C(O)—N($C_1$-$C_4$ alkyl)$_2$, ($C_1$-$C_4$ alkyl)-C(O)OH, C(O)—$NH_2$ or oxetane.

In some embodiments, the compound wherein B has the structure:

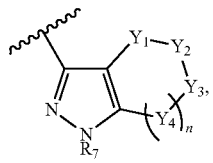

wherein n is 1;

$R_7$ is H, $C_1$-$C_4$ alkyl, or oxetane;

$Y_1$, $Y_3$ and $Y_4$ are each $CH_2$ or $C(CH_3)_2$; and $Y_2$ is O, $SO_2$, or N—$R_{10}$, wherein $R_{10}$ is H, $C_1$-$C_4$ alkyl, $C_1$-$C_4$ cycloalkyl, ($C_1$-$C_4$ alkyl)-$CF_1$, ($C_1$-$C_4$ alkyl)-$OCH_3$, ($C_1$-$C_4$ alkyl)-halogen, $SO_2$—($C_1$-$C_4$ alkyl), $SO_2$—($C_4$-$C_4$ alkyl)-$CF_3$, $SO_2$—($C_1$-$C_4$ alkyl)-$OCH_3$, $SO_2$—($C_1$-$C_4$ alkyl)-halogen, C(O)—($C_1$-$C_4$ alkyl), C(O)—($C_1$-$C_4$ alkyl)-$CF_3$, C(O)—($C_1$-$C_4$ alkyl)-$OCH_3$, C(O)—($C_1$-$C_4$ alkyl)-halogen, C(O)—NH—($C_1$-$C_4$ alkyl), C(O)—N($C_1$-$C_4$ alkyl)$_2$, ($C_1$-$C_4$ alkyl)-C(O)OH, C(O)—$NH_2$ or oxetane.

In some embodiments, the compound wherein B has the structure:

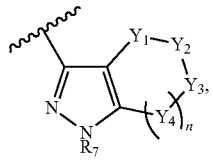

wherein n is 2;

$R_7$ is H, $C_1$-$C_4$ alkyl, or oxetane;

$Y_1$, $Y_3$ and each occurrence of $Y_4$ are each $CH_2$ or $C(CH_3)_2$; and $Y_2$ is O, $SO_2$, or $N-R_{10}$, wherein $R_{10}$ is H, $C_1$-$C_4$ alkyl, $C_1$-$C_4$ cycloalkyl, ($C_1$-$C_4$ alkyl)-$CF_3$, ($C_1$-$C_4$ alkyl)-$OCH_3$, ($C_1$-$C_4$ alkyl)-halogen, $SO_2$—($C_1$-$C_4$ alkyl), $SO_2$—($C_1$-$C_4$ alkyl)-$CF_3$, $SO_2$—($C_1$-$C_4$ alkyl)-$OCH_3$, $SO_2$—($C_1$-$C_4$ alkyl)-halogen, C(O)—($C_1$-$C_4$ alkyl), C(O)—($C_1$-$C_4$ alkyl)-$CF_3$, C(O)—($C_1$-$C_4$ alkyl)-$OCH_3$, C(O)—($C_1$-$C_4$ alkyl-halogen, C(O)—NH—($C_1$-$C_4$ alkyl), C(O)—N($C_1$-$C_4$ alkyl)$_2$, ($C_1$-$C_4$ alkyl)-C(O)OH, C(O)—$NH_2$ or oxetane.

In some embodiments, the compound wherein B has the structure:

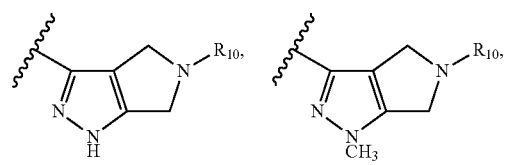
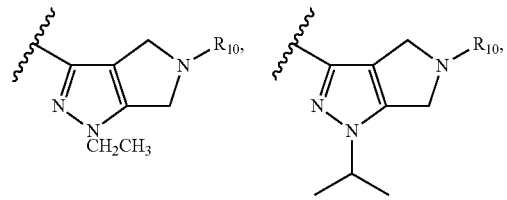
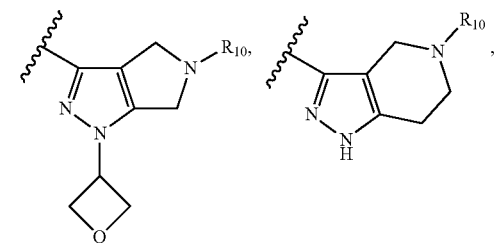
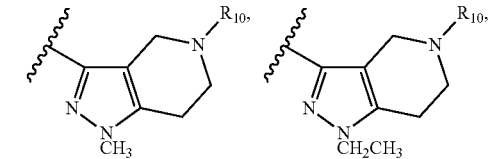
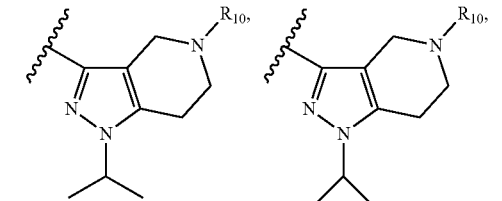
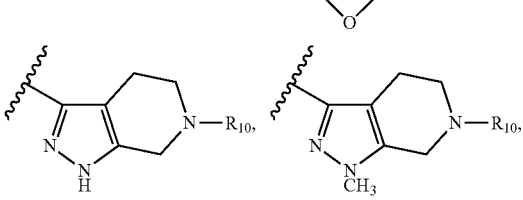
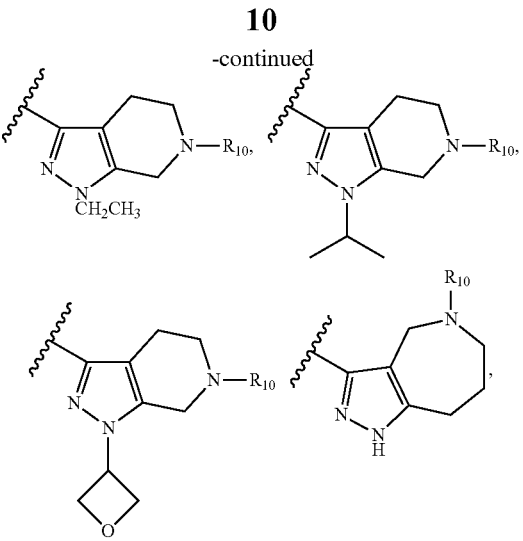
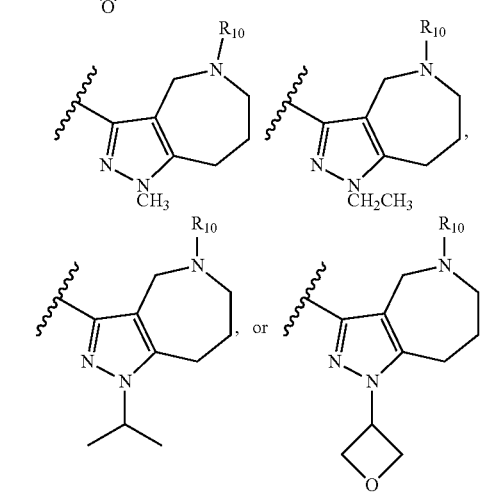

In some embodiments, the compound wherein $R_{10}$ is H, $CH_3$, $CH_2CH_3$, $CH_2CH_2CH_3$, $CH(CH_3)_2$, $CH_2CH(CH_3)_2$, t-Bu, $CH_2OCH_3$, $CH_2CF_3$, $CH_2Cl$, $CH_2F$, $CH_2CH_2OCH_3$, $CH_2CH_2CF_3$, $CH_2CH_2Cl$, $CH_2CH_2F$, or

In some embodiments, the compound wherein $R_{10}$ is $SO_2$—$CH_3$, $SO_2$—$CH_2CH_3$, $SO_2$—$CH_2CH_2CH_3$, $SO_2$—$CH(CH_3)_2$, $SO_2$—$CH_2CH(CH_3)_2$, $SO_2$-t-Bu, $SO_2$—$CH_2OCH_3$, $SO_2$—$CH_2CF_3$, $SO_2$—$CH_2Cl$, $SO_2$—$CH_2F$, $SO_2$—$CH_2CH_2OCH_3$, $SO_2$—$CH_2CH_2CF_3$, $SO_2$—$CH_2CH_2Cl$, $SO_2$—$CH_2CH_2F$, or

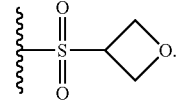

In some embodiments, the compound wherein $R_{10}$ is C(O)—$CH_3$, C(O)—$CH_2CH_3$, C(O)—$CH_2CH_2CH_3$, C(O)—$CH(CH_3)_2$, C(O)—$CH_2CH(CH_3)_2$, C(O)-t-Bu, C(O)—$CH_2OCH_3$, C(O)—$CH_2CF_3$, C(O)—$CH_2Cl$, C(O)—

CH$_2$F, C(O)—CH$_2$CH$_2$OCH$_3$, C(O)—CH$_2$CH$_2$CF$_3$, C(O)—CH$_2$CH$_2$Cl, C(O)—CH$_2$CH$_2$F,

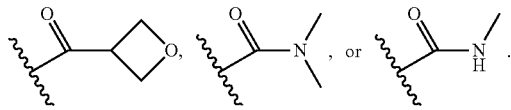

In some embodiments, the compound wherein B has the structure:

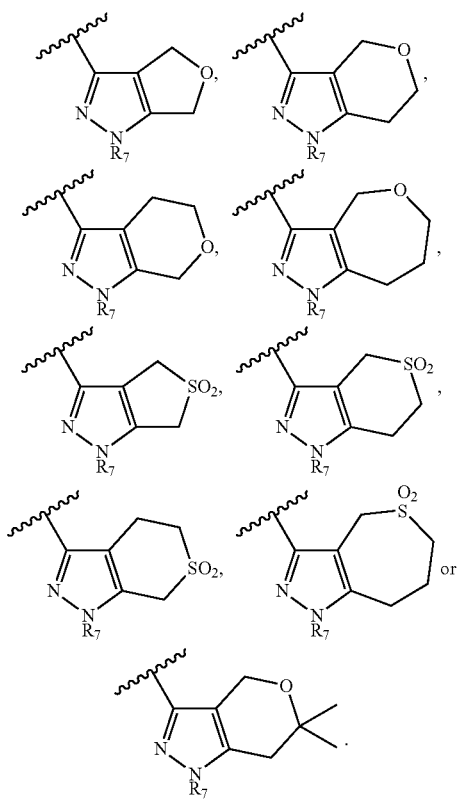

In some embodiments, the compound wherein R$_7$ is H, CH$_3$, CH$_2$CH$_3$, CH(CH$_3$)$_2$, or

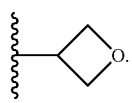 [SMILES: *C1COC1]

In some embodiments, the compound wherein B has the structure:

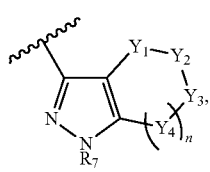

wherein
n is 1;
R$_7$ is H, C$_1$-C$_4$ alkyl, or oxetane;
Y$_1$ and Y$_4$ are each CH$_2$; and
Y$_2$ is C=O and Y$_3$ is N—R$_{10}$, or Y$_3$ is C=O and Y$_2$ is N—R$_{10}$,
wherein
R$_{10}$ is H or C$_1$-C$_4$ alkyl.

In some embodiments, the compound wherein B has the structure:

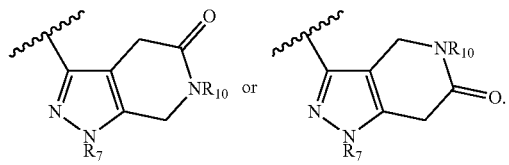

In some embodiments, the compound wherein R$_7$ is H, CH$_3$, CH$_2$CH$_3$, CH(CH$_3$)$_2$, or

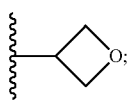 [SMILES: *C1COC1]

and each R$_{10}$ is H or CH$_3$.

In some embodiments, the compound wherein B has the structure:

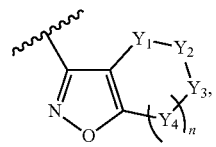

wherein
n is 1;
Y$_1$ and Y$_4$ are each CH$_2$; and
one of Y$_2$ or Y$_3$ is CH$_2$ and the other of Y$_2$ or Y$_3$ is O, SO$_2$, or N—R$_{10}$,
wherein
R$_{10}$ is H, C$_1$-C$_4$ alkyl, C$_1$-C$_4$ cycloalkyl, (C$_1$-C$_4$ alkyl)-CF$_3$, (C$_1$-C$_4$ alkyl)-OCH$_3$, (C$_1$-C$_4$ alkyl)-halogen, SO$_2$—(C$_1$-C$_4$ alkyl), SO$_2$—(C$_1$-C$_4$ alkyl)-CF$_3$, SO$_2$—(C$_1$-C$_4$ alkyl)-OCH$_3$, SO$_2$—(C$_1$-C$_4$ alkyl)-halogen, C(O)—(C$_1$-C$_4$ alkyl), C(O)—(C$_1$-C$_4$ alkyl)-CF$_3$, C(O)—(C$_1$-C$_4$ alkyl)-OCH$_3$, C(O)—(C$_1$-C$_4$ alkyl)-halogen, C(O)—NH—(C$_1$-C$_4$ alkyl), C(O)—N(C$_1$-C$_4$ alkyl)$_2$, C$_1$-C$_4$ alkyl-C(O)OH, or oxetane.

In some embodiments, the compound wherein B has the structure:

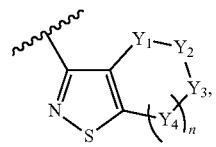

wherein
n is 1;
Y$_1$ and Y$_4$ are each CH$_2$; and
one of Y$_2$ or Y$_3$ is CH$_2$ and the other of Y$_2$ or Y$_3$ is O, SO$_2$, or N—R$_{10}$, wherein R$_{10}$ is H, C$_1$-C$_4$ alkyl, C$_1$-C$_4$ cycloalkyl, (C$_1$-C$_4$ alkyl)-CF$_3$, (C$_1$-C$_4$ alkyl)-OCH$_3$, (C$_1$-C$_4$ alkyl)-halogen, SO$_2$—(C$_1$-C$_4$ alkyl), SO$_2$—(C$_1$-C$_4$ alkyl)-CF$_3$, SO$_2$—(C$_1$-C$_4$ alkyl)-OCH$_2$, SO$_2$—(C$_1$-C$_4$ alkyl)-halogen, C(O)—(C$_1$-C$_4$ alkyl), C(O)—(C$_1$-C$_4$ alkyl)-CF$_3$, C(O)—(C$_1$-C$_4$ alkyl)-OCH), C(O)—(C$_1$-C$_4$ alkyl)-halogen, C(O)—NH—(C$_1$-C$_4$ alkyl), C(O)—N(C$_1$-C$_4$ alkyl)$_2$, C$_1$-C$_4$ alkyl)-C(O)OH, or oxetane.

In some embodiments, the compound wherein B has the structure:

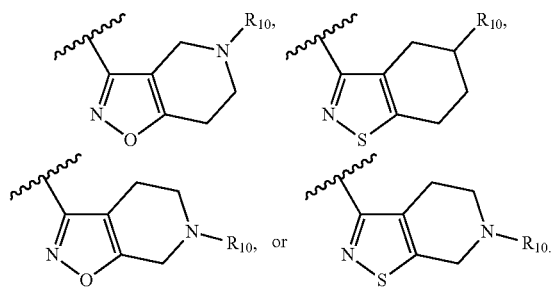

In some embodiments, the compound wherein R$_{10}$ is H, CH$_3$, CH$_2$CH$_3$, CH$_2$CH$_2$CH$_3$, CH(CH$_3$)$_2$, CH$_2$CH(CH$_3$)$_2$, t-Bu, CH$_2$OCH$_3$, CH$_2$CF$_3$, CH$_2$Cl, CH$_2$F, CH$_2$CH$_2$OCH$_3$, CH$_2$CH$_2$CF$_3$, CH$_2$CH$_2$Cl, CH$_2$CH$_2$F, or

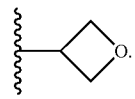

In some embodiments, the compound wherein R$_{10}$ is SO$_2$—CH$_3$, SO$_2$—CH$_2$CH$_3$, SO$_2$—CH$_2$CH$_2$CH$_3$, SO$_2$—CH(CH$_3$)$_2$, SO$_2$—CH$_2$CH(CH$_3$)$_2$, SO$_2$-t-Bu, SO$_2$—CH$_2$OCH$_3$, SO$_2$—CH$_2$CF$_3$, SO$_2$—CH$_2$Cl, SO$_2$—CH$_2$F, SO$_2$—CH$_2$CH$_2$OCH$_3$, SO$_2$—CH$_2$CH$_2$CF$_3$, SO$_2$—CH$_2$CH$_2$Cl, SO$_2$—CH$_2$CH$_2$F, or

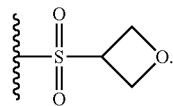 [SMILES: *S(=O)(=O)C1COC1]

In some embodiments, the compound wherein R$_{10}$ is C(O)—CH$_3$, C(O)—CH$_2$CH$_3$, C(O)—CH$_2$CH$_2$CH$_3$, C(O)—CH(CH$_3$)$_2$, C(O)—CH$_2$CH(CH$_3$)$_2$, C(O)-t-Bu, C(O)—CH$_2$OCH$_3$, C(O)—CH$_2$CF$_3$, C(O)—CH$_2$Cl, C(O)—CH$_2$F, C(O)—CH$_2$CH$_3$OCH$_3$, C(O)—CH$_2$CH$_2$CF$_3$, C(O)—CH$_2$CH$_2$Cl, C(O)—CH$_2$CH$_2$F,

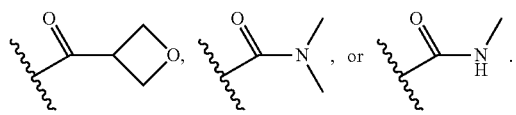

In some embodiments, the compound wherein
β, δ, ε, and φ are present;
α and χ are absent;
Z$_1$ is N;
Z$_2$ is O or N—R$_7$,
  wherein R$_7$ is H, C$_1$-C$_4$ alkyl, or oxetane; and
X is C.

In some embodiments, the compound wherein B has the structure:

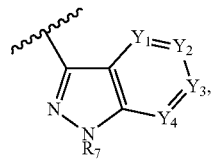

wherein

R$_7$ is H, C$_1$-C$_4$ alkyl, or oxetane; and
Y$_1$, Y$_2$, Y$_3$ and Y$_4$ are each independently CR$_8$ or N,
  wherein each R$_8$ is independently H, halogen, C$_1$-C$_4$ alkyl, C$_1$-C$_4$ cycloalkyl, O—(C$_1$-C$_4$ alkyl), C(O)OH, C(O)—NH$_2$, C(O)—N(CH$_3$)$_2$, C(O)—NHCH$_3$, NHC(O)—N(CH$_3$)$_2$, CN, or CF$_3$, In some embodiments, the compound wherein
Y$_1$, Y$_2$, Y$_3$ and Y$_4$ are each CH;
Y$_1$, Y$_2$, Y$_3$ are each CH and Y$_4$ is N;
Y$_1$, Y$_2$, Y$_4$ are each CH and Y$_3$ is N;
Y$_1$, Y$_3$, Y$_4$ are each CH and Y$_2$ is N; or
Y$_2$, Y$_3$, Y$_4$ are each CH and Y$_1$ is N.

In some embodiments, the compound wherein B has the structure:

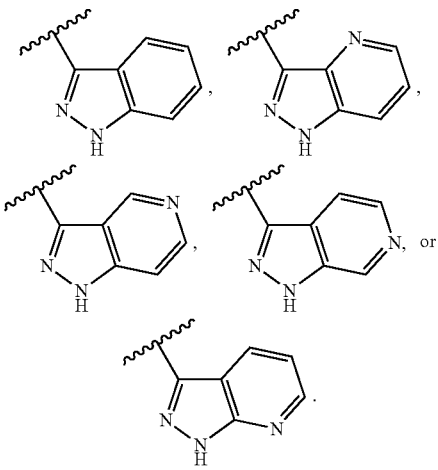

In some embodiments, the compound wherein B has the structure:

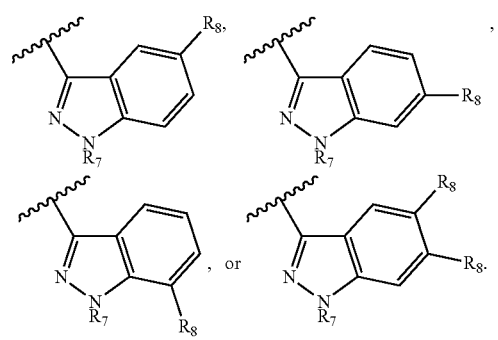

In some embodiments, the compound wherein R$_7$ is H, CH$_2$CH$_3$, CH$_3$, CH(CH$_3$)$_2$, or

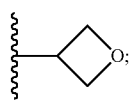 [SMILES: *C1COC1]
and each $R_8$ is independently H, Cl, Br, F, $OCH_3$, $OCH_2CH_3$, $CF_3$, CN, $CH_3$, $CH_3CH_3$, C(O)OH, C(O)—$NH_2$, C(O)—$N(CH_3)_2$, C(O)—$NHCH_3$, or NHC(O)—$N(CH_3)_2$.

In some embodiments, the compound wherein B has the structure:

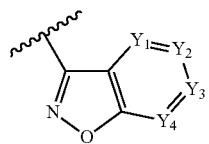

wherein $Y_1$, $Y_2$, $Y_3$ and $Y_4$ are each independently $CR_8$ or N,
wherein $R_8$ is H, halogen, $C_1$-$C_4$ alkyl, $C_1$-$C_4$ cycloalkyl, O—($C_1$-$C_4$ alkyl), C(O)OH, C(O)—$NH_2$, C(O)—$N(CH_3)_2$, C(O)—$NHCH_3$, NHC(O)—$N(CH_3)_2$, CN, or $CF_3$, In some embodiments, the compound wherein $Y_1$, $Y_2$, $Y_3$ and $Y_4$ are each CH;

$Y_1$, $Y_2$, $Y_3$ are each CH and $Y_4$ is N;

$Y_1$, $Y_2$, $Y_4$ are each CH and $Y_3$ is N;

$Y_1$, $Y_3$, $Y_4$ are each CH and $Y_2$ is N; or $Y_2$, $Y_3$, $Y_4$ are each CH and $Y_1$ is N.

In some embodiments, the compound wherein B has the structure:

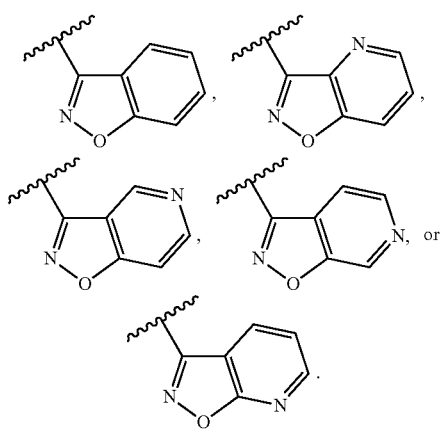

In some embodiments, the compound wherein
α and β are present;
χ, δ, ε, and φ are absent;
$Z_1$ is N;
$Z_2$ is N; and
X is N.

In some embodiments, the compound wherein B has the structure:

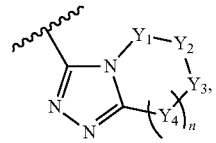

wherein
n is 1;
$Y_1$ and $Y_4$ are each $CH_2$; and
one of $Y_2$ or $Y_3$ is $CH_2$ and the other of $Y_2$ or $Y_3$ is O, $SO_2$, or N—$R_{10}$,
wherein
$R_{10}$ is H, $C_1$-$C_4$ alkyl, C1-C4 cycloalkyl, ($C_1$-$C_4$ alkyl)-$CF_3$, ($C_1$-$C_4$ alkyl)-$OCH_3$, ($C_1$-$C_4$ alkyl)-halogen, $SO_2$—($C_1$-$C_4$ alkyl), $SO_2$—($C_1$-$C_4$ alkyl)-$CF_3$, $SO_2$—($C_1$-$C_4$ alkyl)-$OCH_3$, $SO_2$—($C_1$-$C_4$ alkyl)-halogen, C(O)—($C_1$-$C_4$ alkyl), C(O)—($C_1$-$C_4$ alkyl)-$CF_3$, C(O)—($C_1$-$C_4$ alkyl)-$OCH_3$, C(O)—($C_1$-$C_4$ alkyl)-halogen, C(O)—NH—($C_1$-$C_4$ alkyl), C(O)—N($C_1$-$C_4$ alkyl)$_2$, ($C_1$-$C_4$ alkyl)-C(O)OH, or oxetane.

In some embodiments, the compound wherein B has the structure:

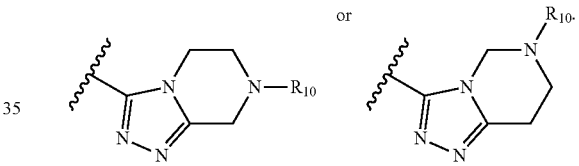

In some embodiments, the compound wherein $R_{10}$ is H, $CH_3$, $CH_2CH_3$, $CH_2CH_2CH_3$, $CH(CH_3)_2$, $CH_2CH(CH_3)_2$, t-Bu, $CH_2OCH_3$, $CH_2CF_3$, $CH_2Cl$, $CH_2F$, $CH_2CH_2OCH_3$, $CH_2CH_2CF_3$, $CH_2CH_2Cl$, $CH_2CH_2F$, or

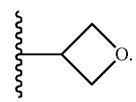

In some embodiments, the compound wherein $R_{10}$ is $SO_2$—$CH_3$, $SO_2$—$CH_2CH_3$, $SO_2$—$CH_2CH_2CH_3$ $SO_2$—$CH(CH_3)_2$, $SO_2$—$CH_2CH(CH_3)_2$, $SO_2$-t-Bu, $SO_2$—$CH_2OCH_3$, $SO_2$—$CH_2CF_3$, $SO_2$—$CH_2Cl$, $SO_2$—$CH_2F$, $SO_2$—$CH_2CH_2OCH_1$, $SO_2$—$CH_2CH_2CF_3$, $SO_2$—$CH_2CH_2Cl$, $SO_2$—$CH_2CH_2F$, or

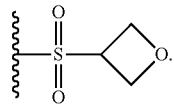 [SMILES: *S(=O)(=O)C1COC1]

In some embodiments, the compound wherein $R_{10}$ is C(O)—$CH_3$, C(O)—$CH_2CH_3$, C(O)—$CH_2CH_2CH_3$, C(O)—$CH(CH_3)_2$, C(O)—$CH_2CH(CH_1)_2$, C(O)-t-Bu, C(O)—$CH_2OCH_3$, C(O)—$CH_2CF_3$, C(O)—$CH_2Cl$, C(O)—

CH$_2$F, C(O)—CH$_2$CH$_2$OCH$_3$, C(O)—CH$_2$CH$_2$CF$_3$, C(O)—CH$_2$CH$_2$Cl, C(O)—CH$_2$CH$_2$F,

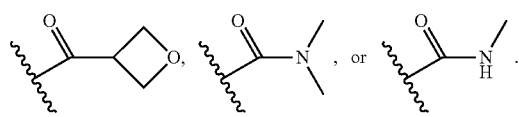

In some embodiments, the compound wherein B has the structure:

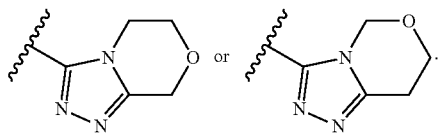 [SMILES: *c1nnc2n1CCOC2 ; "or" ; *c1nnc2n1COCC2]

In some embodiments, the compound wherein α, β, ε, and φ are present;
χ and δ are absent;
Z$_1$ is N;
Z$_2$ is N; and
X is N.

In some embodiments, the compound wherein 13 has the structure:

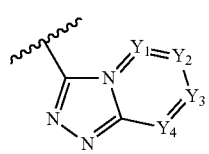

wherein
Y$_1$, Y$_2$, Y$_3$ and Y$_4$ are each independently CR$_8$ or N,
wherein each R$_8$ is independently H, halogen, C$_1$-C$_4$ alkyl, C$_1$-C$_4$ cycloalkyl, O(C$_1$-C$_4$ alkyl), CN, CF$_3$, C(O)OH, C(O)—NH$_2$, C(O)—N(CH$_3$)$_2$, C(O)—NHCH$_3$, or NHC(O)—N(CH$_3$)$_2$ In some embodiments, the compound wherein B has the structure:

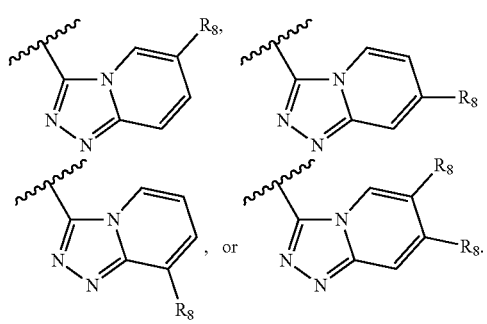

In some embodiments, the compound wherein each R$_8$ is independently H, Cl, Br, F, OCH$_3$, OCH$_2$CH$_3$, CF$_3$, CN, CH$_3$, CH$_3$CH$_3$, C(O)OH, C(O)—NH$_2$, C(O)—N(CH$_3$)$_2$, C(O)—NHCH$_3$, NHC(O)—NHCH$_3$, NHC(O)—N(CH$_3$)$_2$, SO$_2$—NHCH$_3$ or SO$_2$—N(CH$_3$)$_2$.

In some embodiments, the compound wherein
α, χ, ε, and φ are present;
β and δ are absent;
Z$_1$ is O or S;
Z$_2$ is N; and
X is C.

In some embodiments, the compound wherein B has the structure:

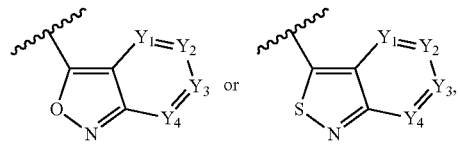

wherein
Y$_1$, Y$_2$, Y$_3$ and Y$_4$ are each independently CR$_8$ or N,
wherein each R$_8$ is independently H, halogen, O—(C$_1$-C$_4$ alkyl), CN, or CF$_3$.

In some embodiments, the compound wherein B has the structure:

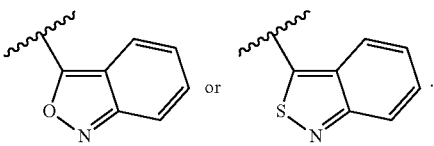 [SMILES: *c1onc2ccccc12 ; "or" ; *c1snc2ccccc12]

In some embodiments, the compound wherein B has the structure:

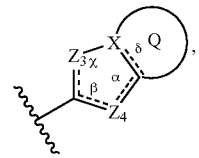

wherein
α, β, χ, and δ are each independently absent or present, and when present each is a bond;
X is C or N;
Z$_3$ is CH, S, O, N or NR$_{11}$,
wherein R$_{11}$ is H or C$_1$-C$_{10}$ alkyl;
Z$_4$ is CH, S, O, N or NR$_{12}$,
wherein R$_{12}$ is H or C$_1$-C$_{10}$ alkyl;
Q is a substituted or unsubstituted 5, 6, or 7 membered ring structure.

In some embodiments of the above compound, the compound wherein
when α is present, then Z$_3$ are N, Z$_4$ is CH, X is N, β and δ are absent, and χ is present;
when α is absent, then Z$_3$ is CH or N, Z$_4$ is NR$_7$, S, or O, X is C, β and δ are present, and χ is absent.

In some embodiments, the compound wherein B has the structure:

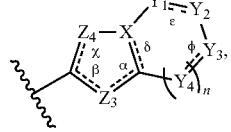

wherein
n is an integer from 0-2;
α, β, χ, δ, ε, and φ are each independently absent or present, and when present each is a bond;

X is C or N;

$Z_3$ is CH, S, O, N or $NR_{11}$,
wherein $R_{11}$ is H or $C_1$-$C_{10}$ alkyl;

$Z_4$ is CH, S, O, N or $NR_{12}$,
wherein $R_{12}$ is H or $C_1$-$C_{10}$ alkyl;

$Y_1$, $Y_2$, $Y_3$, and each occurrence of $Y_4$ are each independently $CR_{13}$, $C(R_{14})_2$, N—$R_{15}$, O, N, $SO_2$, or C=O,
wherein
$R_{13}$ is H, halogen, $C_1$-$C_{10}$ alkyl, $C_3$-$C_6$ cycloalkyl, O—($C_1$-$C_{10}$ alkyl), C(O)OH, C(O)O($C_1$-$C_{10}$ alkyl), C(O)—$NH_2$, C(O)—NH($C_1$-$C_4$ alkyl), C(O)—NH($C_1$-$C_4$ alkyl)$_2$, NHC(O)—NH($C_1$-$C_{10}$ alkyl), NHC(O)—N($C_1$-$C_4$ alkyl)$_2$, $SO_2$—NH($C_1$-$C_{10}$ alkyl), $SO_2$—N($C_1$-$C_{10}$ alkyl)$_2$, CN, $CF_3$, imidazole, morpholino, or pyrrolidine $R_{14}$ is H or $C_1$-$C_{10}$ alkyl;

$R_{15}$ is H, $C_1$-$C_{10}$ alkyl, $C_3$-$C_6$ cycloalkyl, ($C_1$-$C_{10}$ alkyl)-$CF_3$, ($C_1$-$C_{10}$ alkyl)-$OCH_3$, ($C_1$-$C_{10}$ alkyl)-halogen, $SO_2$—($C_1$-$C_{10}$ alkyl), $SO_2$—($C_1$-$C_{10}$ alkyl)-$CF_3$, $SO_2$—($C_1$-$C_{10}$ alkyl)-$OCH_3$, $SO_2$—($C_1$-$C_{10}$ alkyl)-halogen, C(O)—($C_1$-$C_{10}$ alkyl), C(O)—($C_1$-$C_{10}$ alkyl)-$CF_3$, C(O)—($C_1$-$C_{10}$ alkyl)-$OCH_3$, C(O)—($C_1$-$C_{10}$ alkyl)-halogen, C(O)—NH—($C_1$-$C_{10}$ alkyl), C(O)—N($C_1$-$C_4$ alkyl)$_2$, ($C_1$-$C_{10}$ alkyl)-C(O)OH, C(O)—$NH_2$ or oxetane.

In some embodiments of the above compound, the compound wherein
when α is present, then $Z_3$ are N, $Z_4$ is CH, X is N, β and δ are absent, and χ is present;
when α is absent, then $Z_3$ is CH or N, $Z_4$ is $NR_{12}$, S, or O, X is C, β and δ are present, and χ is absent;
when ε and φ are each present, then n=1, and each of $Y_1$, $Y_2$, $Y_3$, and $Y_4$ are independently C—$R_{13}$ or N;
when ε and φ are each absent, then n=0, 1 or 2, each of $Y_1$, $Y_2$, $Y_3$, and each occurrence of $Y_4$ are independently $C(R_{14})_2$, N—$R_{15}$, O, or $SO_2$.

In some embodiments, the compound wherein
α, χ, ε, and φ are each present, β and δ are each absent, $Z_3$ is CH, $Z_4$ is N; and X is N; or
χ, δ, ε, and φ are each present, α and β are each absent, $Z_3$ is CH, $Z_4$ is N—$R_{12}$; and X is C; or
χ, δ, ε, and φ are each present, α and β are each absent, $Z_3$ is N, $Z_4$ is N—$R_{12}$, S or O; and X is C.

In some embodiments, the compound wherein B has the structure:

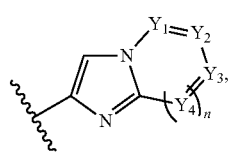

wherein
n is 1; and
$Y_1$, $Y_2$, $Y_3$, and $Y_4$ are each C—$R_{13}$ or N,
wherein $R_{13}$ is H, halogen, $C_1$-$C_4$ alkyl, $C_1$-$C_4$ cycloalkyl, O—($C_1$-$C_4$ alkyl), C(O)OH, C(O)—$NH_2$, C(O)—N($CH_3$)$_2$, C(O)—$NHCH_3$, NHC(O)—N($CH_3$)$_2$, CN, $CF_3$, imidazole, morpholino, or pyrrolidine.

In some embodiments, the compound wherein $Y_1$, $Y_2$, $Y_3$, and $Y_4$ are each C—$R_{13}$; or $Y_1$ is N, and $Y_2$, $Y_3$, and $Y_4$ are each C—$R_{13}$.

In some embodiments, the compound wherein B has the structure:

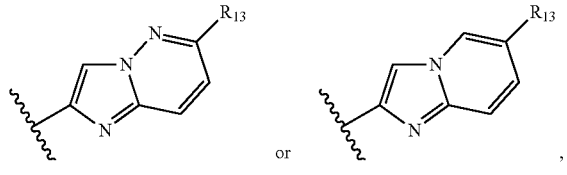

wherein is $R_{13}$ is H, halogen, $C_1$-$C_4$ alkyl, $C_1$-$C_4$ cycloalkyl, O—($C_1$-$C_4$ alkyl), $C_1$-$C_4$ cycloalkyl, C(O)OH, C(O)—$NH_2$, C(O)—N($CH_3$)$_2$, C(O)—$NHCH_3$, NHC(O)—N($CH_3$)$_2$, CN, $CF_3$, imidazole, morpholino, or pyrrolidine.

In some embodiments, the compound wherein B has the structure:

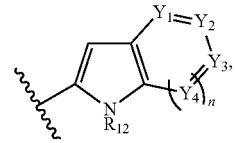

wherein
n is 1;
$R_{12}$ is H or $C_1$-$C_4$ alkyl;
$Y_1$, $Y_2$, $Y_3$, and $Y_4$ are each C—$R_{13}$ or N,
wherein $R_{13}$ is H, halogen, $C_1$-$C_4$ alkyl, $C_1$-$C_4$ cycloalkyl, O—($C_1$-$C_4$ alkyl), C(O)OH, C(O)—$NH_2$, C(O)—N($CH_3$)$_2$, C(O)—$NHCH_3$, NHC(O)—N($CH_3$)$_2$, CN, $CF_3$ imidazole, morpholino, or pyrrolidine.

In some embodiments, the compound wherein B has the structure:

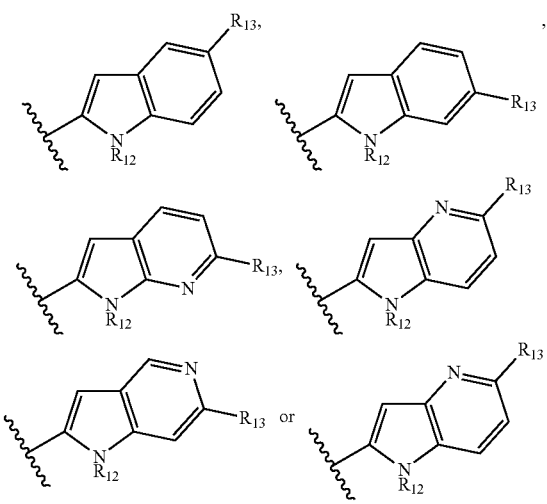

In some embodiments, the compound wherein $R_{13}$ is H, $CH_3$, $CF_3$, $OCH_3$, F, Cl,

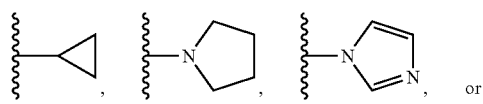 or

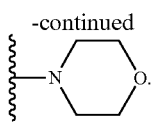

In some embodiments, the compound wherein B has the structure:

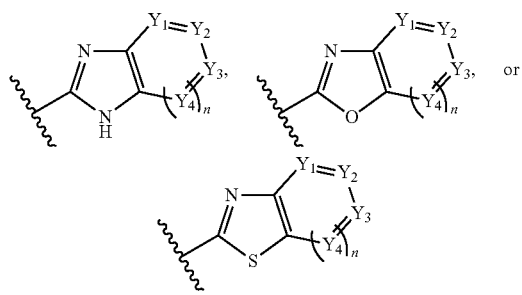

wherein
n is 1; and
$Y_1$, $Y_2$, $Y_3$, and $Y_4$ are each C—$R_{13}$ or N,
  wherein $R_{13}$ is H, halogen, $C_1$-$C_4$ alkyl, $C_1$-$C_4$ cycloalkyl, O—($C_1$-$C_4$ alkyl), C(O)OH, C(O)—$NH_2$, C(O)—$N(CH_3)_2$, C(O)—$NHCH_3$, NHC(O)—$N(CH_3)_2$, CN, $CF_3$, imidazole, morpholino, or pyrrolidine.

In some embodiments, the compound wherein
$Y_1$, $Y_2$, $Y_3$, and $Y_4$ are each C—$R_{13}$, or
one of $Y_1$, $Y_2$, $Y_3$, or $Y_4$ is N and the other three of $Y_1$, $Y_2$, $Y_3$, or $Y_4$ are each C—$R_{13}$,
  wherein each $R_{13}$ is H.

In some embodiments, the compound wherein B has the structure:

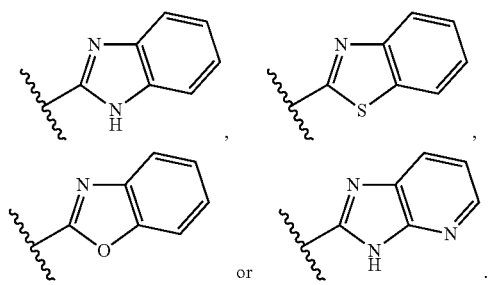

In some embodiments, the compound wherein B has the structure:

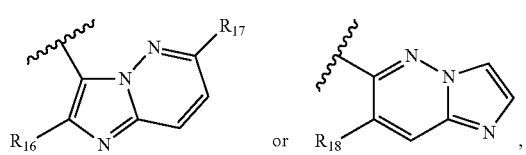

wherein $R_{16}$, $R_{17}$, and $R_{18}$ are each H, halogen, $C_1$-$C_4$ alkyl or $C_1$-$C_4$ cycloalkyl.

In some embodiments, the compound wherein B has the structure:

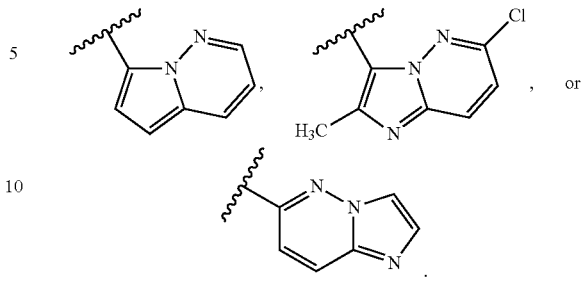

In some embodiments, the compound wherein B is a substituted or unsubstituted monocycle or heteromonocycle.

In some embodiments, the compound wherein B is a substituted or unsubstituted imidazole, pyridazine, pyrazole, pyrazine, thiadiazole, or triazole.

In some embodiments, the compound wherein B has the structure:

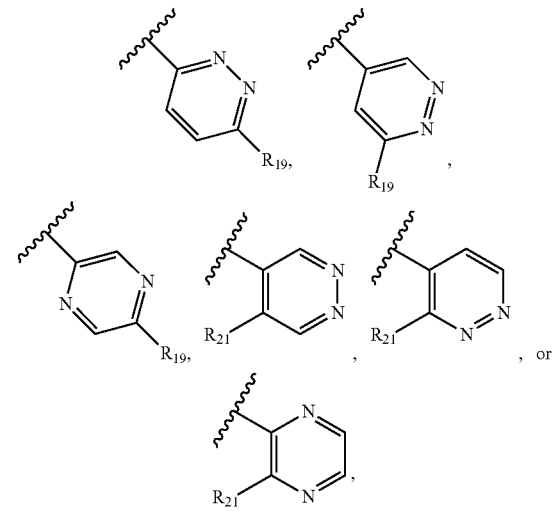

wherein $R_{19}$, is H, halogen CN, $CF_3$, OH, $NH_2$, $C_1$-$C_4$ alkyl, $C_3$-$C_6$ cycloalkyl, O($C_1$-$C_4$ alkyl), C(O)$NH_2$, C(O)NH($C_1$-$C_4$ alkyl), C(O)N($C_1$-$C_4$ alkyl)$_2$; C(O)OH, C(O)O($C_1$-$C_4$ alkyl), C(O)($C_1$-$C_4$ alkyl), C(O)NH($SO_2$)—($C_1$-$C_4$ alkyl), C(O)NH($SO_2$)—($C_3$-$C_6$ cycloalkyl), C(O)NH($SO_2$)-(aryl), O($SO_2$)—$NH_2$, NHC(O)—NH($C_1$-$C_4$ alkyl), NHC(O)—N($C_1$-$C_4$ alkyl)$_2$, $SO_2$—($C_1$-$C_4$ alkyl) or tetrazole.

In some embodiments, the compound wherein $R_{19}$, is H, Cl, Br, F, $OCH_3$, $OCH_2CH_3$, $CF_3$, CN, $CH_3$, $CH_3CH_3$, COOH, or $COOCH_3$.

In some embodiments, the compound wherein B has the structure:

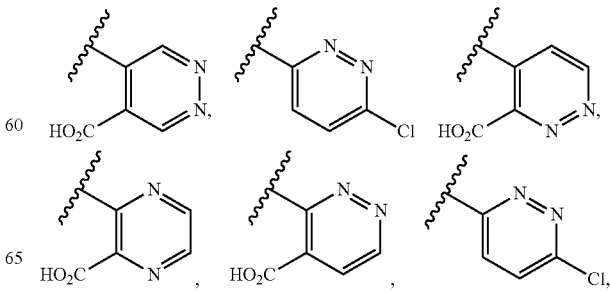

-continued

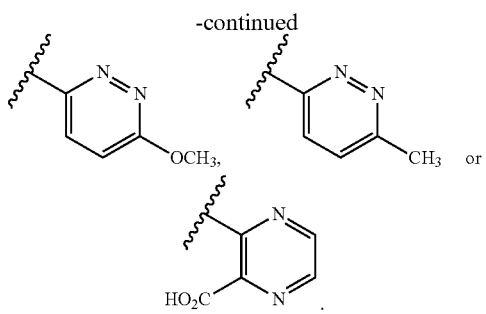

In some embodiments, the compound wherein B has the structure:

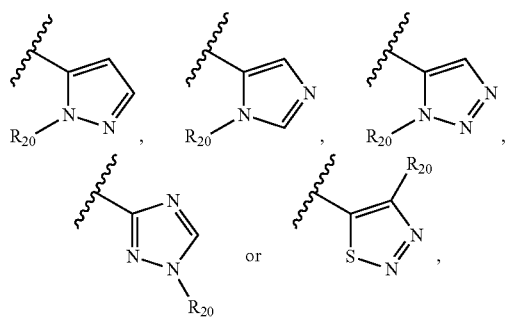

wherein
$R_{20}$ is H, halogen, $C_1$-$C_4$ alkyl, $C_3$-$C_6$ cycloalkyl, O—($C_1$-$C_4$ alkyl), C(O)OH, C(O)—$NH_2$, C(O)—$N(CH_3)_2$, C(O)—$NHCH_3$, NHC(O)—$N(CH_3)_2$, CN or $CF_3$.

In some embodiments, the compound wherein
$R_{20}$ is H, $CH_3$, or $CH_2CH_3$; and
$R_{21}$ is H, Cl, Br, F, $OCH_3$, $OCH_2CH_3$, $CF_3$, CN, $CH_3$, or $CH_3CH_3$.

In some embodiments, the compound wherein B is a substituted or unsubstituted phenyl, pyridine, pyrimidine, benzyl, pyrrolidine, sulfolane, oxetane, $CO_2H$ or ($C_1$-$C_4$ alkyl)-$CO_2H$,
or B is

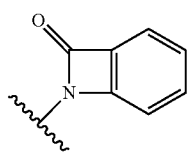

In some embodiments, the compound wherein B has the structure:

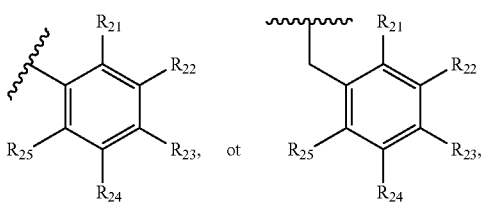

wherein $R_{21}$, $R_{22}$, $R_{23}$, $R_{24}$, and $R_{25}$ are each independently
H, halogen CN, $CF_3$, OH, $NH_2$, $C_1$-$C_{10}$ alkyl, $C_3$-$C_6$ cycloalkyl, O($C_1$-$C_4$ alkyl), C(O)$NH_2$, C(O)NH($C_1$-$C_{10}$ alkyl), C(O)N($C_1$-$C_4$ alkyl)$_2$, C(O)OH, C(O)O($C_1$-$C_{10}$ alkyl), C(O)($C_1$-$C_{10}$ alkyl), C(O)NH($SO_2$)—($C_1$-$C_4$ alkyl), C(O)NH($SO_2$)—($C_3$-$C_6$ cycloalkyl), C(O)NH($SO_2$)-(aryl), O($SO_2$)—$NH_2$, NHC(O)—NH($C_1$-$C_{10}$ alkyl), NHC(O)—N($C_1$-$C_4$ alkyl)$_2$, $SO_2$—($C_1$-$C_{10}$ alkyl) or tetrazole.

In some embodiments, the compound wherein B has the structure:

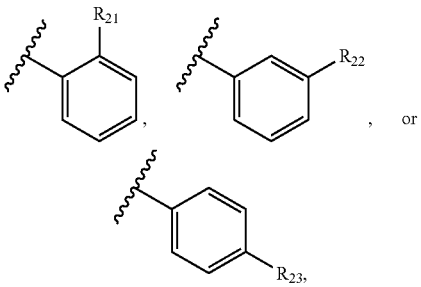

wherein $R_{21}$, $R_{22}$, and $R_{23}$ are each independently
H, halogen, OH, $CF_3$, $NH_2$, $C_1$-$C_4$ alkyl, $C_3$-$C_6$ cycloalkyl, O($C_1$-$C_4$ alkyl), C(O)$NH_2$, C(O)NH($C_1$-$C_4$ alkyl), C(O)N($C_1$-$C_4$ alkyl)$_2$, C(O)OH, C(O)O($C_1$-$C_4$ alkyl), C(O)($C_1$-$C_4$ alkyl), C(O)NH($SO_2$)—($C_1$-$C_4$ alkyl), C(O)NH($SO_2$)—($C_3$-$C_6$ cycloalkyl), C(O)NH($SO_2$)-(aryl), or O($SO_2$)—$NH_2$, $SO_2$—($C_1$-$C_4$ alkyl).

In some embodiments, the compound wherein $R_{21}$, $R_{22}$, and $R_{23}$ are each independently F, Cl, $CH_3$, $CF_3$, $OCH_3$, OH, $SO_2$—$CH_3$, C(O)$NH_2$, C(O)OH, C(O)$OCH_3$,

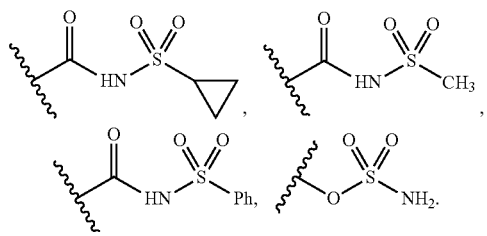

In some embodiments, the compound wherein B has the structure:

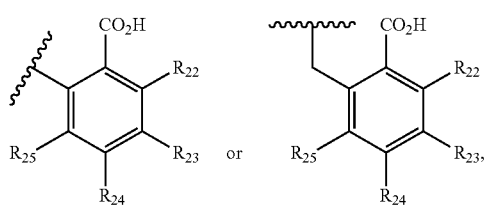

wherein $R_{22}$, $R_{23}$, $R_{24}$ and $R_{25}$ are each independently
H, halogen, OH, $CF_3$, $NH_2$, $C_1$-$C_4$ alkyl, $C_3$-$C_6$ cycloalkyl, O($C_1$-$C_4$ alkyl), C(O)$NH_2$, C(O)NH($C_1$-$C_4$ alkyl), C(O)N($C_1$-$C_4$ alkyl)$_2$, C(O)OH, C(O)O($C_1$-$C_4$ alkyl), C(O)($C_1$-$C_4$ alkyl), C(O)NH($SO_2$)—($C_1$-$C_4$ alkyl), C(O)NH($SO_2$)—($C_3$-$C_6$ cycloalkyl), C(O)NH($SO_2$)-(aryl), O($SO_2$)—$NH_2$, or $SO_2$—($C_1$-$C_4$ alkyl).

In some embodiments, the compound wherein $R_{22}$, $R_{23}$, $R_{24}$, and $R_{25}$ are each independently H, F, Cl, $CF_3$, $CH_3$, $OCH_3$, OH, $SO_2$—$CH_3$, C(O)$NH_2$, C(O)OH, C(O)$OCH_3$,

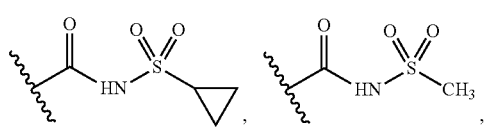

-continued

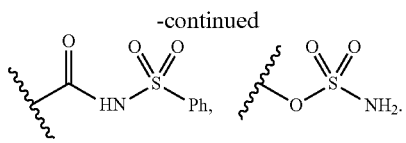

In some embodiments, the compound wherein $R_{22}$, $R_{24}$, $R_{25}$ are each H and $R_{23}$ is F, Cl, $CH_3$, $CF_3OCH_3$, OH, $SO_2$—$CH_3$, $C(O)NH_2$, $C(O)OH$, $C(O)OCH_3$,

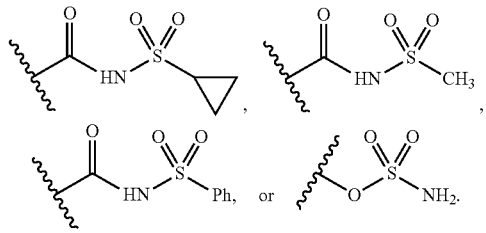

In some embodiments, the compound wherein B has the structure:

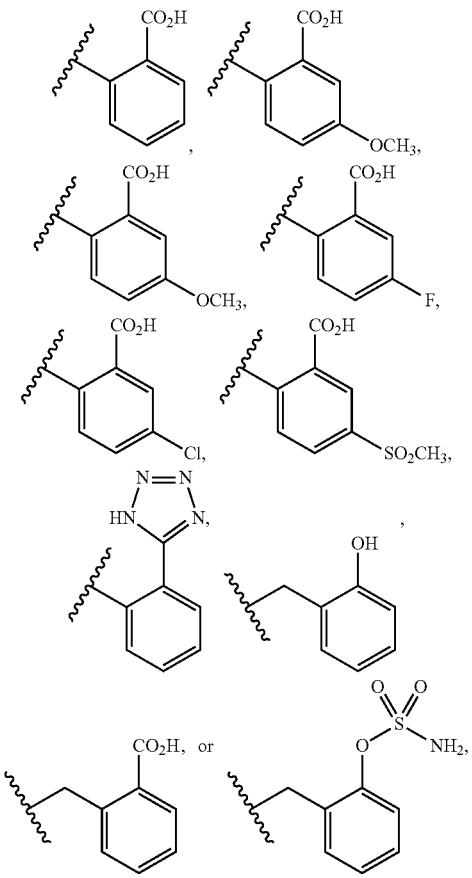

In some embodiments, the compound wherein B has the structure:

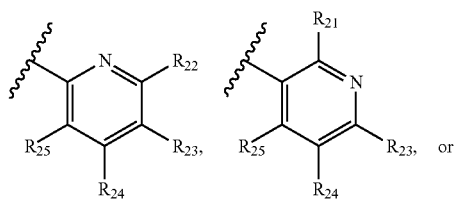

-continued

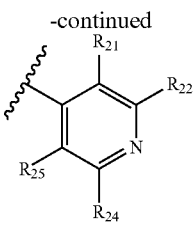

wherein $R_{21}$, $R_{22}$, $R_{23}$, $R_{24}$, and $R_{25}$ are each independently
H, halogen CN, $CF_3$, OH, $NH_2$, $C_1$-$C_{10}$ alkyl, $C_1$-$C_6$ cycloalkyl, $O(C_1$-$C_{10}$ alkyl), $C(O)NH_2$, $C(O)NH(C_1$-$C_{10}$ alkyl), $C(O)N(C_1$-$C_4$ alkyl)$_2$, $C(O)OH$, $C(O)O(C_1$-$C_{10}$ alkyl), $C(O)(C_1$-$C_{10}$ alkyl), $C(O)NH(SO_2)$—$(C_1$-$C_{10}$ alkyl), $C(O)NH(SO_2)$—$(C_3$-$C_6$ cycloalkyl), $C(O)NH(SO_2)$-(aryl), $O(SO_2)$—$NH_2$, $NHC(O)$—$NH(C_1$-$C_{10}$ alkyl), $NHC(O)$—$N(C_1$-$C_4$ alkyl)$_2$, $SO_2$—$(C_1$-$C_{10}$ alkyl).

In some embodiments, the compound wherein B has the structure:

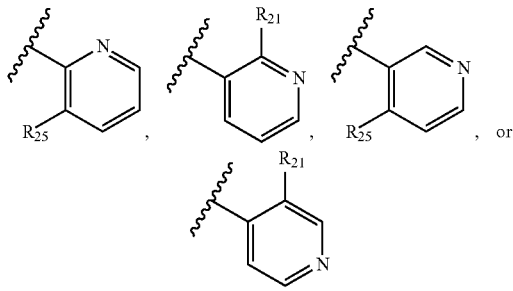

wherein $R_{21}$ and $R_{25}$ are each independently
H, halogen, OH, $NH_2$, $C_1$-$C_4$ alkyl, $C_3$-$C_6$ cycloalkyl, $O(C_1$-$C_4$ alkyl), $C(O)NH_2$, $C(O)NH(C_1$-$C_4$ alkyl), $C(O)N(C_1$-$C_4$ alkyl)$_2$, $C(O)OH$, $C(O)O(C_1$-$C_4$ alkyl), $C(O)(C_1$-$C_4$ alkyl), $C(O)NH(SO_2)$—$(C_1$-$C_4$ alkyl), $C(O)NH(SO_2)$—$(C_3$-$C_6$ cycloalkyl), $C(O)NH(SO_2)$-(aryl), or $O(SO_2)$—$NH_2$, $SO_2$—$(C_1$-$C_4$ alkyl).

In some embodiments, the compound wherein $R_{21}$ and $R_{25}$ are each independently F, Cl, $CF_3$, $CH_3$, $OCH_3$, OH, $SO_2$—$CH_3$, $C(O)NH_2$, $C(O)OH$, $C(O)OCH_3$,

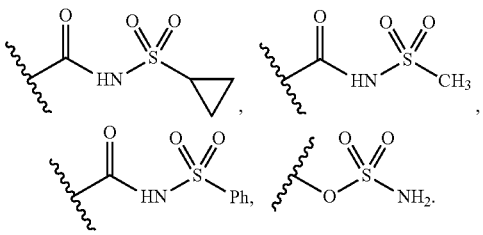

In some embodiments, the compound wherein B has the structure:

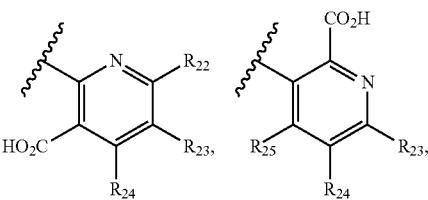

-continued

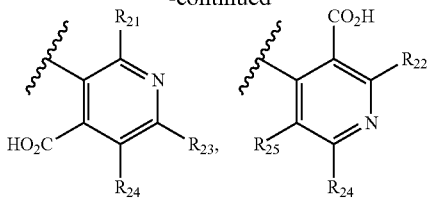

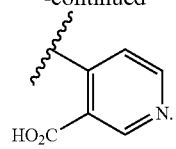

or wherein $R_{22}$, $R_{23}$, $R_{24}$ and $R_{25}$ are each independently

H, halogen, OH, $NH_2$, $C_1$-$C_4$ alkyl, $C_3$-$C_6$ cycloalkyl, O($C_1$-$C_4$ alkyl), C(O)$NH_2$, C(O)NH($C_1$-$C_4$ alkyl), C(O)N($C_1$-$C_4$ alkyl)$_2$, C(O)OH, C(O)O($C_1$-$C_4$ alkyl), C(O)($C_1$-$C_4$ alkyl), C(O)NH($SO_2$)—($C_1$-$C_4$ alkyl), C(O)NH($SO_2$)—($C_3$-$C_5$ cycloalkyl), C(O)NH($SO_2$)-(aryl), or O($SO_2$)—$NH_2$, $SO_2$—($C_1$-$C_4$ alkyl).

In some embodiments, the compound wherein $R_{21}$, $R_{22}$, $R_{23}$, $R_{24}$ and $R_{25}$ are each independently H, F, Cl, $CF_3$, $CH_3$, $OCH_3$, OH, $SO_2$—$CH_3$, C(O)$NH_2$, C(O)OH, C(O)$OCH_3$,

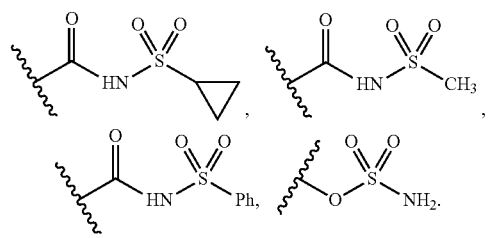

In some embodiments, the compound wherein $R_{22}$, $R_{24}$, $R_{25}$ are each H and $R_{23}$ is F, Cl, $CF_3$, $CH_3$, $OCH_3$, OH, $SO_2$—$CH_3$, C(O)$NH_2$, C(O)OH, C(O)$OCH_3$,

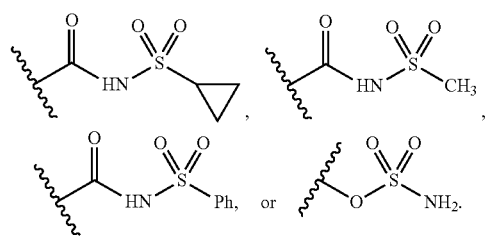

In some embodiments, the compound wherein B has the structure:

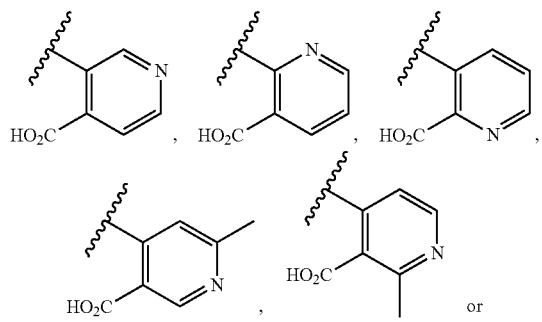

In some embodiments, the compound wherein B has the structure:

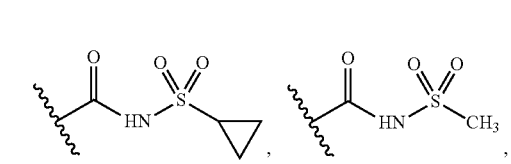

wherein $R_{21}$, $R_{22}$, $R_{23}$, $R_{24}$, and $R_{25}$ are each independently H, halogen CN, $CF_3$, OH, $NH_2$, $C_1$-$C_{10}$ alkyl, $C_3$-$C_6$ cycloalkyl, O($C_1$-$C_{10}$ alkyl), C(O)$NH_2$, C(O)NH($C_1$-$C_{10}$ alkyl), C(O)N($C_1$-$C_4$ alkyl)$_2$, C(O)OH, C(O)O($C_1$-$C_{18}$ alkyl), C(O)($C_1$-$C_{10}$ alkyl), C(O)NH($SO_2$)—($C_1$-$C_{10}$ alkyl), C(O)NH($SO_2$)—($C_3$-$C_6$ cycloalkyl), C(O)NH($SO_2$)-(aryl), O($SO_2$)—$NH_2$, NHC(O)—NH($C_1$-$C_{10}$ alkyl), NHC(O)—N($C_1$-$C_4$ alkyl)$_2$, $SO_2$—($C_1$-$C_{10}$ alkyl).

In some embodiments, the compound wherein B has the structure:

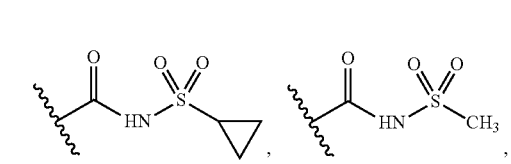

wherein $R_{21}$, $R_{22}$, $R_{24}$ and $R_{25}$, are each independently

H, halogen, OH, $NH_2$, $C_1$-$C_4$ alkyl, $C_3$-$C_6$ cycloalkyl, O($C_1$-$C_4$ alkyl), C(O)$NH_2$, C(O)NH($C_1$-$C_4$ alkyl), C(O)N($C_1$-$C_4$ alkyl)$_2$, C(O)OH, C(O)O($C_1$-$C_4$ alkyl), C(O)($C_1$-$C_4$ alkyl), C(O)NH($SO_2$)—($C_1$-$C_4$ alkyl), C(O)NH($SO_2$)—($C_3$-$C_6$ cycloalkyl), C(O)NH($SO_2$)-(aryl), or O($SO_2$)—$NH_2$, $SO_2$—($C_1$-$C_4$ alkyl).

In some embodiments, the compound wherein $R_{21}$, $R_{22}$, $R_{24}$ and $R_{25}$ are each independently H, F, Cl, $CF_3$, $CH_3$, $OCH_3$, OH, $SO_2$—$CH_3$, C(O)$NH_2$, C(O)OH, C(O)$OCH_3$, -continued

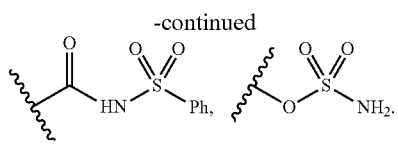

In some embodiments, the compound wherein B has the structure

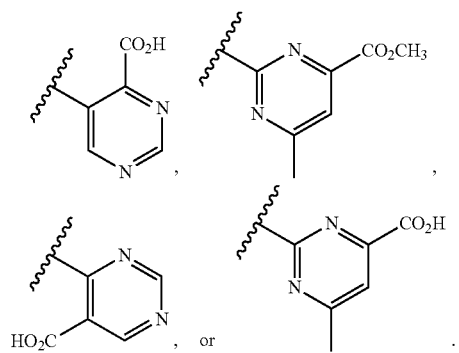

, or

In some embodiments, the compound wherein B has the structure:

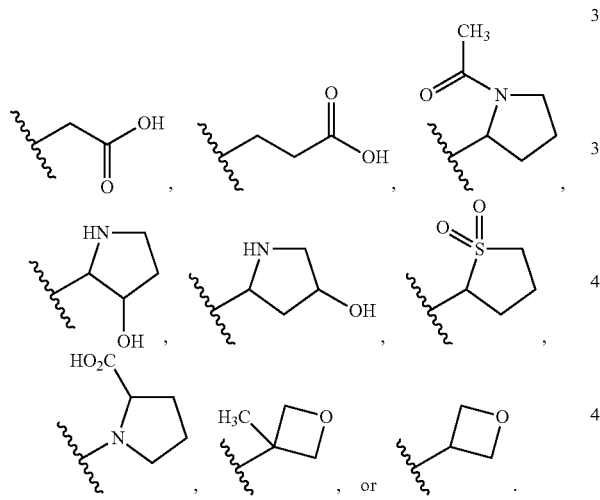

, or

In some embodiments, the compound wherein
ψ is absent is or present;
$R_1$, $R_2$, $R_3$, $R_4$, and $R_5$ are each H, t-Bu, Cl, F, or $CF_3$; and
$R_6$ is absent or present, and when present is H, OH or F.

In some embodiments, the compound wherein
ψ is absent;
$R_1$, $R_2$, $R_3$, and $R_4$ are each H,
$R_5$ is $CF_3$ or t-Bu; and
$R_6$ is H.

In some embodiments, the compound wherein
ψ is present;
$R_1$, $R_2$, $R_3$, and $R_4$ are each H,
$R_5$ is $CF_3$ or t-Bu; and
$R_6$ is absent.

In some embodiments, the compound having the structure:

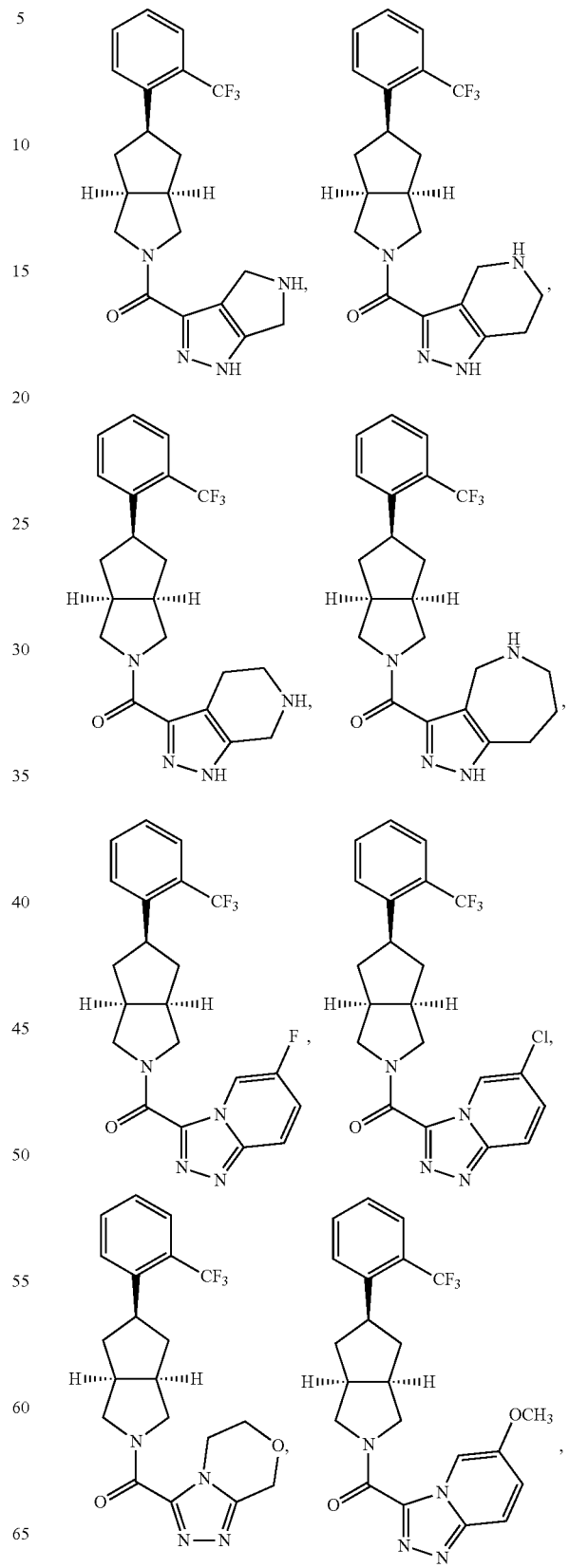

-continued
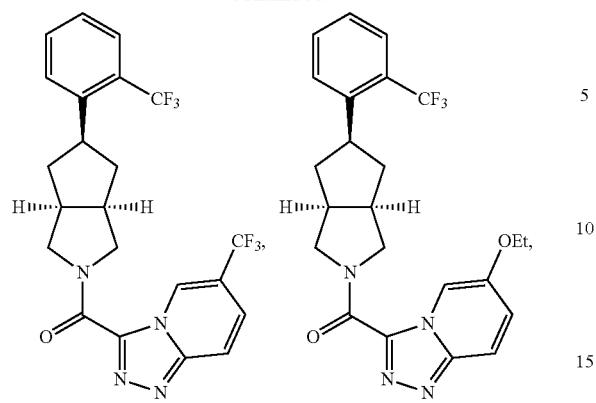
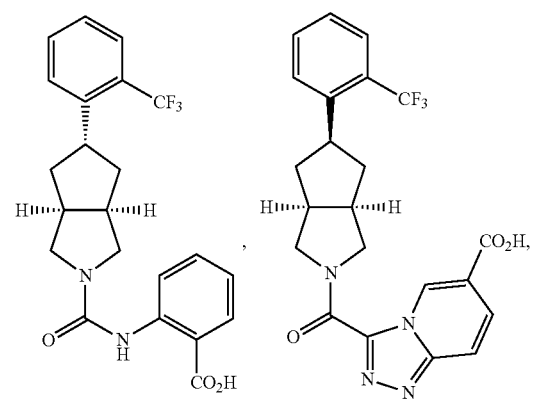
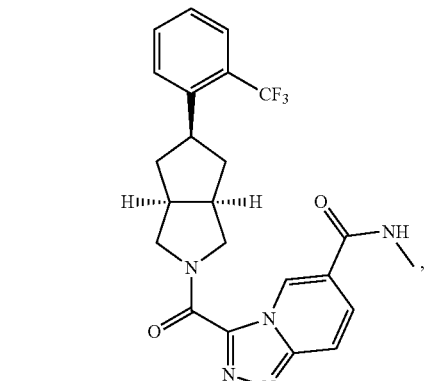
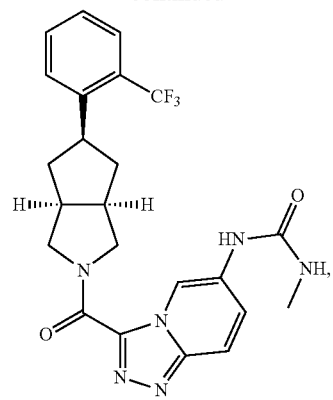 [SMILES: CNC(=O)Nc1ccc2nnc(C(=O)N3C[C@H]4C[C@@H](c5ccccc5C(F)(F)F)C[C@H]4C3)n2c1]
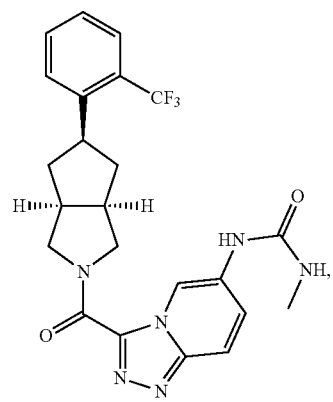
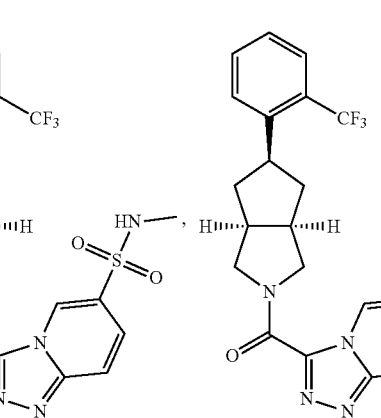
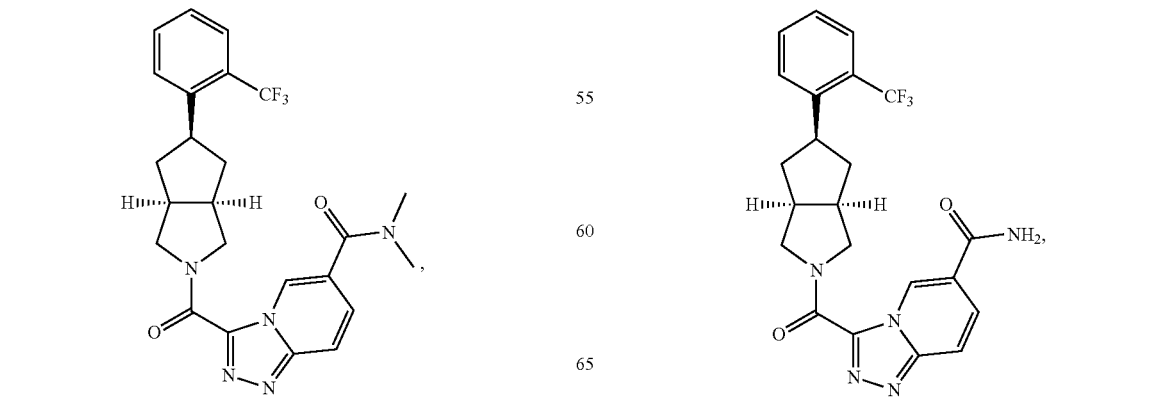

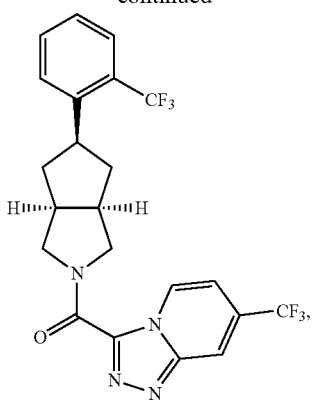
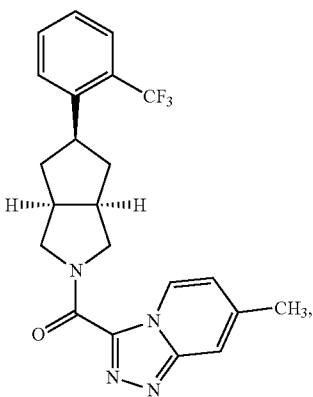
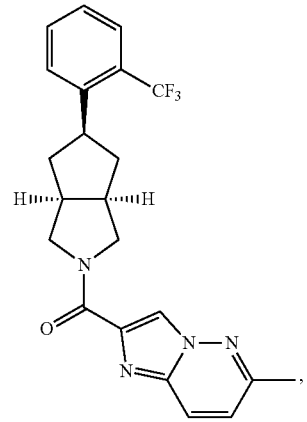
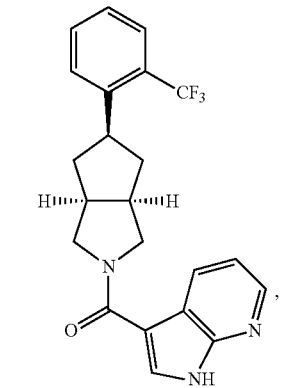
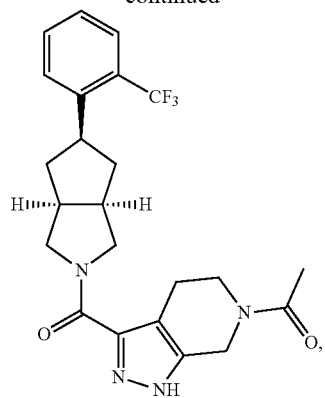
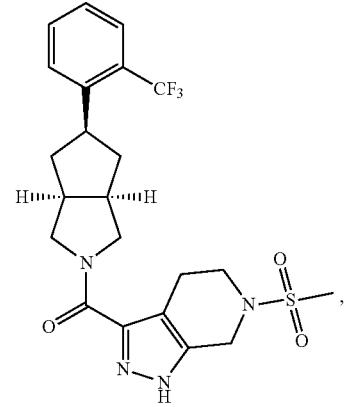
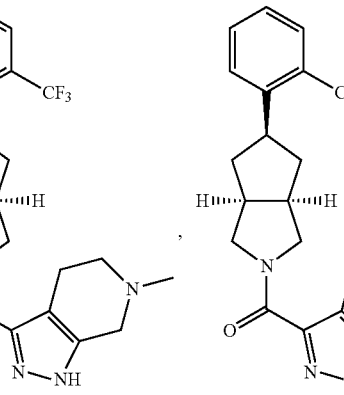
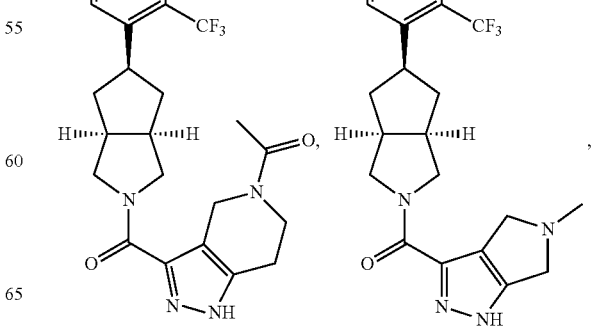

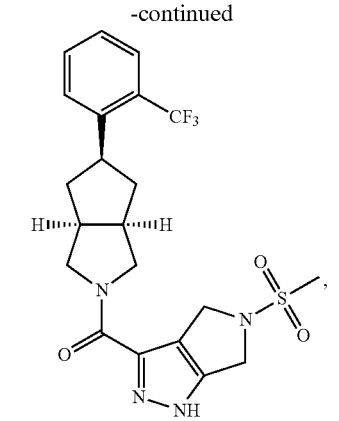
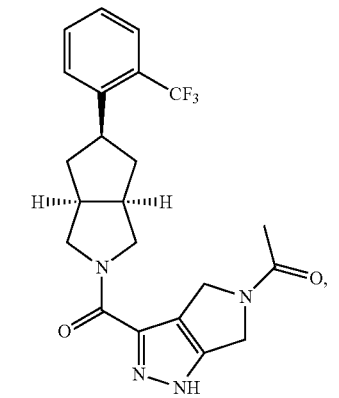
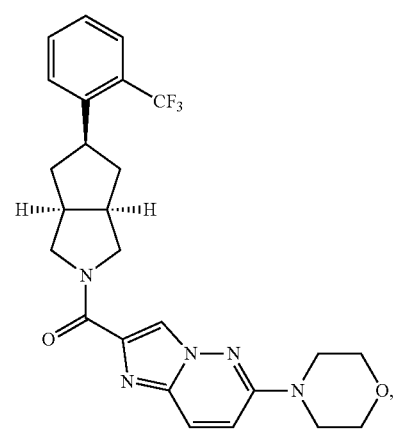
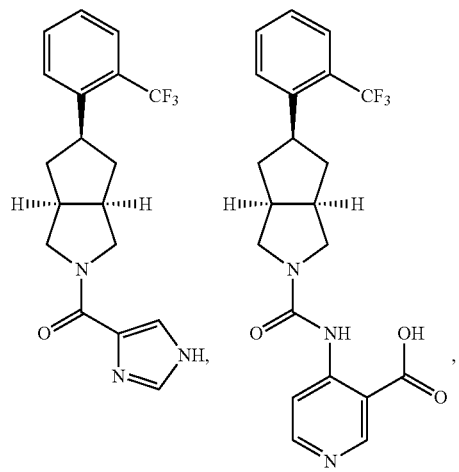
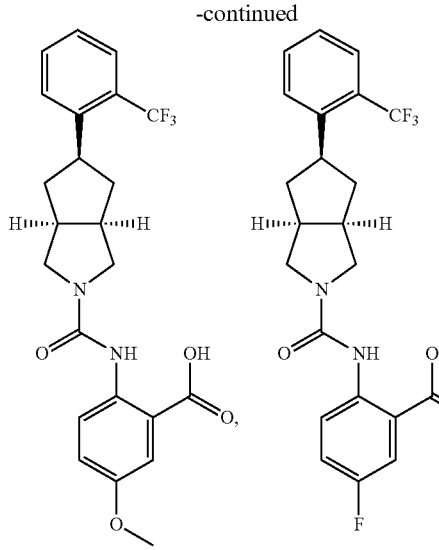
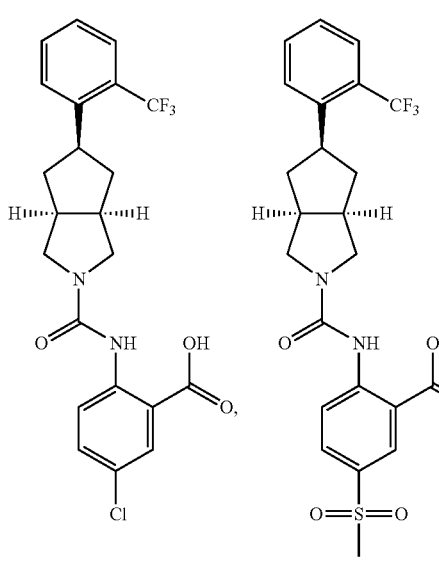
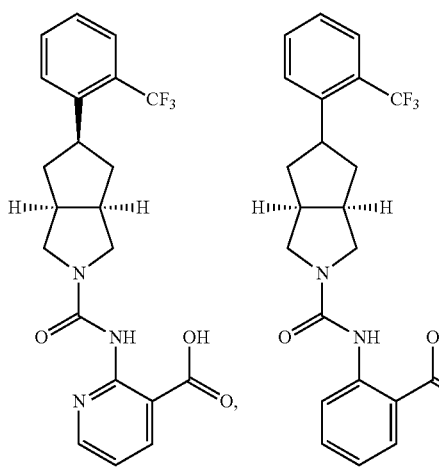

-continued
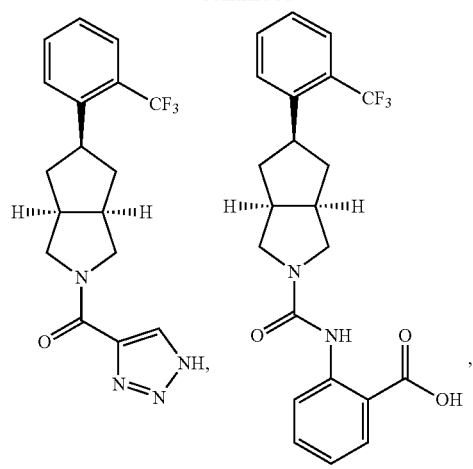
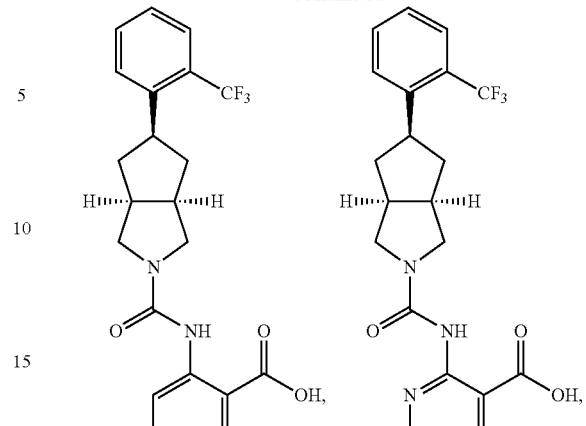
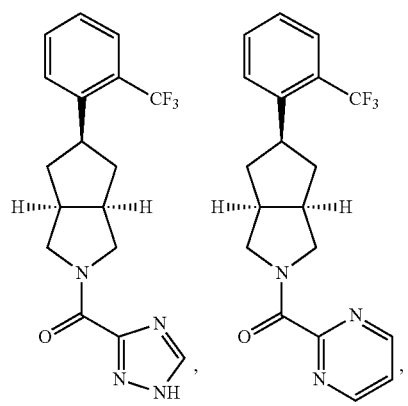
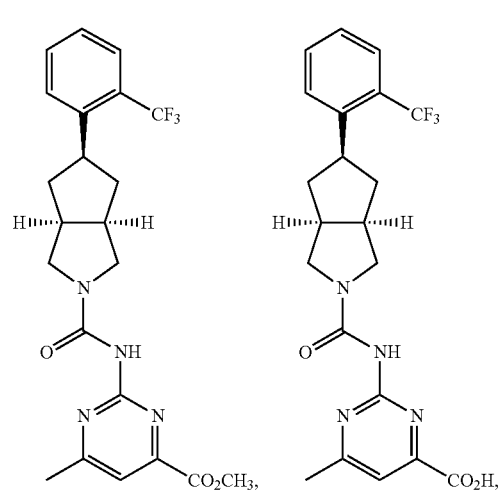
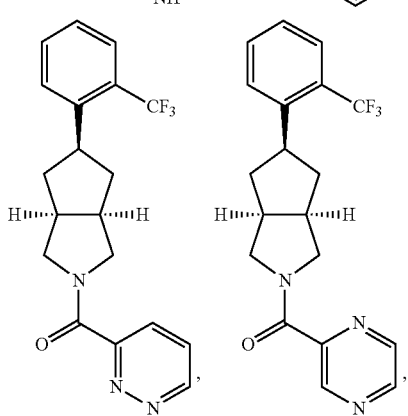
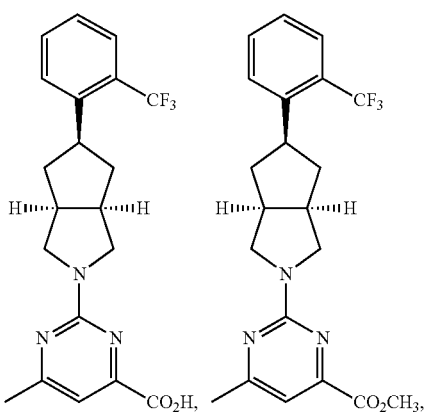
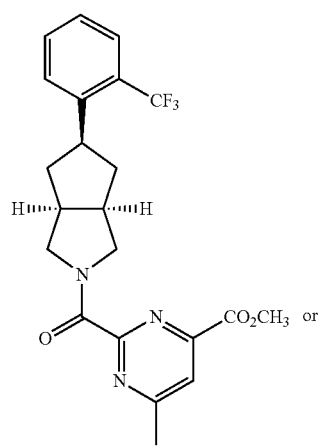

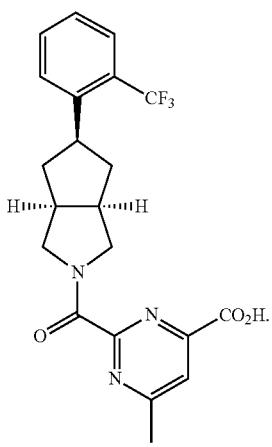 [SMILES: Cc1cc(C(=O)O)nc(C(=O)N2C[C@H]3C[C@@H](c4ccccc4C(F)(F)F)C[C@H]3C2)n1]

The present invention provides a pharmaceutical composition comprising a compound of the present invention and a pharmaceutically acceptable carrier.

The present invention provides a method for treating a disease characterized by excessive lipofuscin accumulation in the retina in a mammal afflicted therewith comprising administering to the mammal an effective amount of a compound of the present invention or a composition of the present invention.

In some embodiments of the method, wherein the disease is further characterized by bisretinoid-mediated macular degeneration.

In some embodiments of the method, wherein the amount of the compound is effective to lower the serum concentration of RBP4 in the mammal.

In some embodiments of the method, wherein the amount of the compound is effective to lower the retinal concentration of a bisretinoid in lipofuscin in the mammal.

In some embodiments of the method, wherein the bisretinoid is A2E. In some embodiments of the method, wherein the bisretinoid is isoA2E. In some embodiments of the method, wherein the bisretinoid is A2-DHP-PE. In some embodiments of the method, wherein the bisretinoid is atRAL di-PE.

In some embodiments of the method, wherein the disease characterized by excessive lipofuscin accumulation in the retina is Age-Related Macular Degeneration.

In some embodiments of the method, wherein the disease characterized by excessive lipofuscin accumulation in the retina is dry (atrophic) Age-Related Macular Degeneration.

In some embodiments of the method, wherein the disease characterized by excessive lipofuscin accumulation in the retina is Stargardt Disease.

In some embodiments of the method, wherein the disease characterized by excessive lipofuscin accumulation in the retina is Best disease.

In some embodiments of the method, wherein the disease characterized by excessive lipofuscin accumulation in the retina is adult vitelliform maculopathy.

In some embodiments of the method, wherein the disease characterized by excessive lipofuscin accumulation in the retina is Stargardt-like macular dystrophy.

In some embodiments, B has the structure:

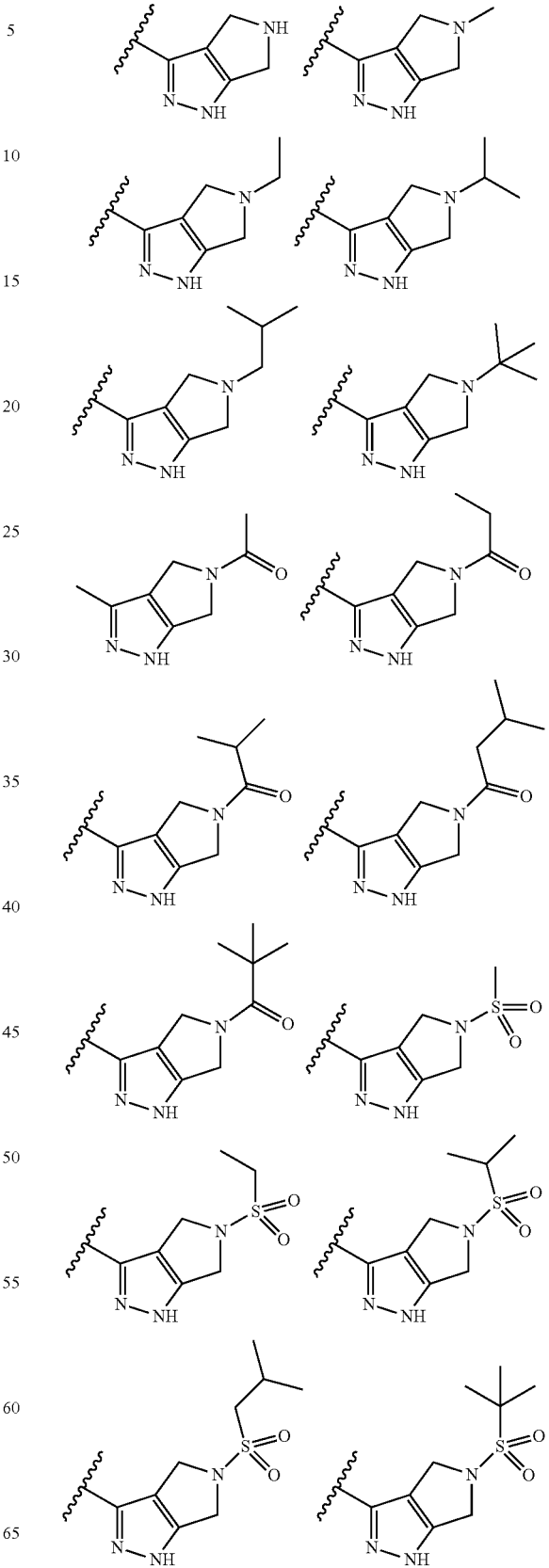

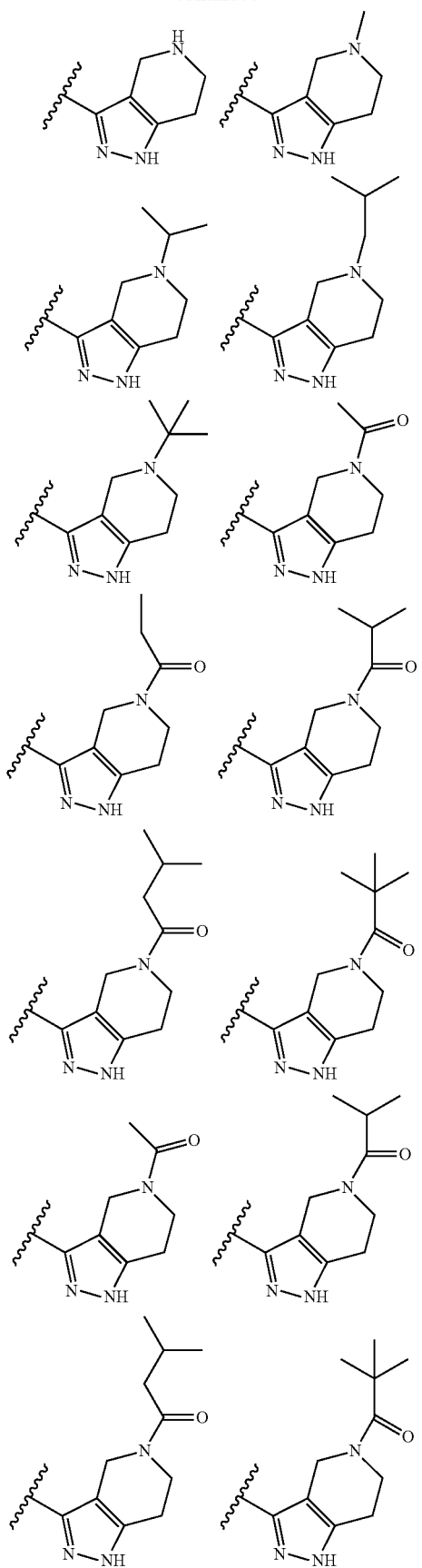
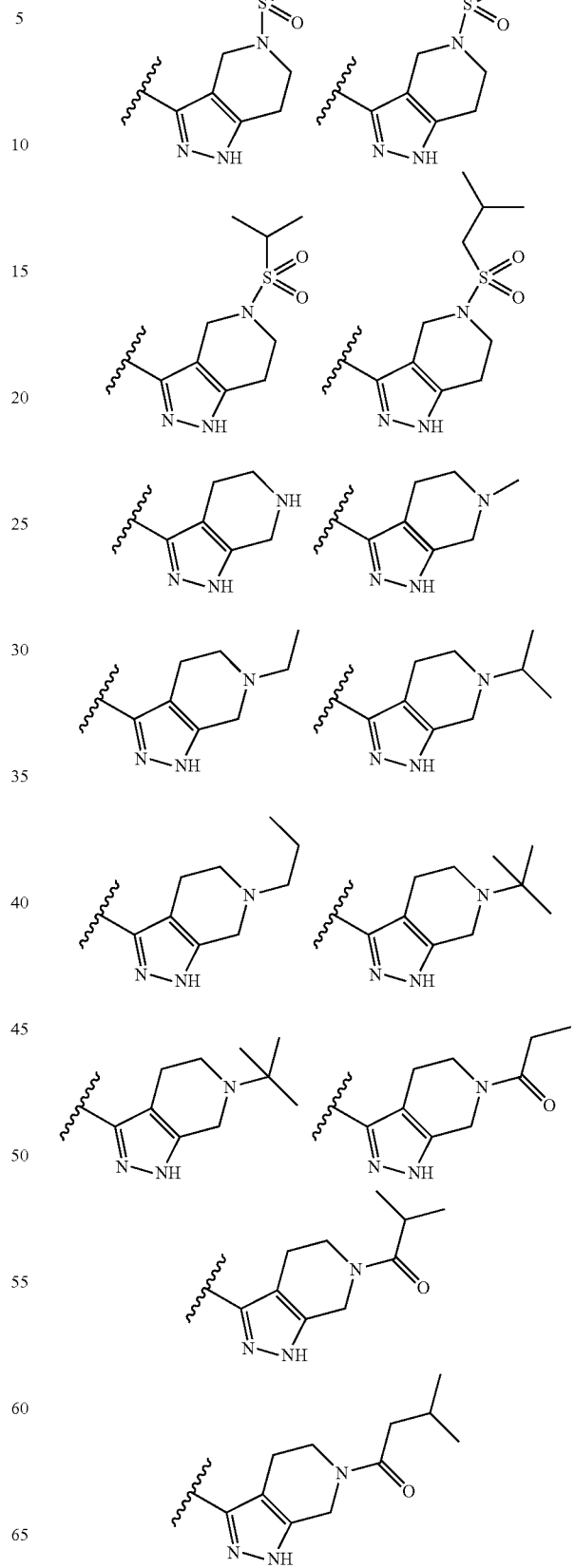

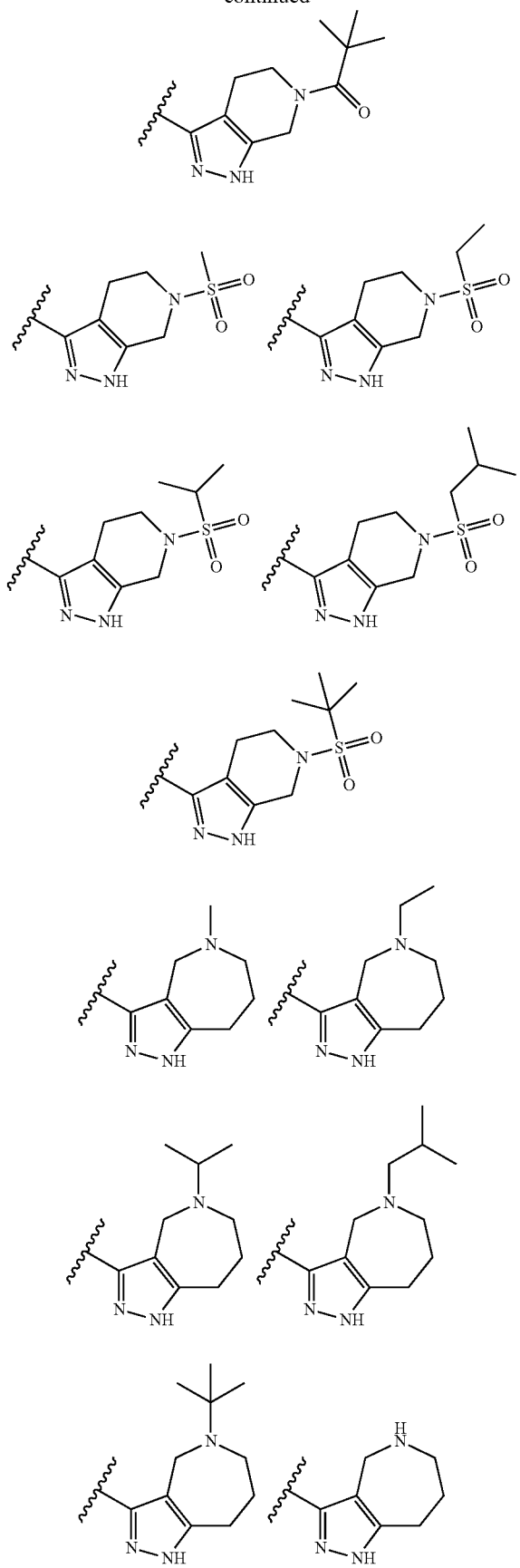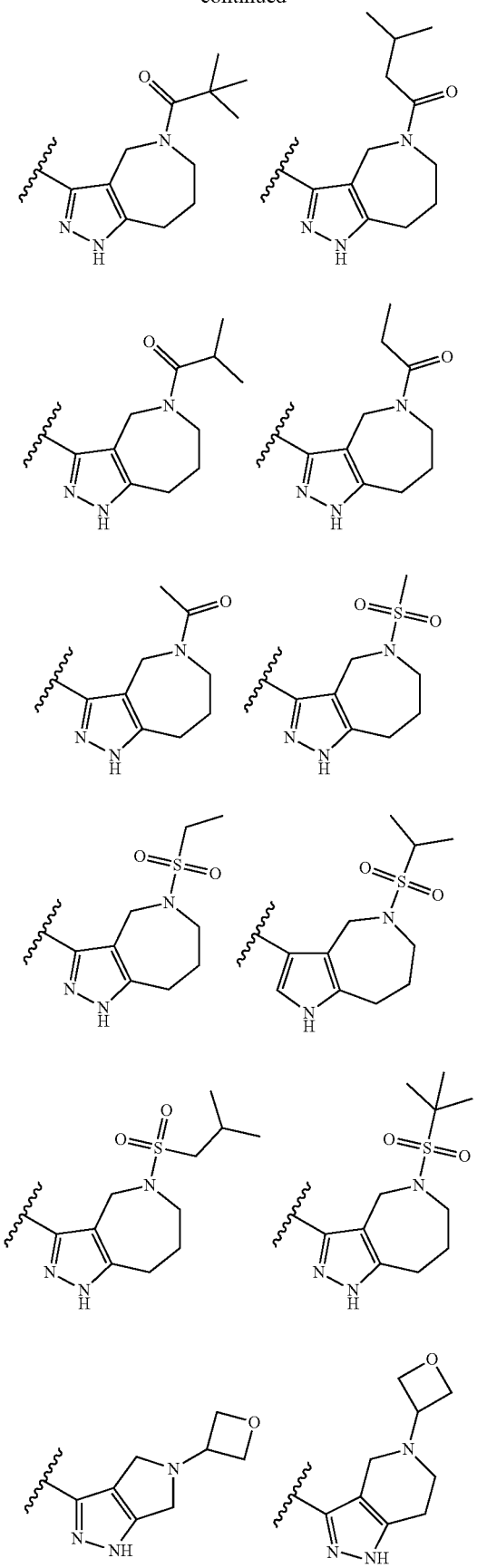

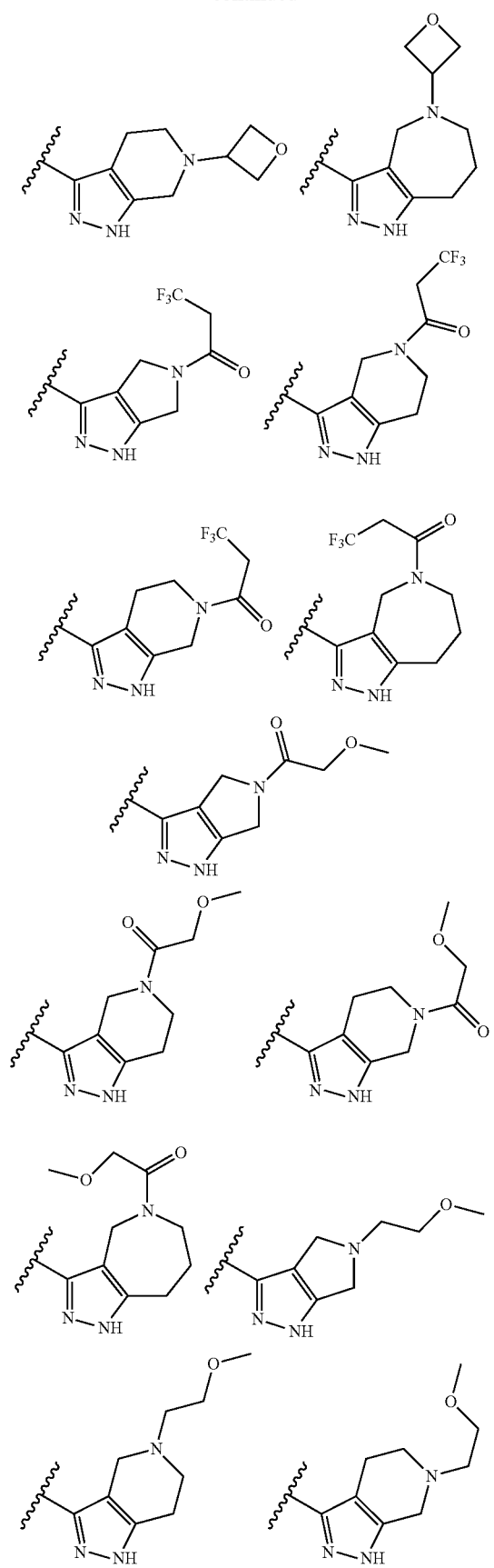
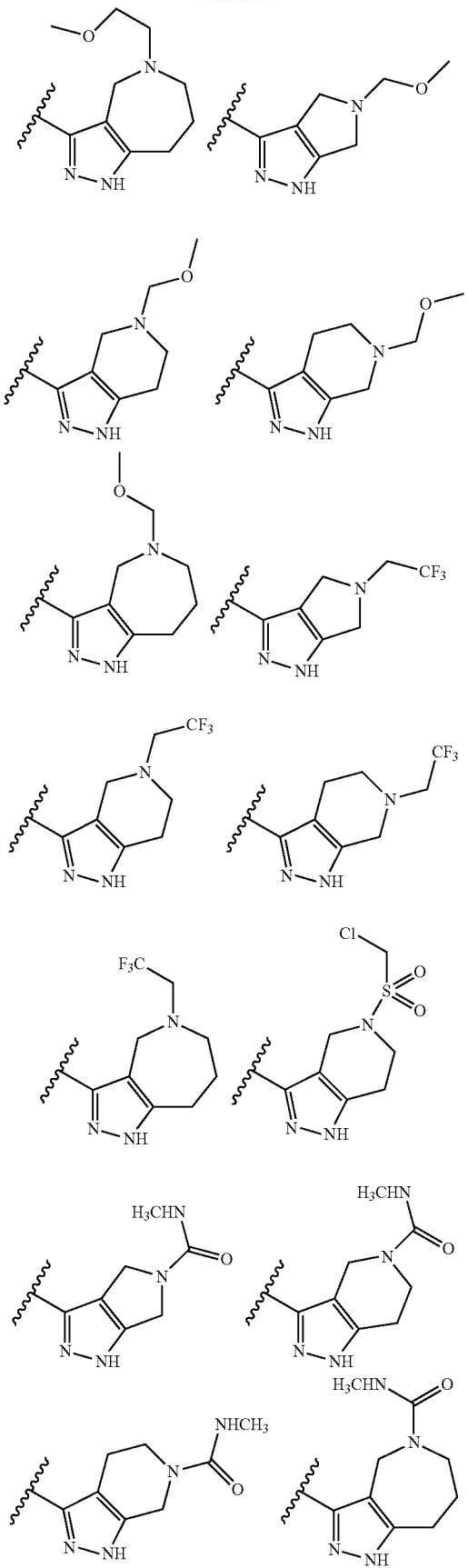

-continued
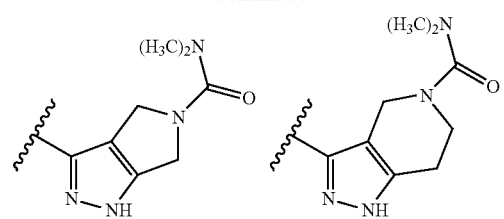
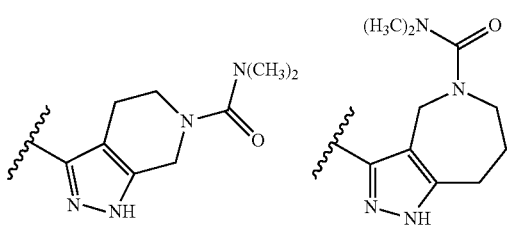
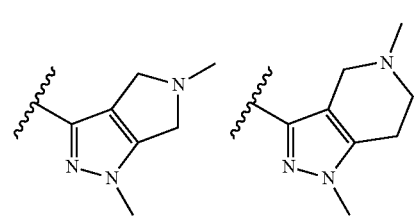
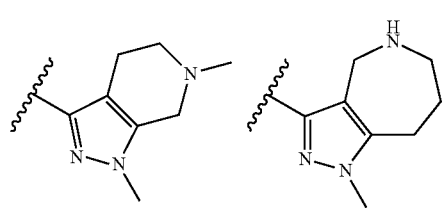
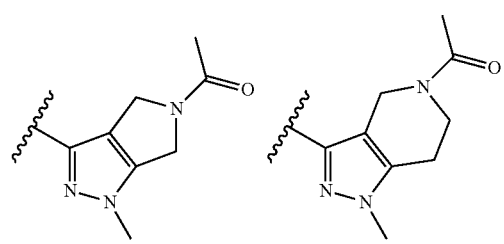
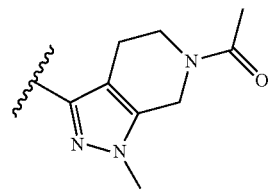
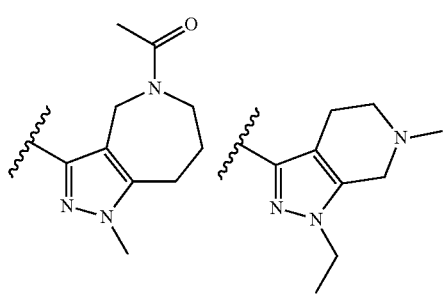
-continued
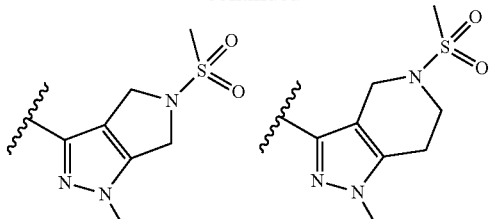
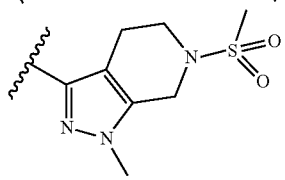
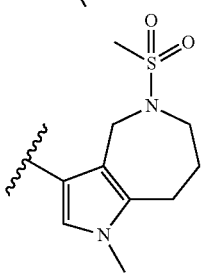
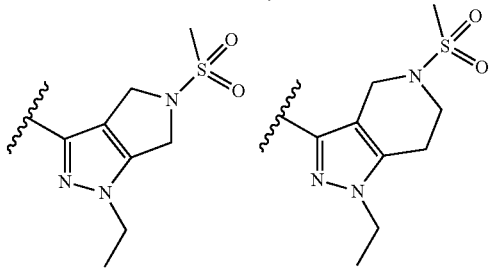
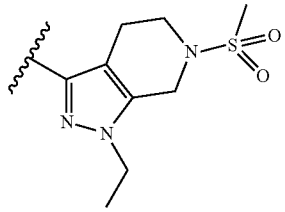
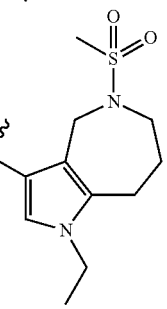
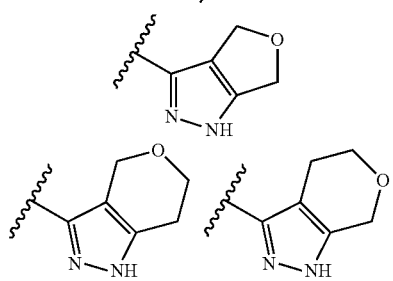

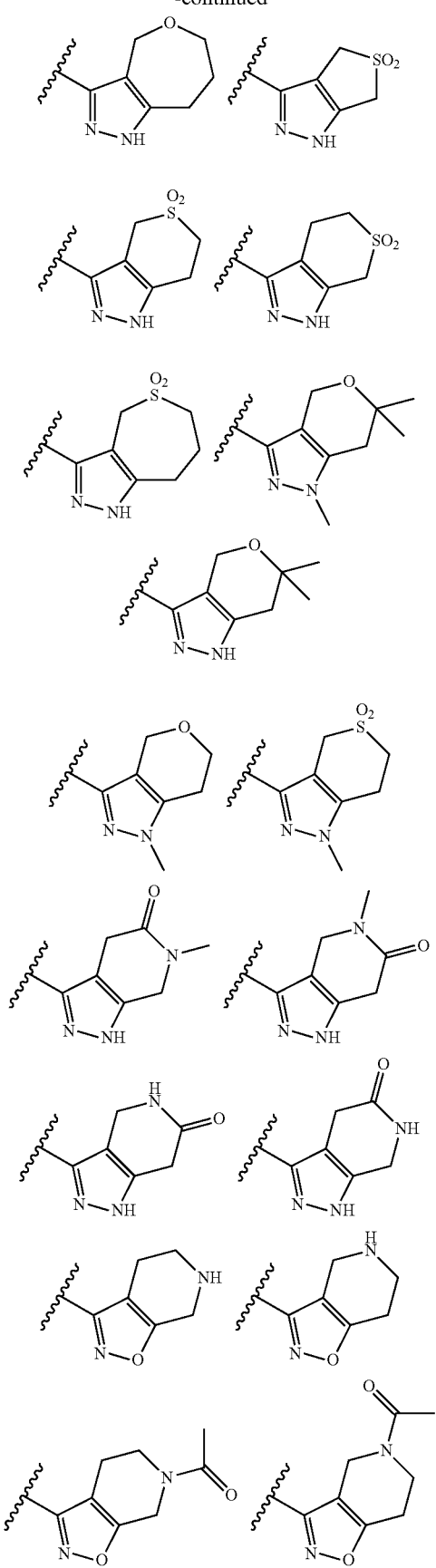
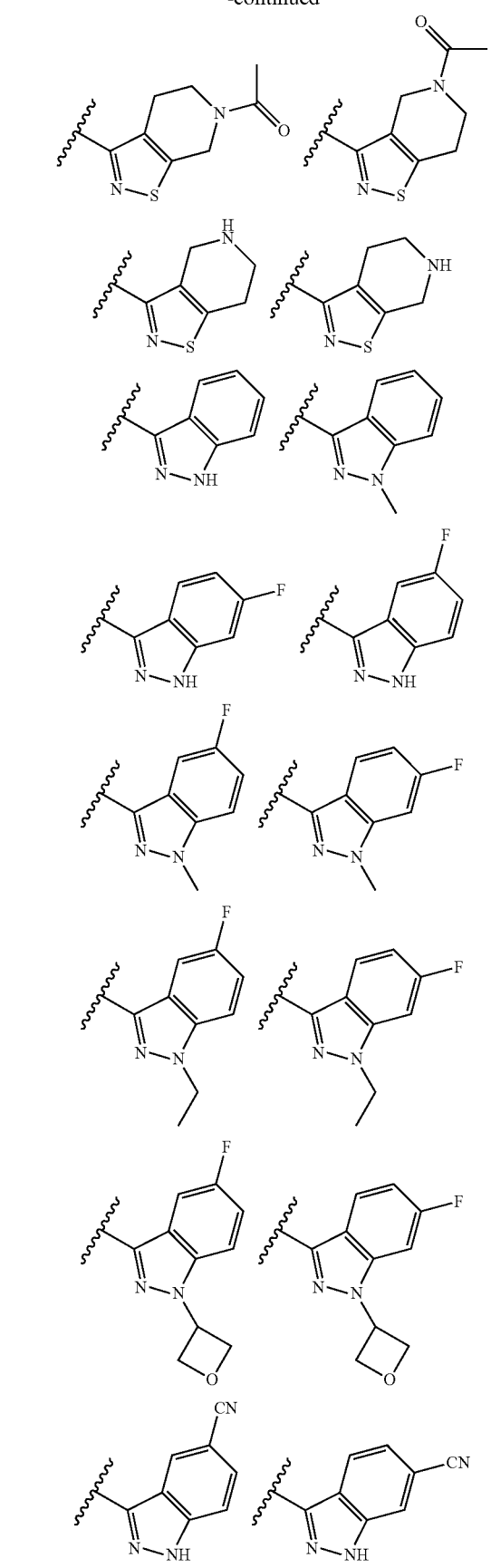

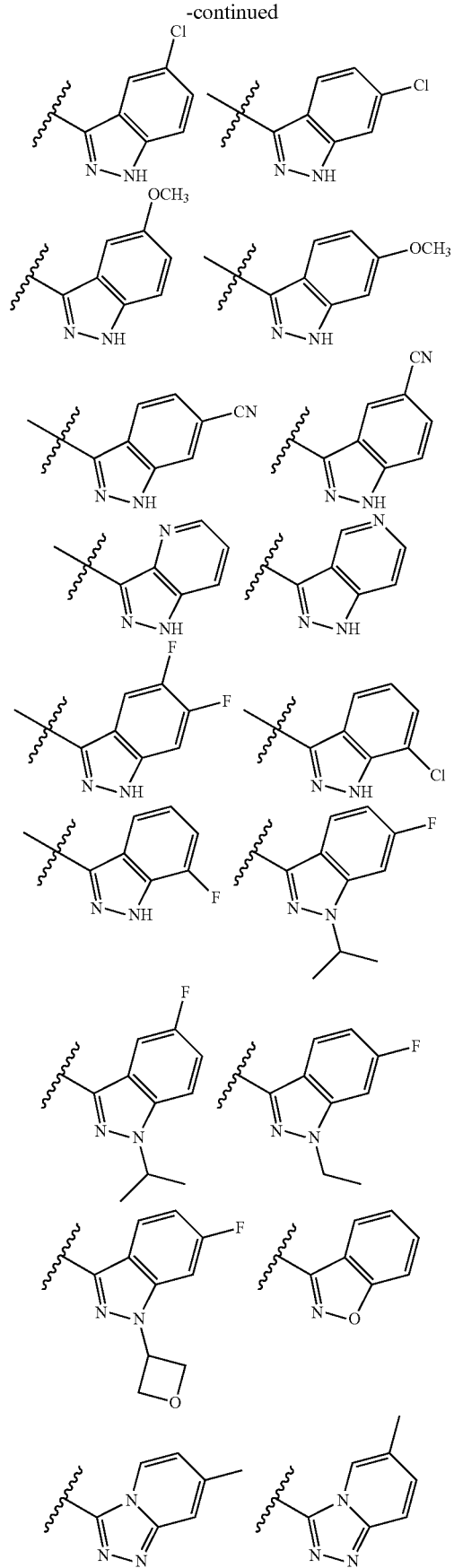
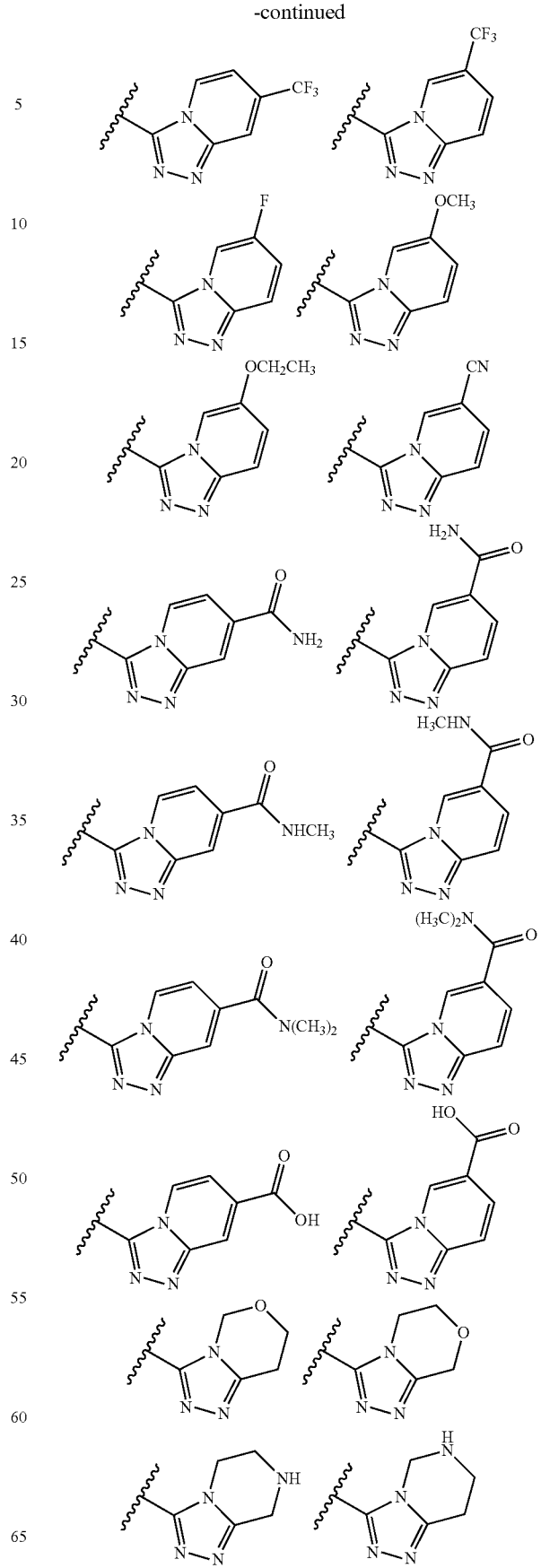

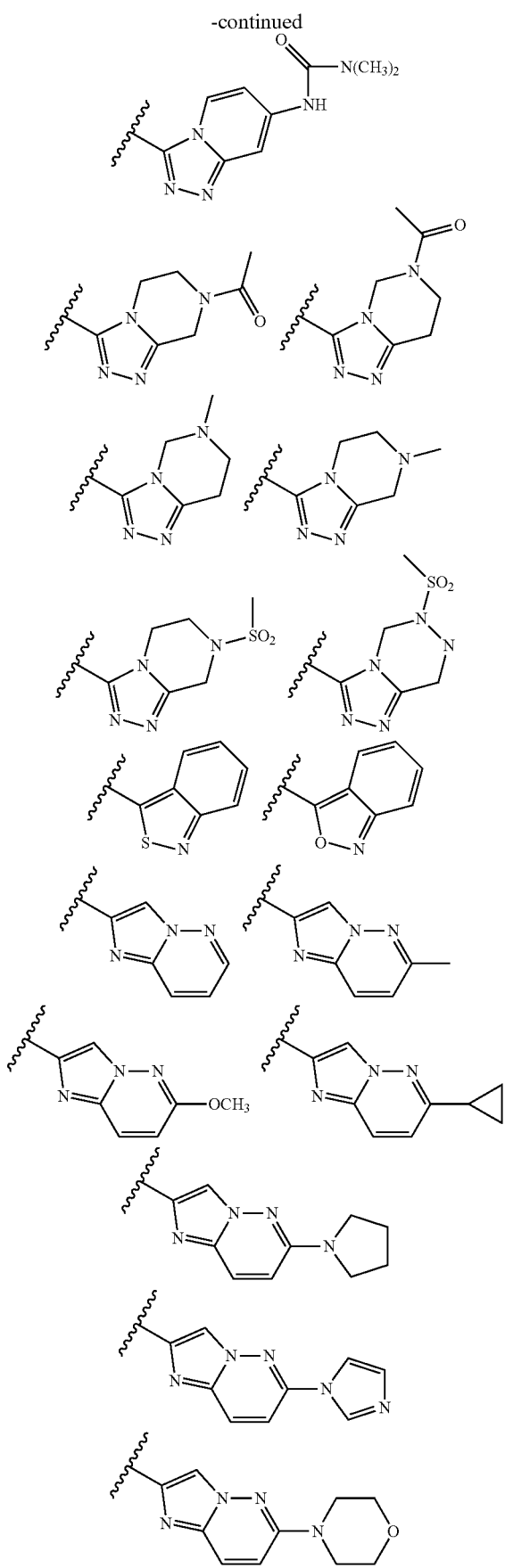
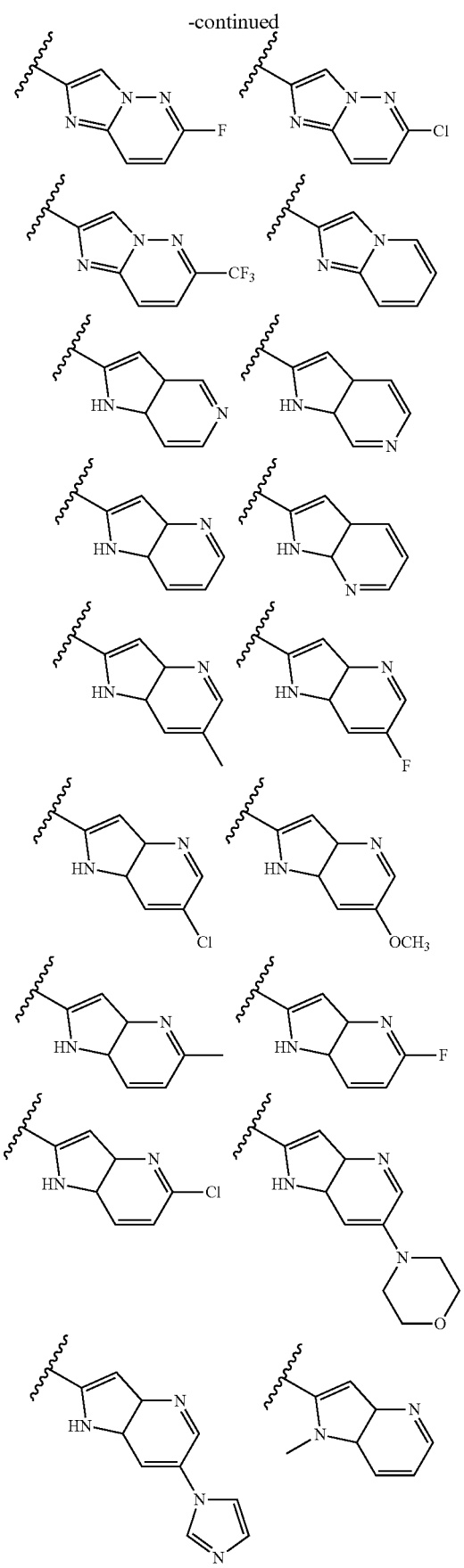

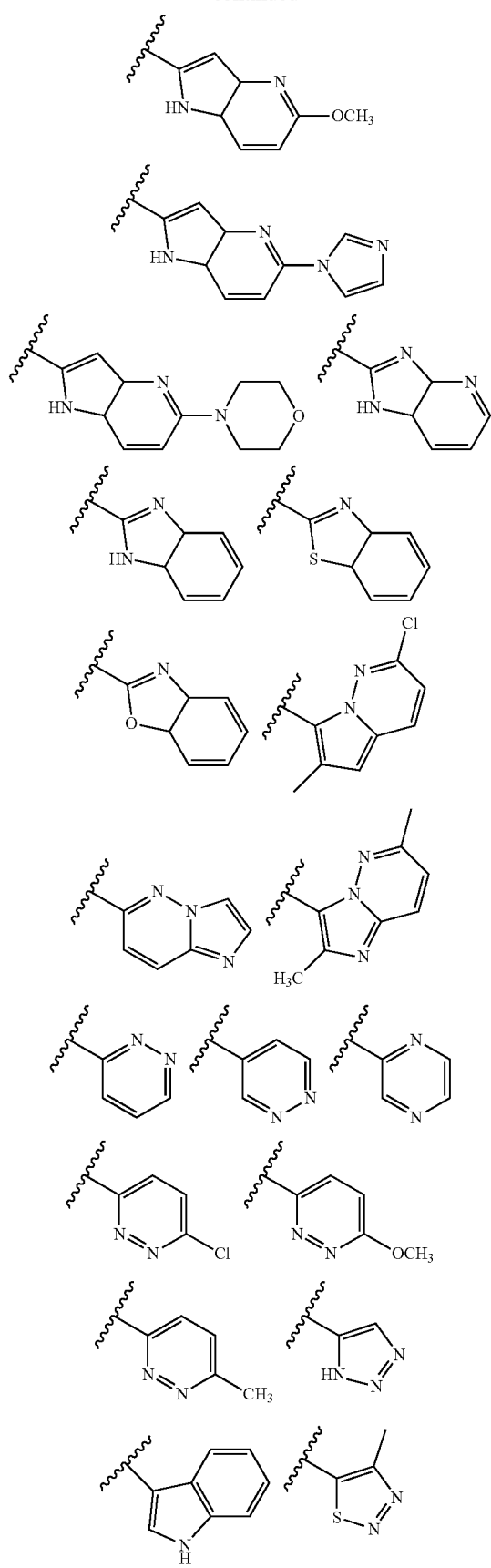
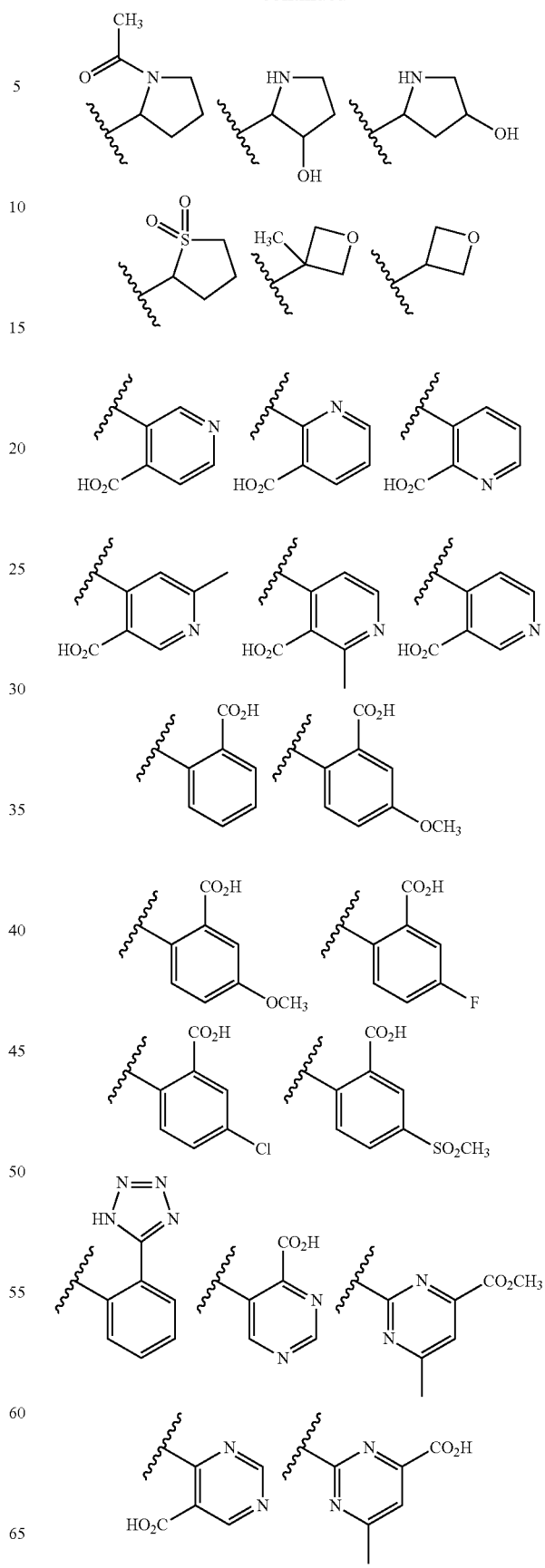

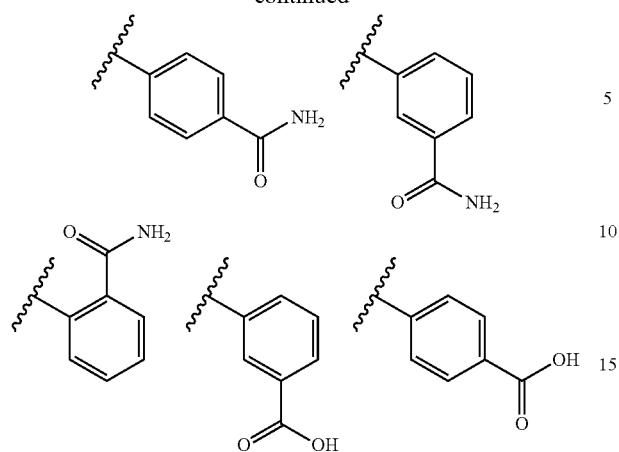
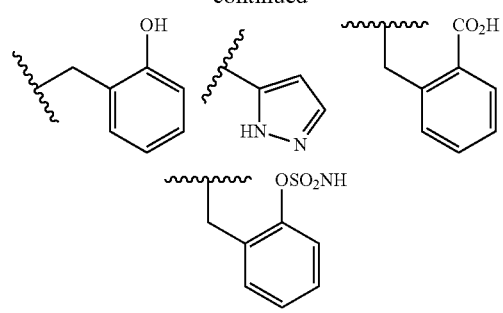
In some embodiments, the compound has the structure:
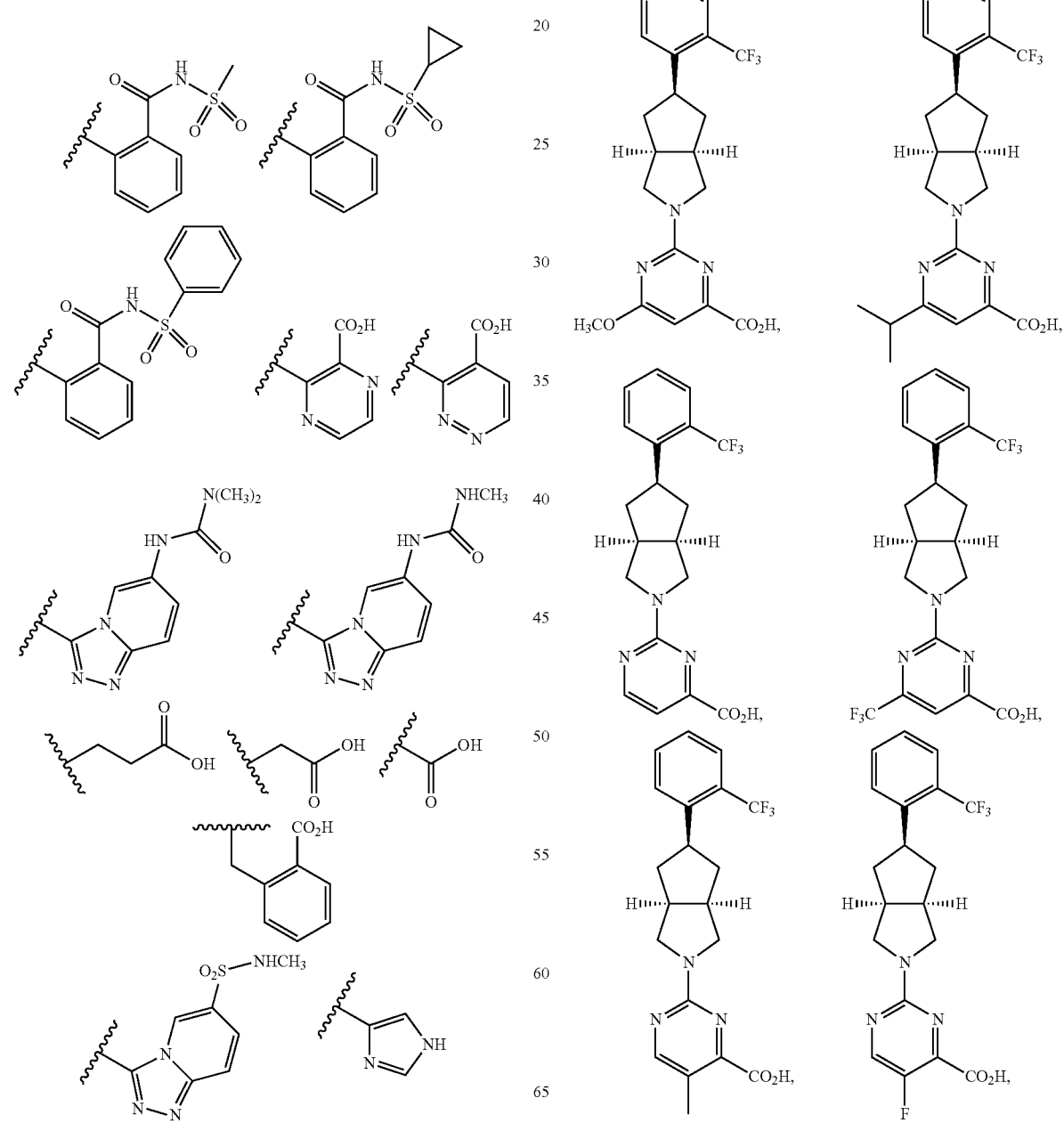

-continued
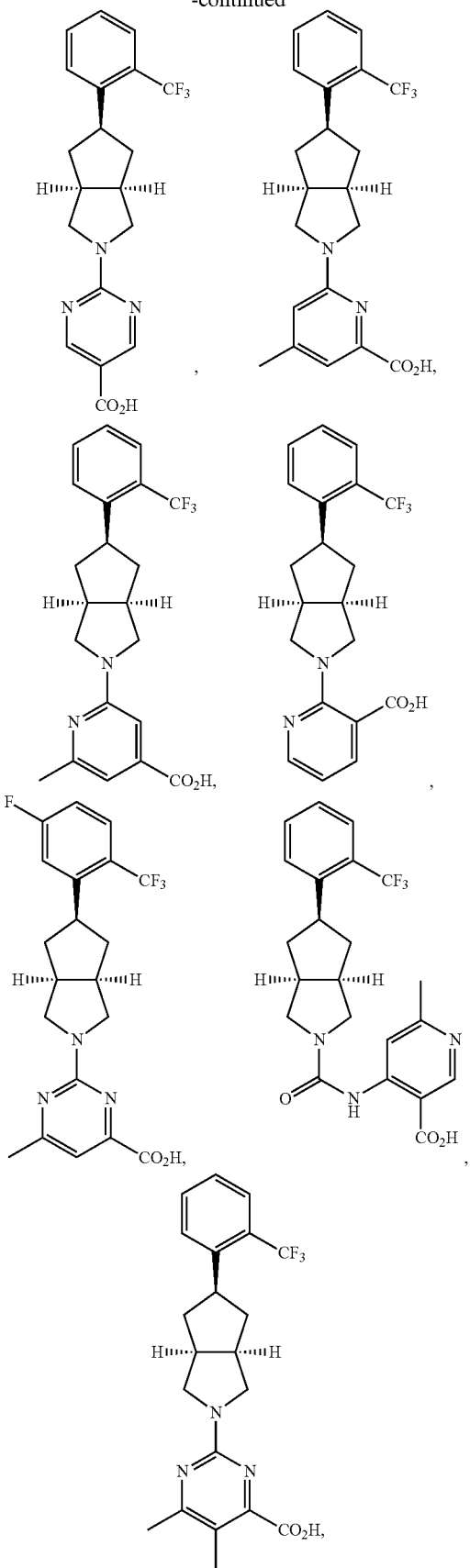
or a pharmaceutically acceptable salt thereof.
In some embodiments of the methods of the present invention, the compound has the structure:
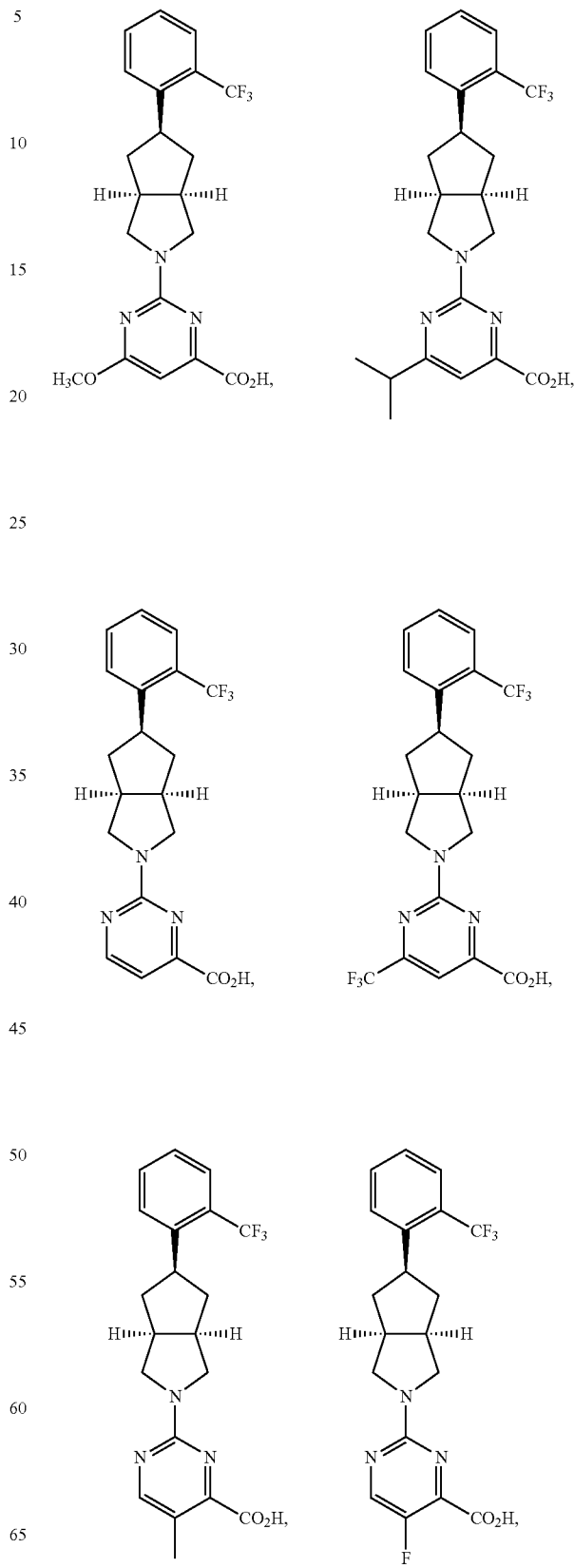

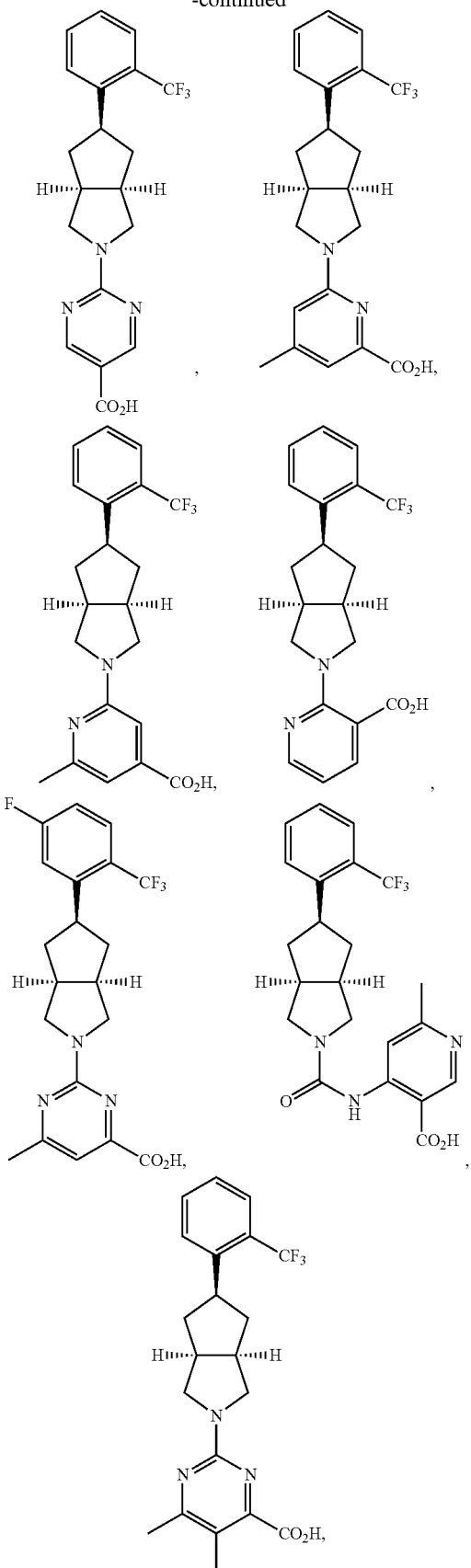

or a pharmaceutically acceptable salt thereof.

In some embodiments, bisretinoid-mediated macular degeneration is Age-Related Macular Degeneration or Stargardt Disease. In some embodiments, the bisretinoid-mediated macular degeneration is Age-Related Macular Degeneration. In some embodiments, the bisretinoid-mediated macular degeneration is dry (atrophic) Age-Related Macular Degeneration.

In some embodiments, the bisretinoid-mediated macular degeneration is Stargardt Disease.

In some embodiments, the bisretinoid-mediated macular degeneration is Best disease.

In some embodiments, the bisretinoid-mediated macular degeneration is adult vitelliform maculopathy.

In some embodiments, the bisretinoid-mediated macular degeneration is Stargardt-like macular dystrophy.

The bisretinoid-mediated macular degeneration may comprise the accumulation of lipofuscin deposits in the retinal pigment epithelium.

Figure 2:
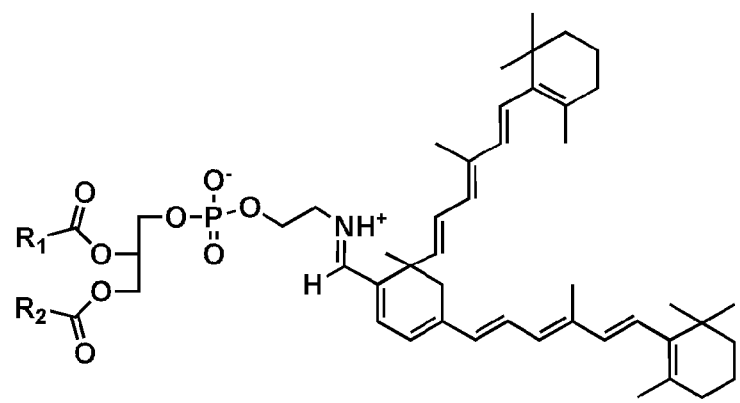
FIG. 2. Structure of bisretinoid atRAL di-PE (all-transretinal dimer-phosphatidyl ethanolamine), a cytotoxic component of retinal lipofuscin. R1 and R2 refer to various fatty acid constituents.
Figure 2:
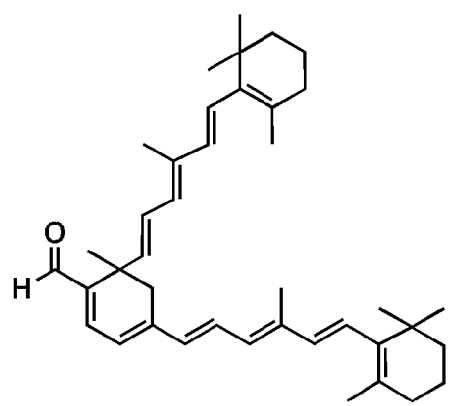
Figure 3:
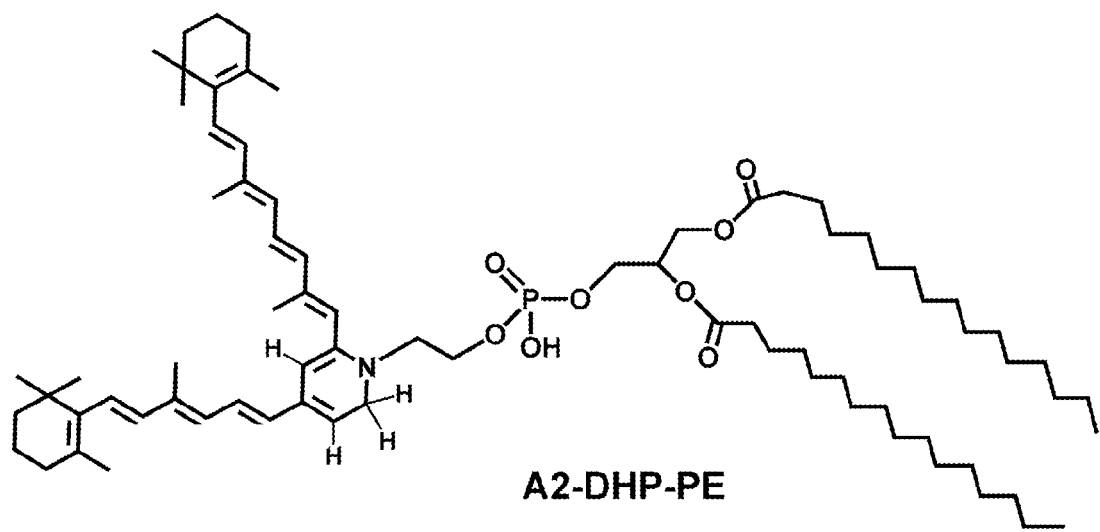
FIG. 3. Structure of bisretinoid A2-DHP-PE, a cytotoxic component of retinal lipofuscin.

As used herein, "bisretinoid lipofuscin" is lipofuscin containing a cytotoxic bisretinoid. Cytotoxic bisretinoids include but are not necessarily limited to A2E, isoA2E, atRAL di-PE, and A2-DHP-PE (FIGS. 1, 2, and 3).

Except where otherwise specified, when the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, and hexyl. Unless otherwise specified contains one to ten carbons. Alkyl groups can be unsubstituted or substituted with one or more substituents, including but not limited to halogen, alkoxy, alkylthio, trifluoromethyl, difluoromethyl, methoxy, and hydroxyl.

As used herein, "$C_1$-$C_4$ alkyl" includes both branched and straight-chain $C_1$-$C_4$ alkyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

As used herein, "heteroalkyl" includes both branched and straight-chain saturated aliphatic hydrocarbon groups having at least 1 heteroatom within the chain or branch.

As used herein, "cycloalkyl" includes cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "heterocycloalkyl" is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains nitrogen, it is understood that the corresponding N-oxides thereof are also encompassed by this definition.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl" as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include but are not limited to phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition. As used herein, "monocycle" includes any stable polycyclic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl. As used herein, "heteromonocycle" includes any monocycle containing at least one heteroatom.

As used herein, "bicycle" includes any stable polycyclic carbon ring of up to 10 atoms that is fused to a polycyclic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene. As used herein, "heterobicycle" includes any bicycle containing at least one heteroatom.

The term "phenyl" is intended to mean an aromatic six membered ring containing six carbons, and any substituted derivative thereof.

The term "benzyl" is intended to mean a methylene attached directly to a benzene ring. A benzyl group is a methyl group wherein a hydrogen is replaced with a phenyl group, and any substituted derivative thereof.

The term "pyridine" is intended to mean a heteroaryl having a six-membered ring containing 5 carbon atoms and 1 nitrogen atom, and any substituted derivative thereof.

The term "pyrimidine" is intended to mean a heteroaryl having a six-membered ring containing 4 carbon atoms and 2 nitrogen atoms wherein the two nitrogen atoms are separated by one carbon atom, and any substituted derivative thereof.

The term "pyridazine" is intended to mean a heteroaryl having a six-membered ring containing 4 carbon atoms and 2 nitrogen atoms wherein the two nitrogen atoms are adjacent to each other, and any substituted derivative thereof.

The term "pyrazine" is intended to mean a heteroaryl having a six-membered ring containing 4 carbon atoms and 2 nitrogen atoms wherein the two nitrogen atoms are separated by two carbon atoms, and any substituted derivative thereof.

The term "pyrrolidine" is intended to mean a non-aromatic five-membered ring containing four carbon atoms and one nitrogen atom, and any substituted derivative thereof.

The term "triazole" is intended to mean a heteroaryl having a five-membered ring containing two carbon atoms and three nitrogen atoms, and any substituted derivative thereof.

The term "imidazole" is intended to mean a heteroaryl having a five-membered ring containing three carbon atoms and two nitrogen atoms, and any substituted derivative thereof.

The term "thiadiazole" is intended to mean a heteroaryl having a five-membered ring containing two carbon atoms, two nitrogen atoms, and one sulfur atom and any substituted derivative thereof.

The term "pyrazole" is intended to mean a heteroaryl having a five-membered ring containing three carbon atoms and two nitrogen atoms wherein the nitrogen atoms are adjacent to each other, and any substituted derivative thereof.

The term "triazine" is intended to mean a heteroaryl having a six-membered ring containing 3 carbon atoms and 3 nitrogen atoms, and any substituted derivative thereof.

The term "indole" is intended to mean a heteroaryl having a five-membered ring fused to a phenyl ring with the five-membered ring containing 1 nitrogen atom directly attached to the phenyl ring.

The term "benzimidazole" is intended to mean a heteroaryl having a five-membered ring fused to a phenyl ring with the five-membered ring containing 2 nitrogen atoms directly attached to the phenyl ring.

The term "oxatane" is intended to mean a non-aromatic four-membered ring containing three carbon atoms and one oxygen atom, and any substituted derivative thereof.

The term "sulfolane" is intended to mean a non-aromatic five-membered ring containing four carbon atoms and one sulfur atom wherein the sulfur atom is doubly bonded to two oxygen atoms and any substituted derivative thereof.

The compounds used in the method of the present invention may be prepared by techniques well know in organic synthesis and familiar to a practitioner ordinarily skilled in the art. However, these may not be the only means by which to synthesize or obtain the desired compounds.

The compounds of present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

The compounds of present invention may be prepared by techniques described herein. The synthetic methods used to prepare Examples 1-46 may be used to prepare additional octahydrocyclopentapyrroles compounds which described herein.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

Another aspect of the invention comprises a compound of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference, Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds of the present invention may be in a salt form. As used herein, a "salt" is a salt of the instant compounds which has been modified by making acid or base salts of the compounds. In the case of compounds used to treat a disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsuiphonate salts and the like. (See, e.g Berge et al. (1977) "Pharmaceutical Salts", *J. Pharm. Sci.* 66:1-19).

A salt or pharmaceutically acceptable salt is contemplated for all compounds disclosed herein.

As used herein, "treating" means preventing, slowing, halting, or reversing the progression of a disease or infection. Treating may also mean improving one or more symptoms of a disease or infection.

The compounds of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Figure 7:
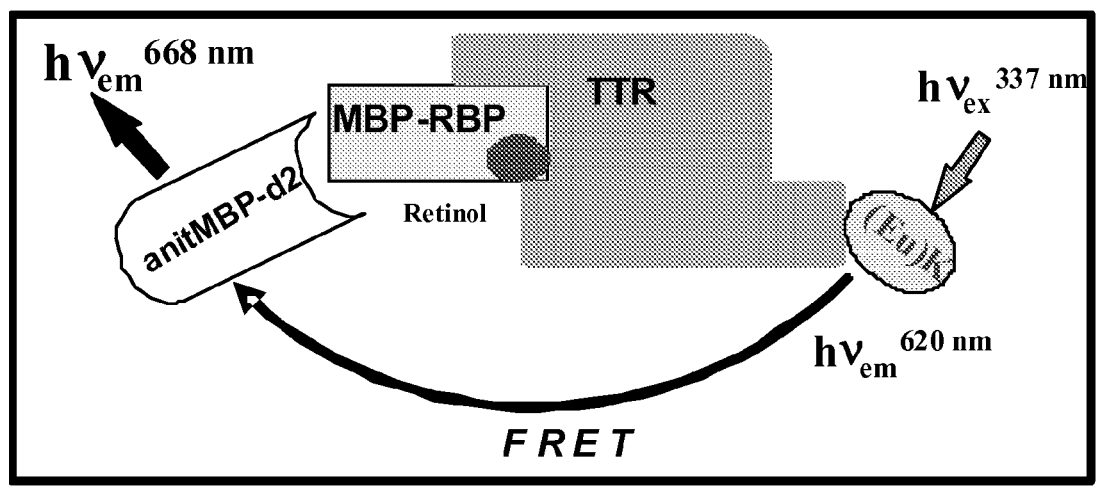
FIG. 7. Schematic depiction of the HTRF-based assay format for characterization of RBP4 antagonists disrupting retinol-induced RBP4-TTR interaction.

Experimental Details
Materials and Methods
TR-FRET Assay for Retinol-Induced RBP4-TTR Interaction Binding of a desired RBP4 antagonist displaces retinol and induces hindrance for RBP4-TTR interaction resulting in the decreased FRET signal (FIG. 7). Bacterially expressed MBP-RBP4 and untagged TTR were used in this assay. For the use in the TR-FRET assay the maltose binding protein (MBP)-tagged human RBP4 fragment (amino acids 19-201) was expressed in the Gold(DE3)pLysS *E. coli* strain (Stratagene) using the pMAL-c4x vector. Following cell lysis, recombinant RBP4 was purified from the soluble fraction using the ACTA FPLC system (GE Healthcare) equipped with the 5-ml the MBP Trap HP column. Human untagged TTR was purchased from Calbiochem. Untagged TTR was labeled directly with $Eu^{3+}$ Cryptate-NHS using the HTRF Cryptate Labeling kit from CisBio following the manufacturer's recommendations. HTRF assay was performed in white low volume 384 well plates (Greiner-Bio) in a final assay volume of 16 μl per well. The reaction buffer contained 10 mM Tris-HCl pH 7.5, 1 mM DTT, 0.05% NP-40, 0.05% Prionex, 6% glycerol, and 400 mM RE. Each reaction contained 60 nM MBP-RBP4 and 2 nM TTR-Eu along with 26.7 nM of anti-MBP antibody conjugated with d2 (Cisbio). Titration of test compounds in this assay was conducted in the presence of 1 μM retinol. All reactions were assembled in the dark under dim red light and incubated overnight at +4° C. wrapped in aluminum foil. TR-FRET signal was measured in the SpectraMax M5e Multimode Plate Reader (Molecular Device). Fluorescence was excited at 337 nm and two readings per well were taken: Reading 1 for time-gated energy transfer from Eu(K) to d2 (337 nm excitation, 668 nm emission, counting delay 75 microseconds, counting window 100 microseconds) and Reading 2 for Eu(K) time-gated fluorescence (337 nm excitation, 620 nm emission, counting delay 400 microseconds, counting window 400 microseconds). The TR-FRET signal was expressed as the ratio of fluorescence intensity: $Flu_{665}/Flu_{620} \times 10,000$.

Scintillation Proximity RBP4 Binding Assay

Untagged human RBP4 purified from urine of tubular proteinuria patients was purchased from Fitzgerald Industries International. It was biotinylated using the EZ-Link Sulfo-NHS-LC-Biotinylation kit from Pierce following the manufacturer's recommendations. Binding experiments were performed in 96-well plates (OptiPlate, PerkinElmer) in a final assay volume of 100 μl per well in SPA buffer (1×PBS, pH 7.4, 1 mM EDTA, 0.1% BSA, 0.5% CHAPS). The reaction mix contained 10 nM $^3$H-Retinol (48.7 Ci/mmol; PerkinElmer), 0.3 mg/well Streptavidin-PVT beads, 50 nM biotinylated RBP4 and a test compound. Nonspecific binding was determined in the presence of 20 μM of unlabeled retinol. The reaction mix was assembled in the dark under dim red light. The plates were sealed with clear tape (TopSeal-A: 96-well microplate, PerkinElmer), wrapped in the aluminum foil, and allowed to equilibrate 6 hours at room temperature followed by overnight incubation at +4° C. Radiocounts were measured using a TopCount NXT counter (Packard Instrument Company).

General Procedures for Preparing 3.3.0 Octahydrocyclopenta[c]pyrrole Amide II

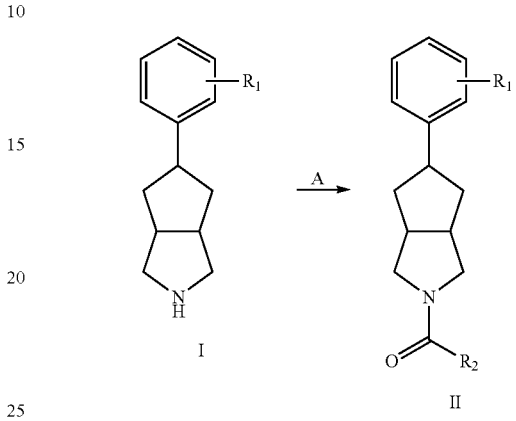

Conditions: A1) carboxylic acid, HBTU, $Et_3N$, DMF; A2) carboxylic acid, EDCI, HOBt, i-$Pr_2$NEt, DMF; A3) acid chloride, $Et_3N$, $CH_2Cl_2$.

General Procedure (GP-A1) for Carboxamide Formation:

A mixture of amine I (1 equiv), desired carboxylic acid (1 equiv), triethylamine ($Et_3N$) (3 equiv), and 2-(1H-benzotriazole-1-yl)-1,1,3,3-tetramethyluronium hexafluoro-phosphate (HBTU) (1.5 equiv) in DMF (0.25 M) was stirred at room temperature until the reaction was complete by TLC or LC-MS. The mixture was diluted with $H_2O$ and extracted with EtOAc. The combined organic extracts were washed with $H_2O$, brine, dried over $Na_2SO_4$, filtered, and concentrated under reduced pressure. The resulting residue was purified by either normal phase silica gel column chromatography (typical eluents included either a mixture of or hexanes and EtOAc or a mixture of $CH_2Cl_2$ and a 90:9:1 mixture of $CH_2C_2/CH_3OH$/concentrated $NH_4OH$) or C-18 reversed phase column chromatography (typical eluents included $CH_3CN$ and $H_2O$) to afford the desired carboxamide II. The product structure was verified by $^1$H NMR and by mass analysis.

General Procedure (GP-A2) for Carboxamide Formation:

A mixture of amine I (1 equiv), desired carboxylic acid (1 equiv), N,N-diisopropylethylamine (i-$Pr_2$NEt) (3 equiv), 1-ethyl-3-(3-dimethylaminutesopropyl)carbodiimide (EDCI) (1.5 equiv) and hydroxybenzotriazole (HOBt) (1.5 equiv) in DMF (0.25 M) was stirred at room temperature until the reaction was complete by TLC or LC-MS. The mixture was diluted with $H_2O$ and extracted with EtOAc. The combined organic extracts were washed with $H_2O$, brine, dried over $Na_2SO_4$, filtered, and concentrated under reduced pressure. The resulting residue was purified by either normal phase silica gel column chromatography (typical eluents included either a mixture of or hexanes and EtOAc or a mixture of $CH_2Cl_2$ and a 90:9:1 mixture of CH$_2$Cl$_2$/CH$_3$OH/concentrated NH$_4$OH) or C-18 reversed phase column chromatography (typical eluents included CH$_3$CN and H$_2$O) to afford the desired carboxamide II. The product structure was verified by $^1$H NMR and by mass analysis.

General Procedure (GP-A3) for Carboxamide Formation:

A mixture of amine I (1 equiv), Et$_3$N (3 equiv), and acid chloride (1 equiv) in CH$_2$Cl$_2$ (0.25 M) was stirred at room temperature until the reaction was complete by TLC or LC-MS. The mixture was washed with H$_2$O, brine, dried over Na$_2$SO$_4$, filtered, and concentrated under reduced pressure. The resulting residue was purified by either normal phase silica gel column chromatography (typical eluents included either a mixture of or hexanes and EtOAc or a mixture of CH$_2$Cl$_2$ and a 90:9:1 mixture of CH$_2$Cl$_2$/CH$_3$OH/concentrated NH$_4$OH) or C-18 reversed phase column chromatography (typical eluents included CH$_3$CN and H$_2$O) to afford the desired carboxamides II. The product structure was verified by $^1$H NMR and by mass analysis.

General Procedures for Preparing (5-Phenylhexahydrocyclopenta[c]pyrrol-2(1H)-yl)(4,5,6,7-tetrahydro-1H-pyrazolo[4,3-c]pyridin-3-yl)methanone Carboxamides IV

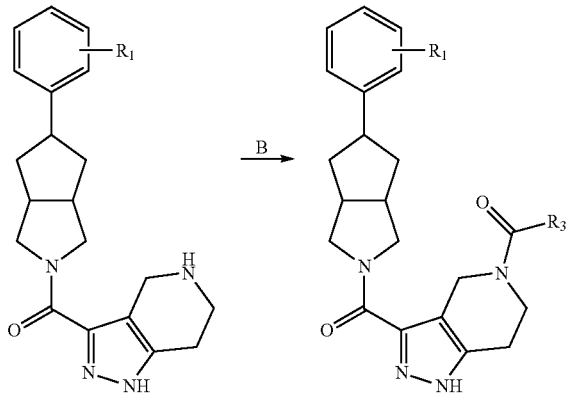

III                    IV

Conditions: B) acid chloride, Et$_3$N, CH$_2$Cl$_2$.

General Procedure (GP-B) for Carboxamide Formation:

A mixture of amine III (1 equiv), desired acid chloride (1 equiv) and Et$_3$N (3 equiv) in CH$_2$Cl$_2$ (0.25 M) was stirred from 0° C. to room temperature until the reaction was complete by TLC or LC-MS. The mixture was diluted with H$_2$O and extracted with CH$_2$Cl$_2$. The combined organic extracts were washed with H$_2$O, brine, dried over Na$_2$SO$_4$, filtered, and concentrated under reduced pressure. The resulting residue was purified by either normal phase silica gel column chromatography (typical eluents included either a mixture of or hexanes and EtOAc or a mixture of CH$_2$Cl$_2$ and a 90:9:1 mixture of CH$_2$Cl$_2$/CH$_3$OH/concentrated NH$_4$OH) or C-18 reversed phase column chromatography (typical eluents included CH$_3$CN and H$_2$O) to afford the desired carboxamides IV. The product structure was verified by $^1$H NMR and by mass analysis.

General Procedures for Preparing (5-Phenylhexahydrocyclopenta[c]pyrrol-2(1H)-yl)(4,5,6,7-tetrahydro-1H-pyrazolo[4,3-c]pyridin-3-yl)methanone Sulfonamides V

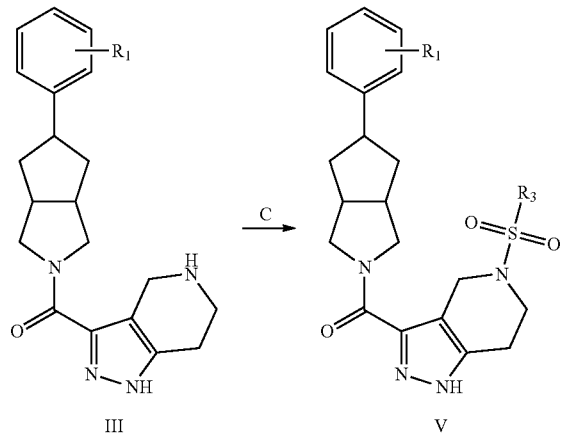

III                    V

Conditions: C) sulfonyl chloride, i-Pr$_2$NEt, CH$_2$Cl$_2$.

General Procedure (GP-C) for Sulfonamide Formation:

A mixture of amine III (1 equiv), desired sulfonyl chloride (1 equiv) and i-Pr$_2$NEt (3 equiv) in CH$_2$Cl$_2$ (0.25 M) was stirred from 0° C. to room temperature until the reaction was complete by TLC or LC-MS. The mixture was diluted with H$_2$O and extracted with CH$_2$Cl$_2$. The combined organic extracts were washed with H$_2$O, brine, dried over Na$_2$SO$_4$, filtered, and concentrated under reduced pressure. The resulting residue was purified by either normal phase silica gel column chromatography (typical eluents included either a mixture of or hexanes and EtOAc or a mixture of CH$_2$Cl$_2$ and a 90:9:1 mixture of CH$_2$Cl$_2$/CH$_3$OH/concentrated NH$_4$OH) or C-18 reversed phase column chromatography (typical eluents included CH$_3$CN and H$_2$O) to afford the desired sulfonamides V. The product structure was verified by $^1$H NMR and by mass analysis.

General Procedures for Preparing Alkylated (5-Phenylhexahydrocyclopenta[c]pyrrol-2(1H)-yl)(4,5,6,7-tetrahydro-1H-pyrazolo[4,3-c]pyridin-3-yl)methanones VI

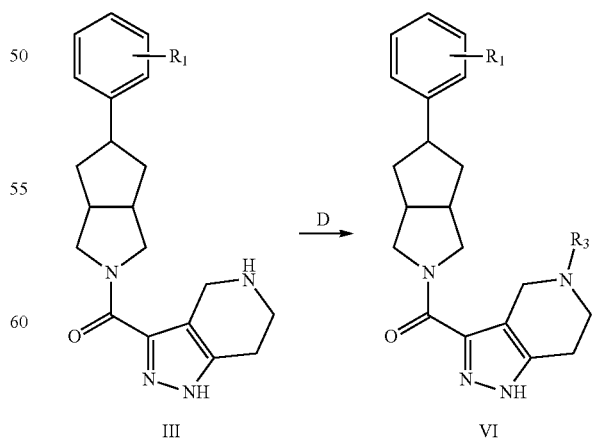

III                    VI

Conditions: D) aldehyde or ketone, NaBH(OAc)$_3$, CH$_2$Cl$_2$.

General Procedure (GP-D) for Sulfonamide Formation:

A mixture of amine III (1 equiv), desired aldehyde or ketone (1.5 equiv) and HOAc (6 equiv) in $CH_2Cl_2$ (0.25 M) was stirred for 16 hours at room temperature. To this was added sodium triacetoxyborohydride ($NaBH(OAc)_3$) and the mixture stirred at room temperature until the reaction was complete by TLC or LC-MS. The mixture was diluted with aqueous, saturated $NaHCO_3$ solution and extracted with $CH_2Cl_2$. The combined organic extracts were washed with $H_2O$, brine, dried over $Na_2SO_4$, filtered, and concentrated under reduced pressure. The resulting residue was purified by either normal phase silica gel column chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) or C-18 reversed phase column chromatography (typical eluents included $CH_3CN$ and $H_2O$) to afford the desired amines VI. The product structure was verified by $^1H$ NMR and by mass analysis.

General Procedures for Preparing (5-Phenylhexahydrocyclopenta[c]pyrrol-2(1H)-yl)(4,5,6,7-tetrahydro-1H-pyrazolo[3,4-c]pyridin-3-yl)methanone Carboxamides VIII

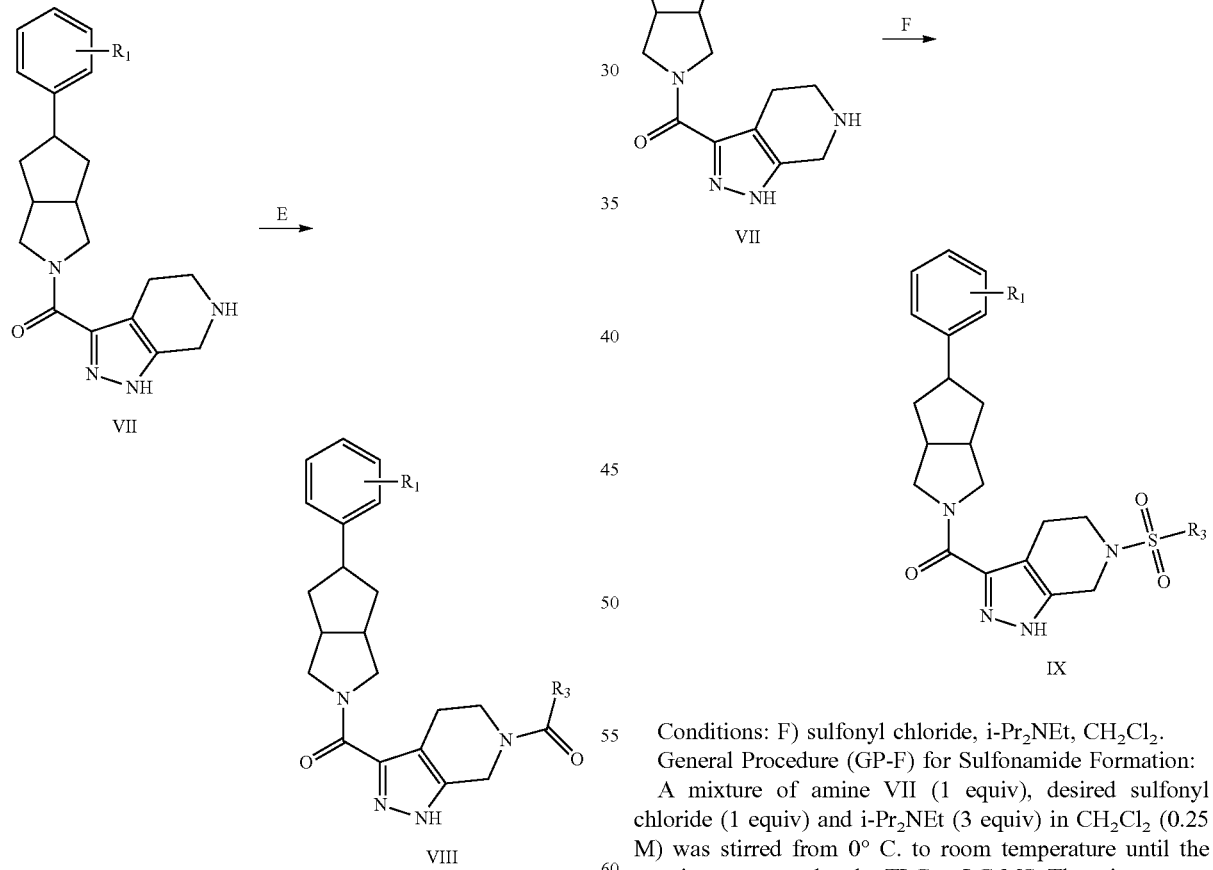

Conditions: E) acid chloride, $Et_3N$, $CH_2Cl_2$.

General Procedure (GP-E) for Carboxamide Formation:

A mixture of amine VII (1 equiv), desired acid chloride (1 equiv) and $Et_3N$ (3 equiv) in $CH_2Cl_2$ (0.25 M) was stirred from 0° C. to room temperature until the reaction was complete by TLC or LC-MS. The mixture was diluted with $H_2O$ and extracted with $CH_2Cl_2$. The combined organic extracts were washed with $H_2O$, brine, dried over $Na_2SO_4$, filtered, and concentrated under reduced pressure. The resulting residue was purified by either normal phase silica gel column chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) or C-18 reversed phase column chromatography (typical eluents included $CH_3CN$ and $H_2O$) to afford the desired carboxamides VIII. The product structure was verified by $^1H$ NMR and by mass analysis.

General Procedures for Preparing (5-Phenylhexahydrocyclopenta[c]pyrrol-2(1H)-yl)(4,5,6,7-tetrahydro-1H-pyrazolo[3,4-c]pyridin-3-yl)methanone Sulfonamides IX

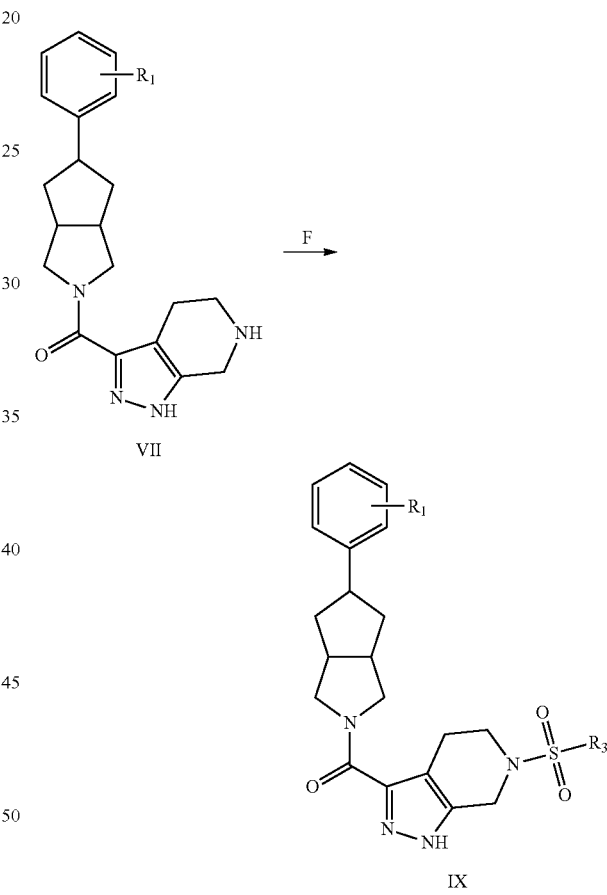

Conditions: F) sulfonyl chloride, i-$Pr_2NEt$, $CH_2Cl_2$.

General Procedure (GP-F) for Sulfonamide Formation:

A mixture of amine VII (1 equiv), desired sulfonyl chloride (1 equiv) and i-$Pr_2NEt$ (3 equiv) in $CH_2Cl_2$ (0.25 M) was stirred from 0° C. to room temperature until the reaction was complete by TLC or LC-MS. The mixture was diluted with $H_2O$ and extracted with $CH_2Cl_2$. The combined organic extracts were washed with $H_2O$, brine, dried over $Na_2SO_4$, filtered, and concentrated under reduced pressure. The resulting residue was purified by either normal phase silica gel column chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) or C-18 reversed phase column chromatography (typical eluents included $CH_3CN$ and $H_2O$) to afford the desired sulfonamides IX. The product structure was verified by $^1H$ NMR and by mass analysis.

General Procedures for Preparing Alkylated (5-Phenylhexahydrocyclopenta[c]pyrrol-2(1H)-yl)(4,5,6,7-tetrahydro-1H-pyrazolo[3,4-c]pyridin-3-yl)methanones X

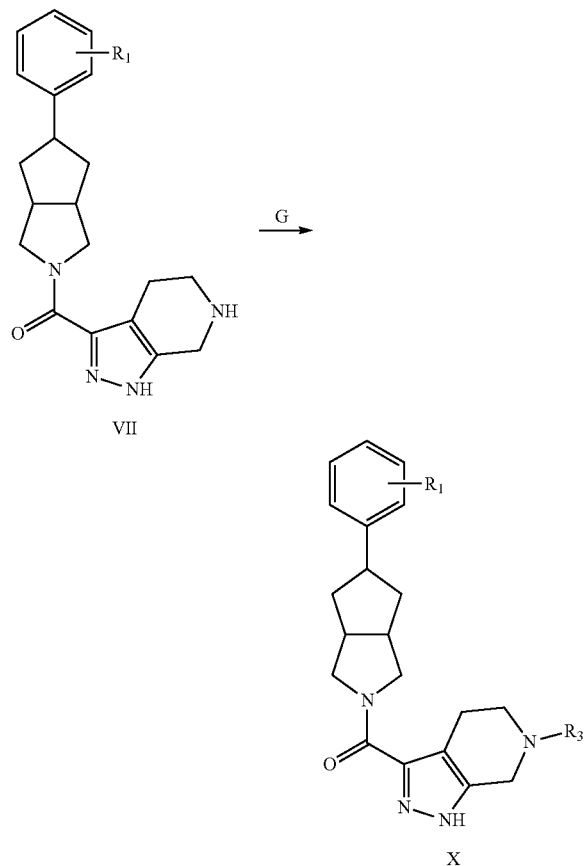

Conditions: G) aldehyde or ketone, $NaBH(OAc)_3$, $CH_2Cl_2$.

General Procedure (GP-G) for Sulfonamide Formation:

A mixture of amine VII (1 equiv), desired aldehyde or ketone (1.5 equiv) and HOAc (6 equiv) in $CH_2Cl_2$ (0.25 M) was stirred for 16 hours at room temperature. To this was added $NaBH(OAc)_3$ and the mixture stirred at room temperature until the reaction was complete by TLC or LC-MS. The mixture was diluted with aqueous, saturated $NaHCO_3$ solution and extracted with $CH_2Cl_2$. The combined organic extracts were washed with $H_2O$, brine, dried over $Na_2SO_4$, filtered, and concentrated under reduced pressure. The resulting residue was purified by either normal phase silica gel column chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) or C-18 reversed phase column chromatography (typical eluents included $CH_3CN$ and $H_2O$) to afford the desired amine X. The product structure was verified by $^1H$ NMR and by mass analysis.

General Procedures for Preparing (5-Phenylhexahydrocyclopenta[c]pyrrol-2(1H)-yl)(1,4,5,6-tetrahydropyrrolo[3,4-c]pyrazol-3-yl)methanone Carboxamides XII

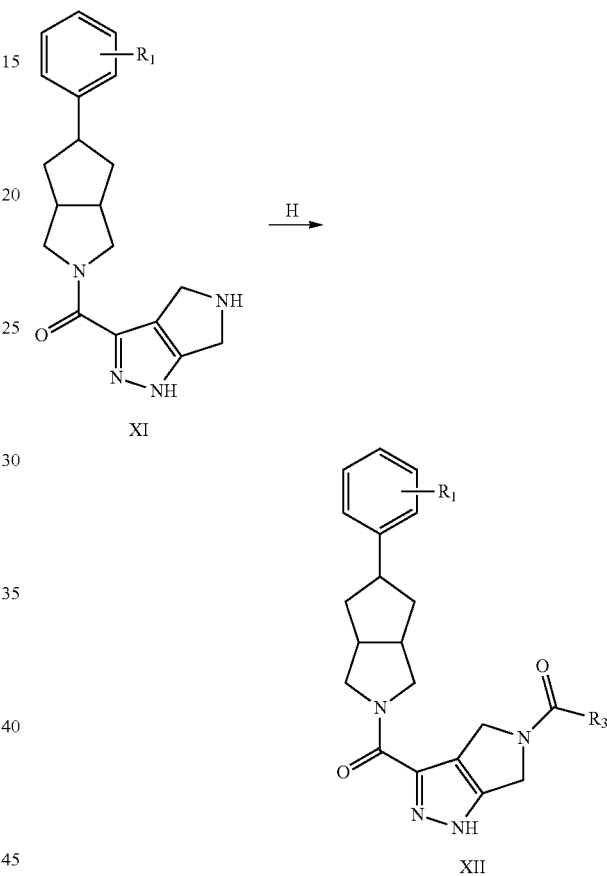

Conditions: H) acid chloride, $Et_3N$, $CH_2Cl_2$.

General Procedure (GP-H) for Carboxamide Formation:

A mixture of amine XI (1 equiv), desired acid chloride (1 equiv) and $Et_3N$ (3 equiv) in $CH_2Cl_2$ (0.25 M) was stirred from 0° C. to room temperature until the reaction was complete by TLC or LC-MS. The mixture was diluted with $H_2O$ and extracted with $CH_2Cl_2$. The combined organic extracts were washed with $H_2O$, brine, dried over $Na_2SO_4$, filtered, and concentrated under reduced pressure. The resulting residue was purified by either normal phase silica gel column chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) or C-18 reversed phase column chromatography (typical eluents included $CH_3CN$ and $H_2O$) to afford the desired carboxamides XII. The product structure was verified by $^1H$ NMR and by mass analysis.

General Procedures for Preparing (5-Phenylhexahydrocyclopenta[c]pyrrol-2(1H)-yl)(1,4,5,6-tetrahydropyrrolo[3,4-c]pyrazol-3-yl)methanone Sulfonamides XIII

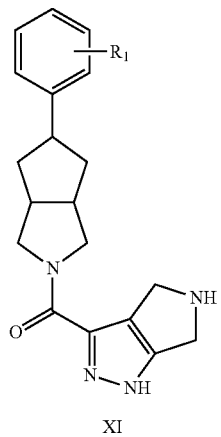

XI

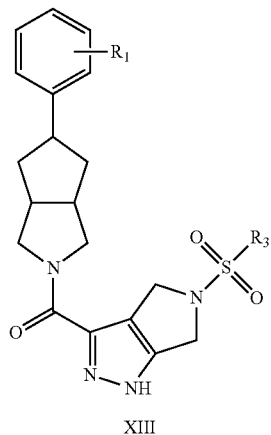

XIII

Conditions: I) sulfonyl chloride, i-Pr$_2$NEt, CH$_2$Cl$_2$.

General Procedure (GP-I) for Sulfonamide Formation:

A mixture of amine XI (1 equiv), desired sulfonyl chloride (1 equiv) and i-Pr$_3$NEt (3 equiv) in CH$_2$Cl$_2$ (0.25 M) was stirred from 0° C. to room temperature until the reaction was complete by TLC or LC-MS. The mixture was diluted with H$_2$O and extracted with CH$_2$Cl$_2$. The combined organic extracts were washed with H$_2$O, brine, dried over Na$_2$SO$_4$, filtered, and concentrated under reduced pressure. The resulting residue was purified by either normal phase silica gel column chromatography (typical eluents included either a mixture of or hexanes and EtOAc or a mixture of CH$_2$Cl$_2$ and a 90:9:1 mixture of CH$_2$Cl$_2$/CH$_3$OH/concentrated NH$_4$OH) or C-18 reversed phase column chromatography (typical eluents included CH$_3$CN and H$_2$O) to afford the desired sulfonamides XIII. The product structure was verified by $^1$H NMR and by mass analysis.

General Procedures for Preparing Alkylated (5-Phenylhexahydrocyclopenta[c]pyrrol-2(1H)-yl)(1,4,5,6-tetrahydropyrrolo[3,4-c]pyrazol-3-yl)methanones XIV

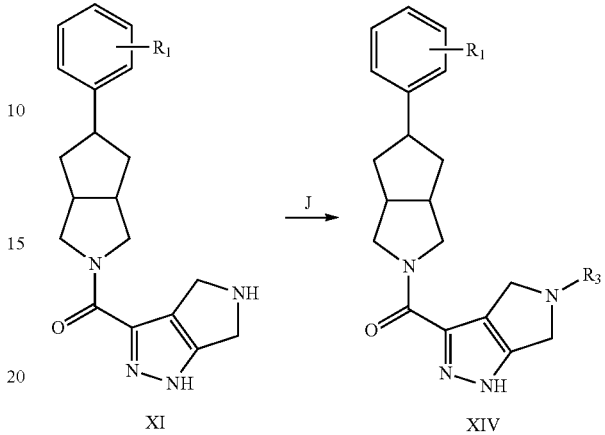

XI    XIV

Conditions: J) aldehyde or ketone, NaBH(OAc)$_3$, CH$_2$Cl$_2$.

General Procedure (GP-J) for Sulfonamide Formation:

A mixture of amine XI (1 equiv), desired aldehyde or ketone (1.5 equiv) and HOAc (6 equiv) in CH$_2$Cl$_2$ (0.25 M) was stirred for 16 hours at room temperature. To this was added NaBH(OAc)$_3$ and the mixture stirred at room temperature until the reaction was complete by TLC or LC-MS. The mixture was diluted with aqueous, saturated NaHCO$_3$ solution and extracted with CH$_2$Cl$_2$. The combined organic extracts were washed with H$_2$O, brine, dried over Na$_2$SO$_4$, filtered, and concentrated under reduced pressure. The resulting residue was purified by either normal phase silica gel column chromatography (typical eluents included either a mixture of or hexanes and EtOAc or a mixture of CH$_2$Cl$_2$ and a 90:9:1 mixture of CH$_2$Cl$_2$/CH$_3$OH/concentrated NH$_4$OH) or C-18 reversed phase column chromatography (typical eluents included CH$_3$CN and H$_2$O) to afford the desired amine XIV. The product structure was verified by $^1$H NMR and by mass analysis.

General Procedures for Preparing 3.3.0 Methyl 2-(hexahydrocyclopenta[c]pyrrol-2(1H)-yl)pyrimidine-4-carboxylate XV

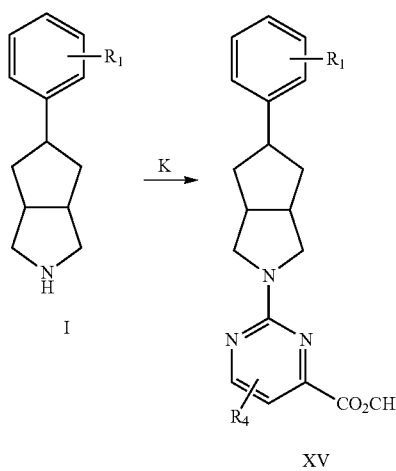

I    XV

Conditions: K1) Et$_3$N, DMF

General Procedure (GP-K1) for 2-Aminopyrimidine Formation:

A mixture of amine I (1 equiv), desired methyl 2-chloropyrimidine-4-carboxylate (1 equiv), and triethylamine (Et$_3$N) (3 equiv) in DMF (0.25 M) was stirred at 60° C. until the reaction was complete by TLC or LC-MS. The mixture was diluted with H$_2$O and extracted with EtOAc. The combined organic extracts were washed with H$_2$O, brine, dried over Na$_2$SO$_4$, filtered, and concentrated under reduced pressure. The resulting residue was purified by either normal phase silica gel column chromatography (typical eluents included either a mixture of or hexanes and EtOAc or a mixture of CH$_2$Cl$_2$ and a 90:9:1 mixture of CH$_2$Cl$_2$/CH$_3$OH/concentrated NH$_4$OH) or C-18 reversed phase column chromatography (typical eluents included CH$_3$CN and H$_2$O) to afford the desired carboxamide XV. The product structure was verified by $^1$H NMR and by mass analysis.

General Procedures for Preparing 3.3.0 2-(Hexahydrocyclopenta[c]pyrrol-2(1H)-yl)pyrimidine-4-carboxylic Acid XVI

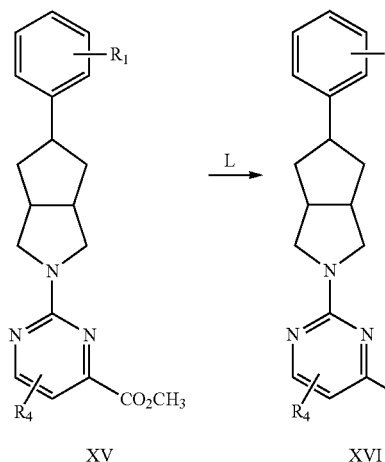

Conditions: L1) 2N NaOH, CH$_3$OH, THF

General Procedure (GP-L1) for Carboxylic Acid Formation:

A mixture of ester XV (1 equiv) and aqueous 2 N NaOH (3 equiv) in a 1:1 mixture of THF and CH$_3$OH (0.25 M) was stirred at room temperature until the reaction was complete by TLC or LC-MS. The mixture was neutralized with 2 N HCl and extracted with CH$_2$Cl$_2$. The combined organic extracts were washed with H$_2$O, brine, dried over Na$_2$SO$_4$, filtered, and concentrated under reduced pressure. The resulting residue was purified by either normal phase silica gel column chromatography (typical eluents included either a mixture of or hexanes and EtOAc or a mixture of CH$_2$Cl$_2$ and a 90:9:1 mixture of CH$_2$Cl$_2$/CH$_3$OH/concentrated NH$_4$OH) or C-18 reversed phase column chromatography (typical eluents included CH$_3$CN and H$_2$O) to afford the desired carboxamide XVI. The product structure was verified by $^1$H NMR and by mass analysis.

Preparation of (3aR,5R,6aS)-5-(2-(Trifluoromethyl)phenyl) octahydrocyclopenta[c]pyrrole Hydrochloride (9)

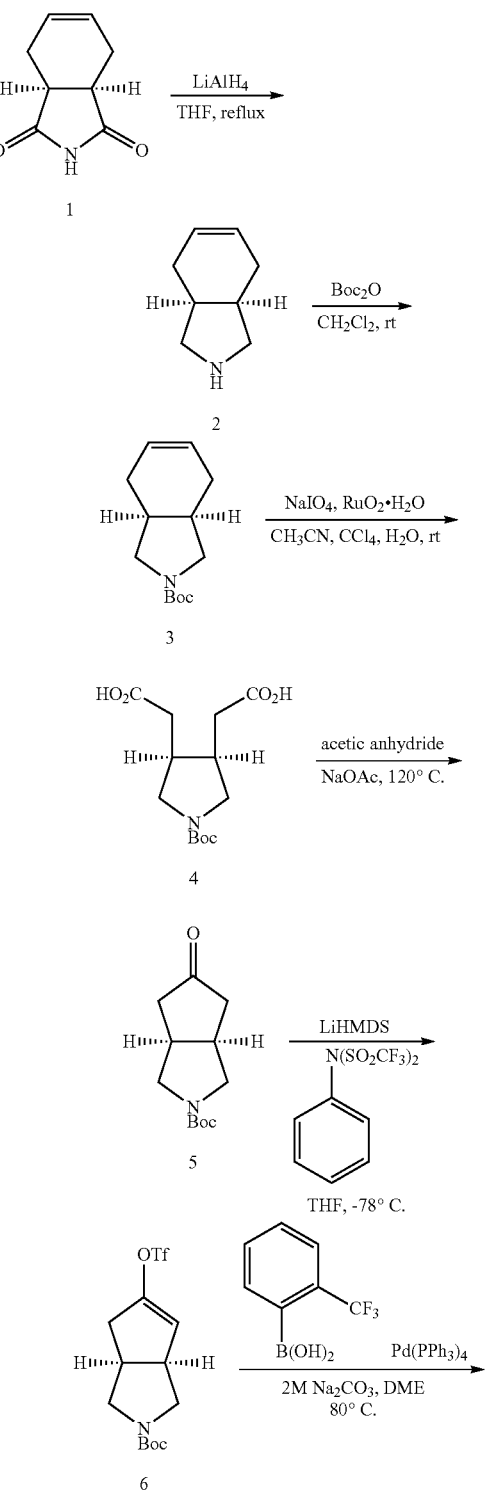

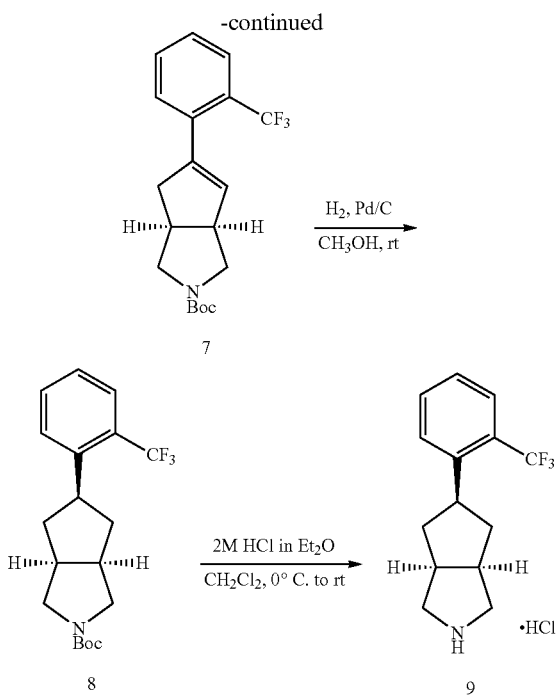

Step A: To a 0° C. cooled solution of lithium aluminum hydride (LiAlH₄) in THF (1.0 M, 800 mL, 0.8 mol) in THF (800 mL) in a 3-L, three-necked, round-bottomed flask equipped with a thermometer was carefully added (3aR, 7aS)-3a,4,7,7a-tetrahydro-1H-isoindole-1,3(2H)-dione (53.7 g, 0.35 mol) portion-wise. An exotherm of ~5° C. occurred upon each addition of the dione. Upon complete addition, the mixture was allowed to warm to room temperature followed by heating at 70° C. for 16 hours. The reaction was allowed to cool back to room temperature and then further cooled to 0° C. The reaction was carefully quenched by slow addition of H₂O (30 mL), 15% aqueous NaOH solution (30 mL), followed by another bolus of H₂O (90 mL). The rate of quenching was done carefully so as to maintain an internal temperature below 25° C. The mixture stirred for 1 hour and was filtered through Celite. The aqueous filtrate was extracted with Et₂O (2×100 mL) and the organic extracts were combined and concentrated under reduced pressure. The resulting residue was purified using a Kugelrohr distillation apparatus to give (3aR,7aS)-2,3,3a,4, 7,7a-hexahydro-1H-isoindole (2) as a clear, colorless oil (19.45 g, 44%): ¹H NMR (500 MHz, CDCl₃) δ 5.29 (s, 2H), 3.88 (bs, 1H), 3.26 (m, 2H), 2.82 (m, 2H), 2.41-2.19 (m, 4H), 1.96 (m, 2H).

Step B: To a 0° C. cooled solution of (3aR,7aS)-2,3,3a, 4,7,7a-hexahydro-1H-isoindole (2, 11.5 g, 93.5 mmol) in CH₂Cl₂ (200 mL) was added di-tert-butyl dicarbonate (24.5 g, 112 mmol) and the mixture was allowed to stir at room temperature for 16 hours. The mixture was washed with H₂O (100 mL), brine (100 mL), dried over Na₂SO₄, filtered, and concentrated under reduced pressure. The residue was purified by flash column chromatography (Isco CombiFlash Rf unit, 330 g Redisep column, 0% to 30% EtOAc in hexanes) to give (3aR,7aS)-tert-butyl 3a,4,7,7a-tetrahydro-1H-isoindole-2(3H)-carboxylate (3) as a an oil (20.10 g, 49%): ¹H NMR (500 MHz, CDCl₃) δ 5.64 (s, 2H), 3.39 (m, 2H), 3.20 (m, 2H), 3.15 (m, 2H), 2.23-2.19 (m, 4H), 1.97 (m, 2H), 1.57 (s, 9H).

Step C: To a 0° C. cooled mixture of (3aR,7aS)-tert-butyl 3a,4,7,7a-tetrahydro-1H-isoindole-2(3H)-carboxylate (3, 66.78 g, 0.224 mol) in CH₃CN (600 mL), CCl₄ (400 mL), and H₂O (800 mL) was added NaIO₄ (192.3 g, 0.899 mol) followed by RuO₂·H₂O (1.19 g, 8.94 mmol). The mixture was stirred at room temperature for 24 hours with mechanical stirring and then filtered through Celite. The filter cake was washed with 10% CH₃OH in CH₂Cl₂ (200 mL) and the biphasic mother liquor was separated. The aqueous phase was further extracted with CH₂Cl₂ (3×150 mL) and the combined organic extracts were washed with H₂O (100 mL), brine (100 mL), dried over Na₂SO₄, filtered, and concentrated under reduced pressure. The residue was filtered through a plug of silica gel using a CH₃OH/CH₂Cl₂ eluent system (2% to 10% CH₃OH in CH₂Cl₂). The filtrate was concentrated under reduced pressure to give 2,2'-((3S,4R)-1-(tert-butoxycarbonyl)pyrrolidine-3,4-diyl)diacetic acid (4) as a solid (46.75 g, 72%): ¹H NMR (500 MHz, DMSO-d₆) δ 12.2 (s, 2H), 3.38 (m, 2H), 3.02 (m, 2H), 2.49 (m, 2H), 2.32 (m, 2H), 2.29 (m, 2H), 1.42 (s, 9H).

Step D: To a suspension of 2,2'-((3S,4R)-1-(tert-butoxycarbonyl)pyrrolidine-3,4-diyl)diacetic acid (4, 6.97 g, 24.3 mmol) in acetic anhydride (50 mL) was added sodium acetate (NaOAc) (1.99 g, 24.3 mmol) and the mixture was heated at 120° C. for 3 hours. The mixture cooled to room temperature and filtered through Celite. The filter cake was washed with Et₂O (5×50 mL) and the mother liquor was concentrated under reduced pressure. The resulting residue was purified by flash column chromatography (Isco CombiFlash Rf unit, 120 g Redisep column, 30% EtOAc in hexanes) to give (3aR,6aS)-tert-butyl 5-oxohexahydrocyclopenta[c]pyrrole-2(1H)-carboxylase (5) as a white foam (2.17 g, 40%): ¹H NMR (500 MHz, CDCl₃) δ 3.69 (m, 2H), 3.22 (m, 2H), 2.91 (m, 2H), 2.50 (m, 2H), 2.17 (m, 2H), 1.46 (s, 9H).

Step E: To a −78° C. cooled solution of (3aR,6aS)-tert-butyl 5-oxohexahydrocyclopenta[c]pyrrole-2(1H)-carboxylate (5, 22.35 g, 99.2 mmol) in THF (500 mL) was slowly added a solution of lithium bis(trimethylsilyl)amide (LiHMDS) in THF (1.0 M, 129 ml). The mixture continued to stir a −78° C. for 30 minutes, then a solution of 1,1,1-trifluoro-N-phenyl-N-((trifluoromethyl)sulfonyl) methane-sulfonamide (49.65 g, 139 mmol) in THF (150 mL) was slowly added. The mixture stirred for an additional 1 hour at −78° C. and was then allowed to stir at room temperature for 2 hours. The mixture was concentrated under reduced pressure and the residue was purified by flash column chromatography (Isco CombiFlash Rf unit, 330 g Redisep column, 0% to 50% EtOAc in hexanes) to give (3aS,6aS)-tert-butyl 5-(((trifluoromethyl)sulfonyl)oxy)-3,3a,6,6a-tetrahydro-cyclopenta[c]pyrrole-2(1H)-carboxylate (6) as a clear, viscous oil (1.56 g, quantitative): ¹H NMR (500 MHz, CDCl₃) δ 5.58 (s, 1H), 3.62 (m, 1H), 3.53 (m, 1H), 3.46 (m, 2H), 3.19 (m, 1H), 2.95 (m, 2H), 2.46 (m, 1H), 1.47 (s, 9H).

Step F: To an N₂ degassed mixture of (3aS,6aS)-tert-butyl 5-(((trifluoromethyl)sulfonyl)oxy)-3,3a,6,6a-tetrahydrocyclopenta[c]pyrrole-2(1H)-carboxylate (6, 14.79 g, 41.4 mmol), 2-trifluoromethylphenylboronic acid (19.70 g, 104 mmol), and a 2 M aqueous solution of Na₂CO₃ (250 mL) in DME (500 mL) was added Pd(PPh₃)₄ (4.80 g, 4.16 mmol). The mixture was heated at 80° C. for 6 hours, then cooled to room temperature and diluted with H₂O (500 mL). The aqueous mixture was extracted with EtOAc (2×200 mL) and the combined organic extracts were washed with H₂O (200 mL), brine (200 mL), dried over Na₂SO₄, filtered, and concentrated under reduced pressure. The residue was purified by flash column chromatography (Isco CombiPlash Rf unit, 330 g Redisep column, 0% to 10% EtOAc in hexanes) to give (3aR,6aS)-tert-butyl 5-(2-(trifluoromethyl)phenyl)-3,3a,6,6a-tetrahydrocyclopenta[c]pyrrole-2(1H)-carboxylate (7) as a clear, viscous oil (13.70 g, 94%): $^1$H NMR (500 MHz, CDCl$_3$) δ 7.65 (m, 1H), 7.47 (m, 2H), 7.25 (m, 1H), 5.58 (s, 1H), 3.85-3.42 (m, 4H), 3.23 (m, 1H), 2.98 (m, 2H), 2.49 (m, 1H), 1.47 (s, 9H).

Step G: A mixture of (3aR,6aS)-tert-butyl 5-(2-(trifluoromethyl)phenyl)-3,3a,6,6a-tetrahydrocyclopenta[c]pyrrole-2(1H)-carboxylate (7, 8.63 g, 24.4 mmol) and 10% Pd/C (1.57 g, wet, 10% w/w) in CH$_3$OH (50 mL) was subjected to an atmosphere of H$_2$ gas (40 psi) using a Parr Shaker apparatus for 16 hours at room temperature. The mixture was filtered through Celite and the filtrate was concentrated under reduced pressure. The resulting residue was purified by flash column chromatography (Isco CombiFlash Rf unit, 40 g Redisep column, 0% to 30% EtOAc in hexanes) to give (3aR,5R,6aS)-tert-butyl 5-(2-(trifluoromethyl)phenyl) hexahydrocyclopenta[c]pyrrole-2(1H)-carboxylate (8) as a clear, viscous oil (0.91 g, 85%): $^1$H NMR (500 MHz, CDCl$_3$) δ 7.69 (m, 1H), 7.51 (m, 2H), 7.25 (m, 1H), 3.49 (m, 5H), 2.75 (m, 2H), 2.92 (m, 2H), (m, 2H), 1.48 (s, 9H).

Step H: To a 0° C. cooled solution of (3aR,5R,6aS)-tert-butyl 5-(2-(trifluoromethyl)phenyl)hexahydrocyclopenta[c]pyrrole-2(1H)-carboxylate (8, 7.94 g, 22.3 mmol) in CH$_2$Cl$_2$ (60 mL) was added a 2 M HCl solution in Et$_2$O (60 mL), and the mixture was allowed to stir at room temperature for 24 hours. The mixture was diluted with Et$_2$O (200 mL) and the precipitated product was filtered to give (3aR,5S,6aS)-5-(2-(trifluoromethyl)phenyl)octahydrocyclopenta[c]pyrrole hydrochloride (9) as a white solid (5.90 g, 91%): $^1$H NMR (500 MHz, CDCl$_3$) δ 10.17 (bs, 1H), 8.06 (m, 1H), 7.59 (m, 1H), 7.53 (m, 1H), 7.27 (m, 1H), 3.42 (m, 2H), 3.38 (m, 3H), 3.01 (m, 2H), 2.36 (m, 2H), 1.96 (m, 2H); MS (ESI+) m/z 256 [M+H]$^+$.

Preparation of (3aR,5S,6aS)-5-(2-(Trifluoromethyl)phenyl) octahydrocyclopenta[c]pyrroleidine (10)

Step A: To a solution of (3aR,6aS)-tert-butyl 5-(2-(trifluoromethyl)phenyl)-3,3a,6,6a-tetrahydrocyclopenta[c]pyrrole-2(1H)-carboxylate (7, 0.680 g, 1.92 mmol) in CH$_2$Cl$_2$ was added trifluoroacetic acid (TFA, 1.5 mL). The mixture was stirred at room temperature for 16 hours and concentrated under reduced pressure. The residue was dissolved in CH$_2$Cl$_2$ (25 mL) and washed with saturated aqueous NaHCO$_3$ solution (25 mL), brine (25 mL), dried over Na$_2$SO$_4$, filtered, and concentrated under reduced pressure. The residue was dissolved in CH$_3$OH (25 mL) and Pd/C was added (10% w/w, Degussa type E101 NE/W, 0.140 g). The mixture was subjected to an atmosphere of H$_2$ (50 psi) for 6 hours and was filtered through Celite. The filtrated was concentrated under reduced pressure and the resulting residue was purified by reversed phase column chromatography (Isco C18 Reversed Phase Gold column, 10% to 30% CH$_3$CN in H$_2$O with 0.05% TFA). The resulting material was dissolved in CH$_2$Cl$_2$ and washed with saturated aqueous NaHCO$_3$, dried over Na$_2$SO$_4$, filtered, and concentrated under reduced pressure to give (3aR,5S,6aS)-5-(2-(trifluoromethyl)phenyl)octahydro-cyclopenta[c]pyrrole (10) as a white solid (0.070 g, 14%): $^1$H NMR (300 MHz, CDCl$_3$) δ 7.61 (d, J=7.8 1H), 7.50 (m, 2H), 7.30-7.24 (m, 1H), 3.54-3.42 (m, 1H), 3.32-3.26 (m, 2H), 2.81-2.68 (m, 2H), 2.51-2.46 (m, 2H), 1.84-1.76 (m, 4H); MS (ESI+) m/z 256 [M+H]$^+$.

Preparation of (4,5,6,7-Tetrahydro-1H-pyrazolo[3,4-c]pyridin-3-yl)((3aR,5R,6aS)-5-(2-(trifluoromethyl)phenyl)hexahydrocyclopenta[c]pyrrol-2(1H)-yl)methanone Hydrochloride (12)

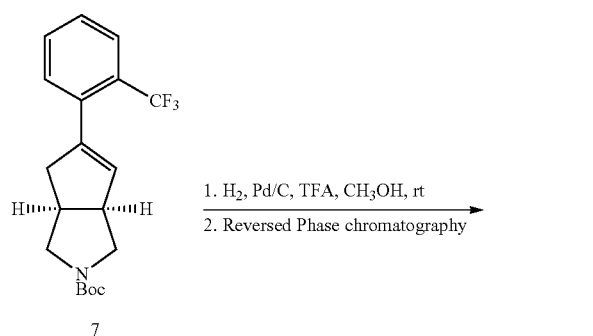

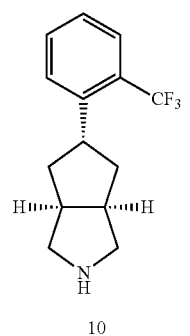

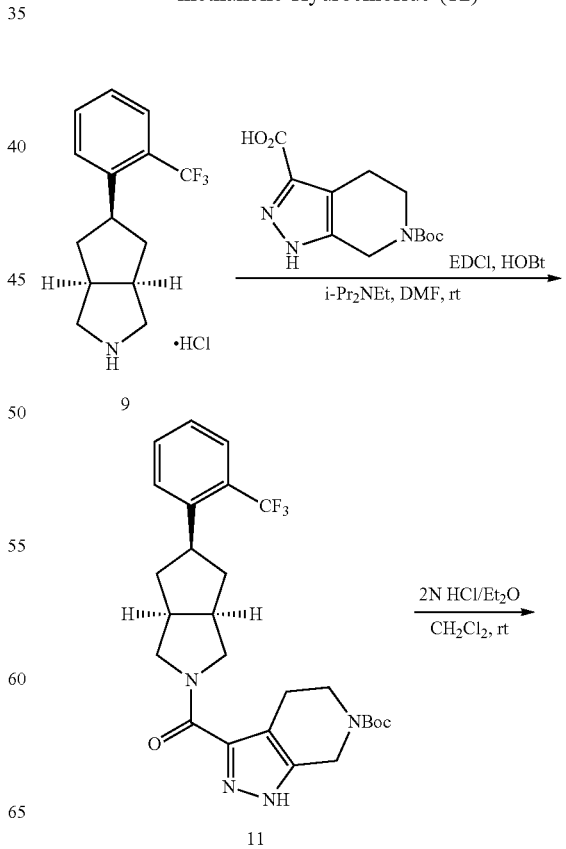

-continued

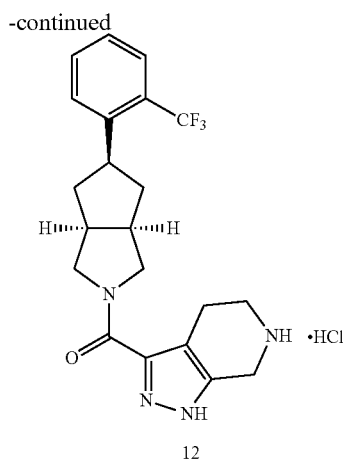

12

Step A: To a solution of (3aR,5r,6aS)-5-(2-(trifluoromethyl) phenyl)octahydrocyclopenta[c]pyrrole hydrochloride (9, 0.292 g, 1.00 mmol), 6-(tert-butoxycarbonyl)-4,5,6,7-tetrahydro-1H-pyrazolo[3,4-c]pyridine-3-carboxylic acid (0.268 g, 1.00 mmol), and i-Pr$_2$NEt (0.52 mL, 3.00 mmol) in DMF (19 mL) under an atmosphere of N$_2$ was added EDCI (0.230 g, 1.20 mmol) and HOBt (0.162 g, 1.20 mmol). The resulting solution was stirred at room temperature for 18 hours. The reaction mixture was diluted with H$_2$O (30 mL). The resulting precipitate was collected by filtration and washed with H$_2$O (50 mL) to provide tert-butyl 3-((3aR,5r,6aS)-5-(2-(trifluoromethyl)phenyl)octahydrocyclopenta[c]pyrrole-2-carbonyl)-4,5-dihydro-1H-pyrazolo[3,4-c]pyridine-6(7H)-carboxylate (11) as an off-white solid (390 mg, 77%): $^1$H NMR (300 MHz, DMSO-d$_4$) δ 12.99 (s, 1H), 7.72-7.57 (m, 3H), 7.43-7.34 (m, 1H), 4.54-4.45 (m, 2H), 4.14-4.00 (m, 2H), 3.76-3.53 (m, 4H), 3.45-3.35 (m, 1H), 2.92-2.63 (m, 4H), 2.30-2.14 (m, 2H), 1.64-1.47 (m, 2H), 1.42 (s, 9H); MS (ESI+) m/z 505 [M+H]$^+$.

Step B: To a suspension of tert-butyl 3-((3aR,5r,6aS)-5-(2-(trifluoromethyl)phenyl)octahydrocyclopenta[c]pyrrole-2-carbonyl)-4,5-dihydro-1H-pyrazolo[3,4-c]pyridine-6(7H)-carboxylate (11, 0.385 g, 0.763 mmol) in a 1:1 CH$_2$Cl$_2$/CH$_3$OH (4.6 mL) was added a 2 N HCl solution in Et$_2$O (4.6 mL) and the resulting solution was stirred at room temperature for 18 h. The mixture was diluted with Et$_2$O (30 mL) and the solids obtained by filtration. The solids were washed with Et$_2$O (30 mL) and dried to provide (4,5,6,7-tetrahydro-1H-pyrazolo[3,4-c]pyridin-3-yl)((3aR,5r,6aS)-5-(2-(trifluoromethyl) phenyl)hexahydrocyclopenta[c]pyrrol-2(1H)-yl)methanone hydrochloride (12) as an off-white solid (320 mg, 95%): $^1$H NMR (300 MHz, DMSO-d$_6$) δ 13.29 (br s, 1H), 9.22-9.11 (m, 2H), 7.71-7.58 (m, 3H), 7.43-7.34 (m, 1H), 4.29-4.21 (m, 2H), 4.11-4.04 (m, 2H), 3.76-3.56 (m, 2H), 3.44-3.30 (m, 3H), 2.99-2.70 (m, 4H), 2.31-2.14 (m, 2H), 1.65-1.46 (m, 2H); MS (ESI+) m/z 405 [M+H]$^+$.

Preparation of (4,5,6,7-Tetrahydro-1H-pyrazolo[4,3-c]pyridin-3-yl)((3aR,5R,6aS)-5-(trifluoromethyl)phenyl)hexahydrocyclopenta[c]pyrrol-2(1H)-yl)methanone Hydrochloride (14)

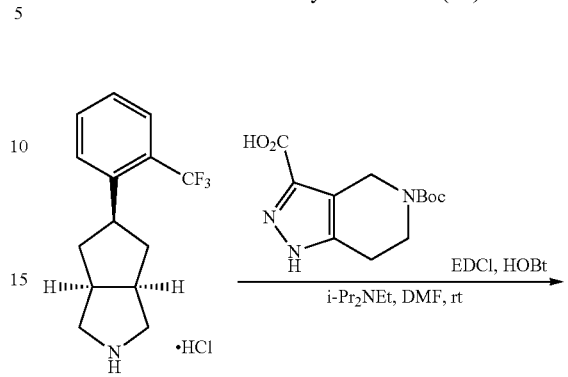

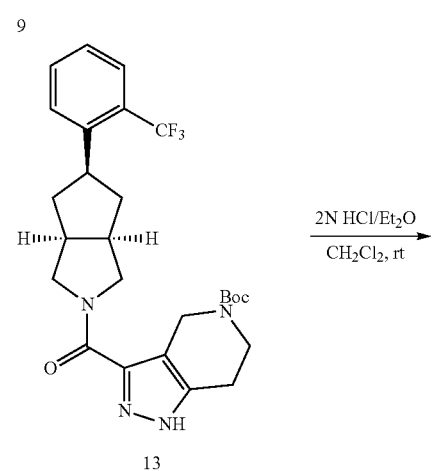

13

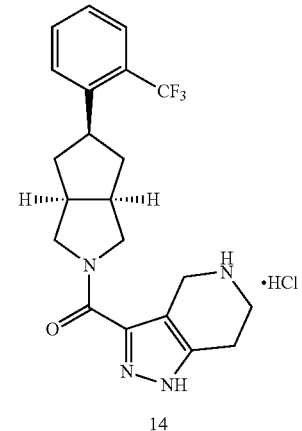

14

Step A: To a solution of (3aR,5R,6aS)-5-(2-(trifluoromethyl)phenyl) octahydrocyclopenta[c]pyrrole hydrochloride (9, 0.271 g, 0.928 mmol), 5-(tert-butoxycarbonyl)-4,5,6,7-tetrahydro-1H-pyrazolo[3,4-c]pyridine-3-carboxylic acid (0.250 g, 0.928 mmol), and i-Pr$_2$NEt (0.49 mL, 2.78 mmol) in DMF (18 mL) under an atmosphere of N$_2$ was added EDCI (0.213 g, 1.11 mmol) and HOBt (0.150 g, 1.11 mmol). The resulting solution was stirred at room temperature for 18 h. The reaction mixture was diluted with H$_2$O (30 mL). The resulting precipitate was collected by filtration and washed with H$_2$O (50 mL). The solids were chromatographed over silica gel (0% to 5% CH$_3$OH in CH$_2$Cl$_2$ with 0.1% NH$_4$OH)

to give tert-butyl 3-((3aR,5R,6aS)-5-(2-(trifluoromethyl)phenyl) octahydrocyclopenta[c]pyrrole-2-carbonyl)-6,7-dihydro-1H-pyrazolo[4,3-c]pyridine-5(4H)-carboxylate (13) as a white solid (384 mg, 82%): ¹H NMR (300 MHz, DMSO-d₆) δ 12.99 (br s, 1H), 7.71-7.58 (m, 3H), 7.43-7.33 (m, 1H), 4.53-4.44 (m, 2H), 4.12-4.01 (m, 2H), 3.74-3.52 (m, 4H), 3.43-3.36 (m, 1H), 2.94-2.61 (m, 4H), 2.31-2.13 (m, 2H), 1.64-1.46 (m, 2H), 1.42 (s, 9H); MS (ESI+) m/z 505 [M+H]⁺.

Step B: To a suspension of tert-butyl 3-((3aR,5r,6aS)-5-(2-(trifluoromethyl)phenyl)octahydrocyclopenta[c]pyrrole-2-carbonyl)-6,7-dihydro-1H-pyrazolo[4,3-c]pyridine-5(4H)-carboxylate (13, 0.384 g, 0.761 mmol) in a 1:1 CH₂Cl₂/CH₃OH (4.6 mL) was added a 2 N HCl solution in Et₂O (4.6 mL) and the resulting solution was stirred at room temperature for 18 hours. The mixture was diluted with Et₂O (50 mL) and the solids obtained by filtration. The solids were washed with Et₂O (30 mL) and dried to provide (4,5,6,7-tetrahydro-1H-pyrazolo[4,3-c]pyridin-3-yl)((3aR,5R,6aS)-5-(2-(trifluoromethyl)phenyl) hexahydro-cyclopenta[c]pyrrol-2(1H)-yl) methanone hydrochloride (14) as a white solid (325 mg, 97%): ¹H NMR (300 MHz, DMSO-d₆) δ 13.29 (br s, 1H), 9.21 (br s, 2H), 7.71-7.58 (m, 3H), 7.43-7.34 (m, 1H), 4.28-4.21 (m, 2H), 4.12-4.05 (m, 2H), 3.76-3.51 (m, 2H), 3.44-3.30 (m, 3H), 2.99-2.69 (m, 4H), 2.31-2.14 (m, 2H), 1.66-1.46 (m, 2H); MS (ESI+) m/z 405 [M+H]⁺.

Preparation of (1,4,5,6-Tetrahydropyrrolo[3,4-c]pyrazol-3-yl)((3aR,5R,6aS)-5-(2-(trifluoromethyl)phenyl)hexahydrocyclopenta[c]pyrrol-2(1H)-yl)methanone Hydrochloride (16)

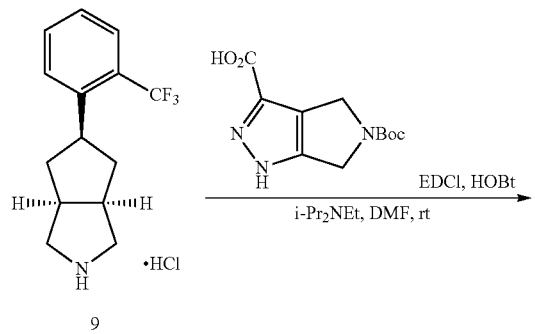

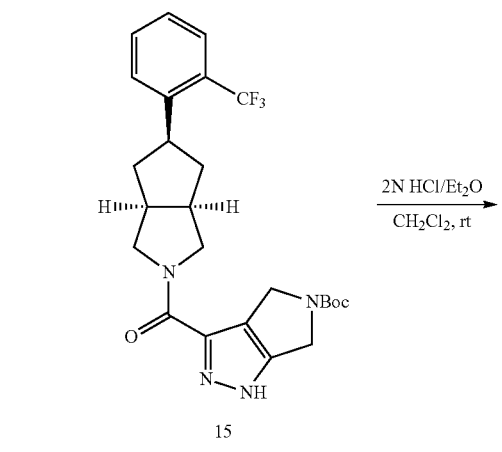

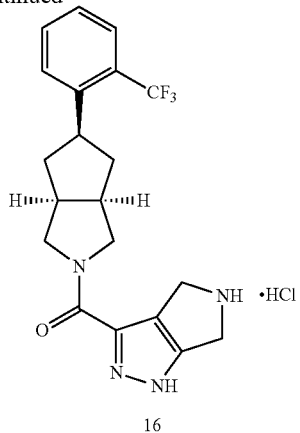

16

Step A: To a solution of (3aR,5R,6aS)-5-(2-(trifluoromethyl)phenyl) octahydrocyclopenta[c]pyrrole hydrochloride (9, 0.300 g, 1.03 mmol), 5-(tert-butoxycarbonyl)-1,4,5,6-tetrahydropyrrolo[3,4-c]pyrazole-3-carboxylic acid (0.260 g, 1.03 mmol), and i-Pr₂NEt (0.389 g, 3.09 mmol) in DMF (20 mL) under an atmosphere of N₂ was added EDCI (0.236 g, 1.23 mmol) and HOBt (0.166 g, 1.23 mmol). The resulting solution was stirred at room temperature for 18 hours. The reaction mixture was diluted with H₂O (50 mL) and the resulting solids collected by filtration. The obtained solids were chromatographed over silica gel (0% to 5% CH₃OH in CH₂Cl₂ with 0.1% NH₄OH) to give tert-butyl 3-((3aR,5Rr,6aS)-5-(2-(trifluoromethyl)phenyl)octahydrocyclopenta[c]pyrrole-2-carbonyl)-4,6-dihydropyrrolo[3,4-c]pyrazole-5(1H)-carboxylate (15) as a white solid (349 mg, 69%): ¹H NMR (300 MHz, DMSO-d₆) δ 13.33-13.10 (m, 1H), 7.75-7.57 (m, 3H), 7.45-7.34 (m, 1H), 4.56-4.31 (m, 4H), 4.13-4.01 (m, 1H), 3.79-3.53 (m, 3H), 3.44-3.34 (m, 1H), 2.93-2.67 (m, 2H), 2.32-2.14 (m, 2H), 1.66-1.48 (m, 2H), 1.47-1.37 (s, 9H); MS (ESI+) m/z 491 [M+H]⁺.

Step B: To a suspension of tert-butyl 3-((3aR,5R,6aS)-5-(2-(trifluoromethyl)phenyl)octahydrocyclopenta[c]pyrrole-2-carbonyl)-4,6-dihydropyrrolo[3,4-c]pyrazole-5(1H)-carboxylate (15, 0.349 g, 0.711 mmol) in CH₂Cl₂ (3.0 mL) was added a 2 N HCl solution in Et₂O (3.0 mL) and the resulting solution was stirred at room temperature for 72 h. The mixture was diluted with Et₂O (30 mL) and the solids obtained by filtration. The solids were washed with Et₂O (30 mL) and dried to provide (1,4,5,6-tetrahydropyrrolo[3,4-c]pyrazol-3-yl)((3aR,5R,6aS)-5-(2-(trifluoromethyl)phenyl)hexahydrocyclopenta[c]pyrrol-2(1H)-yl)methanone hydrochloride as a yellow-green foam (274 mg, 90%): ¹H NMR (300 MHz, DMSO-d₆) δ 10.25 (br s, 2H), 7.75-7.69 (m, 1H), 7.68-7.59 (m, 2H), 7.45-7.35 (m, 1H), 4.46-4.27 (m, 4H), 3.95-3.81 (m, 1H), 3.78-3.52 (m, 3H), 3.46-3.29 (m, 2H), 2.99-2.69 (m, 2H), 2.30-2.12 (m, 2H), 1.67-1.46 (m, 2H); MS (ESI+) m/z 391 [M+H]⁺.

Example 1: 2-((3aR,5R,6aS)-5-(2-(Trifluoromethyl) phenyl)octahydrocyclopenta[c]pyrrole-2-carboxamido)benzoic Acid (17)

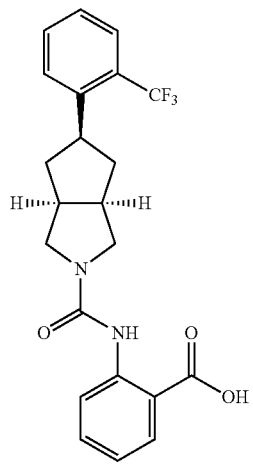

Step A: To a solution of (3aR,5S,6aS)-5-(2-(trifluoromethyl)phenyl)octahydrocyclopenta[c]pyrrole (0.640 g, 2.50 mmol) in CH$_2$Cl$_2$ (50 mL) was added methyl 2-isocyanatobenzoate (0.442 g, 2.50 mmol) and the mixture stirred at room temperature for 16 hours. The mixture was concentrated under reduced pressure and the resulting residue was purified by flash column chromatography (Isco CombiFlash Rf unit, 40 g Redisep column, 0% to 30% EtOAc in hexanes) to give methyl 2-((3aR,5R,6aS)-5-(2-(trifluoromethyl)phenyl) octahydrocyclopenta[c]pyrrole-2-carboxamido)benzoate as a white solid (0.700 g, 64%): MS (ESI+) m/z 433 [M+H].

Step B: To a solution of methyl 2-((3aR,5R,6aS)-5-(2-(trifluoromethyl)phenyl)octahydrocyclopenta[c]pyrrole-2-carboxamido)benzoate (0.700 g, 1.61 mmol) in CH$_3$OH (20 mL) and THF (20 mL) was added aqueous 2 N NaOH (10 mL). The mixture was stirred for 16 hours and concentrated under reduced pressure. The residue was diluted with H$_2$O (25 mL), and acidified with 2 N HCl to pH 5 and the resulting precipitate was filtered to give 2-((3aR,5R,6aS)-5-(2-(trifluoromethyl) phenyl)octahydrocyclopenta[c]pyrrole-2-carboxamido)benzoic acid as a white solid (0.668 g, 98%): mp 95-100° C.; $^1$H NMR (500 MHz, DMSO-d$_6$) δ %): mp 157-161° C.; $^1$H NMR (300 MHz, DMSO-d$_6$) δ 13.46 (br s, 1H), 10.79 (s, 1H), 8.53 (d, J=8.5 Hz, 1H), 7.96 (dd, J=8.0, 1.5 Hz, 1H), 7.77-7.01 (m, 5H), 6.99 (m, 1H), 3.65-3.62 (m, 2H), 3.47-3.38 (m, 3H), 2.86 (br s, 2H), 2.27-2.22 (m, 2H), 1.66-1.59 (m, 2H); MS (ESI+) m/z 419 [M+H]$^+$.

Example 2: (1H-1,2,4-Triazol-3-yl)((3aR,5R,6aS)-5-(2-(trifluoromethyl)phenyl)hexahydrocyclopenta[c]pyrrol-2(1H)-yl) methanone (19)

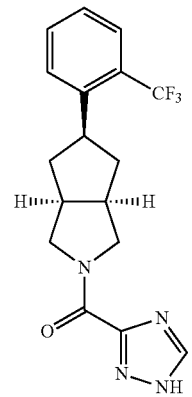

Step A: Following general procedure GP-A1, (3aR,5S,6aS)-5-(2-(trifluoromethyl)phenyl)octahydrocyclopenta[c] pyrrole hydrochloride and 1H-1,2,4-triazole-3-carboxylic acid were converted to (1H-1,2,4-triazol-3-yl)((3aR,5R,6aS)-5-(2-(trifluoromethyl)phenyl) hexahydrocyclopenta[c]pyrrol-2(1H)-yl)methanone as a white solid (0.071 g, 52%): $^1$H NMR (500 MHz, CDCl$_3$) δ 12.7.1 (bs, 1H), 8.12 (bs, 1H), 7.67 (m, 1H), 7.49 (m, 2H), 7.26 (m, 1H), 4.43 (m, 2H), 3.93 (m, 2H), 3.53 (m, 1H), 3.08-2.81 (m, 2H), 2.42 (m, 2H), 1.65 (m, 2H); ESI MS m/z 351 [M+H]$^+$.

Example 3: (6-Fluoro-[1,2,4]triazolo[4,3-a]pyridin-3-yl)((3aR,5R,6aS)-5-(2(trifluoromethyl)phenyl) hexahydrocyclopenta[c]pyrrol-2(1N)-yl)methanone (19)

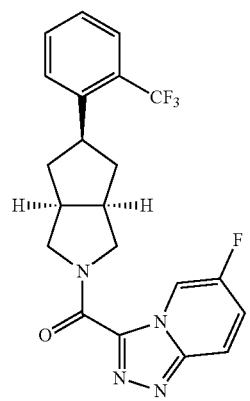

Step A: To a solution of ethyl 6-fluoro-[1,2,4]triazolo[4,3-a]pyridine-3-carboxylate (0.050 g, 0.239 mmol) in THF (4 mL) was added a solution of LiOH.H$_2$O (0.030 g, 0.717 mmol) in H$_2$O (3 mL). The mixture was stirred for 20 minutes, acidified with 2 N HCl to pH 6, and concentrated under reduced pressure. To the residue were added (3aR,5R,6aS)-5-(2-(trifluoromethyl)phenyl)octahydrocyclopenta [c]pyrrole hydrochloride (0.070 g, 0.239 mmol), benzotriazole-1-yl-oxy-tris-(dimethylaminuteso)-phosphonium hexafluorophosphate (0.211 g, 0.478 mmol), i-Pr$_2$NEt (0.093 g, 0.717 mmol), and DMF (4 mL). The mixture was stirred at room temperature for 16 h and poured into H$_2$O. The mixture was extracted with EtOAc (30 mL) and the organic layer was washed with brine (2×30 mL), dried over Na₂SO₄, filtered, and concentrated under reduced pressure. The resulting residue was chromatographed over silica gel (0% to 50% EtOAc in hexanes) and freeze dried to give (6-fluoro-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone as a white solid (0.073 g, 73%): mp 139-141° C.; ¹H NMR (300 MHz, CDCl₃) δ9.43 (m, 1H), 7.92-7.87 (m, 1H), 7.62 (d, J=8.1 Hz, 1H), 7.54-7.47 (m, 2H), 7.43-7.36 (m, 1H), 7.28 (m, 1H), 4.53-4.41 (m, 2H), 4.00-3.85 (m, 2H), 3.63-3.53 (m, 2H), 2.47-2.36 (m, 2H), 1.73-1.60 (m, 2H); MS (ESI+) m/z 419 [M+H]⁺.

Example 4: (6,8-Dihydro-5H-[1,2,4]triazolo[3,4-o][1,4]oxazin-3-yl)((3aR,5R,6aS)-5-(2-(trifluoromethyl)phenyl)hexahydrocyclopenta[C]pyrrol-2(1H)-yl)methanone (20)

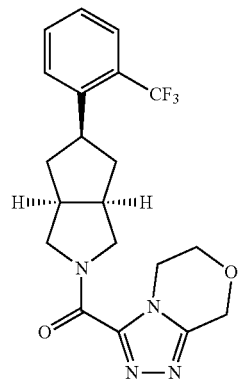

Step A: To a solution of ethyl 6,8-dihydro-5H-[1,2,4]triazolo[3,4-c][1,4]oxazine-3-carboxylate (0.070 g, 0.355 mmol) in THF (3 mL) was added a solution of LiOH.H₂O (0.030 g, 0.710 mmol) in H₂O (2 mL). The mixture was stirred for 20 minutes, acidified with 2 N HCl to pH 6 and concentrated under reduced pressure. To the residue were added (3aR,5R,6aS)-5-(2-(trifluoromethyl)phenyl)octahydrocyclopenta[c]pyrrole hydrochloride (0.104 g, 0.355 mmol), benzotriazole-1-yl-oxy-tris-(dimethylaminuteso)-phosphonium hexafluorophosphate (0.314 g, 0.710 mmol), N,N-diisopropylethylamine (0.138 g, 1.07 mmol), and DMF (3 mL). The mixture was stirred at room temperature for 16 h and poured into H₂O. The mixture was extracted with EtOAc (30 mL) and the organic layer was washed with brine (2×30 mL), dried over Na₂SO₄, filtered, and concentrated under reduced pressure. The resulting residue was chromatographed over silica gel (0% to 100% EtOAc in hexanes) and freeze dried to give (6-methoxy-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl) methanone as a white solid (0.052 g, 36%); mp 161-162° C.; ¹H NMR (300 MHz, CDCl₃) δ 7.61 (d, J=7.8 Hz, 1H), 7.51 (m, 2H), 7.31-7.25 (m, 1H), 5.03 (s, 2H), 4.54-4.47 (m, 2H), 4.38-4.27 (m, 2H), 4.08-4.00 (m, 2H), 3.91-3.74 (m, 2H), 3.62-3.50 (m, 1H), 3.01-2.80 (m, 2H), 2.44-2.32 (m, 2H), 1.69-1.56 (m, 4H); MS (ESI+) m/z 407 [M+H]⁺.

Example 5: (6-Methoxy-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (21)

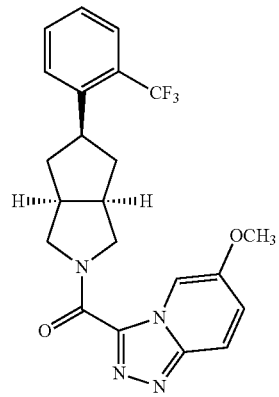 [SMILES: COc1ccc2nnc(C(=O)N3C[C@H]4C[C@@H](c5ccccc5C(F)(F)F)C[C@H]4C3)n2c1]

Step A: To a solution of ethyl 6-methoxy-[1,2,4]triazolo[4,3-a]pyridine-3-carboxylate (0.016 g, 0.316 mmol) in THF (5 mL) was added a solution of LiOH.H₂O (0.040 g, 0.948 mmol) in H₂O (3 mL). The mixture was stirred for 20 minutes, acidified with 2 N HCl to pH 6 and concentrated under reduced pressure. To the residue were added (3aR,5R,6aS)-5-(2-(trifluoromethyl)phenyl)octahydrocyclopenta[c]pyrrole hydrochloride (0.092 g, 0.316 mmol), benzotriazole-1-yl-oxy-tris-(dimethylaminuteso)-phosphonium hexafluorophosphate (0.280 g, 0.632 mmol), i-Pr₂NEt (0.123 g, 0.948 mmol), and DMF (3 mL). The mixture was stirred at room temperature for 16 h and poured into H₂O. The mixture was extracted with EtOAc (30 mL) and the organic layer was washed with brine (2×30 mL), dried over Na₂SO₄, filtered, and concentrated under reduced pressure. The resulting residue was chromatographed over silica gel (0% to 50% EtOAc in hexanes) and freeze dried to give (6-methoxy-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone as an off-white solid (0.098 g, 78%): mp 147-152° C.; ¹H NMR (300 MHz, CDCl₃) (δ 9.00 (m, 1H), 7.78 (dd, J=9.9, 0.6 Hz, 1H), 7.63-7.47 (m, 3H), 7.30-7.21 (3H), 4.54-4.42 (m, 2H), 4.00-3.85 (m, 5H), 3.66-3.53 (m, 1H), 3.04-2.87 (m, 2H), 2.46-2.36 (m, 2H), 1.74-1.61 (m, 2H); MS (ESI+) m/z 431 [M+H]⁺.

Example 6: (6-Chloro-(1,2,4)triazolo[4,3-a]pyridin-3-yl)((3aR,5R,6aS)-5-(2-(trifluoromethyl)phenyl)hexahydrocyclopenta[c]pyrrol-2(1H)-yl)methanone (22)

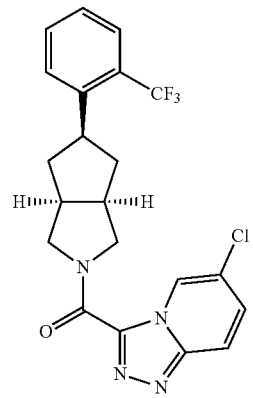 [SMILES: O=C(c1nnc2ccc(Cl)cn12)N1C[C@H]2C[C@@H](c3ccccc3C(F)(F)F)C[C@H]2C1]

Step A: To a solution of ethyl 6-chloro-[1,2,4]triazolo[4,3-a]pyridine-3-carboxylate (0.058 g, 0.257 mmol) in THF (4 mL) was added a solution of LiOH.H$_2$O (0.032 g, 0.771 mmol) in H$_2$O (2 mL). The mixture was stirred for 30 minutes, acidified with 2 N HCl to pH 6 and concentrated under reduced pressure. To the residue were added (3aR,5R,6aS)-5-(2-(trifluoromethyl)phenyl)octahydrocyclopenta[c]pyrrole hydrochloride (0.075 g, 0.257 mmol), benzotriazole-1-yl-oxy-tris-(dimethylaminuteso)-phosphonium hexafluorophosphate (0.227 g, 0.514 mmol), i-Pr$_2$NEt (0.100 g, 0.771 mmol), and DMF (2 mL). The mixture was stirred at room temperature for 16 h and poured into H$_2$O. The mixture was extracted with EtOAc (30 mL) and the organic layer was washed with brine (2×30 mL), dried over Na$_2$SO$_4$, filtered, and concentrated under reduced pressure. The resulting residue was chromatographed over silica gel (0% to 40% EtOAc in hexanes) and freeze dried to give (6-chloro-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone as a white solid (0.042 g, 37%): mp 147-150° C.; $^1$H NMR (500 MHz, CDCl$_2$) δ 9.54 (m, 1H), 7.84 (m, 1H), 7.62 (d, J=8.0 Hz, 1H), 7.53-7.48 (m, 2H), 7.41 (dd, J=10.0, 2.0 Hz, 1H), 7.28 (t, J=8.0 Hz, 1H), 4.50-4.41 (m, 2H), 3.99-3.86 (m, 2H), 3.63-3.55 (m, 1H), 3.04-2.87 (m, 2H), 2.44-2.37 (m, 2H), 1.70-1.62 (m, 2H); MS (ESI+) m/z 435 [M+H]$^+$.

Example 7: (6-(Trifluoromethyl)-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (23)

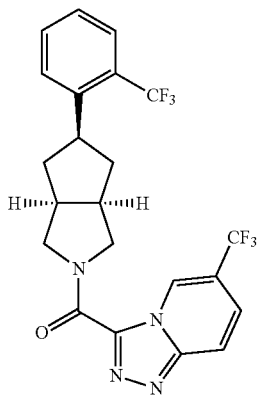 [SMILES: CCOc1ccc2nnc(C(=O)N3C[C@H]4C[C@@H](c5ccccc5C(F)(F)F)C[C@H]4C3)n2c1]

Step A: To a solution of ethyl 6-(trifluoromethyl)-[1,2,4]triazolo[4,3-a]pyridine-3-carboxylate (0.072 g, 0.278 mmol) in THF (3 mL) was added a solution of LiOH.H$_2$O (0.035 g, 0.834 mmol) in H$_2$O (1 mL). The mixture was stirred for 30 minutes, acidified with 2 N HCl to pH 6 and concentrated under reduced pressure. To the residue were added (3aR,5R,6aS)-5-(2-(trifluoromethyl)phenyl) octahydrocyclopenta[c]pyrrole hydrochloride (0.081 g, 0.278 mmol), benzotriazole-1-yl-oxy-tris-(dimethylaminuteso)-phosphonium hexafluorophosphate (0.246 g, 0.556 mmol), i-Pr$_2$NEt (0.108 g, 0.834 mmol), and DMF (2 mL). The mixture was stirred at room temperature for 16 h and poured into H$_2$O. The mixture was extracted with EtOAc (30 mL) and the organic layer was washed with brine (2×30 mL), dried over Na$_2$SO$_4$, filtered, and concentrated under reduced pressure. The resulting residue was chromatographed over silica gel (0% to 40% EtOAc in hexanes) and freeze dried to give (6-(trifluoromethyl)-[1,2,4]triazolo[4,3-a]pyridin-3-yl)((3aR,5R,6aS)-5-(2-(trifluoromethyl) phenyl)hexahydrocyclopenta[c]pyrrol-2(1H)-yl)methanone as a white solid (0.087 g, 66%): mp 154-156° C.; $^1$H NMR (300 MHz, CDCl$_3$) δ 9.88 (m, 1H), 8.00 (d, J=9.6 Hz, 1H), 7.63-7.49 (m, 4H), 7.27 (m, 1H), 4.53-4.41 (m, 2H), 4.02-3.86 (m, 2H), 3.65-3.50 (m, 1H), 3.06-2.89 (m, 2H), 2.48-2.36 (m, 2H), 1.72-1.61 (m, 2H); MS (ESI+) m/z 469 [M+H]$^+$.

Example 8: (6-Ethoxy-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (24)

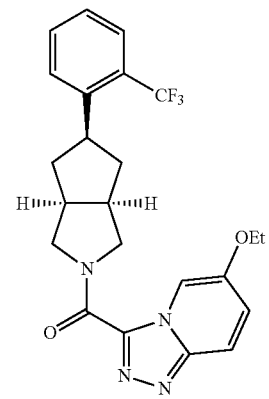

Step A: To a solution of ethyl 6-ethoxy-[1,2,4]triazolo[4,3-a]pyridine-3-carboxylate (0.072 g, 0.306 mmol) in THF (3 mL) was added a solution of LiOH.H$_2$O (0.038 g, 0.918 mmol) in H$_2$O (1 mL). The mixture was stirred for 30 minutes, acidified with 2 N HCl to pH 6 and concentrated under reduced pressure. To the residue were added (3aR,5R,6aS)-5-(2-(trifluoromethyl)phenyl)octahydrocyclopenta[c]pyrrole hydrochloride (0.089 g, 0.306 mmol), benzotriazole-1-yl-oxy-tris-(dimethylaminuteso)-phosphonium hexafluorophosphate (0.271 g, 0.612 mmol), i-Pr$_2$NEt (0.119 g, 0.918 mmol), and DMF (3 mL). The mixture was stirred at room temperature for 16 h and poured into H$_2$O. The mixture was extracted with EtOAc (30 mL) and the organic layer was washed with brine (2×30 mL), dried over Na$_2$SO$_4$, filtered, and concentrated under reduced pressure. The resulting residue was chromatographed over silica gel (0% to 30% EtOAc in hexanes) and freeze dried to give (6-ethoxy-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone as an off-white solid (0.107 g, 78%): mp 110-112° C.; $^1$H NMR (300 MHz, CDCl$_3$) δ 8.98

(d, J=1.5 Hz, 1H), 7.77 (m, 1H), 7.61 (d, J=7.8 Hz, 1H), 7.54-7.47 (m, 2H), 7.30-7.23 (m, 2H), 4.54-4.42 (m, 2H), 4.10 (q, J=6.9 Hz, 2H), 3.99-3.84 (m, 2H), 3.65-3.52 (m, 1H), 3.06-2.84 (m, 2H), 2.46-2.35 (m, 2H), 1.74-1.60 (m, 2H), 1.48 (t, J=6.9 Hz, 3H); MS (ESI+) m/z 445 [M+H]+.

Example 9: 2-((3aR,5S,6aS)-5-(2-(Trifluoromethyl) phenyl)octahydrocyclopenta[c]pyrrole-2-carboxamido)benzoic Acid (25)

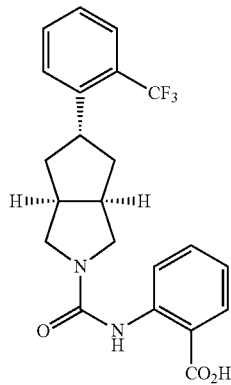 [SMILES: O=C(O)c1ccccc1NC(=O)N1C[C@H]2C[C@H](c3ccccc3C(F)(F)F)C[C@H]2C1]

Step A: To a solution of (3aR,5S,6aS)-5-(2-(trifluoromethyl)phenyl)octahydrocyclopenta[c]pyrrole (10, 0.030 g, 0.118 mmol) in CH2Cl2 (2 mL) was added methyl 2-isocyanatobenzoate (0.021 g, 0.118 mmol). The mixture was stirred for 2 hours and then chromatographed over silica gel (0% to 50% EtOAc in hexanes) to give methyl 2-((3aR,5S,6aS)-5-(2-(trifluoromethyl)phenyl)octahydro-cyclopenta[c]pyrrole-2-carboxamido)benzoate as a white solid (0.052 g, 100%): 1H NMR (300 MHz, CDCl3) δ10.53 (s, 1H), 8.67 (m, 1H), 8.01 (dd, J=8.0, 1.6 Hz, 1H), 7.62-7.46 (m, 4H), 7.28 (m, 1H), 6.99-6.94 (m, 1H), 3.92 (m, 5H), 3.79-3.67 (m, 1H), 3.38-3.33 (m, 2H), 3.07 (m, 2H), 2.11-1.93 (m, 4H); MS (ESI+) m/z 433 [M+H]+.

Step C: To a solution of methyl methyl 2-((3aR,5S,6aS)-5-(2-(trifluoromethyl)phenyl)octahydrocyclopenta[c]pyrrole-2-carboxamido)benzoate (0.052 g, 0.120 mmol) in THF (3 mL) and methanol (1 mL) was added a solution of LiOH.H2O (0.015 g, 0.360 mmol) in H2O (1 mL). The mixture was stirred for 6 hours, acidified to pH 2 with 2 N HCl and poured into H2O. The mixture was extracted with CH2Cl2 (30 mL) and the organic layer was washed with brine, dried over Na2SO4, filtered, and concentrated under reduced pressure. The residue was chromatographed over silica gel (0 to 10% CH3OH in CH2Cl2) and freeze dried to give 2-((3aR,5S,6aS)-5-(2-(trifluoromethyl)phenyl) octahydrocyclopenta[c]pyrrole-2-carboxamido)benzoic acid as a white solid (0.049 g, 98%): mp 172-174° C.; 1H NMR (300 MHz, CDCl3) δ8.67 (d, J=8.7 Hz, 1H), 8.07 (dd, J=8.1, 1.5 Hz, 1H), 7.62-7.45 (m, 4H), 7.28 (m, 1H), 7.02-6.96 (m, 1H), 3.94-3.87 (m, 2H), 3.79-3.67 (m, 1H), 3.38 (dd, J=10.8, 4.8 Hz, 2H), 3.07 (m, 2H), 2.10-1.93 (m, 4H); MS (ESI+) m/z 419 [M+H]+.

Example 10: 3-((3aR,5R,6aS)-5-(2-(trifluoromethyl) phenyl)octahydrocyclopenta[c]pyrrole-2-carbonyl)-[1,2,4]triazolo[4,3-a]pyridine-6-carboxylic Acid (26)

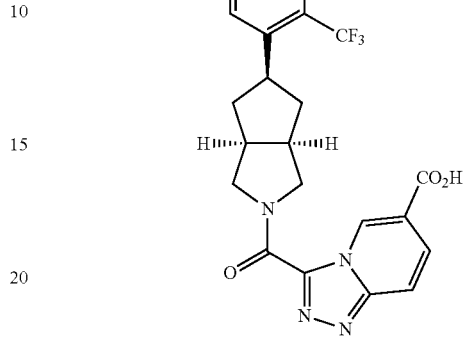

Step A: To a solution of ethyl 6-bromo-[1,2,4]triazolo[4,3-a]pyridine-3-carboxylate (0.485 g, 1.80 mmol) in THF (15 mL) was added a solution of LiOH.H2O (0.076 g, 1.80 mmol) in H2O (5 mL). The mixture was stirred for 20 minutes, acidified with 2 N HCl to pH 6 and concentrated under reduced pressure. To the residue were added (3aR,5R,6aS)-5-(2-(trifluoromethyl)phenyl) octahydrocyclopenta[c]pyrrole hydrochloride (0.525 g, 1.80 mmol), benzotriazole-1-yl-oxy-tris-(dimethylaminuteso)-phosphonium hexafluorophosphate (1.20 g, 2.7 mmol), i-Pr2NEt (0.698 g, 5.40 mmol), and DMF (15 mL). The mixture was stirred at room temperature for 16 hours and poured into H2O. The mixture was extracted with EtOAc (150 mL) and the organic layer was washed with brine (2×150 mL), dried over Na2SO4, filtered, and concentrated under reduced pressure. The resulting residue was chromatographed over silica gel (0% to 50% EtOAc in hexanes) to give (6-bromo-[1,2,4]triazolo[4,3-a]pyridin-3-yl)((3aR,5R,6aS)-5-(2-(trifluoromethyl)phenyl) hexahydrocyclopenta[c]pyrrol-2(1H)-yl) methanone as a white solid (0.485 g, 56%): 1H NMR (300 MHz, CDCl3) δ 9.65 (m, 1H), 7.98 (dd, J=9.6, 0.9 Hz, 1H), 7.62 (d, J=7.9 Hz, 1H), 7.53-7.47 (m, 3H), 7.28 (m, 1H), 4.51-4.39 (m, 2H), 4.00-3.85 (m, 2H), 3.64-3.52 (m, 1H), 3.07-2.84 (m, 2H), 2.50-2.33 (m, 2H), 1.72-1.60 (m, 2H); MS (ESI+) m/z 479 [M+H]+.

Step B: (6-bromo-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (0.080 g, 0.167 mmol), molybdenum hexacarbonyl (0.066 g, 0.251 mmol), Pd(OAc)2 (0.0037 g, 0.0167 mmol), xantphos (0.014 g, 0.0251 mmol), CH3OH (0.054 g, 1.67 mmol), Cs2CO3(109 g, 0.334 mmol), and 1,4-dioxane (2 mL) was heated at 80° C. for 2 hours in a sealed vessel and then allowed to cool to room temperature. The mixture was chromatographed over silica gel (0% to 60% EtOAc in hexanes) to give methyl 3-((3aR,5R,6aS)-5-(2-(trifluoromethyl)phenyl) octahydrocyclopenta[c]pyrrole-2-carbonyl)-[1,2,4]triazolo[4,3-a]pyridine-6-carboxylate as a white solid (0.024 g, 31%): 1H NMR (300 MHz, CDCl3) δ 10.12 (s, 1H), 8.00-7.87 (m, 2H), 7.63-7.47 (m, 3H), 7.28 (m, 1H), 4.52-4.21 (m, 2H), 4.03-3.88 (m, 5H), 3.65-3.53 (m, 1H), 3.06-2.89 (m, 2H), 2.47-2.36 (m, 2H), 1.73-1.61 (m, 2H); MS (ESI+) m/z 459 [M+H]+.

Step C: To a solution of 3-((3aR,5R,6aS)-5-(2-(trifluoromethyl)phenyl)octahydrocyclopenta[c]pyrrole-2-carbonyl)-[1,2,4]triazolo[4,3-a]pyridine-6-carboxylate (0.024 g, 0.0523 mmol) in THF (2 mL) was added a solution of LiOH.H₂O (0.004 g, 0.105 mmol) in H₂O (1 mL). The mixture was stirred for 30 minutes, acidified with 2 N HCl to pH 6, and purified by C-18 reverse phase column chromatography (10% to 60% CH₃CN in H₂O) to give 3-((3aR,5R,6aS)-5-(2-(trifluoromethyl)phenyl) octahydrocyclopenta[c]pyrrole-2-carbonyl)-[1,2,4]triazolo[4,3-a]pyridine-6-carboxylic acid as a white solid (0.020 g, 86%): $^1$H NMR (300 MHz, DMSO-d₆) δ 9.51 (s, 1H), 7.98 (d, J=9.3 Hz, 1H), 7.80-7.74 (m, 2H), 7.66-7.61 (m, 2H), 7.38 (t, J=7.5 Hz, 1H), 4.29-4.18 (m, 2H), 3.88-3.78 (m, 2H), 3.41 (m, 1H), 2.97-2.82 (m, 2H), 2.32-2.19 (m, 2H), 1.71-1.66 (m, 2H); MS (ESI+) m/z 445 [M+H]⁺.

Example 11: N-Methyl-3-((3aR,5R,6aS)-5-(2-(trifluoromethyl)phenyl)octahydrocyclopenta[c]pyrrole-2-carbonyl)-[1,2,4]triazolo[4,3-a]pyridine-6-carboxamide (27)

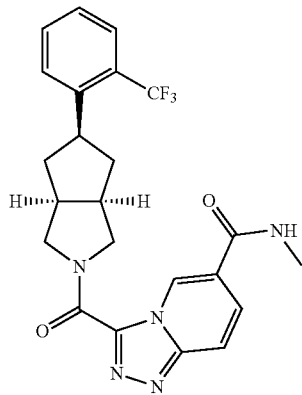 [SMILES: CNC(=O)c1ccc2nnc(C(=O)N3C[C@H]4C[C@@H](c5ccccc5C(F)(F)F)C[C@H]4C3)n2c1]

Step A: A mixture of (6-bromo-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (0.066 g, 0.138 mmol), molybdenum hexacarbonyl (0.054 g, 0.207 mmol), Pd(OAc)₂ (0.0015 g, 0.0007 mmol), xantphos (0.008 g, 0.0138 mmol), methylamine (0.040 g, 0.414 mmol, 33% in ethanol), i-Pr₂NEt (0.054 g, 0.414 mmol), and 1,4-dioxane (2 mL) was heated at 80° C. for 2 hours in a sealed vessel and allowed to cool to room temperature. The mixture was chromatographed over silica gel (0% to 10% CH₂OH in CH₂Cl₂) and further purified by C-18 reverse phase column chromatography (10% to 60% CH₃CN in H₂O) to give N-methyl-3-((3aR,5R,6aS)-5-(2-(trifluoromethyl)phenyl) octahydrocyclopenta[c]pyrrole-2-carbonyl)-[1,2,4]triazolo[4,3-a]pyridine-6-carboxamide as a white solid (0.034 g, 54%): mp 164-168° C.; $^1$H NMR (300 MHz, CDCl₃) δ 9.83 (n, 1H), 7.91 (m, 2H), 7.62 (d, J=8.0 Hz, 1H), 7.53-7.47 (m, 2H), 7.28 (m, 1H), 6.31 (br s, 1H), 4.48 (m, 2H), 4.00-3.85 (m, 2H), 3.66-3.53 (m, 1H), 3.05 (d, J=4.9 Hz, 3H), 3.01-2.88 (m, 2H), 2.48-2.37 (m, 2H), 1.73-1.62 (m, 2H); MS (ESI+) m/z 458 [M+H]⁺.

Example 12: N,N-Dimethyl-3-((3aR,5R,6aS)-5-(2-(trifluoromethyl)phenyl)octahydrocyclopenta[c]pyrrole-2-carbonyl)-[1,2,4]triazolo[4,3-a]pyridine-6-carboxamide (28)

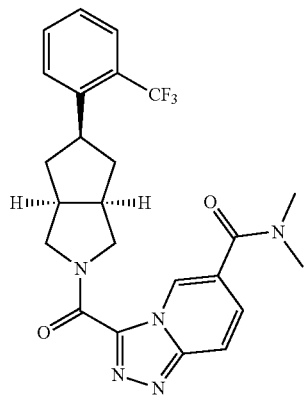 [SMILES: CN(C)C(=O)c1ccc2nnc(C(=O)N3C[C@H]4C[C@@H](c5ccccc5C(F)(F)F)C[C@H]4C3)n2c1]

Step A: A mixture of 6-bromo-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (0.066 g, 0.138 mmol), molybdenum hexacarbonyl (0.054 g, 0.207 mmol), Pd(OAc)₂ (0.0015 g, 0.0007 mmol), xantphos (0.008 g, 0.0138 mmol), dimethylamine hydrochloride (0.056 g, 0.690 mmol), i-Pr₂NEt (0.125 g, 0.966 mmol), and 1,4-dioxane (2 mL) was heated at 80° C. for 2 hours in a sealed vessel and allowed to cool to room temperature. The mixture was chromatographed over silica gel (0% to 10% CH₃OH in CH₂Cl₂) and further purified by C-18 reverse phase column chromatography (10% to 60% CH₃CN in H₂O) to give N,N-dimethyl-3-((3aR,5R,6aS)-5-(2-(trifluoromethyl)phenyl)octahydrocyclopenta[c]pyrrole-2-carbonyl)-[1,2,4]triazolo[4,3-a]pyridine-6-carboxamide as a white solid (0.047 g, 72%): mp 83-87° C.; $^1$H NMR (300 MHz, CDCl₃) δ 9.56 (m, 1H), 7.92 (dd, J=9.4, 1.0 Hz, 1H), 7.62 (d, J=7.8 Hz, 1H), 7.55-7.47 (m, 3H), 7.28 (m, 1H), 4.52-4.40 (m, 2H), 3.99-3.85 (m, 2H), 3.64-3.52 (m, 1H), 3.14 (s, 6H), 3.07-2.84 (m, 2H), 2.47-2.36 (m, 2H), 1.72-1.59 (m, 2H); MS (ESI+) m/z 472 [M+H]⁺.

Example 13: 1-Methyl-3-(3-((3aR,5R,6aS)-5-(2-(trifluoromethyl)phenyl)octahydrocyclopenta[c]pyrrole-2-carbonyl)-[1,2,4]triazolo[4,3-a]pyridin-6-yl) urea (29)

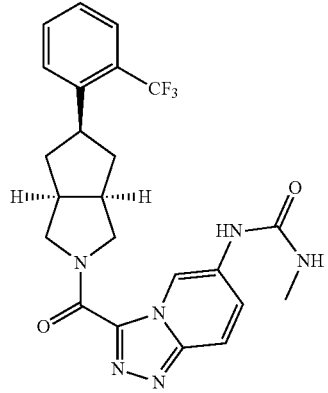 [SMILES: CNC(=O)Nc1ccc2nnc(C(=O)N3C[C@H]4C[C@@H](c5ccccc5C(F)(F)F)C[C@H]4C3)n2c1]

Step A: A mixture of 6-bromo-[1,2,4]triazolo[4,3-a]pyridin-3-yl)((3aR,5R,6aS)-5-(2-(trifluoromethyl)phenyl) hexahydrocyclopenta[c]pyrrol-2(1H)-yl)methanone (0.066 g, 0.138 mmol), Pd(OAc)$_2$ (0.003 g, 0.0138 mmol), xantphos (0.012 g, 0.0207 mmol), methylurea (0.020 g, 0.276 mmol), Cs$_2$CO$_3$ (0.067 g, 0.207 mmol), and 1,4-dioxane (2 mL) was heated at 110° C. for 6 hours and cooled to room temperature. The mixture was chromatographed over silica gel (0% to 10% CH$_3$OH in CH$_2$Cl$_2$) and further purified by C-18 reverse phase column chromatography (10% to 60% CH$_3$CN in H$_2$O) to give 1-methyl-3-(3-((3aR,5R,6aS)-5-(2-(trifluoromethyl)phenyl) octahydrocyclopenta[c]pyrrole-2-carbonyl)-[1,2,4]triazolo[4,3-a]pyridin-6-yl)urea as a white solid (0.010 g, 15%): mp 230-236° C.; $^1$H NMR (300 MHz, CDCl$_3$) δ 9.48 (s, 1H), 7.78 (d, J=9.2 Hz, 1H), 7.62-7.47 (m, 4H), 7.06 (s, 1H), 5.09 (s, 1H), 4.41 (m, 2H), 3.97-3.83 (m, 2H), 3.57 (m, 1H), 3.00-2.87 (m, 5H), 2.45-2.36 (m, 2H), 1.63 (m, 2H); MS (ESI+) m/z 473 [M+H]$^+$.

Example 14: 1,1-Dimethyl-3-(3-((3aR,5R,6aS)-5-(2-(trifluoromethyl)phenyl)octahydrocyclopenta[c]pyrrole-2-carbonyl)-[1,2,4]triazolo[4,3-a]pyridin-6-yl) urea (30)

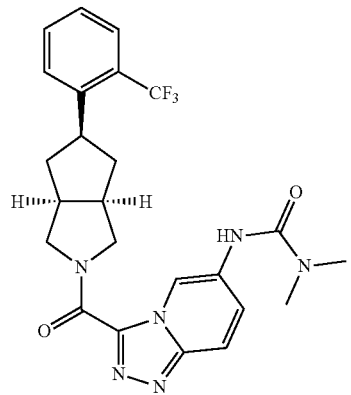 [SMILES: CN(C)C(=O)Nc1ccc2nnc(C(=O)N3C[C@H]4C[C@@H](c5ccccc5C(F)(F)F)C[C@H]4C3)n2c1]

Step A: A mixture of 6-bromo-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (0.066 g, 0.138 mmol), Pd(OAc)$_2$ (0.003 g, 0.0138 mmol), xantphos (0.012 g, 0.0207 mmol), N,N-dimethylurea (0.018 g, 0.207 mmol), Cs$_2$CO$_3$ (0.067 g, 0.207 mmol), and 1,4-dioxane (2 mL) was heated at 100° C. for 6 hours and cooled to room temperature. The mixture was chromatographed over silica gel (0% to 10% CH$_3$OH in CH$_2$Cl$_2$) and further purified by C-18 reverse phase column chromatography (10% to 60% CH$_3$CN in H$_2$O) to give 1,1-dimethyl-3-(3-((3aR,5R,6aS)-5-(2-(trifluoromethyl)phenyl) octahydrocyclopenta[c]pyrrole-2-carbonyl)-[1,2,4]triazolo[4,3-a]pyridin-6-yl)urea as a white solid (0.023 g, 34%): mp 110-115° C.; $^1$H NMR (300 MHz, CDCl$_3$) δ9.43 (m, 1H), 7.79 (m, 1H), 7.69-7.47 (m, 4H), 7.30-7.25 (m, 1H), 4.48-4.37 (m, 2H), 3.97-3.83 (m, 2H), 3.63-3.51 (m, 1H), 3.06 (s, 6H), 3.02-2.83 (m, 2H), 2.45-2.34 (m, 2H), 1.72-1.59 (m, 2H); MS (ESI+) m/z 487 [M+H]$^+$.

Example 15: N-Methyl-3-((3aR,5R,6aS)-5-(2-(trifluoromethyl)phenyl)octahydrocyclopenta[c]pyrrole-2-carbonyl)-[1,2,4]triazolo[4,3-a]pyridine-6-sulfonamide (31)

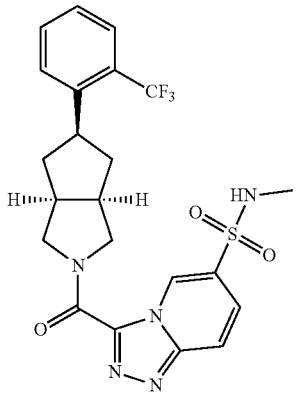 [SMILES: CNS(=O)(=O)c1ccc2nnc(C(=O)N3C[C@H]4C[C@@H](c5ccccc5C(F)(F)F)C[C@H]4C3)n2c1]

Step A: A mixture of 6-bromo-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (0.090 g, 0.188 mmol), Pd(OAc)$_2$ (0.0042 g, 0.0188 mmol), xantphos (0.016 g, 0.0282 mmol), benzyl mercaptan (0.035 g, 0.282 mmol), i-Pr$_2$NEt (0.073 g, 0.564 mmol), and 1,4-dioxane (2 mL) was heated at 110° C. for 16 hours and cooled to room temperature. The mixture was chromatographed over silica gel (0% to 50% EtOAc in hexanes) to give (6-(benzylthio)-[1,2,4]triazolo[4,3-a]pyridin-3-yl)((3aR,5R,6aS)-5-(2-(trifluoromethyl)phenyl) hexahydrocyclopenta[c]pyrrol-2(1H)-yl)methanone as a mixture with unreacted benzyl mercaptan (0.090 g in a ratio of 1:1.4): thick oil; MS (ESI+) m/z 523 [M+H]$^+$.

Step B: The material obtained in Step A was dissolved in HOAc (3 mL) and H$_2$O (1 mL). N-Chlorosuccinimide (NCS, 0.040 g, 0.296 mmol) was added and the mixture was stirred for 3 hours then concentrated under reduced pressure. The residue was partitioned between saturated aqueous Na$_2$CO$_3$ (50 mL) and CH$_2$Cl$_2$ (50 mL). The organic layer was separated and washed with brine (50 mL), dried over Na$_2$SO$_4$, filtered, and concentrated under reduced pressure. The resulting residue was chromatographed over silica gel (0% to 50% EtOAc in hexanes) to give 3-((3aR,5R,6aS)-5-(2-(trifluoromethyl) phenyl)octahydrocyclopenta[c]pyrrole-2-carbonyl)-[1,2,4]triazolo[4,3-a]pyridine-6-sulfonyl chloride as a mixture with unreacted NCS (0.032 g): thick oil; $^1$H NMR (300 MHz, CDCl$_3$) δ10.28 (m, 1H), 8.08 (dd, J=9.7, 0.8 Hz, 1H), 7.89 (dd, J=9.7, 1.9 Hz, 1H), 7.62 (d, J=7.8 Hz, 1H), 7.53-7.47 (m, 2H), 7.29 (m, 1H), 4.51-4.40 (m, 2H), 4.03-3.87 (m, 2H), 3.66-3.53 (m, 1H), 3.10-2.86 (m, 2H), 2.49-2.37 (m, 2H), 1.72-1.60 (m, 2H); MS (ESI+) m/z 499 [M+H]$^+$.

Step C: The material obtained in Step B was dissolved in CH$_2$Cl$_2$ (1 mL) and cooled to 0° C. A mixture of methylamine (33% in EtOH, 0.018 g, 0.192 mmol) and N,N-diisopropylethylamine (0.025 g, 0.192 mmol) in CH$_2$Cl$_2$ (1 mL) was added. The mixture was stirred at room temperature for 2 hours and then concentrated under reduced pressure. The residue was chromatographed by C-18 reverse phase column chromatography (10% to 50% CH$_3$CN in H$_2$O) to give N-methyl-3-((3aR,5R,6aS)-5-(2-(trifluoromethyl)phenyl)octahydrocyclopenta[c]pyrrole-2-carbonyl)-[1,2,4]triazolo[4,3-a]pyridine-6-sulfonamide as a white solid (6.0 mg, 6% over three steps): mp 148-152° C.; $^1$H NMR (300 MHz, CDCl$_2$) δ10.0 (m, 1H), 7.99 (dd, J=9.6, 0.8

Hz, 1H), 7.73 (dd, J=9.6, 1.7 Hz, 1H), 7.62 (d, J=7.2 Hz, 1H), 7.54-7.47 (m, 2H), 7.28 (m, 1H), 4.59 (q, J=5.2 Hz, 1H), 4.50-4.39 (m, 2H), 4.01-3.86 (m, 2H), 3.65-3.53 (m, 1H), 3.08-2.86 (m, 2H), 2.81 (d, J=5.3 Hz, 3H), 2.48-2.36 (m, 2H), 1.71-1.60 (m, 2H); MS (ESI+) m/z 494 [M+H]+.

Example 16: 3-((3aR,5R,6aS)-5-(2-(Trifluoromethyl)phenyl)octahydrocyclopenta[c]pyrrole-2-carbonyl)-[1,2,6]triazolo[4,3-a]pyridine-6-carbonitrile (32)

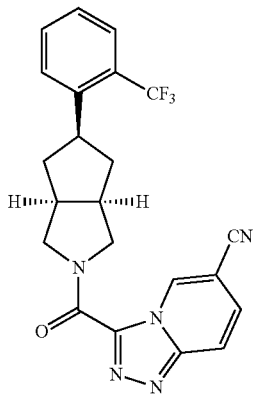 [SMILES: N#Cc1ccc2nnc(C(=O)N3C[C@H]4C[C@@H](c5ccccc5C(F)(F)F)C[C@H]4C3)n2c1]

Step A: A mixture of 6-bromo-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (0.080 g, 0.167 mmol), ZnCN$_2$ (0.039 g, 0.335 mmol), Pd(PPh$_3$)$_4$ (0.019 g, 0.0167 mmol), and DMF (2 mL) was heated at 130° C. under microwave irradiation for 30 minutes. After cooling to room temperature, the mixture was diluted with H$_2$O (50 mL) and extracted with EtOAc (50 mL). The organic extract was washed with brine (2×50 mL), dried over Na$_2$SO$_4$, filtered, and concentrated under reduced pressure. The resulting residue was chromatographed over silica gel (0% to 50% EtOAc in hexanes) to give 3-((3aR,5R,6aS)-5-(2-(trifluoromethyl)phenyl)octahydrocyclopenta[c]pyrrole-2-carbonyl)-[1,2,4]triazolo[4,3-a]pyridine-6-carbonitrile as a white solid (0.073 g, 100%): mp 60-65° C.; $^1$H NMR (300 MHz, CDCl$_3$) δ9.98 (m, 1H), 7.99 (dd, J=9.5, 0.9 Hz, 1H), 7.63 (d, J=7.8 Hz, 1H), 7.53-7.47 (m, 3H), 7.28 (m, 1H), 4.51-4.40 (m, 2H), 4.02-3.86 (m, 2H), 3.66-3.54 (m, 1H), 3.09-2.86 (m, 2H), 2.49-2.37 (m, 2H), 1.71-1.60 (m, 2H); MS (ESI+) m/z 426 [M+H]+.

Example 17: 3-((3aR,5R,6aS)-5-(2-(Trifluoromethyl)phenyl)octahydrocyclopenta[c]pyrrole-2-carbonyl)-[1,2,4]triazolo[4,3-a]pyridine-6-carboxamide (33)

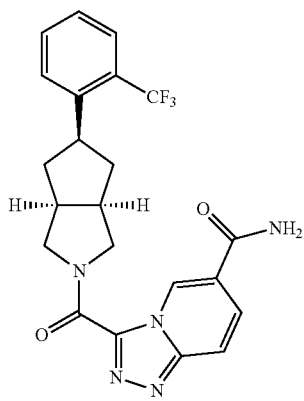 [SMILES: NC(=O)c1ccc2nnc(C(=O)N3C[C@H]4C[C@@H](c5ccccc5C(F)(F)F)C[C@H]4C3)n2c1]

Step A: To a solution of 3-((3aR,5R,6aS)-5-(2-(trifluoromethyl)phenyl)octahydrocyclopenta[c]pyrrole-2-carbonyl)-[1,2,4]triazolo[4,3-a]pyridine-6-carbonitrile (0.038 g, 0.0893 mmol) in THF (3 mL) was added a solution of LiOH.H$_2$O (0.007 g, 0.179 mmol) in H$_2$O (1 mL). The mixture was stirred for 20 minutes, acidified with 2 N HCl to pH 6 and purified by C-18 reverse phase column chromatography (10% to 60% CH$_3$CN in H$_2$O) to give 3-((3aR,5R,6aS)-5-(2-(trifluoromethyl)phenyl) octahydrocyclopenta[c]pyrrole-2-carbonyl)-[1,2,4]triazolo[4,3-a]pyridine-6-carboxamide as a white solid (0.031 g, 77%): mp 238-243° C.; $^1$H NMR (300 MHz, DMSO-d$_6$) δ 9.95 (s, 1H), 8.87 (br s, 2H), 7.95 (d, J=9.2 Hz, 1H), 7.74-7.63 (m, 3H), 7.40 (t, J=7.6 Hz, 1H), 7.01 (d, J=9.1 Hz, 1H), 4.01-3.94 (m, 2H), 3.82-3.68 (m, 3H), 3.45-3.31 (m, 1H), 2.85 (m, 2H), 2.32-2.15 (m, 2H), 1.66-1.52 (m, 2H); MS (ESI+) m/z 444 [M+H]+.

Example 18: (7-(Trifluoromethyl)-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (34)

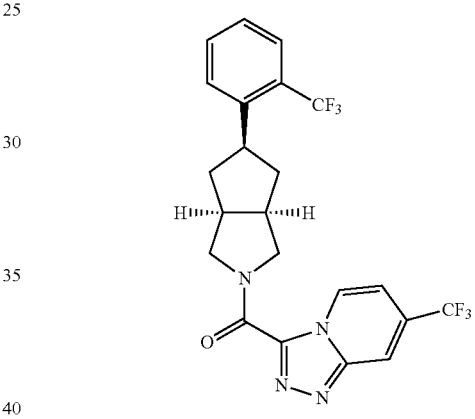

Step A: To a solution of ethyl 7-(trifluoromethyl)-[1,2,4]triazolo[4,3-a]pyridine-3-carboxylate (0.072 g, 0.278 mmol) in THF (3 mL) was added a solution of LiOH.H$_2$O (0.035 g, 0.834 mmol) in H$_2$O (1 mL). The mixture was stirred for 20 minutes, acidified with 2 N HCl to pH 6 and concentrated under reduced pressure. To the residue were added (3aR,5R,6aS)-5-(2-(trifluoromethyl)phenyl) octahydrocyclopenta[c]pyrrole hydrochloride (9, 0.081 g, 0.278 mmol), benzotriazole-1-yl-oxy-tris-(dimethylaminuteso)-phosphonium hexafluorophosphate (0.184 g, 0.417 mmol), i-Pr$_2$NEt (0.108 g, 0.834 mmol), and DMF (2 mL). The mixture was stirred at room temperature for 16 hours and poured into H$_2$O. The mixture was extracted with EtOAc (30 mL) and the organic layer was washed with brine (2×30 mL), dried over Na$_2$SO$_4$, filtered, and concentrated under reduced pressure. The resulting residue was chromatographed over silica gel (0% to 40% EtOAc in hexanes) and freeze dried to give (7-(trifluoromethyl)-[1,2,4]triazolo[4,3-a]pyridin-3-yl) ((3aR,5R,6aS)-5-(2-(trifluoromethyl)phenyl) hexahydrocyclopenta[c]pyrrol-2(1H)-yl)methanone as an off-white solid (0.072 g, 55%): mp 130-132° C.; $^1$H NMR (300 MHz, CDCl$_3$) δ9.98 (d, J=7.4 Hz, 1H), 8.22 (m, 1H), 7.63-7.47 (m, 3H), 7.28 (m, 1H), 7.18 (dd, J=7.4, 1.7 Hz, 1H), 4.53-4.41 (m, 2H), 4.02-3.86 (m, 2H), 3.66-3.54 (m, 1H), 3.09-2.86 (m, 2H), 2.48-2.37 (m, 2H), 1.73-1.60 (m, 2H); MS (ESI+) m/z 469 [M+H]+.

Example 19: (7-Methyl-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone (35a)

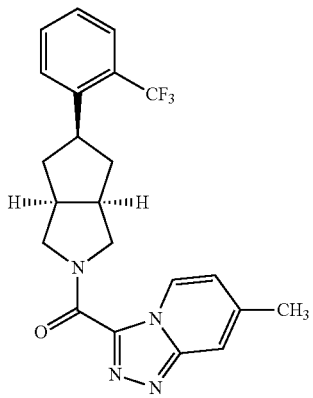 [SMILES: Cc1ccn2c(C(=O)N3C[C@H]4C[C@@H](c5ccccc5C(F)(F)F)C[C@H]4C3)nnc2c1]

Step A: To a solution of ethyl 7-methyl-[1,2,4]triazolo[4,3-a]pyridine-3-carboxylate (0.067 g, 0.326 mmol) in THF (3 mL) was added a solution of LiOH.H$_2$O (0.041 g, 0.978 mmol) in H$_2$O (1 mL). The mixture was stirred for 20 minutes, acidified with 2 N HCl to pH 6 and concentrated under reduced pressure. To the residue were added (3aR,5R,6aS)-5-(2-(trifluoromethyl)phenyl)octahydrocyclopenta[c]pyrrole hydrochloride (9, 0.095 g, 0.326 mmol), benzotriazole-1-yl-oxy-tris-(dimethylaminuteso)-phosphonium hexafluorophosphate (0.216 g, 0.489 mmol), i-Pr$_2$NEt (0.119 g, 0.978 mmol), and DMF (2 mL). The mixture was stirred at room temperature for 16 h and poured into H$_2$O. The mixture was extracted with EtOAc (30 mL) and the organic layer was washed with brine (2×30 mL), dried over Na$_2$SO$_4$, filtered, and concentrated under reduced pressure. The resulting residue was chromatographed over silica gel (0% to 70% EtOAc in hexanes) and freeze dried to give (7-methyl-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone as a white solid (0.103 g, 76%): mp 176-180° C.; $^1$H NMR (300 MHz, CDCl$_3$) δ9.29 (d, J=7.2 Hz, 1H), 7.62-7.46 (m, 4H), 7.26 (m, 1H), 6.85 (dd, J=7.2, 1.5 Hz, 1H), 4.53-4.40 (m, 2H), 3.99-3.84 (m, 2H), 3.64-3.52 (m, 1H), 3.06-2.83 (m, 2H), 2.48 (s, 3H), 2.46-2.35 (m, 2H), 1.73-1.60 (m, 2H); MS (ESI+) m/z 415 [M+H]$^+$.

Example 20: (6-methyl-[1,2,4]triazolo[4,3-a]pyridin-3-yl)((3aR,5r,6aS)-5-(2-(trifluoromethyl)phenyl)hexahydrocyclopenta[c]pyrrol-2(1H)-yl)methanone (35b)

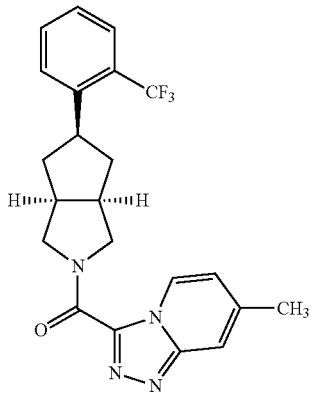

Step A: To a solution of ethyl 6-methyl-[1,2,4]triazolo[4,3-a]pyridine-3-carboxylate (0.067 g, 0.326 mmol) in THF (3 mL) is added a solution of LiOH.H$_2$O (0.041 g, 0.978 mmol) in H$_2$O (1 mL). The mixture is stirred for 20 minutes, acidified with 2 N HCl to pH 6 and concentrated under reduced pressure. To the residue are added (3aR,5R,6aS)-5-(2-(trifluoromethyl)phenyl)octahydrocyclopenta[c]pyrrole hydrochloride (9, 0.095 g, 0.326 mmol), benzotriazole-1-yl-oxy-tris-(dimethylaminuteso)-phosphonium hexafluorophosphate (0.216 g, 0.489 mmol), i-Pr$_2$NEt (0.119 g, 0.978 mmol), and DMF (2 mL). The mixture is stirred at room temperature for 16 h and poured into H$_2$O. The mixture is extracted with EtOAc (30 mL) and the organic layer was washed with brine (2×30 mL), dried over Na$_2$SO$_4$, filtered, and concentrated under reduced pressure. The resulting residue is chromatographed over silica gel (0% to 70% EtOAc in hexanes) and is freeze dried to give (6-methyl-[1,2,4]triazolo[4,3-a]pyridin-3-yl)((3aR,5R,6aS)-5-(2-(trifluoromethyl)phenyl)hexahydrocyclopenta[c]pyrrol-2(1H)-yl)methanone as a white solid.

Example 21: Pyrimidin-2-yl((3aR,5R,6aS)-5-(2-(trifluoromethyl)phenyl)hexahydrocyclopenta[c]pyrrol-2(1H)-yl)methanone (36)

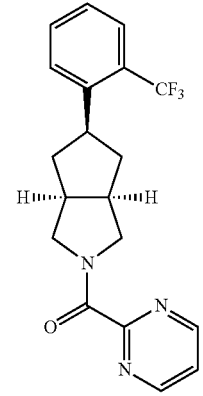

Step A: Following general procedure GP-A2, (3aR,5R,6aS)-5-(2-(trifluoromethyl)phenyl)octahydrocyclopenta[c]pyrrole hydrochloride and pyrimidine-2-carboxylic acid were converted to pyrimidin-2-yl((3aR,5R,6aS)-5-(2-(trifluoromethyl)phenyl)hexahydrocyclopenta[c]pyrrol-2(1H)-yl)methanone as a white solid (127 mg, 76%): mp 84-92° C.; $^1$H NMR (300 MHz, DMSO-d$_6$) δ 8.92 (d, J=8.5 Hz, 2H), 7.75-7.58 (m, 4H), 7.45-7.36 (m, 1H), 3.74-3.64 (m, 2H), 3.55-3.46 (m, 1H), 3.42-3.29 (m, 1H), 3.28-3.21 (m, 1H), 2.94-2.71 (m, 2H), 2.33-2.21 (m, 1H), 2.18-2.07 (m, 1H), 1.65-1.44 (m, 2H); MS (ESI+) m/z 362 [M+H]$^+$.

Example 22: Pyridazin-3-yl((3aR,5R,6aS)-5-(2-(trifluoromethyl)phenyl)hexahydrocyclopenta[c]pyrrol-2(1H)-yl)methanone (37)

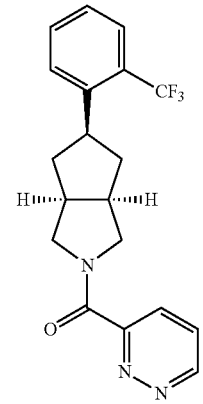 [SMILES: O=C(c1cccnn1)N1C[C@H]2C[C@@H](c3ccccc3C(F)(F)F)C[C@H]2C1]

Step A: Following general procedure GP-A2, (3aR,5R,6aS)-5-(2-(trifluoromethyl)phenyl)octahydrocyclopenta[c]pyrrole hydrochloride and pyridazine-3-carboxylic were converted to pyridazin-3-yl((3aR,5r,6aS)-5-(2-(trifluoromethyl)phenyl)hexahydrocyclopenta[c]pyrrol-2(1H)-yl)methanone as a clear viscous oil (109 mg, 66%): $^1$H NMR (500 MHz, DMSO-d$_6$) δ 9.32 (dd, J=5.0, 2.0 Hz, 1H), 7.98 (dd, J=8.5, 1.5 Hz, 1H), 7.87-7.84 (m, 1H), 7.74 (d, J=8.0 Hz, 1H), 7.67-7.62 (m, 2H), 7.42-7.37 (m, 1H), 3.84-3.78 (m, 2H), 3.74-3.69 (m, 1H), 3.65-3.60 (m, 1H), 3.42-3.33 (m, 1H), 2.87-2.79 (m, 2H), 2.30-2.23 (m, 1H), 2.19-2.12 (m, 1H), 1.66-1.52 (m, 2H); MS (ESI+) m/z 362 [M+H]$^+$.

Example 23: (Pyrazin-2-yl((3aR,5r,6aS)-5-(2-(trifluoromethyl)phenyl)hexahydrocyclopenta[c]pyrrol-2(1H)-yl)methanone (38)

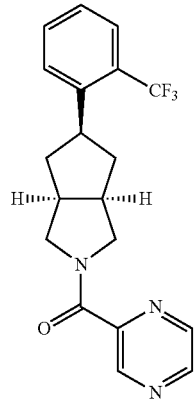 [SMILES: O=C(c1cnccn1)N1C[C@H]2C[C@@H](c3ccccc3C(F)(F)F)C[C@H]2C1]

Step A: Following general procedure GP-A1, (3aR,5R,6aS)-5-(2-(trifluoromethyl)phenyl)octahydrocyclopenta[c]pyrrole hydrochloride and pyrazine-2-carboxylic were converted to pyrazin-2-yl((3aR,5R,6aS)-5-(2-(trifluoromethyl)phenyl)hexahydrocyclopenta[c]pyrrol-2(1H)-yl)methanone as a clear oil (53.1 mg, 64%): $^1$H NMR (500 MHz, DMSO-d$_6$) δ 8.98 (d, J=1.5 Hz, 1H), 8.76 (d, J=2.5 Hz, 1H), 8.70-8.69 (m, 1H), 7.73 (d, J=8.5 Hz, 1H), 7.67-7.62 (m, 2H), 7.42-7.37 (m, 1H), 3.86-3.80 (m, 1H), 3.78-3.72 (m, 1H), 3.71-3.62 (m, 2H), 3.42-3.32 (m, 1H), 2.87-2.77 (m, 2H), 2.29-2.22 (m, 1H), 2.19-2.12 (m, 1H), 1.64-1.51 (m, 2H); MS (ESI+) m/z 362 [M+H]$^+$.

Example 24: (6-Morpholinoimidazo[1,2-b]pyridazin-2-yl)((3aR,5R,6aS)-5-(2-(trifluoromethyl)phenyl)hexahydrocyclopenta[c]pyrrol-2(1H)-yl)methanone (39)

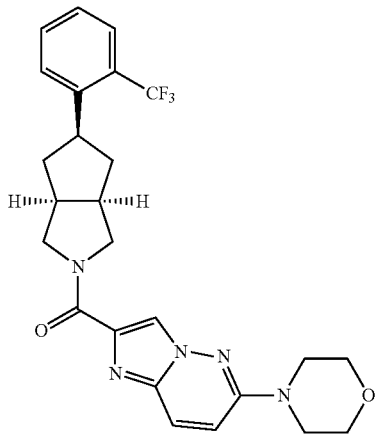 [SMILES: O=C(c1cn2nc(N3CCOCC3)ccc2n1)N1C[C@H]2C[C@@H](c3ccccc3C(F)(F)F)C[C@H]2C1]

Step A: Following general procedure GP-A1, (3aR,5R,6aS)-5-(2-(trifluoromethyl)phenyl)octahydrocyclopenta[c]pyrrole hydrochloride and 6-chloroimidazo[1,2-b]pyridazine-2-carboxylic acid were converted to (6-chloroimidazo[1,2-b]pyridazin-2-yl)((3aR,5R,6aS)-5-(2-(trifluoromethyl)phenyl) hexahydrocyclopenta[c]pyrrol-2(1H)-yl) methanone (134 mg, 63%) as an off-white solid: $^1$H NMR (300 MHz, DMSO-d$_6$) δ 8.72 (d, J=0.6 Hz, 1H), 8.31 (dd, J=9.6, 0.6 Hz, 1H), 7.73-7.59 (m, 3H), 7.47 (d, J=9.6 Hz, 1H), 7.42-7.35 (m, 1H), 4.19-4.14 (m, 2H), 3.80-3.65 (m, 2H), 3.45-3.30 (m, 1H), 2.92-2.75 (m, 2H), 2.32-2.15 (m, 2H), 1.67-1.49 (m, 2H); MS (ESI+) m/z 435 [M+H]$^+$.

Step B: A mixture of (6-chloroimidazo[1,2-b]pyridazin-2-yl)((3aR,5r,6aS)-5-(2-(trifluoromethyl)phenyl)hexahydrocyclopenta[c]pyrrol-2(1H)-yl)methanone (0.064 g, 0.147 mmol) and morpholine (3.0 mL) was heated at 120° C. for 2 hours. The mixture cooled to room temperature and was concentrated under reduced pressure. The resulting residue was chromatographed over silica gel (0% to 3% CH$_3$OH in CH$_2$Cl$_2$ with 0.1% NH$_4$OH) to give a residue that was chromatographed over silica gel (0% to 3% CH$_3$OH in CH$_2$Cl$_2$ with 0.01% NH$_4$OH) to give (6-morpholinoimidazo[1,2-b]pyridazin-2-yl)((3aR,5R,6aS)-5-(2-(trifluoromethyl)phenyl) hexahydrocyclopenta[c]pyrrol-2(1H)-yl)methanone as an off-white solid (26.4 mg, 37%): mp 218-223° C.; $^1$H NMR (500 MHz, DMSO-d$_4$) δ 8.23 (s, 1H), 7.94 (d, J=10 Hz, 1H), 7.68 (d, J=8.0 Hz, 1H), 7.67-7.60 (m, 2H), 7.41-7.36 (m, 1H), 7.27 (d, J=10.5 Hz, 1H), 4.24-4.13 (m, 2H), 3.76-3.62 (m, 6H), 3.50-3.46 (m, 4H), 3.44-3.34 (m, 1H), 2.92-2.72 (m, 2H), 2.30-2.18 (m, 2H), 1.63-1.51 (m, 2H); MS (ESI+) m/z 486 [M+H]$^+$.

Example 25: (6-Methylimidazo[1,2-b]pyridazin-2-yl)((3aR,5R,6aS)-5-(2-(trifluoromethyl)phenyl)hexahydrocyclopenta[c]pyrrol-2(1H)-yl)methanone (40)

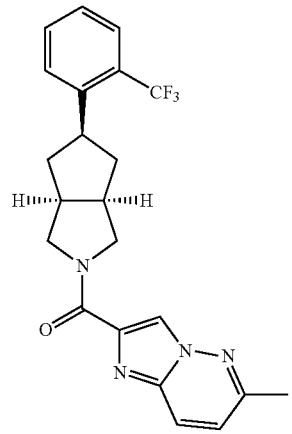 [SMILES: Cc1ccc2nc(C(=O)N3C[C@H]4C[C@@H](c5ccccc5C(F)(F)F)C[C@H]4C3)cn2n1]

Step A: To a solution of (6-chloroimidazo[1,2-b]pyridazin-2-yl)((3aR,5R,6aS)-5-(2-(trifluoromethyl)phenyl)hexahydrocyclopenta[c]pyrrol-2(1H)-yl)methanone (0.050 g, 0.115 mmol) in THF (0.5 mL) and NMP (44 μL) under N$_2$ atmosphere. To this was added Fe(acac)$_3$ (0.004 g, 0.0115 mmol) and the resulting solution was cooled to 0° C. A 1.4 M solution of CH$_2$MgBr in THF/toluene (0.12 mL, 0.173 mmol) was added dropwise. The solution was warmed to room temperature. After 1.5 hours, an additional 1.4 M solution of CH$_3$MgBr in THF/toluene (0.04 mL) was added. The reaction was stirred for 20 minutes then carefully diluted with EtOAc (3 mL) and 1 N HCl was added. The mixture was basified with saturated NaHCO$_3$ and extracted with EtOAc (3×30 mL). The combined organic extracts were concentrated under reduced pressure. The resulting residue was chromatographed over silica gel (0% to 5% CH$_3$OH in CH$_2$Cl$_2$ with 0.1% NH$_4$OH) to give (6-methylimidazo[1,2-b]pyridazin-2-yl)((3aR,5R,6aS)-5-(2-(trifluoromethyl)phenyl)hexahydrocyclopenta[c]pyrrol-2(1H)-yl)methanone as a white solid (24.5 mg, 51%): mp 167-169° C.; $^1$H NMR (500 MHz, DMSO-d$_4$) δ 8.52 (s, 1H), 8.08 (d, J=9.0 Hz, 1H), 7.70 (d, J=8.0 Hz, 1H), 7.66-7.60 (m, 2H), 7.41-7.36 (m, 1H), 7.22 (d, J=9.5 Hz, 1H), 4.23-4.15 (m, 2H), 3.77-3.65 (m, 2H), 3.44-3.34 (m, 1H), 2.93-2.74 (m, 2H), 2.54 (s, 3H), 2.30-2.18 (m, 2H), 1.64-1.51 (m, 2H); MS (ESI+) m/z 415 [M+H]$^+$.

Example 26: (1H-Pyrazolo[3,4-b]pyridin-3-yl)((3aR,5R,6aS)-5-(2-(trifluoromethyl)phenyl)hexahydrocyclopenta[c]pyrrol-2(1H)-yl)methanone (41)

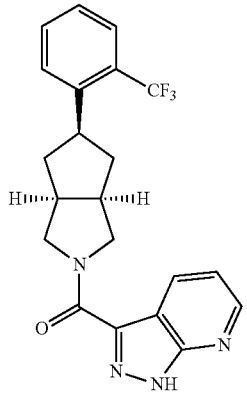 [SMILES: O=C(c1n[nH]c2ncccc12)N1C[C@H]2C[C@@H](c3ccccc3C(F)(F)F)C[C@H]2C1]

Step A: Following general procedure GP-A2, (3aR,5R,6aS)-5-(2-(trifluoromethyl)phenyl)octahydrocyclopenta[c]pyrrole hydrochloride and 1H-pyrazolo[3,4-b]pyridine-3-carboxylic acid were converted to (1H-pyrazolo[3,4-b]pyridin-3-yl)((3aR,5r,6aS)-5-(2-(trifluoromethyl)phenyl)hexahydrocyclopenta[c]pyrrol-2(1H)-yl)methanone as a white solid (49 mg, 51%): mp 218-220° C.; $^1$H NMR (500 MHz, DMSO-d$_6$) δ 14.13 (s, 1H), 8.59 (dd, J=4.5, 2.0 Hz, 1H), 8.55 (dd, J=8.0, 1.5 Hz, 1H), 7.72 (d, J=8.0 Hz, 1H), 7.66-7.59 (m, 2H), 7.41-7.36 (m, 1H), 7.34-7.31 (m, 1H), 4.22-4.11 (m, 2H), 3.85-3.78 (m, 1H), 3.76-3.70 (m, 1H), 3.46-3.37 (m, 1H), 2.96-2.77 (m, 2H), 2.31-2.19 (m, 2H), 1.68-1.57 (m, 2E); MS (ESI+) m/z 401 [M+H]$^+$.

Example 27: 1-(3-((3aR,5R,6aS)-5-(2-(Trifluoromethyl)phenyl)octahydrocyclopenta[c]pyrrole-2-carbonyl)-4,5-dihydro-1H-pyrazolo[3,4-c]pyridin-6(7H)-yl)ethanone (42)

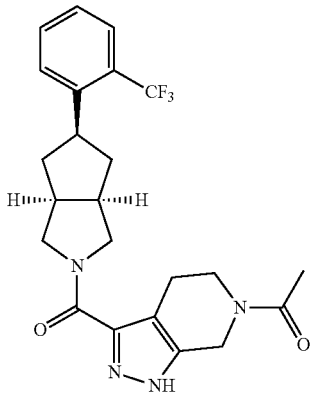 [SMILES: CC(=O)N1CCc2c(C(=O)N3C[C@H]4C[C@@H](c5ccccc5C(F)(F)F)C[C@H]4C3)n[nH]c2C1]

Step A: Following general procedure GP-E, (3aR,5R,6aS)-5-(2-(trifluoromethyl)phenyl)octahydrocyclopenta[c]pyrrole hydrochloride and acetyl chloride were converted to 1-(3-((3aR,5R,6aS)-5-(2-(trifluoromethyl)phenyl) octahydrocyclopenta[c]pyrrole-2-carbonyl)-4,5-dihydro-1H-pyrazolo[3,4-c]pyridin-6(7H)-yl)ethanone as a white solid (48 mg, 60%): mp 207-213° C.; $^1$H NMR (500 MHz, DMSO-d$_6$) δ 13.00-12.94 (m, 1H), 7.71-7.60 (m, 3H), 7.42-7.36 (m, 1H), 4.66-4.52 (m, 2H), 4.12-3.99 (m, 2H), 3.76-3.85 (m, 4H), 3.44-3.34 (m, 1H), 2.87-2.80 (m, 1H), 2.79-2.70 (m, 2H), 2.69-2.62 (m, 1H), 2.29-2.15 (m, 2H), 2.11-2.04 (m, 3H), 1.62-1.48 (m, 2H); MS (ESI+) m/z 447 [M+H]$^+$.

Example 28: (6-(Methylsulfonyl)-4,5,6,7-tetrahydro-1H-pyrazolo[3,4-c]pyridin-3-yl)((3aR,5R,6aS)-5-(2-(trifluoromethyl)phenyl)hexahydrocyclopenta[c]pyrrol-2(1H)-yl)methanone (43)

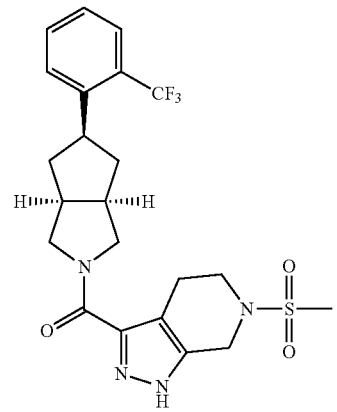 [SMILES: CS(=O)(=O)N1CCc2c(C(=O)N3C[C@H]4C[C@@H](c5ccccc5C(F)(F)F)C[C@H]4C3)n[nH]c2C1]

Step A: Following general procedure GP-F, (3aR,5R,6aS)-5-(2-(trifluoromethyl)phenyl)octahydrocyclopenta[c]pyrrole hydrochloride and methanesulfonyl chloride were converted to (6-(methylsulfonyl)-4,5,6,7-tetrahydro-1H-pyrazolo[3,4-c]pyridin-3-yl)((3aR,5R,6aS)-5-(2-(trifluoromethyl)phenyl)hexahydrocyclopenta[c]pyrrol-2(1H)-yl)methanone as a white solid (78.6 mg, 89%): mp 212-215° C.; $^1$H NMR (500 MHz, DMSO-d$_6$) δ 13.04 (s, 1H), 7.70-7.59 (m, 3H), 7.41-7.36 (m, 1H), 4.43-4.34 (m, 2H), 4.11-4.02 (m, 2H), 3.72-3.58 (m, 2H), 3.52-3.34 (m, 3H), 2.93 (s, 3H), 2.88-2.71 (m, 4H), 2.37-2.17 (m, 2H), 1.61-1.50 (m, 2H); MS (ESI+) m/z 483 [M+H]$^+$.

Example 29: (6-Methyl-4,5,6,7-tetrahydro-1H-pyrazolo[3,4-c]pyridin-3-yl)((3aR,5R,6aS)-5-(2-(trifluoromethyl)phenyl)hexahydrocyclopenta[c]pyrrol-2(1H)-yl)methanone (44)

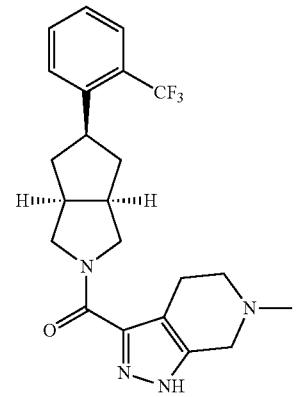 [SMILES: CN1CCc2c(C(=O)N3C[C@H]4C[C@@H](c5ccccc5C(F)(F)F)C[C@H]4C3)n[nH]c2C1]

Step A: Following general procedure GP-G, (3aR,5R,6aS)-5-(2-(trifluoromethyl)phenyl)octahydrocyclopenta[c]pyrrole hydrochloride and formaldehyde were converted to (6-methyl-4,5,6,7-tetrahydro-1H-pyrazolo[3,4-c]pyridin-3- yl)((3aR,5R,6aS)-5-(2-(trifluoromethyl) phenyl)hexahydrocyclopenta[c]pyrrol-2(1H)-yl) methanone as a white solid (88.2 mg, 55%): ¹H NMR (500 MHz, DMSO-d₆) δ 12.80 (s, 1H), 7.69-7.60 (m, 3H), 7.42-7.36 (m, 1H), 4.09-3.97 (m, 2H), 3.69-3.57 (m, 2H), 3.47 (s, 2H), 3.43-3.32 (m, 1H), 2.88-2.71 (m, 2H), 2.70-2.66 (m, 2H), 2.64-2.57 (m, 2H), 2.36 (s, 3H), 2.28-2.16 (m, 2H), 1.59-1.48 (m, 2H); MS (ESI+) m/z 419 [M+H]⁺.

Example 30: 1-(3-((3aR,5R,6aS)-5-(2-(Trifluoromethyl)phenyl)octahydrocyclopenta[c]pyrrole-2-carbonyl)-6,7-dihydro-1H-pyrazolo[4,3-c]pyridin-5(4H)-yl)ethanone (45)

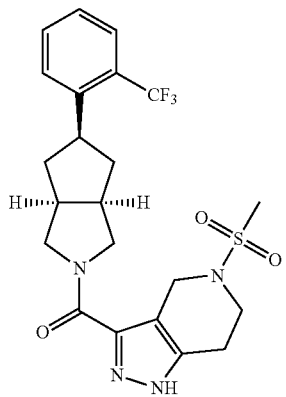 [SMILES: CS(=O)(=O)N1CCc2[nH]nc(C(=O)N3C[C@H]4C[C@@H](c5ccccc5C(F)(F)F)C[C@H]4C3)c2C1]

Step A: Following general procedure GP-C, (4,5,6,7-tetrahydro-1H-pyrazolo[4,3-c]pyridin-3-yl)((3aR,5R,6aS)-5-(2-(trifluoromethyl) phenyl)hexahydrocyclopenta[c]pyrrol-2(1H)-yl)methanone hydrochloride and methanesulfonyl chloride were converted to 1-(3-((3aR,5R,6aS)-5-(2-(trifluoromethyl)phenyl)octahydrocyclopenta[c]pyrrole-2-carbonyl)-6,7-dihydro-1H-pyrazolo[4,3-c]pyridin-5(4R)-yl)ethanone as a white solid (77.2 mg, 86%): mp 215-219° C.; ¹H NMR (500 MHz, DMSO-d₆) δ 13.04 (s, 1H), 7.71-7.60 (m, 3H), 7.41-7.36 (m, 1H), 4.44-4.34 (m, 2H), 4.12-4.02 (m, 2H), 3.73-3.58 (m, 2H), 3.53-3.33 (m, 3H), 2.93 (s, 3H), 2.88-2.71 (m, 4H), 2.30-2.17 (m, 2H), 1.62-1.49 (m, 2H); MS (ESI+) m/z 483 [M+H]⁺.

Example 31: 1-(3-((3aR,5R,6aS)-5-(2-(Trifluoromethyl)phenyl)octahydrocyclopenta[c]pyrrole-2-carbonyl)-6,7-dihydro-1H-pyrazolo[4,3-c]pyridin-5(4H)-yl)ethanone (46)

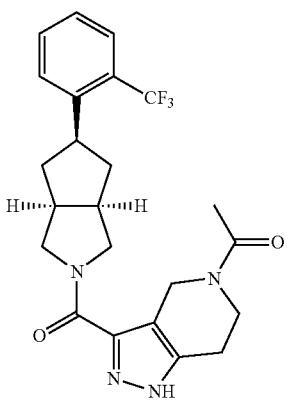 [SMILES: CC(=O)N1CCc2[nH]nc(C(=O)N3C[C@H]4C[C@@H](c5ccccc5C(F)(F)F)C[C@H]4C3)c2C1]

Step A: Following general procedure GP-B, (4,5,6,7-tetrahydro-1H-pyrazolo[4,3-c]pyridin-3-yl)((3aR,5R,6aS)-5-(2-(trifluoromethyl) phenyl)hexahydrocyclopenta[c]pyrrol-2(1H)-yl)methanone hydrochloride and acetyl chloride were converted to 1-(3-((3aR,5R,6aS)-5-(2-(trifluoromethyl)phenyl) octahydrocyclopenta[c]pyrrole-2-carbonyl)-4,5-dihydro-1H-pyrazolo[3,4-c]pyridin-6(7H)-yl)ethanone as a white solid (57.2 mg, 69%): mp 191-199° C.; ¹H NMR (500 MHz, DMSO-d₆) δ 13.01-12.94 (s, 1H), 7.70-7.60 (m, 3H), 7.41-7.36 (m, 1H), 4.66-4.51 (m, 2H), 4.12-3.99 (m, 2H), 3.75-3.58 (m, 4H), 3.44-3.33 (m, 1H), 2.89-2.70 (m, 3H), 2.68-2.62 (m, 1H), 2.29-2.16 (m, 2H), 2.11-2.04 (m, 3H), 1.62-1.47 (m, 2H); MS (ESI+) m/z 447 [M+H]⁺; HPLC>99% purity (Method I).

Example 32: (5-Methyl-1,4,5,6-tetrahydropyrrolo[3,4-c]pyrazol-3-yl)((3aR,5R,6aS)-5-(2-(trifluoromethyl)phenyl)hexahydrocyclopenta[c]pyrrol-2(1H)-yl)methanone (47)

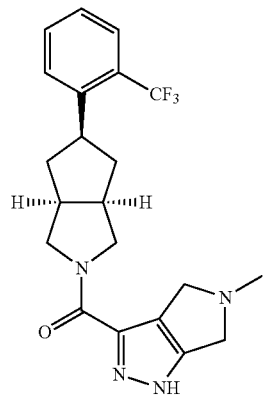 [SMILES: CN1Cc2[nH]nc(C(=O)N3C[C@H]4C[C@@H](c5ccccc5C(F)(F)F)C[C@H]4C3)c2C1]

Step A: Following general procedure GP-J, (1,4,5,6-tetrahydropyrrolo[3,4-c]pyrazol-3-yl)((3aR,5r,6aS)-5-(2-(trifluoromethyl) phenyl)hexahydrocyclopenta[c]pyrrol-2(1H)-yl)methanone hydrochloride and formaldehyde were converted to (5-methyl-1,4,5,6-tetrahydropyrrolo[3,4-c]pyrazol-3-yl)((3aR,5R,6aS)-5-(2-(trifluoromethyl)phenyl) hexahydrocyclopenta[c]pyrrol-2(1H)-yl)methanone as a white solid (33 mg, 27%): mp 156-159° C.; ¹H NMR (500 MHz, DMSO-d₆) δ 12.95 (s, 1H), 7.70-7.67 (m, 1H), 7.66-7.61 (m, 2H), 7.41-7.36 (m, 1H), 4.12-3.48 (m, 8H), 3.42-3.33 (m, 1H), 2.89-2.69 (m, 2H), 2.28-2.14 (m, 2H), 1.62-1.47 (m, 2H); MS (ESI+) m/z 405 [M+H]⁺.

Example 33: (5-(Methylsulfonyl)-1,4,5,6-tetrahydropyrrolo[3,4-c]pyrazol-3-yl)((3aR,5R,6aS)-5-(2-(trifluoromethyl)phenyl) hexahydrocyclopenta[c]pyrrol-2(1H)-yl)methanone (48)

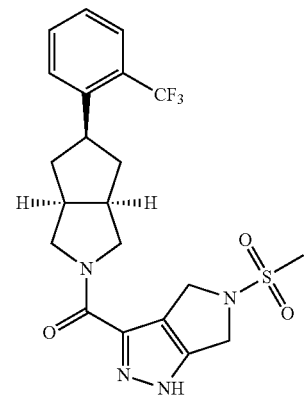 [SMILES: CS(=O)(=O)N1Cc2[nH]nc(C(=O)N3C[C@H]4C[C@@H](c5ccccc5C(F)(F)F)C[C@H]4C3)c2C1]

Step A: Following general procedure GP-I, (1,4,5,6-tetrahydropyrrolo[3,4-c]pyrazol-3-yl)((3aR,5r,6aS)-5-(2-(trifluoromethyl)phenyl)hexahydrocyclopenta[c]pyrrol-2(1H)- yl)methanone hydrochloride and methanesulfonyl chloride were converted to (5-(methylsulfonyl)-1,4,5,6-tetrahydropyrrolo[3,4-c]pyrazol-3-yl)((3aR,5R,6aS)-5-(2-(trifluoromethyl)phenyl) hexahydrocyclopenta[c]pyrrol-2(1H)-yl)methanone (49 mg, 62%) as a white solid: mp 202-205° C.; $^1$H NMR (500 MHz, DMSO-d$_6$) δ 13.41-13.18 (m, 1H), 9.04 (m, 1H), 7.74-7.60 (m, 3H), 7.42-7.35 (m, 1H), 4.62-4.50 (m, 2H), 4.46-4.41 (m, 2H), 4.14-4.03 (m, 1H), 3.82-3.55 (m, 3H), 3.44-3.33 (m, 1H), 3.05-2.99 (m, 3H), 2.91-2.70 (m, 2H), 2.29-2.18 (m, 2H), 1.62-1.49 (m, 2H); MS (ESI+) m/z 469 [M+H]$^+$.

Example 34: 1-(3-((3aR,5R,6aS)-5-(2-(Trifluoromethyl)phenyl)octahydro-cyclopenta[c]pyrrole-2-carbonyl)pyrrolo[3,4-c]pyrazol-5(1H,4H,6H)-yl)ethanone (49)

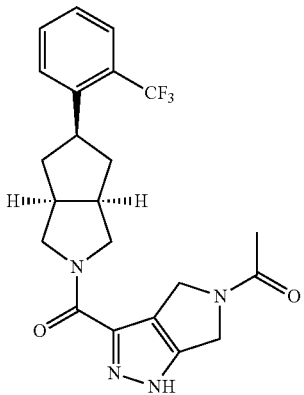 [SMILES: CC(=O)N1Cc2[nH]nc(C(=O)N3C[C@H]4C[C@@H](c5ccccc5C(F)(F)F)C[C@H]4C3)c2C1]

Step A: Following general procedure GP-H, (1,4,5,6-tetrahydropyrrolo[3,4-c]pyrazol-3-yl)((3aR,5r,6aS)-5-(2-(trifluoromethyl)phenyl)hexahydrocyclopenta[c]pyrrol-2(1H)-yl)methanone hydrochloride and acetyl chloride were converted to 1-(3-((3aR,5R,6aS)-5-(2-(trifluoromethyl)phenyl)octahydrocyclopenta [c]pyrrole-2-carbonyl)pyrrolo[3,4-c]pyrazol-5(1H,4H,6H)-yl)ethanone as a white solid (20 mg, 28%): $^1$H NMR (500 MHz, DMSO-d$_6$) δ 13.36-13.14 (m, 1H), 7.74-7.58 (m, 3H), 7.43-7.35 (m, 1H), 4.78-4.70 (m, 1H), 4.65-4.60 (m, 1H), 4.57-4.46 (m, 1H), 4.41-4.37 (m, 1H), 4.10-4.05 (m, 1H), 3.80-3.57 (m, 3H), 3.43-3.33 (m, 1H), 2.92-2.71 (m, 2H), 2.28-2.18 (m, 2H), 2.07-2.01 (m, 3H), 1.61-1.50 (m, 2H); MS (ESI+) m/z 433 [M+H]$^+$.

Example 35: 4-((3aR,5R,6aS)-5-(2-(Trifluoromethyl)phenyl)octahydrocyclopenta[c]pyrrole-2-carboxamido)nicotinic acid (50)

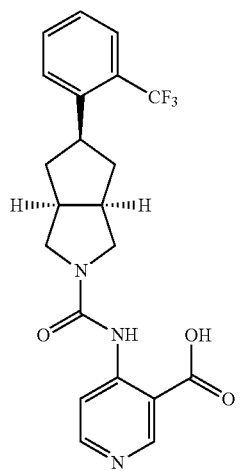

Step A: To a solution of triphosgene (0.148 g, 0.500 mmol) in CH$_2$Cl$_2$ (3.0 mL) under N$_2$, cooled to −78° C., was slowly added pyridine (0.158 g, 2.00 mmol) and the resulting solution was stirred at −78° C. for 10 minutes. A solution of (3aR,5r,6aS)-5-(2-(trifluoromethyl)phenyl)octahydrocyclopenta[c]pyrrole hydrochloride (9, 0.292 g, 1.00 mmol) in CH$_2$Cl$_2$ (2.0 mL) was added and the resulting solution was stirred at −78° C. for 30 minutes. The solution was warmed to room temperature and stirred for 2 h. The reaction was diluted with 1 N HCl (8 mL) and extracted with CH$_2$Cl$_2$ (3×30 mL). The combined organic extracts were washed with saturated NaHCO$_3$ solution (40 mL) and concentrated under reduced pressure. The resulting residue was chromatographed over silica gel (0% to 30% EtOAc in hexanes) to give (3aR,5r,6aS)-5-(2-(trifluoromethyl)phenyl)hexahydrocyclopenta[c]pyrrole-2(1H)-carbonyl chloride as a light yellow solid (170 mg, 53%): $^1$H NMR (300 MHz, DMSO-d$_6$) δ 7.81 (d, J=8.4 Hz, 1H), 7.69-7.60 (m, 2H), 7.44-7.35 (m, 1H), 3.85-3.75 (m, 1H), 3.71-3.54 (m, 2H), 3.51-3.43 (m, 1H), 3.42-3.36 (m, 1H), 2.91-2.75 (m, 2H), 2.25-2.12 (m, 2H), 1.70-1.55 (m, 2H); MS (ESI+) m/z 318 [M+H]$^+$.

Step B: To a solution of (3aR,5R,6aS)-5-(2-(trifluoromethyl)phenyl)hexahydrocyclopenta[c]pyrrole-2(1H)-carbonyl chloride (0.170 g, 0.536 mmol) in THF (3.0 mL) was added i-Pr$_2$NEt (0.064 g, 0.536 mmol) and methyl 4-aminonicotinate (0.081 g, 0.536 mmol) and the resulting solution was heated at 68° C. for 4 hours. The reaction was diluted with H$_2$O (20 mL) and extracted with EtOAc (3×30 mL). The combined organic extracts were concentrated under reduced pressure. The resulting residue was chromatographed over silica gel (0 to 5% CH$_3$OH in CH$_2$Cl$_2$ with 0.1% NH$_4$OH) to give methyl 4-((3aR,5R,6aS)-5-(2-(trifluoromethyl)phenyl)octahydrocyclopenta[c]pyrrole-2-carboxamido)nicotinate as a white solid (140 mg, 60%): $^1$H NMR (300 MHz, DMSO-d$_6$) δ 10.46 (br s, 1H), 8.98 (d, J=0.3 Hz, 1H), 8.53 (d, J=6.0 Hz, 1H), 8.46 (d, J=6.3 Hz, 1H), 7.79 (d, J=8.1 Hz, 1H), 7.68-7.59 (m, 2H), 7.43-7.35 (m, 1H), 3.91 (s, 3H), 3.75-3.61 (m, 2H), 3.52-3.35 (m, 3H), 2.94-2.81 (m, 2H), 2.31-2.17 (m, 2H), 1.72-1.56 (m, 2H); MS (ESI+) m/z 434 [M+H]$^+$.

Step C: To a solution of methyl 4-((3aR,5R,6aS)-5-(2-(trifluoromethyl)phenyl)octahydrocyclopenta[c]pyrrole-2-carboxamido)nicotinate (0.138 g, 0.311 mmol) in THF (6.2 mL) and CH$_3$OH (3.2 mL) was added a solution of LiOH.H$_2$O (0.130 g, 3.11 mmol) in H$_2$O (1.6 mL). The mixture stirred for 3 hours, then acidified to pH 4 with 2 N HCl, and diluted with H$_2$O (50 mL). The resulting solids were collected by filtration and dried to provide 4-((3aR,5R,6aS)-5-(2-(trifluormethyl)phenyl)octahydrocyclopenta [c]pyrrole-2-carboxamido)nicotinic acid as a light yellow solid (130 mg, >99%): mp 245-255° C. decomp.; $^1$H NMR (500 MHz, DMSO-d$_6$) δ 14.43-12.71 (m, 1H), 8.92 (m, 1H), 8.53 (d, J=6.5 Hz, 1H), 8.44 (d, J=7.5 Hz, 1H), 7.76 (d, J=8.0 Hz, 1H), 7.67-7.59 (m, 2H), 7.42-7.36 (m, 1H), 3.75-3.62 (m, 2H), 3.53-3.35 (m, 3H), 2.93-2.79 (m, 2H), 2.28-2.20 (m, 2H), 1.67-1.58 (m, 2H); MS (ESI+) m/z 420 [M+H]$^+$.

Example 36: 5-methoxy-2-((3aR,5R,6aS)-5-(2-(Trifluoromethyl)phenyl)octahydrocyclopenta[c]pyrrole-2-carboxamido)benzoic acid (51)

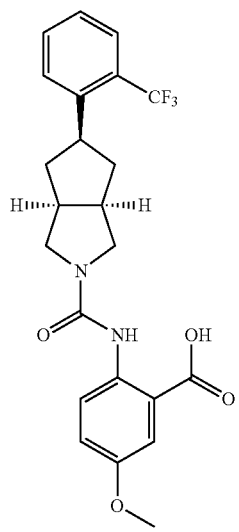

Step A: To a solution of (3aR,5R,6aS)-5-(2-(trifluoromethyl) phenyl)hexahydrocyclopenta[c]pyrrole-2(1H)-carbonyl chloride (0.100 g, 0.315 mmol) in THF (1.8 mL) was added i-Pr$_2$NEt (0.041 g, 0.315 mmol) and methyl 2-amino-5-methoxybenzoate (0.057 g, 0.315 mmol). The resulting solution was heated at 68° C. for 18 h. The reaction was diluted with H$_2$O (30 mL) and extracted with EtOAc (4×30 mL). The combined organic extracts were concentrated under reduced pressure. The resulting residue was chromatographed over silica gel (0% to 100% EtOAc in hexanes) to give methyl 5-methoxy-2-((3aR,5R,6aS)-5-(2-(trifluoromethyl)phenyl)octahydrocyclopenta[c]pyrrole-2-carboxamido)benzoate as a white film (94.9 mg, 65%): $^1$H NMR (500 MHz, CDCl$_3$) δ 10.27 (s, 1H), 8.59 (d, J=9.5 Hz, 1H), 7.60 (d, J=8.0 Hz, 1H), 7.55-7.46 (m, 3H), 7.30-7.26 (m, 1H), 7.13 (dd, J=9.5, 3.5 Hz, 1H), 3.92 (s, 3H), 3.81 (s, 3H), 3.76-3.72 (m, 2H), 3.59-3.48 (m, 3H), 2.93-2.85 (m, 2H), 2.41-2.33 (m, 2H), 1.68-1.60 (m, 2H); MS (ESI+) m/z 463 [M+H]$^+$.

Step B: To a solution of methyl 5-methoxy-2-((3aR,5R,6aS)-5-(2-(trifluoromethyl)phenyl)octahydrocyclopenta[c]pyrrole-2-carboxamido) benzoate (0.092 g, 0.199 mmol) in THF (3.9 mL) and CH3OH (2.0 mL) was added a solution of LiOH.H$_2$O (0.084 g, 1.99 mmol) in H$_2$O (1.0 mL). The mixture was stirred for 2 hours, then acidified with 2 N HCl, and diluted with H$_2$O (50 mL). The resulting solids were collected by filtration to provide 5-methoxy-2-((3aR,5R,6aS)-5-(2-(trifluoromethyl)phenyl)octahydrocyclopenta[c]pyrrole-2-carboxamido)benzoic acid as a white solid (77.2 mg, 86%): mp 176-179° C. decomp.; $^1$H NMR (500 MHz, DMSO-d$_6$) δ 13.56 (s, 1H), 10.42 (br s, 1H), 8.43 (d, J=9.0 Hz, 1H), 7.75 (d, J=8.0 Hz, 1H), 7.67-7.59 (m, 2H), 7.43 (d, J=3.0 Hz, 1H), 7.42-7.36 (m, 1H), 7.18 (dd, J=9.5, 3.0 Hz, 1H), 3.75 (s, 3H), 3.65-3.58 (m, 2H), 3.46-3.36 (m, 3H), 2.90-2.79 (m, 2H), 2.28-2.19 (m, 2H), 1.66-1.57 (m, 2H); MS (ESI+) m/z 449 [M+H]$^+$.

Example 37: 5-Fluoro-2-((3aR,5R,6aS)-5-(2-(trifluoromethyl)phenyl)octahydrocyclopenta[c]pyrrole-2-carboxamido)benzoic acid (52)

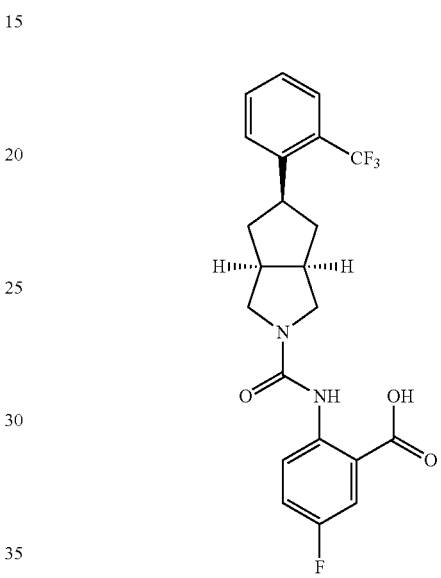

Step A: To a solution of (3aR,5R,6aS)-5-(2-(trifluoromethyl)phenyl)hexahydrocyclopenta[c]pyrrole-2(1H)-carbonyl chloride (0.100 g, 0.315 mmol) in THF (1.8 mL) was added i-Pr$_2$NEt (0.041 g, 0.315 mmol) and methyl 2-amino-5-fluorobenzoate (0.064 g, 0.378 mmol). The resulting solution was heated at 68° C. for 5 h. The reaction was diluted with H$_2$O (30 mL) and extracted with EtOAc (4×30 mL). The combined organic extracts were concentrated under reduced pressure. The resulting residue was chromatographed over silica gel (0% to 10% EtOAc in hexanes) to give methyl 5-fluoro-2-((3aR,5R,6aS)-5-(2-(trifluoromethyl)phenyl)octahydrocyclopenta[c]pyrrole-2-carboxamido)benzoate as a light orange film (101 mg, crude): MS (ESI+) m/z 451 [M+H]$^+$.

Step B: To a solution of methyl 5-fluoro-2-((3aR,5R,6aS)-5-(2-(trifluoromethyl)phenyl)octahydrocyclopenta[c]pyrrole-2-carboxamido)benzoate (0.101 g, 0.224 mmol) in THF (4.4 mL) and CH3OH (2.3 mL) was added a solution of LiOH.H$_2$O (0.094 g, 2.24 mmol) in H$_2$O (1.2 mL). The mixture stirred for 18 hours, then acidified with 2 N HCl, diluted with H$_2$O (20 mL), and extracted with EtOAc (3×30 mL). The combined organic extracts were concentrated under reduced pressure. The resulting residue was chromatographed by reverse phase column (0% to 100% CH₃CN in H₂O). Followed by preparative HPLC (Phenomenex Luna C18 (2), 250.0×50.0 mm, 15 micron, H₂O with 0.05% TFA and CH₃CN with 0.05% TFA) to provide 5-fluoro-2-((3aR,5r,6aS)-5-(2-(trifluoromethyl)phenyl)octahydrocyclopenta[c]pyrrole-2-carboxamido)benzoic acid as a white solid (11 mg, 12%): mp 176-180° C.; ¹H NMR (500 MHz, DMSO-d₆) δ 13.83 (br s, 1H), 10.65 (br s, 1H), 8.57-8.51 (m, 1H), 7.75 (d, J=8.5 Hz, 1H), 7.69-7.59 (m, 3H), 7.46-7.36 (m, 2H), 3.67-3.58 (m, 2H), 3.47-3.36 (m, 3H), 2.90-2.81 (m, 2H), 2.28-2.20 (m, 2H), 1.68-1.58 (m, 2H); MS (ESI+) m/z 437 [M+H]⁺.

Example 38: 5-Chloro-2-((3aR,5R,6aS)-5-(2-(trifluoromethyl)phenyl)octahydrocyclopenta[c]pyrrole-2-carbonamido)benzoic acid (53)

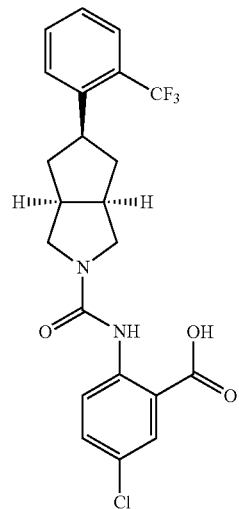

Step A: To a solution of methyl 2-amino-5-chlorobenzoate (0.0.58 g, 0.315 mmol) in DMF (2.7 mL) cooled to −10° C. under N₂ was added NaH (60% in mineral oil, 0.019 g, 0.473 mmol) and the resulting solution was stirred at −10° C. for 20 minutes. A solution of (3aR,5R,6aS)-5-(2-(trifluoromethyl)phenyl)hexahydrocyclopenta[c]pyrrole-2(1H)-carbonyl chloride (0.100 g, 0.315 mmol) in DMF (0.55 mL) was added and the reaction allowed to warm to room temperature and was stirred for 2.5 h. The reaction was carefully diluted with H₂O (30 mL), made acidic to pH 2 with 2 N HCl, and extracted with EtOAc (4×30 mL). The combined organic extracts were washed with brine (4×30 mL) and concentrated under reduced pressure. The resulting residue was chromatographed over silica gel (0% 10% CH₃OH in CH₂Cl₂ with 0.1% AcOH) followed by reverse phase column chromatography (0% to 100% CH₃CN in H₂O). The obtained residue was purified with preparative TLC (Analtech, 20×20 cm, 1000 microns, with 5% CH₃OH in CH₂Cl₂) to give 5-chloro-2-((3aR,5R,6aS)-5-(2-(trifluoromethyl)phenyl) octahydrocyclopenta[c]pyrrole-2-carboxamido)benzoic acid as a white solid (21 mg, 23%): mp 188-193° C.; ¹H NMR (500 MHz, DMSO-d₆) δ 13.92 (br s, 1H), 10.85 (br s, 1H), 8.56 (d, J=9.5 Hz, 1H), 7.90 (s, 1H), 7.76 (d, J=8.0 Hz, 1H), 7.68-7.54 (m, 3H), 7.42-7.35 (m, 1H), 3.67-3.58 (m, 2H), 3.48-3.35 (m, 3H), 2.90-2.80 (m, 2H), 2.28-2.19 (m, 2H), 1.67-1.53 (m, 2H); MS (ESI+) m/z 453 [M+H]⁺.

Example 39: 5-(Methylsulfonyl)-2-((3aR,5R,6aS)-5-(2-(trifluoromethyl)phenyl)octahydrocyclopenta[c]pyrrole-2-carboxamido)benzoic acid (54)

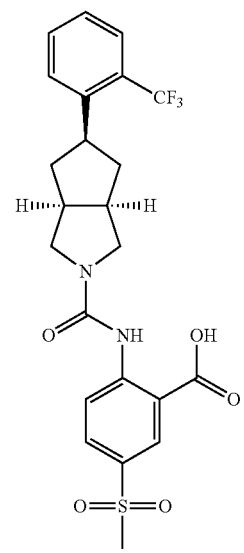

Step A: To a solution of methyl 2-amino-5(methylsulfonyl)benzoate (0.116 g, 0.506 mmol) in DMF (4.4 mL) cooled to −10° C. under N₂ was added NaH (60% in mineral oil, 0.024 g, 0.606 mmol) and the resulting solution was stirred at −10° C. for 30 minutes. A solution of (3aR,5R,6aS)-5-(2-(trifluoromethyl)phenyl)hexahydrocyclopenta[c]pyrrole-2(1H)-carbonyl chloride (0.192 g, 0.606 mmol) in DMF (1.1 mL) was added and the reaction allowed to warm to room temperature and was stirred for 2 hours. The reaction was carefully diluted with H₂O (20 mL), made acidic to pH 2 with 2 N HCl, and extracted with EtOAc (3×40 mL). The combined organic extracts were washed with brine (2×30 mL) and concentrated under reduced pressure. The resulting residue was chromatographed over silica gel (0% to 70% EtOAc in hexanes) followed by reverse phase column chromatography (0% to 100% CH₂CN in H₂O) to give methyl 5-(methylsulfonyl)-2-((3aR,5R,6aS)-5-(2-(trifluoromethylphenyl)octahydrocyclopenta[c]pyrrole-2-carboxamido)benzoate as a white film (76.2 mg, 29%): ¹H NMR (300 MHz, CDCl₃) δ 10.91 (br s, 1H), 8.93 (d, J=9.3 Hz, 1H), 8.61 (d, J=2.1 Hz, 1H), 8.01 (dd, J=9.0, 2.4 Hz, 1H), 7.62 (d, J=7.8 Hz, 1H), 7.55-7.47 (m, 2H), 7.33-7.27 (m, 1H), 3.97 (s, 3H), 3.86-3.73 (m, 2H), 3.64-3.47 (m, 3H), 3.06 (s, 3H), 2.98-2.86 (m, 2H), 2.46-2.33 (m, 2H), 1.71-1.58 (m, 2H); MS (ESI+) m/z 511 [M+H]⁺.

Step B: To a solution of methyl 5-(methylsulfonyl)-2-((3aR,5R,6aS)-5-(2-(trifluoromethyl)phenyl)octahydrocyclopenta[c]pyrrole-2-carboxamido)benzoate (0.075 g, 0.147 mmol) in THF (2.9 mL) and CH₃OH (1.5 mL) was added a solution of LiOH.H₂O (0.062 g, 1.47 mmol) in H₂O (0.74 mL). The mixture was stirred for 5 hours, then acidified to pH 2 with 2 N HCl and diluted with H₂O (30 mL). The resulting precipitate was collected by filtration and dried to provide 5-(methylsulfonyl)-2-((3aR,5R,6aS)-5-(2-(trifluoromethyl)phenyl) octahydrocyclopenta[c]pyrrole-2-carboxamido)benzoic acid as a white solid (52 mg, 71%): mp 175-181° C.; ¹H NMR (500 MHz, DMSO-d₆) δ 14.09 (br s, 1H), 11.09 (br s, 1H), 8.77 (d, J=9.0 Hz, 1H), 8.42 (d, J=2.5 Hz, 1H), 8.04 (dd, J=9.0, 2.5 Hz, 1H), 7.77 (d, J=8.0 Hz, 1H), 7.67-7.60 (m, 2H), 7.42-7.37 (m, 1H), 3.72-3.64 (m, 2H), 3.52-3.46 (m, 2H), 3.45-3.32 (m, 1H), 3.20 (s, 3H), 2.92-2.84 (m, 2H), 2.28-2.20 (m, 2H), 1.69-1.59 (m, 2H); MS (ESI+) m/z 497 [M+H]⁺.

Example 40: 2-((3aR,5R,6aS)-5-(2-(Trifluoromethyl)phenyl)octahydrocyclopenta[c]pyrrole-2-carboxamido)nicotinic acid (55)

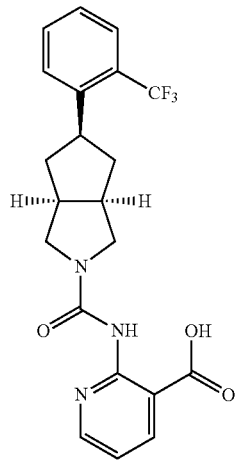

Step A: A solution of (3aR,5R,6aS)-5-(2-(trifluoromethyl)phenyl)hexahydrocyclopenta[c]pyrrole-2(1H)-carbonyl chloride (0.300 g, 0.946 mmol) in 7 N NH₃ in CH₃OH (4.0 mL) was stirred for 1 hour. The reaction was concentrated with Et₂ and dried to provide (3aR,5R,6aS)-5-(2-(trifluoromethyl)phenyl)hexahydrocyclopenta[c]pyrrole-2(1H)-carboxamide as a white solid (323 mg, >99%): MS (ESI+) m/z 299 [m+H]⁺.

Step B: To a solution of (3aR,5R,6aS)-5-(2-(trifluoromethyl)phenyl)hexahydrocyclopenta[c]pyrrole-2(1H)-carboxamide (0.100 g, 0.338 mmol), methyl 2-chloronicotinate (0.087 g, 0.507 mmol) and Cs₂CO₃ (0.134 g, 0.473 mmol) in deoxygenated toluene (4.0 mL) was added Pd(OAc)₂ (0.022 g, 0.0338 mmol) and racemic BINAP (0.042 g, 0.0676 mmol) and the resulting solution was heated at reflux for 2 hours. The resulting solution was cooled and filtered through Celite, which was rinsed with EtOAc. The filtrate was washed with brine (3×30 mL) and concentrated under reduced pressure. The resulting residue was chromatographed over silica gel (0% to 5% CH₃OH in CH₂Cl₂ with 0.01% NH₄OH) to give methyl 2-((3aR,5r,6aS)-5-(2-(trifluoromethyl)phenyl)octahydrocyclopenta[c]pyrrole-2-carboxamido)nicotinate as a light orange film (46 mg, 31%): ¹H NMR (300 MHz, DMSO-d₆) δ 10.41 (br s, 1H), 8.69 (dd, J=4.8, 1.8 Hz, 1H), 8.32 (dd, J=7.8, 1.8 Hz, 1H), 7.61 (d, J=7.8 Hz, 1H), 7.57-7.47 (m, 2H), 7.31-7.27 (m, 1H), 7.00 (dd, J=7.8, 4.8 Hz, 1H), 3.95 (s, 3H), 3.84-3.74 (m, 2H), 3.68-3.60 (m, 2H), 3.58-3.43 (m, 1H), 2.95-2.83 (m, 2H), 2.43-2.32 (m, 2H), 1.72-1.57 (m, 2H); MS (ESI+) m/z 434 [M+H]⁺.

Step C: To a solution of methyl 2-((3aR,5R,6aS)-5-(2-(trifluoromethyl)phenyl)octahydrocyclopenta[c]pyrrole-2-carboxamido)nicotinate (0.039 g, 0.090 mmol) in THF (4.0 mL) and CH₃OH (1.9 mL) was added a solution of LiOH.H₂O (0.037 g, 0.900 mmol) in H₂O (1.1 mL). The mixture stirred for 3 hours, then neutralized with 2 N HCl and extracted with CH₂Cl₂ (4×20 mL). The combined organic extracts were concentrated under reduced pressure and the resulting residue was chromatographed by reverse phase column chromatography (0% to 60% CH₃CN in H₂O) to give 2-((3aR,5R,6aS)-5-(2-(trifluoromethyl)phenyl)octahydrocyclopenta[c]pyrrole-2-carboxamido)nicotinic acid as a white solid (21 mg, 55%): mp 129-133° C.; ¹H NMR (300 MHz, DMSO-d₆) δ 14.00 (br s, 14), 8.45-8.30 (m, 2H), 7.76 (d, J=7.8 Hz, 1H), 7.70-7.60 (m, 2H), 7.45-7.34 (m, 1H), 7.17-7.09 (m, 1H), 3.69-3.58 (m, 2H), 3.56-3.46 (m, 2H), 3.45-3.16 (m, 1H), 2.94-2.76 (m, 2H), 2.31-2.17 (m, 2H), 1.70-1.54 (m, 2H); MS (ESI+) m/z 420 [M+H]⁺.

Example 41: 2-((3aS,6aR)-5-(2-(Trifluoromethyl)phenyl)-1,2,3,3a,4,6a-hexahydrocyclopenta[c]pyrrole-2-carboxamido)benzoic acid (56)

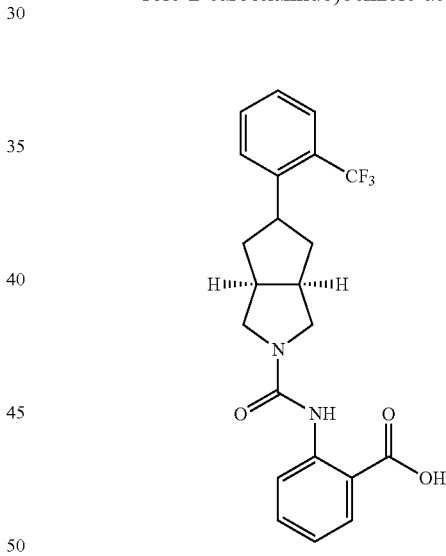

Step A: To a solution of (3aR,6aS)-tert-butyl 5-(2-(trifluoromethyl)phenyl)-3,3a,6,6a-tetrahydrocyclopenta[c]pyrrole-2(1H)-carboxylate (7, 120 mg, 0.34 mmol) in CH₂Cl₂ (3 mL) was added a TFA (3 mL) and the resulting solution was stirred at room temperature for 3 hours. The reaction was concentrated under reduced pressure to provide the TFA salt of (3aS,6aR)-5-(2-(trifluoromethyl)phenyl)-1,2,3,3a,4,6a-hexahydrocyclopenta[c]pyrrole as an off-white solid (146 mg, >99%): ¹H NMR (300 MHz, CDCl₃) δ 9.21 (br s, 1H), 8.18 (br s, 1H), 7.67 (d, J=7.8 Hz, 1H), 7.51-7.34 (m, 3H), 5.57 (s, 1H), 3.82 (br s, 1H), 3.62-3.54 (m, 2H), 3.39-3.09 (m, 4H), 2.62-2.56 (m, 1H).

Step B: A solution of (3aS,6aR)-5-(2-(trifluoromethyl)phenyl)-1,2,3,3a,4,6a-hexahydrocyclopenta[c]pyrrole TFA salt (159 mg, 0.43 mmol), methyl 2-isocyanatobenzoate (91 mg, 0.51 mmol), and Et₃N (0.14 mL, 1.0 mmol) in CH₂Cl₂

(6 mL) stirred for 64 hours at room temperature. After this time, the reaction was diluted with saturated aqueous NaHCO₃ (30 mL) and extracted with dichloromethane (3×10 mL). The combined organic extracts were washed with brine, dried over Na$_2$SO$_4$, filtered, and concentrated under reduced pressure. The resulting residue was chromatographed over silica gel (0% to 100% EtOAc in hexanes) to give methyl 2-((3aS,6aR)-5-(2-(trifluoromethyl)phenyl)-1,2,3,3a,4,6a-hexahydrocyclopenta[c]pyrrole-2-carboxamido)benzoate as an off-white solid (114 mg, 62%): ¹H NMR (300 MHz, CDCl₃) δ 8.66 (dd, J=8.4, 0.9 Hz, 1H), 8.02-7.98 (m, 1H), 7.66-7.64 (m, 1H), 7.54-7.34 (m, 4H), 6.99-6.93 (m, 1H), 5.67 (br s, 1H), 4.02-3.90 (m, 4H), 3.81-3.67 (m, 3H), 3.37-3.31 (m, 1H), 3.16-2.97 (m, 2H), 2.58-2.53 (m, 1H).

Step C: To a stirring solution of methyl 2-((3aS,6aR)-5-(2-(trifluoromethyl)phenyl)-1,2,3,3a,4,6a-hexahydrocyclopenta[c]pyrrole-2-carboxamido)benzoate (114 mg, 0.26 mmol) in CH₂OH (4 mL) and THF (4 mL) was added a solution of LiOH.H₂O (110 mg, 2.62 mmol) in H₂O (2 mL). The mixture stirred for 4 hours at room temperature, was diluted with additional H₂O (10 mL), and acidified with 2 N HCl to pH 6. The resulting solids were collected by filtration and dried under reduced pressure to provide 2-((3aS,6aR)-5-(2-(trifluoromethyl)phenyl)-1,2,3,3a,4,6a-hexahydrocyclopenta[c]pyrrole-2-carboxamido)benzoic acid as a white solid (85 mg, 79%): mp 148-152° C.; ¹H NMR (500 MHz, DMSO-d₆) δ13.50 (br s, 1H), 10.74 (s, 1H), 8.50 (d, J=8.5 Hz, 1H), 7.96-7.94 (m, 1H), 7.73-7.42 (m, 6H), 7.01-6.98 (m, 1H), 5.68 (s, 1H), 3.83-3.79 (m, 1H), 3.64-3.55 (m, 3H), 3.31-2.96 (m, 3H), MS (ESI−) m/z 415 [M−H]⁻.

Example 42: (1H-1,2,3-Triazol-4-yl)((3aR,5R,6aS)-5-(2-(trifluoromethyl)phenyl)hexahydrocyclopenta[c]pyrrol-2(1H)-yl)methanone (57)

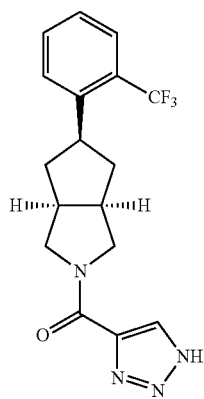

Step A: Following general procedure GP-A1, (3aR,6aS)-5-(2-(trifluoromethyl)phenyl)octahydrocyclopenta[c]pyrrole hydrochloride and 1H-1,2,3-triazole-5-carboxylic acid were converted to (1H-1,2,3-triazol-4-yl)((3aR,5R,6aS)-5-(2-(trifluoromethyl)-phenyl) hexahydrocyclopenta[c]pyrrol-2(1H)-yl)methanone as a white solid (0.039 g, 53%): 163-165° C.; ¹H NMR (300 MHz, DMSO-d₆) δ 15.46 (br s, 1H), 8.32 (br s, 1H), 7.73-7.60 (m, 3H), 7.41-7.36 (m, 1H), 4.04-4.02 (m, 1H), 3.76-3.61 (m, 2H), 3.98-3.96 (m, 1H), 2.89-2.78 (m, 2H), 2.26-2.22 (m, 2H), 1.64-1.53 (m, 2H); MS (ESI+) m/z 351 [M+H]⁺.

Example 43: Methyl 6-methyl-2-((3aR,5r,6aS)-5-(2-(trifluoromethyl)phenyl)hexahydrocyclopenta[c]pyrrol-2(1H)-yl)pyrimidine-4-carboxylate (58)

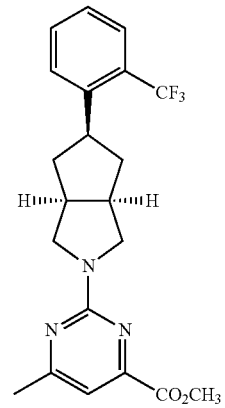 [SMILES: COC(=O)c1cc(C)nc(N2C[C@H]3C[C@@H](c4ccccc4C(F)(F)F)C[C@H]3C2)n1]

The above compound was prepared according to General Procedure GP-K1.

Example 44: Preparation of 6-Methyl-2-((3aR,5R,6aS)-5-(2-(trifluoromethyl)phenyl)hexahydrocyclopenta[c]pyrrol-2(1H)-yl)pyrimidine-4-carboxylic Acid (59)

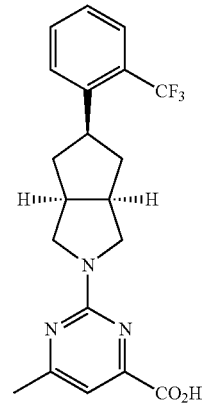

Step A: To a solution of (3aR,5R,6aS)-5-(2-(trifluoromethyl)phenyl)octahydrocyclopenta[c]pyrrole hydrochloride (9, 1.0 g, 3.43 mmol) and Et₃N (1.43 mL, 10.29 mmol) in DMF (50 mL) was added a methyl 2-chloro6-methylpyrimidine-4-carboxylate (0.641 g, 3.43 mmol) and the resulting solution was stirred at 60° C. for 16 hours. The reaction was diluted with H₂O (200 mL) and extracted with EtOAc (3×100 mL). The combined organic extracts were washed with H₂O (3×100 mL), brine (100 mL), dried over Na₂SO₄, filtered, and concentrated under reduced pressure. The resulting residue was chromatographed over silica gel (0% to 30% EtOAc in hexanes) to give methyl 6-methyl-2-((3aR,5R,6aS)-5-(2-(trifluoromethyl)phenyl) hexahydrocyclopenta[c]pyrrol-2(1H)-yl)pyrimidine-4-carboxylate as an off-white solid (1.20 g, 86%): ¹H NMR (300 MHz, CDCl₃) δ 7.61 (m, 1H), 7.58 (m, 2H), 7.23 (m, 1H), 7.05 (s, 1H), 3.95 (s, 3H), 3.82 (m, 4H), 3.59 (m, 1H), 2.92 (m, 2H), 2.44 (s, 3H), 2.40 (m, 2H), 1.69 (m, 2H); MS (ESI+) m/z 406 [M+H]⁺.

Step B: A solution of methyl 6-methyl-2-((3aR,5R,6aS)-5-(2-(trifluoromethyl)phenyl)hexahydrocyclopenta[c]pyrrol-2(1H)-yl)pyrimidine-4-carboxylate (1.2 g, 2.95 mmol) and 2 N NaOH (20 mL) in a 1:1 mixture of CH₃OH/THF (40 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to give 6-methyl-2-((3aR,5r,6aS)-5-(2-(trifluoromethyl)phenyl)hexahydrocyclopenta[c]pyrrol-2 (1H)-yl)pyrimidine-4-carboxylic acid as an off-white solid (1.0 g, 86%): $^1$H NMR (300 MHz, CDCl$_3$) δ 7.62 (m, 1H), 7.53 (m, 2H), 7.27 (m, 2H), 7.13 (s, 1H), 3.84 (m, 4H), 3.83.56 (m, 1H), 2.99 (m, 2H), 2.48 (s, 3H), 2.41 (m, 2H), 1.67 (m, 2H); MS (ESI+) m/z 392 [M+H]$^+$.

Example 45: 5-((3aR,5r,6aS)-5-(2-(trifluoromethyl)phenyl)octahydrocyclopenta[c]pyrrole-2-carboxamido)pyridazine-4-carboxylic acid (60)

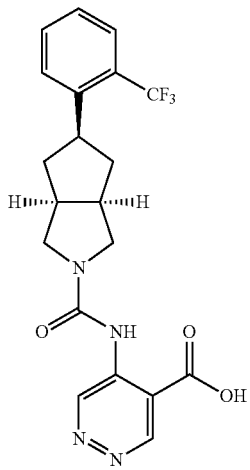 [SMILES: O=C(O)c1cnncc1NC(=O)N1C[C@H]2C[C@@H](c3ccccc3C(F)(F)F)C[C@H]2C1]

The above compound was prepared according to the method described hereinabove for the synthesis of compound 50.

Example 46: 3-((3aR,5r,6aS)-5-(2-(trifluoromethyl)phenyl)octahydrocyclopenta[c]pyrrole-2-carboxamido)pyrazine-2-carboxylic acid (61)

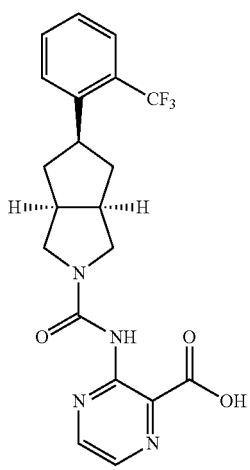

The above compound was prepared according to the method described hereinabove for the synthesis of compound 50.

Example 47: Preparation of 6-Methoxy-2-((3aR,5r,6aS)-5-(2-(trifluoromethyl)phenyl)hexahydrocyclopenta[c]pyrrol-2(1H)-yl)pyrimidine-4-carboxylic Acid (62)

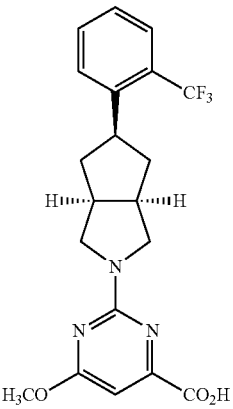

Step A: To a solution of (3aR,5R,6aS)-5-(2-(trifluoromethyl)phenyl)octahydrocyclopenta[c]pyrrole hydrochloride (9, 0.500 g, 1.71 mmol) and Et$_3$N (0.52 mL, 5.14 mmol) in DMF (20 mL) was added methyl 2-chloro-6-methoxypyrimidine-4-carboxylate (0.346 g, 1.71 mmol) and the resulting solution was stirred at 60° C. for 16 hours. The reaction was diluted with H$_2$O (200 mL) and extracted with EtOAc (3×100 mL). The combined organic extracts were washed with H$_2$O (3×100 mL), brine (100 mL), dried over Na$_2$SO$_4$, filtered, and concentrated under reduced pressure. The resulting residue was chromatographed over silica gel (0% to 30% EtOAc in hexanes) to give methyl 6-methoxy-2-((3aR,5r,6aS)-5-(2-(trifluoromethyl)phenyl)hexahydrocyclopenta[c]pyrrol-2(1H)-yl)pyrimidine-4-carboxylate as an off-white solid (0.590 g, 82%): MS (ESI+) m/z 422 [M+H]$^+$.

Step B: A solution of 6-methoxy-2-((3aR,5r,6aS)-5-(2-(trifluoromethyl)phenyl)hexahydrocyclopenta[c]pyrrol-2 (1H)-yl)pyrimidine-4-carboxylate (0.500 g, 1.18 mmol) and 2 N NaOH (10 mL) in a 1:1 mixture of CH$_3$OH/THF (20 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to give 6-methoxy-2-((3aR,5r,6aS)-5-(2-(trifluoromethyl)phenyl)hexahydrocyclopenta[c]pyrrol-2 (1H)-yl)pyrimidine-4-carboxylic acid as an off-white solid (0.415 g, 86%): $^1$H NMR (300 MHz, CDCl$_3$) δ 7.73 (m, 1H), 7.64 (m, 2H), 7.36, (m, 1H), 6.51, (s, 1H), 3.90 (s, 3H), 3.76 (m, 2H), 3.72, (m, 2H), 2.88 (m, 2H), 2.22 (m, 2H), 1.67 (m, 2H); MS (ESI+) m/z 408 [M+H]$^+$.

Example 48: Preparation of 6-Isopropyl-2-((3aR,5r, 6aS)-5-(2-(trifluoromethyl)phenyl)hexahydrocyclopenta[c]pyrrol-2(1H)-yl)pyrimidine-4-carboxylic Acid (63)

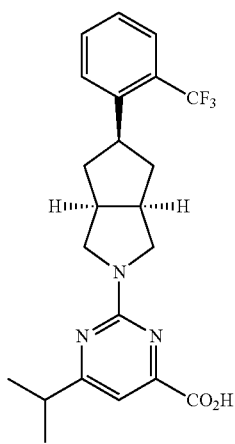 [SMILES: CC(C)c1cc(C(=O)O)nc(N2C[C@H]3C[C@@H](c4ccccc4C(F)(F)F)C[C@H]3C2)n1]

Step A: To a solution of (3aR,5R,6aS)-5-(2-(trifluoromethyl)phenyl)octahydrocyclopenta[c]pyrrole hydrochloride (9, 0.500 g, 1.71 mmol) and Et₃N (0.52 mL, 5.14 mmol) in DMF (20 mL) was added methyl 2-chloro-6-isopropylpyrimidine-4-carboxylate (0.367 g, 1.71 mmol) and the resulting solution was stirred at 60° C. for 16 hours. The reaction was diluted with H₂O (200 mL) and extracted with EtOAc (3×100 mL). The combined organic extracts were washed with H₂O (3×100 mL), brine (100 mL), dried over Na₂SO₄, filtered, and concentrated under reduced pressure. The resulting residue was chromatographed over silica gel (0% to 30% EtOAc in hexanes) to give methyl 6-isopropyl-2-((3aR,5r,6aS)-5-(2-(trifluoromethyl)phenyl) hexahydrocyclopenta[c]pyrrol-2(1H)-yl)pyrimidine-4-carboxylate as an off-white solid (0.555 g, 75%): MS (ESI+) m/z 434 [M+H]⁺.

Step B: A solution of methyl 6-isopropyl-2-((3aR,5r,6aS)-5-(2-(trifluoromethyl)phenyl)hexahydrocyclopenta[c]pyrrol-2(1H)-yl)pyrimidine-4-carboxylate (0.500 g, 1.15 mmol) and 2 N NaOH (10 mL) in a 1:1 mixture of CH₃OH/THF (20 mL) stirred at room temperature for 16 hours. The mixture was carefully neutralized at 0° C. with 2 N HCl and extracted with CH₂Cl₂ (3×10 mL). The combined organic extracts were washed with brine, dried over Na₂SO₄, filtered, and concentrated under reduced pressure. The resulting residue was chromatographed over silica gel (0% to 10% CH₃OH in CH₂Cl₂) to give 6-isopropyl-2-((3aR,5r,6aS)-5-(2-(trifluoromethyl)phenyl) hexahydrocyclopenta[c]pyrrol-2(1H)-yl)pyrimidine-4-carboxylic acid as an off-white solid (0.396 g, 82%): ¹H NMR (300 MHz, DMSO-d₆) δ 13.21 (bs, 1H), 7.72 (m, 1H), 7.65, (m, 2H), 7.39 (m, 2H), 7.01, (s, 1H), 3.75 (m, 2H), 3.71, (m, 2H), 3.42 (m, 1H), 2.90, (m, 3H), 2.49 (m, 2H), 1.66 (m, 2H), 1.23 (s, 6H); MS (ESI+) m/z 420 [M+H]⁺.

Example 49: Preparation of 2-((3aR,5r,6aS)-5-(2-(Trifluoromethyl)phenyl)hexahydrocyclopenta[c]pyrrol-2(1H)-yl)pyrimidine-4-carboxylic Acid (64)

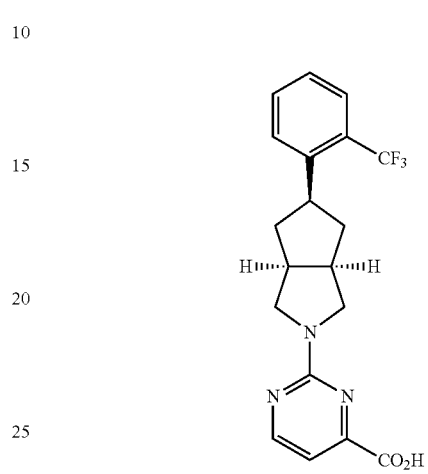

Step A: To a solution of (3aR,5R,6aR)-5-(2-(trifluoromethyl)phenyl)octahydrocyclopenta[c]pyrrole hydrochloride (9, 0.050 g, 0.17 mmol) and Et₃N (0.05 mL, 0.51 mmol) in DMF (10 mL) was added methyl 2-chloropyrimidine-4-carboxylate (0.029 g, 0.17 mmol) and the resulting solution was stirred at 60° C. for 16 hours. The reaction was diluted with H₂O (200 mL) and extracted with EtOAc (3×100 mL). The combined organic extracts were washed with H₂O (3×100 mL), brine (100 mL), dried over Na₂SO₄, filtered, and concentrated under reduced pressure. The resulting residue was chromatographed over silica gel (0% to 30% EtOAc in hexanes) to give methyl 2-((3aR,5r,6aS)-5-(2-(trifluoromethyl)phenyl)hexahydrocyclopenta[c]pyrrol-2 (1H)-yl)pyrimidine-4-carboxylate as an off-white solid (0.055 g, 77%): MS (ESI+) m/z 392 [M+H]⁺.

Step B: A solution of methyl 2-((3aR,5r,6aS)-5-(2-(trifluoromethyl)phenyl)hexahydrocyclopenta[c]pyrrol-2(1H)-yl)pyrimidine-4-carboxylate (0.050 g, 0.12 mmol) and 2 N NaOH (5 mL) in a 1:1 mixture of CH₃OH/THF (10 mL) stirred at room temperature for 16 hours. The mixture was carefully neutralized at 0° C. with 2 N HCl and extracted with CH₂Cl₂ (3×10 mL). The combined organic extracts were washed with brine, dried over Na₂SO₄, filtered, and concentrated under reduced pressure. The resulting residue was chromatographed over silica gel (0% to 10% CH₃OH in CH₂Cl₂) to give 2-((3aR,5r,6aS)-5-(2-(trifluoromethyl)phenyl)hexahydrocyclopenta[c]pyrrol-2(1H)-yl)pyrimidine-4-carboxylic acid as an off-white solid (0.044 g, 92%): ¹H NMR (300 MHz, DMSO-d₆) δ 8.56 (s, 1H), 7.71 (m, 1H), 7.65 (m, 2H), 7.39 (m, 1H), 7.06 (s, 1H), 3.73 (m, 2H), 3.64

(m, 2H), 3.43 (m, 1H), 2.86 (m, 2H), 2.30 (m, 2H), 1.64 (m, 2H); MS (ESI+) m/z 378 [M+H]+.

Example 50: Preparation of 6-(Trifluoromethyl)-2-((3aR,5r,6aS)-5-(2-(trifluoromethyl)phenyl)hexahydrocyclopenta[c]pyrrol-2(1H)-yl)pyrimidine-4-carboxylic Acid (65)

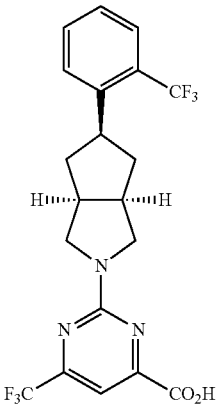 [SMILES: O=C(O)c1cc(C(F)(F)F)nc(N2C[C@H]3C[C@@H](c4ccccc4C(F)(F)F)C[C@H]3C2)n1]

Step A: To a solution of (3aR,5R,6aS)-5-(2-(trifluoromethyl)phenyl)octahydrocyclopenta[c]pyrrole hydrochloride (9, 0.050 g, 0.17 mmol) and Et$_3$N (0.05 mL, 0.51 mmol) in DMF (10 mL) was added methyl 2-chloro-6-(trifluoromethyl)pyrimidine-4-carboxylate (0.041 g, 0.17 mmol) and the resulting solution was stirred at 60° C. for 16 hours. The reaction was diluted with H$_2$O (200 mL) and extracted with EtOAc (3×100 mL). The combined organic extracts were washed with H$_2$O (3×100 mL), brine (100 mL), dried over Na$_2$SO$_4$, filtered, and concentrated under reduced pressure. The resulting residue was chromatographed over silica gel (0% to 30% EtOAc in hexanes) to give methyl 6-(trifluoromethyl)-2-((3aR,5r,6aS)-5-(2-(trifluoromethyl) phenyl) hexahydrocyclopenta[c]pyrrol-2(1H)-yl)pyrimidine-4-carboxylate as an off-white solid (0.066 g, 85%): MS (ESI+) m/z 460 [M+H]+.

Step B: A solution of methyl 6-(trifluoromethyl)-2-((3aR, 5r,6aS)-5-(2-(trifluoromethyl)phenyl)hexahydrocyclopenta [c]pyrrol-2(1H)-yl)pyrimidine-4-carboxylate (0.050 g, 0.13 mmol) and 2 N NaOH (5 mL) in a 1:1 mixture of CH$_3$OH/THF (10 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to give 6-(trifluoromethyl)-2-((3aR,5r, 6aS)-5-(2-(trifluoromethyl)phenyl)hexahydrocyclopenta[c] pyrrol-2(1H)-yl)pyrimidine-4-carboxylic acid as an off-white solid (0.053 g, 92%): $^1$H NMR (500 MHz, DMSO-d$_6$) δ 13.92 (bs, 1H), 7.57 (m, 1H), 7.65 (m, 1H), 7.59 (m, 1H), 7.40 (m, 1H), 7.33 (s, 1H), 3.78 (m, 2H), 3.68 (m, 2H), 3.30 (m, 1H), 2.93 (m, 2H), 2.29 (m, 2H), 1.64 (m, 2H); MS (ESI+) m/z 446 [M+H]+.

Example 51: Preparation of 5-Methyl-2-((3aR,5r, 6aS)-5-(2-(trifluoromethyl)phenyl)hexahydrocyclopenta[c]pyrrol-2(1H-yl)pyrimidine-4-carboxylic Acid (66)

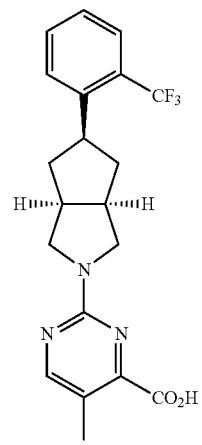

Step A: To a solution of (3aR,5R,6aS)-5-(2-(trifluoromethyl)phenyl)octahydrocyclopenta[c]pyrrole hydrochloride (9, 0.050 g, 0.17 mmol) and Et$_3$M (0.05 mL, 0.51 mmol) in DMF (10 mL) was added methyl 2-chloro-5-methylpyrimidine-4-carboxylate (0.031 g, 0.17 mmol) and the resulting solution was stirred at 60° C. for 16 hours. The reaction was diluted with H$_2$O (200 mL) and extracted with EtOAc (3×100 mL). The combined organic extracts were washed with H$_2$O (3×100 mL), brine (100 mL), dried over Na$_2$SO$_4$, filtered, and concentrated under reduced pressure. The resulting residue was chromatographed over silica gel (0% to 30% EtOAc in hexanes) to give methyl 5-methyl-2-((3aR, 5r,6aS)-5-(2-(trifluoromethyl)phenyl) hexahydrocyclopenta [c]pyrrol-2(1H)-yl)pyrimidine-4-carboxylate as an off-white solid (0.015 g, 22%): MS (ESI+) m/z 406 [M+H]+.

Step B: A solution of methyl 5-methyl-2-((3aR,5r,6aS)-5-(2-(trifluoromethyl)phenyl)hexahydrocyclopenta[c]pyrrol-2(1H)-yl)pyrimidine-4-carboxylate (0.015 g, 0.04 mmol) and 2 N NaOH (5 mL) in a 1:1 mixture of CH$_3$OH/THF (10 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to 5-methyl-2-((3aR,5r,6aS)-5-(2-(trifluoromethyl)phenyl)hexahydrocyclopenta[c]pyrrol-2(1H)-yl)pyrimidine-4-carboxylic acid as an off-white solid (0.013 g, 92%): $^1$H NMR (300 MHz, CD$_3$OD) δ 8.12 (s, 1H), 7.67-7.78 (m, 3H), 7.31 (m, 1H), 3.41-3.61 (m, 5H), 2.91 (m, 2H), 2.34 (m, 4H), 2.15 (s, 3H), 1.67 (m, 2H); MS (ESI+) m/z 392 [M+H]+.

Example 52: Preparation of 5-Fluoro-2-((3aR,5r,6aS)-5-(2-(trifluoromethyl)phenyl)hexahydrocyclopenta[c]pyrrol-2(1H-yl)pyrimidine-4-carboxylic Acid (67)

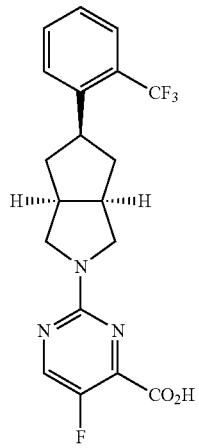 [SMILES: O=C(O)c1nc(N2C[C@H]3C[C@@H](c4ccccc4C(F)(F)F)C[C@H]3C2)ncc1F]

Step A: To a solution of (3aR,5R,6aS)-5-(2-(trifluoromethyl)phenyl)octahydrocyclopenta[c]pyrrole hydrochloride (9, 0.050 g, 0.17 mmol) and Et$_3$N (0.05 mL, 0.51 mmol) in DMF (10 mL) was added methyl 2-chloro-5-fluoropyrimidine-4-carboxylate (0.032 g, 0.17 mmol) and the resulting solution was stirred at 60° C. for 16 hours. The reaction was diluted with H$_2$O (200 mL) and extracted with EtOAc (3×100 mL). The combined organic extracts were washed with H$_2$O (3×100 mL), brine (100 mL), dried over Na$_2$SO$_4$, filtered, and concentrated under reduced pressure. The resulting residue was chromatographed over silica gel (0% to 30% EtOAc in hexanes) to give methyl 5-fluoro-2-((3aR,5r,6aS)-5-(2-(trifluoromethyl)phenyl)hexahydrocyclopenta[c]pyrrol-2(1H)-yl)pyrimidine-4-carboxylate as an off-white solid (0.030 g, 42%): MS (ESI+) m/z 410 [M+H]+.

Step B: A solution of methyl methyl 5-fluoro-2-((3aR,5r,6aS)-5-(2-(trifluoromethyl)phenyl)hexahydrocyclopenta[c]pyrrol-2(1H)-yl)pyrimidine-4-carboxylate (0.030 g, 0.07 mmol) and 2 N NaOH (5 mL) in a 1:1 mixture of CH$_3$OH/THF (10 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to 5-fluoro-2-((3aR,5r,6aS)-5-(2-(trifluoromethyl)phenyl)hexahydrocyclopenta[c]pyrrol-2(1H)-yl)pyrimidine-4-carboxylic acid as an off-white solid (0.026 g, 93%): $^1$H NMR (500 MHz, DMSO-d$_6$) δ 8.15 (s, 1H), 7.65-7.69 (m, 3H), 7.37 (m, 1H), 3.57 (m, 4H), 3.38 (m, 1H), 2.84 (m, 2H), 2.28 (m, 2H), 1.59 (m, 2H); MS (ESI+) m/z 394 [M+H]+.

Example 53: Preparation of 2-((3aR,5r,6aS)-5-(2-(Trifluoromethyl)phenyl)hexahydrocyclopenta[c]pyrrol-2(1H-yl)pyrimidine-5-carboxylic Acid (68)

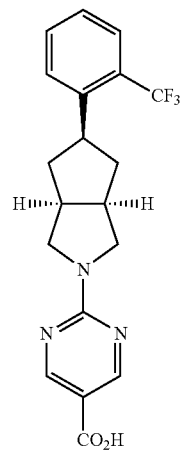

Step A: To a solution of (3aR,5R,6aS)-5-(2-(trifluoromethyl)phenyl)octahydrocyclopenta[c]pyrrole hydrochloride (9, 0.050 g, 0.17 mmol) and Et$_3$N (0.05 mL, 0.51 mmol) in DMF (10 mL) was added methyl 2-chloropyrimidine-5-carboxylate (0.029 g, 0.17 mmol) and the resulting solution was stirred at 60° C. for 16 hours. The reaction was diluted with H$_2$O (200 mL) and extracted with EtOAc (3×100 mL). The combined organic extracts were washed with H$_2$O (3×100 mL), brine (100 mL), dried over Na$_2$SO$_4$, filtered, and concentrated under reduced pressure. The resulting residue was chromatographed over silica gel (0% to 30% EtOAc in hexanes) to give methyl 2-((3aR,5r,6aS)-5-(2-(trifluoromethyl)phenyl)hexahydro-cyclopenta[c]pyrrol-2(1H)-yl)pyrimidine-5-carboxylate as an off-white solid (0.035 g, 52%): MS (ESI+) m/z 392 [M+H]+.

Step B: A solution of methyl 2-((3aR,5r,6aS)-5-(2-(trifluoromethyl)phenyl)hexahydrocyclopenta[c]pyrrol-2(1H)-yl)pyrimidine-5-carboxylate (0.030 g, 0.07 mmol) and 2 N NaOH (5 mL) in a 1:1 mixture of CH$_2$OH/THF (10 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to 2-((3aR,5r,6aS)-5-(2-(trifluoromethyl)phenyl)hexahydrocyclopenta[c]pyrrol-2(1H)-yl)pyrimidine-5-carboxylic acid as an off-white solid (0.026 g, 91%): $^1$H NMR (500 MHz, CDCl$_2$) δ 8.90 (bs, 1H), 7.32-7.51 (m, 3H), 7.21 (m, 3H), 3.41-3.91 (m, 5H), 2.89 (m, 2H), 2.32 (m, 2H), 1.64 (m, 2H); MS (ESI+) m/z 378 [M+H]+.

Example 54: Preparation of 4-Methyl-6-((3aR,5r,6aS)-5-(2-(trifluoromethyl)phenyl)hexahydrocyclopenta[c]pyrrol-2(1H)-yl)picolinic Acid (69)

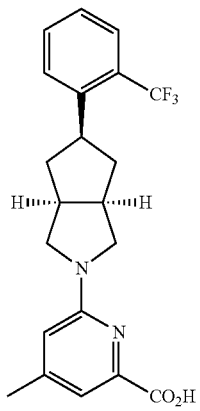

Step A: A mixture of (3aR,5R,6aS)-5-(2-(trifluoromethyl)phenyl)octahydrocyclopenta[c]pyrrole hydrochloride (9, 0.158 g, 0.54 mmol), methyl 6-chloro-4-methylnicotinate (0.100 g, 0.54 mmol), Pd(OAc)$_2$ (0.011 g, 0.05 mmol), Xanphos (0.011 g), and Cs$_2$CO$_2$ (0.050 g, 0.15 mmol) in toluene (10 mL) was stirred at 110° C. for 16 hours. The reaction was diluted with H$_2$O (200 mL) and extracted with EtOAc (3×100 mL). The combined organic extracts were washed with H$_2$O (3×100 mL), brine (100 mL), dried over Na$_2$SO$_4$, filtered, and concentrated under reduced pressure. The resulting residue was chromatographed over silica gel (0% to 30% EtOAc in hexanes) to give methyl 4-methyl-6-((3aR,5r,6aS)-5-(2-(trifluoromethyl)phenyl) hexahydrocyclopenta[c]pyrrol-2(1H)-yl)picolinate as an off-white solid (0.129 g, 59%).

Step B: A solution of methyl 4-methyl-6-((3aR,5r,6aS)-5-(2-(trifluoromethyl)phenyl)hexahydrocyclopenta[c]pyrrol-2(1H)-yl)picolinate (0.129 g, 0.07 mmol) and 2 N NaOH (10 mL) in a 1:1 mixture of CH$_3$OH/THF (20 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to give 4-methyl-6-((3aR,5r,6aS)-5-(2-(trifluoromethyl)phenyl)hexahydrocyclopenta[c]pyrrol-2(1H)-yl)picolinic acid as an off-white solid (0.106 g, 88%): $^1$H NMR (500 MHz, DMSO-d$_6$) δ 12.51 (bs, 1H), 7.71 (m, 3H), 7.61 (m, 1H), 7.14 (s, 1H), 6.62 (s, 1H), 3.55 (m, 4H), 3.34 (m, 4H), 2.88 (m, 2H), 2.29 (m, 5H), 1.62 (m, 2H): MS (ESI+) m/z 391 [M+H]$^+$.

Example 55: Preparation of 2-Methyl-6-((3aR,5r,6aS)-5-(2-(trifluoromethyl)phenyl)hexahydrocyclopenta[c]pyrrol-2(1H)-yl)isonicotinic Acid (70)

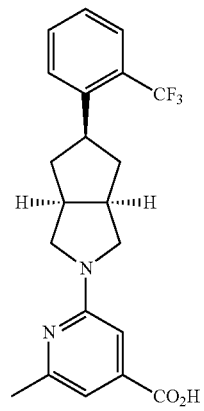

Step A: A mixture of (3aR,5R,6aS)-5-(2-(trifluoromethyl)phenyl)octahydrocyclopenta[c]pyrrole hydrochloride (9, 0.160 g, 0.55 mmol), methyl 2-chloro-6-methylisonicotinate (0.101 g, 0.55 mmol), Pd(OAc)$_2$ (0.011 g, 0.05 mmol), Xanphos (0.011 g), and Cs$_2$CO$_3$ (0.050 g, 0.15 mmol) in toluene (10 mL) was stirred at 110° C. for 16 hours. The reaction was diluted with H$_2$O (200 mL) and extracted with EtOAc (3×100 mL). The combined organic extracts were washed with H$_2$O (3×100 mL), brine (100 mL), dried over Na$_2$SO$_4$, filtered, and concentrated under reduced pressure. The resulting residue was chromatographed over silica gel (0% to 30% EtOAc in hexanes) to give methyl 2-methyl-6-((3aR,5r,6aS)-5-(2-(trifluoromethyl)phenyl) hexahydrocyclopenta[c]pyrrol-2(1H)-yl)isonicotinate as an off-white solid (0.140 g, 63%).

Step B: A solution of methyl 2-methyl-6-((3aR,5r,6aS)-5-(2-(trifluoromethyl)phenyl)hexahydrocyclopenta[c]pyrrol-2(1H)-yl)isonicotinate (0.140 g, 0.08 mmol) and 2 N NaOH (10 mL) in a 1:1 mixture of CH$_3$OH/THF (20 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to give 2-methyl-6-((3aR,5r,6aS)-5-(2-(trifluoromethyl)phenyl)hexahydrocyclopenta[c]pyrrol-2(1H)-yl)isonicotinic acid as an off-white solid (0.124 g, 86%): $^1$H NMR (500 MHz, DMSO-d$_6$) δ 12.81 (bs, 1H), 7.77 (s, 1H), 7.66 (m, 3H), 7.40 (m, 1H), 6.60 (s, 1H), 3.52 (m, 4H), 3.45 (m, 1H), 2.80 (m, 2H), 2.36 (s, 3H), 2.24 (m, 2H), 1.60 (m, 2H); MS (ESI+) m/z 391 [M+H]$^+$.

Example 56: Preparation of 2-((3aR,5r,6aS)-5-(2-(Trifluoromethyl)phenyl)hexahydrocyclopenta[c]pyrrol-2(1H)-yl)nicotinic Acid (71)

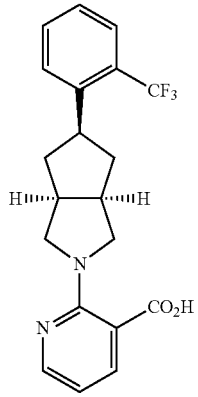 [SMILES: O=C(O)c1cccnc1N1C[C@H]2C[C@@H](c3ccccc3C(F)(F)F)C[C@H]2C1]

Step A: A mixture of (3aR,5R,6aS)-5-(2-(trifluoromethyl)phenyl)octahydrocyclopenta[c]pyrrole hydrochloride (9, 0.160 g, 0.55 mmol), methyl 2-chloronicotinate (0.071 g, 0.41 mmol), Pd(OAc)2 (0.011 g, 0.05 mmol), Xanphos (0.011 g), and Cs$_2$CO$_3$ (0.050 g, 0.15 mmol) in toluene (10 mL) was stirred at 110° C. for 16 hours. The reaction was diluted with H$_2$O (200 mL) and extracted with EtOAc (3×100 mL). The combined organic extracts were washed with H$_2$O (3×100 mL), brine (100 mL), dried over Na$_2$SO$_4$, filtered, and concentrated under reduced pressure. The resulting residue was chromatographed over silica gel (0% to 30% EtOAc in hexanes) to give methyl 2-((3aR,5r,6aS)-5-(2-(trifluoromethyl)phenyl) hexahydrocyclopenta[c]pyrrol-2(1H)-yl)nicotinate as an off-white solid (0.07 g, 33%).

Step B: A solution of 2-((3aR,5r,6aS)-5-(2-(trifluoromethyl)phenyl)hexahydrocyclopenta[c]pyrrol-2(1H)-yl)nicotinate (0.70 g, 0.18 mmol) and 2 N NaOH (10 mL) in a 1:1 mixture of CH$_3$OH/THF (20 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to give 2-((3aR,5r,6aS)-5-(2-(trifluoromethyl)phenyl)hexahydrocyclopenta[c]pyrrol-2(1H)-yl)nicotinic acid as an off-white solid (0.057 g, 85%): $^1$H NMR (500 MHz, DMSO-d$_6$) δ 8.20 (s, 1H), 7.79 (m, 1H), 7.63 (m, 3H), 7.39 (m, 1H), 6.71 (s, 1H), 3.53 (m, 4H), 3.48 (m, 1H), 2.80 (m, 2H), 2.24 (m, 2H), 1.61 (m, 2H): MS (ESI-+) m/z 377 [M+H]$^+$.

Example 57: Preparation of 2-((3aR,5r,6aS)-5-(5-Fluoro-2-(trifluoromethyl)phenyl)hexahydrocyclopenta[c]pyrrol-2(1H)-yl)-6-methylpyrimidine-4-carboxylic Acid (72)

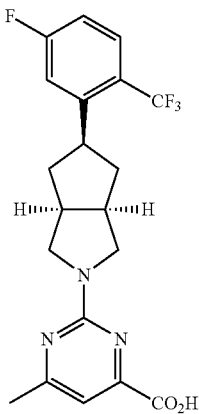

Step A: To an N$_2$ degassed mixture of (3aS,6aS)-tert-butyl 5-(((trifluoromethyl)sulfonyl)oxy)-3,3a,6,6a-tetrahydrocyclopenta[c]pyrrole-2(1H)-carboxylate (6, 5.0 g, 14.0 mmol), (5-fluoro-2-(trifluoromethyl)phenyl)boronic acid (2.91 g, 14.0 mmol), and a 2 M aqueous solution of Na$_2$CO$_3$ (100 mL) in DME (200 mL) was added Pd(PPh$_3$)$_4$ (0.500 g, 1.4 mmol). The mixture was heated at 80° C. for 6 hours, then cooled to room temperature and diluted with H$_2$O (500 mL). The aqueous mixture was extracted with EtOAc (2×200 mL) and the combined organic extracts were washed with H$_2$O (200 mL), brine (200 mL), dried over Na$_2$SO$_4$, filtered, and concentrated under reduced pressure. The residue was purified by flash column chromatography (Isco CombiFlash Rf unit, 330 g Redisep column, 0% to 10% EtOAc in hexanes) to give (3aR,6aS)-tert-butyl 5-(5-fluoro-2-(trifluoromethyl)phenyl)-3,3a,6,6a-tetrahydrocyclopenta[c]pyrrole-2(1H)-carboxylate as a clear, viscous oil (4.88 g, 94%).

Step B: A mixture of 5-(5-fluoro-2-(trifluoromethyl)phenyl)-3,3a,6,6a-tetrahydrocyclopenta[c]pyrrole-2(1H)-carboxylate (4.8 g, 12.9 mmol) and 10% Pd/C (1.57 g, wet, 10% w/w) in CH$_3$OH (50 mL) was subjected to an atmosphere of H$_2$ gas (40 psi) using a Parr Shaker apparatus for 16 hours at room temperature. The mixture was filtered through Celite and the filtrate was concentrated under reduced pressure. The resulting residue was purified by flash column chromatography (Isco CombiFlash Rf unit, 40 g Redisep column, 0% to 30% EtOAc in hexanes) to give (3aR,5r,6aS)-tert-butyl 5-(5-fluoro-2-(trifluoromethyl)phenyl)hexahydrocyclopenta[c]pyrrole-2(1H)-carboxylate as a clear, viscous oil (4.5 g, 95%).

Step C: To a 0° C. cooled solution of 3aR,5r,6aS)-tert-butyl 5-(5-fluoro-2-(trifluoromethyl)phenyl)hexahydrocyclopenta[c]pyrrole-2(1H)-carboxylate (4.50 g, 12.1 mmol) in CH$_2$Cl$_2$ (60 mL) was added a 2 M HCl solution in Et$_2$O (100 mL), and the mixture was allowed to stir at room temperature for 24 hours. The mixture was diluted with Et$_2$O (200 mL) and the precipitated product was filtered to give (3aR,5r,6aS)-5-(5-fluoro-2-(trifluoromethyl)phenyl)octahydro-cyclopenta[c]pyrrole hydrochloride as a white solid (3.45 g, 92%): MS (ESI+) m/z 274 [M+H]$^+$.

Step D: To a solution of (3aR,5r,6aS)-5-(5-fluoro-2-(trifluoromethyl)phenyl)octahydrocyclopenta[c]pyrrole hydrochloride (1.0 g, 3.23 mmol) and Et$_3$N (1.43 mL, 10.29 mmol) in DMF (50 mL) was added a methyl 2-chloropyrimidine-4-carboxylate (0.641 g, 3.43 mmol) and the resulting solution was stirred at 60° C. for 16 hours. The reaction was diluted with H$_2$O (200 mL) and extracted with EtOAc (3×100 mL). The combined organic extracts were washed with H$_2$O (3×100 mL), brine (100 mL), dried over Na$_2$SO$_4$, filtered, and concentrated under reduced pressure. The resulting residue was chromatographed over silica gel (0% to 30% EtOAc in hexanes) to give methyl 2-((3aR,5r,6aS)-5-(5-fluoro-2-(trifluoromethyl)phenyl)hexahydro-cyclopenta[c]pyrrol-2(1H)-yl)-6-methylpyrimidine-4-carboxylate as an off-white solid (1.14 g, 84%): MS (ESI+) m/z 424 [M+H]$^+$.

Step E: A solution of methyl 2-((3aR,5r,6aS)-5-(5-fluoro-2-(trifluoromethyl)phenyl)hexahydrocyclopenta[c]pyrrol-2(1H)-yl)-6-methylpyrimidine-4-carboxylate (1.0 g, 2.36 mmol) and 2 N NaOH (20 mL) in a 1:1 mixture of CH$_3$OH/THF (40 mL) stirred at room temperature for 16 hours. The mixture was carefully neutralized at 0° C. with 2 N HCl and extracted with CH$_2$Cl$_2$ (3×10 mL). The combined organic extracts were washed with brine, dried over Na$_2$SO$_4$, filtered, and concentrated under reduced pressure. The resulting residue was chromatographed over silica gel (0% to 10% CH$_3$OH in CH$_2$Cl$_2$) to give 2-((3aR,5r,6aS)-5-

(5-fluoro-2-(trifluoromethyl)phenyl)hexahydrocyclopenta[c]pyrrol-2(1H)-yl)-6-methylpyrimidine-4-carboxylic acid as an off-white solid (0.831 g, 86%): $^1$H NMR (500 MHz, DMSO-$d_6$) δ 7.74 (m, 1H), 7.54 (m, 1H), 7.24 (m, 1H), 6.63 (s, 1H), 3.63 (m, 4H), 3.58 (m, 1H), 2.82 (m, 2H), 2.36 (m, 2H), 2.27 (s, 3H), 1.61 (m, 2H); MS (ESI+) m/z 410 $[M+H]^+$.

Example 58: Preparation of 6-Methyl-4-((3aR,5r,6aS)-5-(2-(trifluoromethyl)phenyl)octahydrocyclopenta[c]pyrrole-2-carboxamido)nicotinic Acid (73)

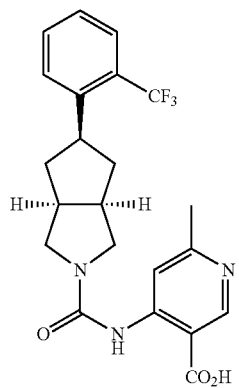

Step A: To a solution of triphosgene (0.148 g, 0.500 mmol) in $CH_2Cl_2$ (3.0 mL) under $N_2$, cooled to −78° C., was slowly added pyridine (0.158 g, 2.00 mmol) and the resulting solution was stirred at −78° C. for 10 minutes. A solution of (3aR,5r,6aS)-5-(2-(trifluoromethyl)phenyl)octahydrocyclopenta[c]pyrrole hydrochloride (0.292 g, 1.00 mmol) in $CH_2Cl_2$ (2.0 mL) was added and the resulting solution was stirred at −78° C. for 30 minutes. The solution was warmed to room temperature and stirred for 2 h. The reaction was diluted with 1 N HCl (8 mL) and extracted with $CH_2Cl_2$ (3×30 mL). The combined organic extracts were washed with saturated $NaHCO_3$ solution (40 mL) and concentrated under reduced pressure. The resulting residue was chromatographed over silica gel (0% to 30% EtOAc in hexanes) to give (3aR,5r,6aS)-5-(2-(trifluoromethyl)phenyl)hexahydrocyclopenta[c]pyrrole-2(1H)-carbonyl chloride as a light yellow solid (170 mg, 53%): $^1$H NMR (300 MHz, DMSO-$d_6$) δ 7.81 (d, J=8.4 Hz, 1H), 7.69-7.60 (m, 2H), 7.44-7.35 (m, 1H), 3.85-3.75 (m, 1H), 3.71-3.54 (m, 2H), 3.51-3.43 (m, 1H), 3.42-3.36 (m, 1H), 2.91-2.75 (m, 2H), 2.25-2.12 (m, 2H), 1.70-1.55 (m, 2H); MS (ESI+) m/z 318 $[M+H]^+$.

Step B: To a solution of (3aR,5R,6aS)-5-(2-(trifluoromethyl)phenyl)hexahydrocyclopenta[c]pyrrole-2(1H)-carbonyl chloride (0.170 g, 0.536 mmol) in THF (3.0 mL) was added i-$Pr_2$NEt (0.064 g, 0.536 mmol) and methyl 4-amino-6-methylnicotinate (0.080 g, 0.536 mmol) and the resulting solution was heated at 68° C. for 4 hours. The reaction was diluted with $H_2O$ (20 mL) and extracted with EtOAc (3×30 mL). The combined organic extracts were concentrated under reduced pressure. The resulting residue was chromatographed over silica gel (0 to 5% $CH_3OH$ in $CH_2Cl_2$ with 0.1% $NH_4OH$) to give methyl 6-methyl-4-((3aR,5r,6aS)-5-(2-(trifluoromethyl)phenyl) octahydrocyclopenta[c] pyrrole-2-carboxamido)nicotinate as a white solid (142 mg, 61%): MS (ESI+) m/z 435 $[M+H]^+$.

Step C: To a solution of methyl 6-methyl-4-((3aR,5r,6aS)-5-(2-(trifluoromethyl)phenyl)octahydrocyclopenta[c]pyrrole-2-carboxamido)nicotinate (0.138 g, 0.311 mmol) in THF (6.2 mL) and $CH_3OH$ (3.2 mL) was added a solution of $LiOH.H_2O$ (0.130 g, 3.11 mmol) in $H_2O$ (1.6 mL). The mixture stirred for 3 hours, then acidified to pH 4 with 2 N HCl, and diluted with $H_2O$ (50 mL). The resulting solids were collected by filtration and dried to provide 6-methyl-4-((3aR,5r,6aS)-5-(2-trifluoromethyl)phenyl)octahydrocyclopenta[c]pyrrole-2-carboxamido)nicotinic acid as a light yellow solid (127 mg, 94%): $^1$H NMR (300 MHz, DMSO-$d_6$) δ 7.77 (m, 4H), 7.41 (m, 2H), 3.68 (m, 2H), 3.25-3.59 (m, 7H), 2.78 (m, 2H), 2.21 (m, 2H), 1.66 (m, 2H); MS (ESI+) m/z 434 $[M+H]^+$.

Example 59: Preparation of 5,6-Dimethyl-2-((3aR,5r,6aS)-5-(2-(trifluoromethyl)phenyl)hexahydrocyclopenta[c]pyrrol-2(1H)-yl)pyrimidine-4-carboxylic Acid (74)

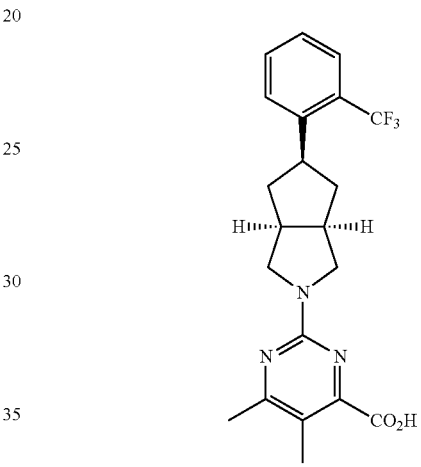

Step A: To a solution of (3aR,5R,6aS)-5-(2-(trifluoromethyl)phenyl)octahydrocyclopenta[c]pyrrole hydrochloride (9, 0.050 g, 0.17 mmol) and $Et_3N$ (0.05 mL, 0.51 mmol) in DMF (10 mL) was added methyl 2-chloro-5,6-dimethylpyrimidine-4-carboxylate (0.037 g, 0.17 mmol) and the resulting solution was stirred at 60° C. for 16 hours. The reaction was diluted with $H_2O$ (200 mL) and extracted with EtOAc (3×100 mL). The combined organic extracts were washed with $H_2O$ (3×100 mL), brine (100 mL), dried over $Na_2SO_4$, filtered, and concentrated under reduced pressure. The resulting residue was chromatographed over silica gel (0% to 30% EtOAc in hexanes) to give methyl 5,6-dimethyl-2-((3aR,5r,6aS)-5-(2-(trifluoromethyl)phenyl) hexahydrocyclopenta[c]pyrrol-2(1H)-yl)pyrimidine-4-carboxylate as an off-white solid (0.026 g, 32%): MS (ESI+) m/z 420 $[M+H]^+$.

Step B: A solution of methyl 5,6-dimethyl-2-((3aR,5r,6aS)-5-(2-(trifluoromethyl)phenyl)hexahydrocyclopenta[c]pyrrol-2(1H)-yl)pyrimidine-4-carboxylate (0.020 g, 0.05 mmol) and 2 N NaOH (5 mL) in a 1:1 mixture of $CH_3OH$/THF (10 mL) stirred at room temperature for 16 hours. The mixture was carefully neutralized at 0° C. with 2 N HCl and extracted with $CH_2Cl_2$ (3×10 mL). The combined organic extracts were washed with brine, dried over $Na_2SO_4$, filtered, and concentrated under reduced pressure. The resulting residue was chromatographed over silica gel (0% to 10% $CH_4OH$ in $CH_2Cl_2$) to methyl 5,6-dimethyl-2-((3aR,5r,6aS)-5-(2-(trifluoromethyl)phenyl)hexahydrocyclopenta[c] pyrrol-2(1H)-yl)pyrimidine-4-carboxylate as an off-white solid (0.017 g, 92%): $^1$H NMR (300 MHz, DMSO-$d_6$) δ 7.72

(m, 3H), 7.32 (m, 1H), 3.62 (m, 4H), 2.89 (m, 2H), 2.43 (s, 3H), 2.23 (m, 2H), 2.09 (s, 3H), 1.66 (m, 2H); MS (ESI+) m/z 406 [M+H]$^+$.

Example 60: RPB4 Binding of Octahydrocyclopentapyrroles Compounds

Various compounds listed in Examples 1-46 (compounds 17-24 and 27-39 and 41-59) were tested in two in vitro assays, RBP4 binding (SPA) and retinol-dependent RBP4-TTR interaction (HTRF) (FIG. 8-9). The compounds binded to RBP4 and/or antagonized retinol-dependent RBP4-TTR interaction. This activity indicates that the compounds reduce the levels of serum RBP4 and retinol.

Additional compounds listed in Examples 47-59 (compounds 62-74) were tested in two in vitro assays, RBP4 binding (SPA) and retinol-dependent RBP4-TTR interaction (HTRF). The compounds binded to RBP4 and/or antagonized retinol-dependent RBP4-TTR interaction (see Table 1 below). This activity indicates that the compounds reduce the levels of serum RBP4 and retinol.

TABLE 1

| Compound # | SPA binding assay for RBP4: IC$_{50}$ (nM) | HTRF assay for antagonists of RBP4-TTR interaction: IC$_{50}$ (nM) |
|---|---|---|
| 62 | 14.3 | 86.7 |
| 63 | 157.9 | 202.8 |
| 64 | 27.2 | 79.6 |
| 65 | 9.5 | 88.0 |
| 66 | 90.0 | 595.7 |
| 67 | 25.9 | 276.5 |
| 68 | 171.5 | 1860 |
| 69 | 14.0 | 294.9 |
| 70 | 53.2 | 228.8 |
| 71 | 43.8 | 381.7 |
| 72 | 54.3 | 49.2 |
| 73 | 23.9 | 235.2 |
| 74 | 48.7 | 123.1 |

Example 61: RPB4 Binding of Additional Octahydrocyclopentapyrroles Compounds An additional aspect of the invention provides analogs of the compounds of Examples 1-46 that are active as RBP4 antagonists. The analogs of Examples 1-46 described herein analogously bind to RBP4 and antagonize retinol-dependent RBP4-TTR interaction.

Additional octahydrocyclopentapyrroles compounds, which are analogs of those described in Example 1-46, are tested in two in vitro assays, RBP4 binding (SPA) and retinol-dependent RBP4-TTR interaction (HTRF). These compounds bind to RBP4 and antagonize retinol-dependent RBP4-TTR interaction. This activity indicates that the compounds reduce the level of serum RBP4 and retinol.

Example 62: Efficacy in a Mammalian Model

The effectiveness of the compounds listed in Example 1-46 are tested in wild-type and Abca4-/- mice. The Abca4-/- mouse model manifests accelerated accumulation of lipofuscin in the RPE and is considered a pre-clinical efficacy model for a drug reducing lipofuscin accumulation. Compounds are orally dosed for 3 weeks at 30 mg/kg. There is a reduction in the serum RBP4 level in treated animals. The levels of A2E/isoA2E and other bisretinoids are reduced in treated mice. The levels of A2-DHP-PE and atRAL di-PE are also reduced.

The effectiveness of the compounds listed in Example 47-59 are tested in wild-type and Abca4-/- mice. The Abca4-/- mouse model manifests accelerated accumulation of lipofuscin in the RPE and is considered a pre-clinical efficacy model for a drug reducing lipofuscin accumulation. Compounds are orally dosed for 3 weeks at 30 mg/kg. There is a reduction in the serum RBP4 level in treated animals. The levels of A2E/isoA2E and other bisretinoids are reduced in treated mice. The levels of A2-DHP-PE and atRAL di-PE are also reduced.

The effectiveness of additional octahydrocyclopentapyrroles compounds, which are analogs of those described in Examples 1-46, are tested in wild-type and Abca4-/- mice. The Abca4-/- mouse model manifests accelerated accumulation of lipofuscin in the RPE and is considered a preclinical efficacy model for a drug reducing lipofuscin accumulation. Compounds are orally dosed for 3 weeks at 30 mg/kg. There is s reduction in the serum RBP4 level in treated animals. The levels of A2E/isoA2E and other bisretinoids are reduced in treated mice. The levels of A2-DHP-PE and atRAL di-PE are also reduced.

Discussion

Age-related macular degeneration (AMD) is the leading cause of blindness in developed countries. Its prevalence is higher than that of Alzheimer's disease. There is no treatment for the most common dry form of AMD. Dry AMD is triggered by abnormalities in the retinal pigment epithelium (RPE) that lies beneath the photoreceptor cells and provides critical metabolic support to these light-sensing cells. RPE dysfunction induces secondary degeneration of photoreceptors in the central part of the retina called the macula. Experimental data indicate that high levels of lipofuscin induce degeneration of RPE and the adjacent photoreceptors in atrophic AMD retinas. In addition to AMD, dramatic accumulation of lipofuscin is the hallmark of Stargardt's disease (STGD), an inherited form of juvenile onset macular degeneration. The major cytotoxic component of RPE lipofuscin is a pyridinium bisretinoid A2E. A2E formation occurs in the retina in a non-enzymatic manner and can be considered a by-product of a properly functioning visual cycle. Given the established cytotoxic affects of A2E on RPE and photoreceptors, inhibition of A2E formation could lead to delay in visual loss in patients with dry AMD and STGD. It was suggested that small molecule visual cycle inhibitors may reduce the formation of A2E in the retina and prolong RPE and photoreceptor survival in patients with dry AMD and STGD. Rates of the visual cycle and A2E production in the retina depend on the influx of all-trans retinol from serum to the RPE. RPE retinol uptake depends on serum retinol concentrations. Pharmacological downregulation of serum retinol is a valid treatment strategy for dry AMD and STGD. Serum retinol is maintained in circulation as a tertiary complex with retinol-binding protein (RBP4) and transthyretin (TTR). Without interacting with TTR, the RBP4-retinol complex is rapidly cleared due to glomerular filtration. Retinol binding to RBP4 is required for formation of the RBP4-TTR complex; apo-RBP4 does not interact with TTR. Importantly, the retinol-binding site on RBP4 is sterically proximal to the interface mediating the RBP4-TTR interaction. Without wishing to be bound by any scientific theory, the data herein show that small molecule RBP4 antagonists displacing retinol from RBP4 and disrupting the RBP4-TTR interaction will reduce serum retinol concentration, inhibit retinol uptake into the retina and act as indirect visual cycle inhibitors reducing formation of cytotoxic A2E.

Serum RBP4 as a Drug Target for Pharmacological Inhibition of the Visual Cycle

Figure 4:
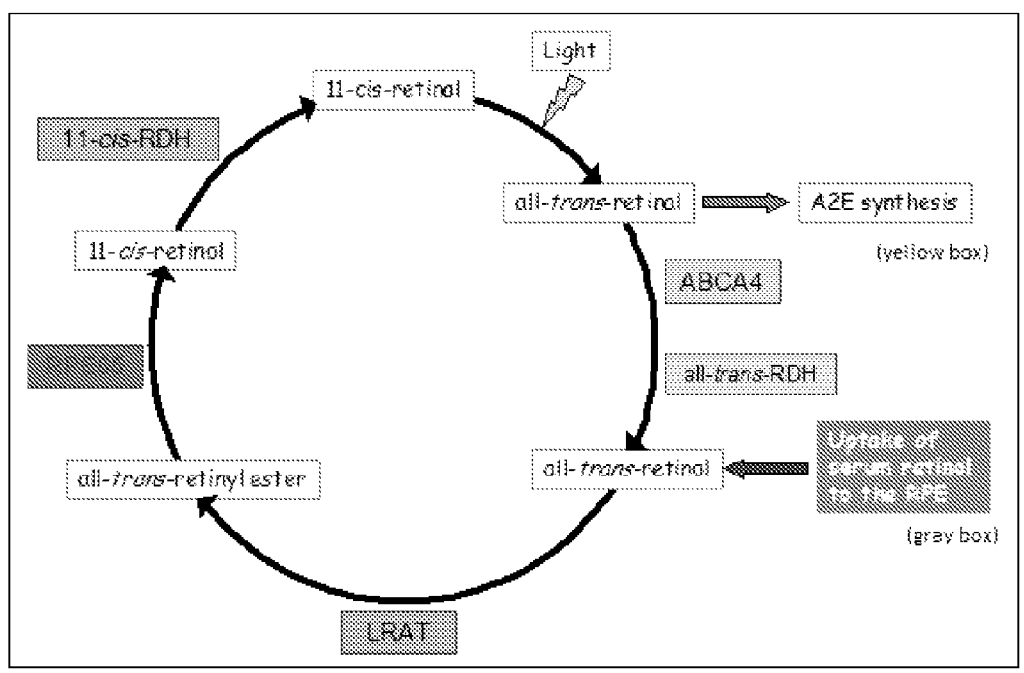
FIG. 4. Visual cycle and biosynthesis of A2E. A2E biosynthesis begins when a portion of all-trans-retinal escapes the visual cycle (yellow box) and non-enzymatically reacts with phosphatidyl-ethanolamine forming the A2E precursor, A2-PE. Uptake of serum retinol to the RPE (gray box) fuels the cycle.
Figure 5:
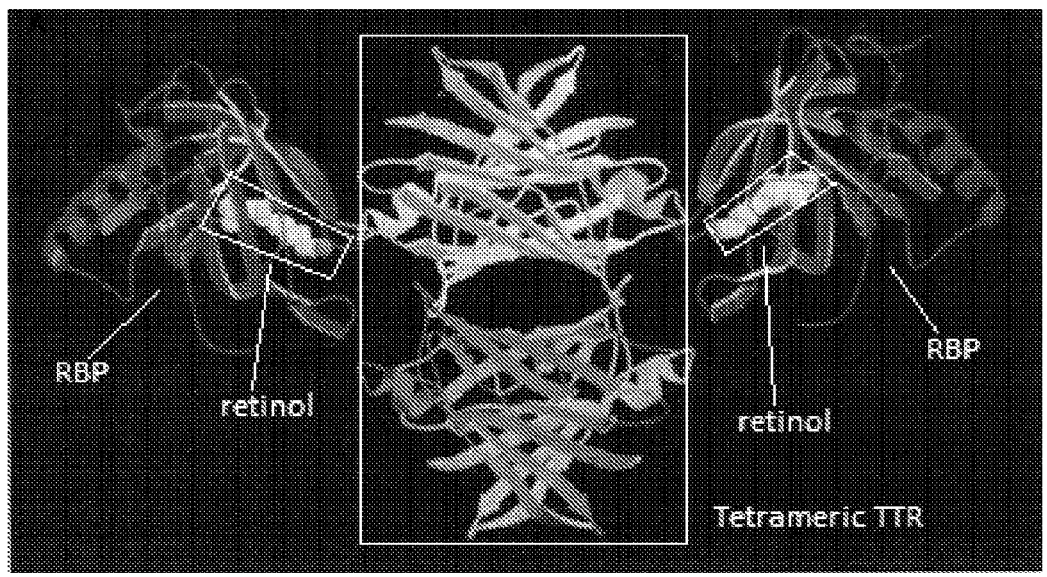
FIG. 5. Three-dimensional structure of the RBP4-TTR-retinol complex. Tetrameic TTR is shown in blue, light blue, green and yellow (large boxed region). RBP is shown in red (unboxed region) and retinol is shown in gray (small boxed region) (28).

As rates of the visual cycle and A2E production in the retina depend on the influx of all-trans retinol from serum to the RPE (FIG. 4), it has been suggested that partial pharmacological down-regulation of serum retinol may represent a target area in dry AMD treatment (11). Serum retinol is bound to retinol-binding protein (RBP4) and maintained in circulation as a tertiary complex with RBP4 and transthyretin (TTR) (FIG. 5). Without interacting with TTR, the RBP4-retinol complex is rapidly cleared from circulation due to glomerular filtration. Additionally, formation of the RBP4-TTR-retinol complex is required for receptor-mediated all-trans retinol uptake from serum to the retina.

Without wishing to be bound by any scientific theory, visual cycle inhibitors may reduce the formation of toxic bisretinoids and prolong RPE and photoreceptor survival in dry AMD. Rates of the visual cycle and A2E production depend on the influx of all-trans retinol from serum to the RPE. Formation of the tertiary retinol-binding protein 4 (RBP4)-transthyretin (TTR)-retinol complex in serum is required for retinol uptake from circulation to the RPE. Retinol-binding site on RBP4 is sterically proximal to the interface mediating the RBP4-TTR interaction. RBP4 antagonists that compete with serum retinol for binding to RBP4 while blocking the RBP4-TTR interaction would reduce serum retinol, slow down the visual cycle, and inhibit formation of cytotoxic bisretinoids.

RBP4 represents an attractive drug target for indirect pharmacological inhibition of the visual cycle and A2E formation. The retinol-binding site on RBP4 is sterically proximal to the interface mediating the RBP4-TTR interaction. Retinol antagonists competing with serum retinol for binding to RBP4 while blocking the RBP4-TTR interaction would reduce serum RBP4 and retinol levels which would lead to reduced uptake of retinol to the retina. The outcome would be visual cycle inhibition with subsequent reduction in the A2E synthesis.

Figure 6:
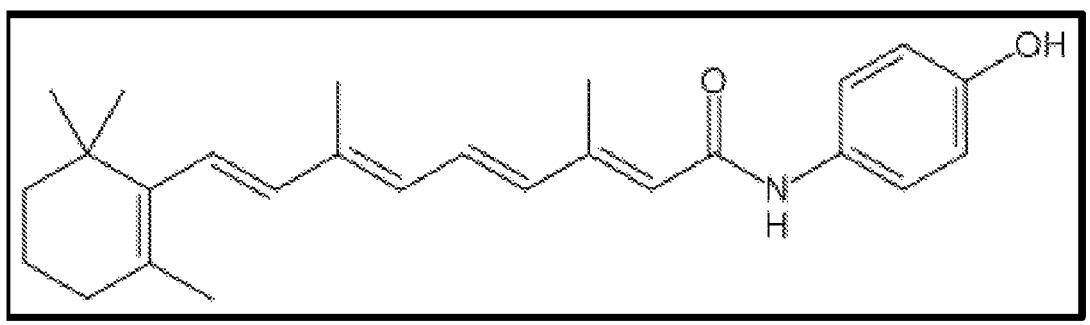
FIG. 6. Structure of fenretinide, [N-(4-hydroxy-phenyl) retinamide, 4HRP], a retinoid RBP4 antagonist.

A synthetic retinoid called fenretinide [N-(4-hydroxyphenyl)retinamide, 4HRP] (FIG. 6) previously considered as a cancer treatment (29) was found to bind to RBP4, displace all-trans retinol from RBP4 (13), and disrupt the RBP4-TTR interaction (13,14).

Fenretinide was shown to reduce serum RBP4 and retinol (15), inhibit ocular all-trans retinal uptake and slow down the visual cycle (11). Importantly, fenretinide administration reduced A2E production in an animal model of excessive bisretinoid accumulation, Abca4−/− mice (11). Pre-clinical experiments with fenretinide validated RBP4 as a drug target for dry AMD. However, fenretinide is non-selective and toxic. Independent of its activity as an antagonist of retinol binding to RBP4, fenretinide is an extremely active inducer of apoptosis in many cell types (16-19), including the retinal pigment epithelium cells (20). It has been suggested that fenretinide's adverse effects are mediated by its action as a ligand of a nuclear receptor RAR (21-24). Additionally, similar to other retinoids, fenretinide is reported to stimulate formation of hemangiosarcomas in mice. Moreover, fenretinide is teratogenic, which makes its use problematic in Stargardt disease patients of childbearing age.

As fenretinide's safety profile may be incompatible with long-term dosing in individuals with blinding but non-life threatening conditions, identification of new classes of RBP4 antagonists is of significant importance. The compounds of the present invention displace retinol from RBP4, disrupt retinol-induced RBP4-TTR interaction, and reduce serum REBP4 levels. The compounds of the present invention inhibit bisretinoid accumulation in the Abca4−/− mouse model of excessive lipofuscinogenesis which indicates usefulness a treatment for dry AMD and Stargardt disease.

The present invention relates to small molecules for treatment of macular degeneration and Stargardt Disease. Disclosed herein is the ophthalmic use of the small molecule as non-retinoid RBP4 antagonists. The compounds of Examples 1-46 have been shown to bind RBP4 in vitro and/or to antagonize RBP4-TTR interaction in vitro at biologically significant concentrations. Additional compounds described herein, which are analogs of Examples 1-46 analogously bind RBP4 in vitro and antagonize RBP4-TTR interaction in vitro at biologically significant concentrations.

Currently, there is no FDA-approved treatment for dry AMD or Stargardt disease, which affects millions of patients. An over the counter, non FDA-approved cocktail of antioxidant vitamins and zinc (AREDS formula) is claimed to be beneficial in a subset of dry AMD patients. There are no treatments for Stargardt disease. The present invention identified non-retinoid RBP4 antagonists that are useful for the treatment of dry AMD and other conditions characterized by excessive accumulation of lipofuscin. Without wishing to be bound by any scientific theory, as accumulation of lipofuscin seems to be a direct cause of RPE and photoreceoptor demise in AMD and STGD retina, the compounds described herein are disease-modifying agents since they directly address the root cause of these diseases. The present invention provides novel methods of treatment that will preserve vision in AMD and Stargardt disease patients, and patients' suffering from conditions characterized by excessive accumulation of lipofuscin.

REFERENCES

1. Petrukhin K. New therapeutic targets in atrophic age-related macular degeneration. Expert Opin. Ther. Targets, 2007, 11(5): 625-639
2. C. Delori, D. G. Goger and C. K. Dorey, Age-related accumulation and spatial distribution of lipofuscin in RPE of normal subjects. Investigative Ophthalmology and Visual Science 42 (2001), pp. 1855-1866
3. F. C. Delori, RPE lipofuscin in aging and age-related macular degeneration. In: G. Coscas and F. C. Piccolino, Editors, Retinal Pigment Epithelium and Macular Disease (Documenta Ophthalmologica) vol. 62, Kluwer Academic Publishers, Dordrecht, The Netherlands (1995), pp. 37-45.
4. C. K. Dorey, G. Wu, D. Ebenstein, A. Garsd and J. J. Waiter, Cell loss in the aging retina. Relationship to lipofuscin accumulation and macular degeneration. Investigative Ophthalmology and Visual Science 30 (1989), pp. 1691-1699.
5. L. Feeney-Burns, E. S. Hilderbrand and S. Eldridge, Aging human RPE: morphometric analysis of macular, equatorial, and peripheral cells. Investigative Ophthalmology and Visual Science 25 (1984), pp. 195-200.
6. F. G. Holz, C. Bellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
7. E. G. Holz, C. Bellmann, M. Margaritidis, F. Schutt, T. P. Otto and H. E. Volcker, Patterns of increased in vivo fundus autofluorescence in the junctional zone of geographic atrophy of the retinal pigment epithelium associated with age-related macular degeneration. Graefe's Archive for Clinical and Experimental Ophthalmology 237 (1999), pp. 145-152.
7. A. von Rückmann, F. W. Fitzke and A. C. Bird, Fundus autofluorescence in age-related macular disease imaged with a laser scanning ophthalmoscope. Investigative Ophthalmology and Visual Science 38 (1997), pp. 478-486.
9. F. G. Holz, C. Bellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
10. Sparrow J R, Fishkin N, Zhou J, Cai B, Jang Y P, Krane S, Itagaki Y, Nakanishi K. A2E, a by product of the visual cycle. Vision Res. 2003 December; 43(28):2983-90
11. Radu R A, Han Y, Bui T V, Nusinowitz S, Bok D, Lichter J, Widder K, Travis G H, Mata N L. Reductions in serum vitamin A arrest accumulation of toxic retinal fluorophores: a potential therapy for treatment of lipofuscin-based retinal diseases. Invest Ophthalmol Vis Sci. 2005 December; 46(12):4393-401
12. Motani A, Wang Z, Conn M, Siegler K, Zhang Y, Liu Q, Johnstone S, Xu H, Thibault S, Wang Y, Fan P, Connors R, Le H, Xu G, Walker N, Shan B, Coward P. Identification and characterization of a non-retinoid ligand for retinol-binding protein 4 which lowers serum retinol-binding protein 4 levels in vivo. J Biol Chem. 2009 Mar. 20; 284(12):7673-80.
13. Berni R, Formelli F. In vitro interaction of fenretinide with plasma retinol-binding protein and its functional consequences. FEBS Lett. 1992 Aug. 10; 308(1):43-5.
14. Schaffer E M, Ritter S J, Smith J E. N-(4-hydroxyphenyl)retinamide (fenretinide) induces retinol-binding protein secretion from liver and accumulation in the kidneys in rats. J Nutr. 1993 September; 123(9):1497-503
15. Adams W R, Smith J E, Green M H. Effects of N-(4-hydroxyphenyl)retinamide on vitamin A metabolism in rats. Proc Soc Exp Biol Med, 1995 February; 208(2):178-85.
16. Puduvalli V K, Saito Y, Xu R, Kouraklis G P, Levin V A, Kyritsis A P. Fenretinide activates caspases and induces apoptosis in gliomas. Clin Cancer Res. 1999 August; 5(8):2230-5
17. Holmes W F, Soprano D R, Soprano K J, Synthetic retinoids as inducers of apoptosis in ovarian carcinoma cell lines. J Cell Physiol. 2004 June; 199(3):317-29
18. Simeone A M, Ekmekcioglu S, Broemeling L D, Grimm E A, Tari A M. A novel mechanism by which N-(4-hydroxyphenyl)retinamide inhibits breast cancer cell growth: the production of nitric oxide. Mol Cancer Ther. 2002 October; 1(12):1009-17
19. Fontana J A, Rishi A K. Classical and novel retinoids: their targets in cancer therapy. Leukemia. 2002 April; 16(4):463-72
20. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65
21. Fontana J A, Rishi A K. Classical and novel retinoids: their targets in cancer therapy. Leukemia. 2002 April; 16(4):463-72
22. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of hems oxygenase-1 and Gadd153. J Cell Physiol. 2006 December; 209(3):854-65
23. Sabichi A L, Xu H, Fischer S. Zou C, Yang X, Steele V E, Kelloff G J, Lotan R, Clifford J L. Retinoid receptor-dependent and independent biological activities of novel fenretinide analogues and metabolites. Clin Cancer Res. 2003 Oct. 1; 9(12):4606-13
24. Clifford J L, Menter D G, Wang M, Lotan R, Lippman S M. Retinoid receptor-dependent and -independent effects of N-(4-hydroxyphenyl)retinamide in F9 embryonal carcinoma cells, Cancer Res. 1999 Jan. 1; 59(1):14-8.
25. Gollapalli D R, Rando R R. The specific binding of retinoic acid to RPE65 and approaches to the treatment of macular degeneration. Proc Natl Acad Sci USA. 2004 Jul. 6; 101(27):10030-5
26. Maiti P, Kong J, Kim S R, Sparrow J R, Allikmets R, Rando R R. Small molecule RPE65 antagonists limit the visual cycle and prevent lipofuscin formation. Biochemistry. 2006 Jan. 24; 45(3):852-60
27. Radu R A, Mata N L, Nusinowitz S, Liu X, Sieving P A, Travis G H. Treatment with isotretinoin inhibits lipofuscin accumulation in a mouse model of recessive Stargardt's macular degeneration. Proc Natl Acad Sci USA. 2003 Apr. 15; 100(8):4742-7
28. Monaco H L, Rizzi M, Coda A. Structure of a complex of two plasma proteins: transthyretin and retinol-binding protein. Science. 1995 May 19; 268(5213):1039-41.
29. Bonanni B, Lazzeroni M, Veronesi U. Synthetic retinoid fenretinide in breast cancer chemoprevention. Expert Rev Anticancer Ther. 2007 April; 7(4):423-32.
30. Sunness J S, Margalit E, Srikumaran D, Applegate C A, Tian Y, Perry D, Hawkins B S, Bressler N M. The long-term natural history of geographic atrophy from age-related macular degeneration: enlargement of atrophy and implications for interventional clinical trials. Ophthalmology. 2007 February; 114(2):271-7.
31. Glickman J F et al. A comparison of ALPHAScreen, TR-FRET, and TRF as assay methods for FXR nuclear receptors. J. Biomol. Screening 2002; 7:3-10
32. Fujimura T et al. Unique properties of coactivator recruitment caused by differential binding of FK614, an anti-diabetic agent, to PPARgamma. Biol. Pharm. Bull. 2006; 29:423-429
33. Zhou G et al. Nuclear receptors have distinct affinities for coactivators: characterization by FRET. Mol. Endocrinol. 1998; 12:1594-1605
34. Cogan U, Kopelman M, Mokady S, Shinitzky M. Binding affinities of retinol and related compounds to retinol binding proteins. Eur J Biochem. 1976 May 17; 65(1):71-8.
35. Decensi A, Torrisi R, Polizzi A, Gesi R, Brezzo V, Rolando M, Rondanina G, Orengo M A, Formelli F, Costa A. Effect of the synthetic retinoid fenretinide on dark adaptation and the ocular surface. J Natl Cancer Inst. 1994 Jan. 19; 86(2):105-10.
36. Conley B, O'Shaughnessy J, Prindiville S, Lawrence J, Chow C, Jones E, Merino M J, Kaiser-Kupfer M I, Caruso R C, Podgor M, Goldspiel B, Venzon D, Danforth D, Wu S, Noone M, Goldstein J, Cowan K H, Zujewski J. Pilot trial of the safety, tolerability, and retinoid levels of N-(4-hydroxyphenyl)retinamide in combination with tamoxifen in patients at high risk for developing invasive breast cancer. J Clin Oncol. 2000 January; 18(2):275-83.

37. Fain G L, Lisman J E. Photoreceptor degeneration in vitamin A deprivation and retinitis pigmentosa: the equivalent light hypothesis. Exp Eye Res. 1993 September; 57(3):335-40.
38. Makimura H, Wei J, Dolan-Looby S E, Ricchiuti V, Grinspoon S. Retinol-Binding Protein Levels are Increased in Association with Gonadotropin Levels in Healthy Women. Metabolism. 2009 April; 58(4): 479-487.
39. Yang Q, Graham T E, Mody N, Preitner F, Peroni O D, Zabolotny J M, Kotani K, Quadro L, Kahn B B. Serum retinol binding protein 4 contributes to insulin resistance in obesity and type 2 diabetes. Nature. 2005 Jul. 21; 436(7049):356-62.
40. Kim S R, Jang Y P, Jockusch S, Fishkin N E, Turro N J, Sparrow J R. The all-trans-retinal dimer series of lipofuscin pigments in retinal pigment epithelial cells in a recessive Stargardt disease model. PNAS. Dec. 4, 2007, Vol. 104, No. 49, 19273-8.
41. Wu Y, Fishkin N E, Pande A, Pande J, Sparrow R J. Novel Lipofuscin Bisretinoids Prominent in Human Retina and in a Model of Recessive Stargardt Disease. Journal of Biological Chemistry. Jul. 24, 2009, Vol. 284, No. 30, 20155-20166.
42. F. G. Holz, C. Bellmann, M. Margaritidis, F. Schutt, T. P. Otto and H. E. Volcker, Patterns of increased in vivo fundus autofluorescence in the junctional zone of geographic atrophy of the retinal pigment epithelium associated with age-related macular degeneration. Graefe's Archive for Clinical and Experimental Ophthalmology 237 (1999), pp. 145-152.

What is claimed is:

1. A compound having the structure:

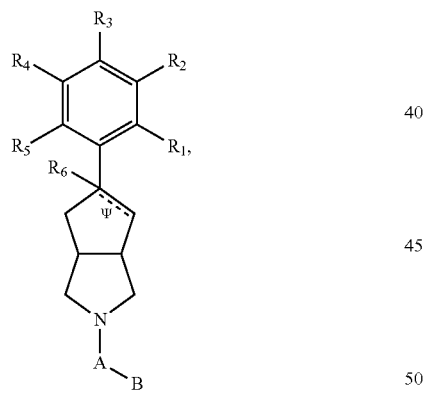

wherein
ψ is absent;
$R_1$, $R_2$, $R_3$, $R_4$, and $R_5$ are each independently H, halogen, $CF_3$ or $C_1$-$C_4$ alkyl;
$R_6$ is absent or present, and when present is H, OH, or halogen;
A is absent or present, and when present is

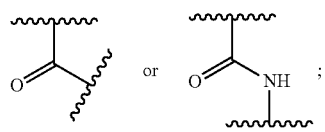

B is substituted or unsubstituted heteromonocycle or heterobicycle; and wherein when ψ is present, then $R_6$ is absent and when ψ is absent, then $R_6$ is present,
or a pharmaceutically acceptable salt thereof.

2. The compound of claim 1 having the structure:

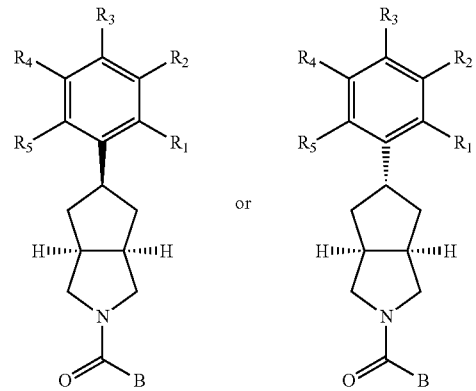

3. The compound of claim 1 having the structure:

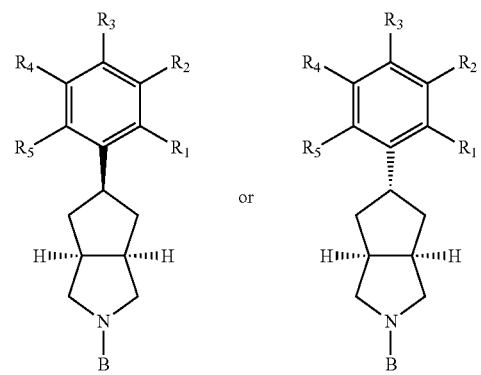

4. The compound of claim 1, wherein B has the structure:

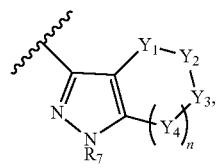

wherein
n is 1;
$R_7$ is H, $C_1$-$C_4$ alkyl, or oxetane;
$Y_1$, $Y_2$ and $Y_4$ are each $CH_2$ or $C(CH_3)_2$; and
$Y_3$ is O, $SO_2$, or N—$R_{10}$,
wherein
$R_{10}$ is H, $C_1$-$C_4$ alkyl, $C_1$-$C_4$ cycloalkyl, ($C_1$-$C_4$ alkyl)-$CF_3$, ($C_1$-$C_4$ alkyl)-$OCH_3$, ($C_1$-$C_4$ alkyl)-halogen, $SO_2$—($C_1$-$C_4$ alkyl), $SO_2$—($C_1$-$C_4$ alkyl)-$CF_3$, $SO_2$—($C_1$-$C_4$ alkyl)-$OCH_3$, $SO_2$—($C_1$-$C_4$ alkyl)-halogen, C(O)—($C_1$-$C_4$ alkyl), C(O)—($C_1$-$C_4$ alkyl)-$CF_3$, C(O)—($C_1$-$C_4$ alkyl)-$OCH_3$, C(O)—($C_1$-$C_4$ alkyl)-halogen, C(O)—NH—($C_1$-$C_4$ alkyl), C(O)—N($C_1$-$C_4$ alkyl)$_2$, ($C_1$-$C_4$ alkyl)-C(O)OH, C(O)—$NH_2$ or oxetane.

5. The compound of claim 4, wherein B has the structure:

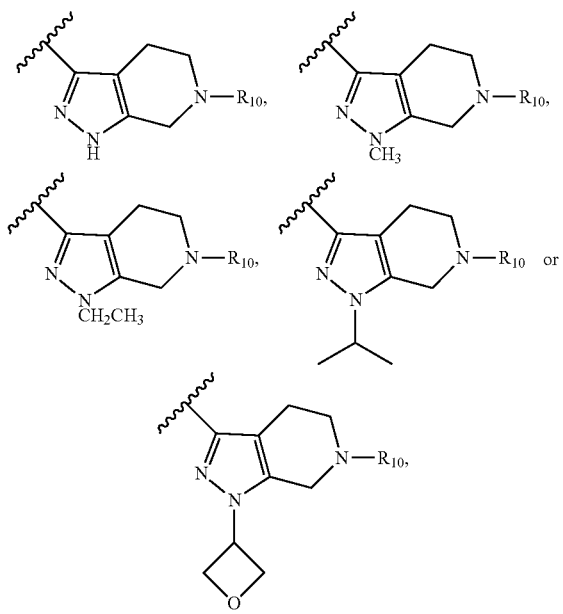

wherein
$R_{10}$ is H, $C_1$-$C_4$ alkyl, $C_1$-$C_4$ cycloalkyl, ($C_1$-$C_4$ alkyl)-$CF_3$, ($C_1$-$C_4$ alkyl)-$OCH_3$, ($C_1$-$C_4$ alkyl)-halogen, $SO_2$—($C_1$-$C_4$ alkyl), $SO_2$—($C_1$-$C_4$ alkyl)-$CF_3$, $SO_2$—($C_1$-$C_4$ alkyl)-$OCH_3$, $SO_2$—($C_1$-$C_4$ alkyl)-halogen, C(O)—($C_1$-$C_4$ alkyl), C(O)—($C_1$-$C_4$ alkyl)-$CF_3$, C(O)—($C_1$-$C_4$ alkyl)-$OCH_3$, C(O)—($C_1$-$C_4$ alkyl)-halogen, C(O)—NH—($C_1$-$C_4$ alkyl), C(O)—N($C_1$-$C_4$ alkyl)$_2$, ($C_1$-$C_4$ alkyl)-C(O)OH, C(O)—$NH_2$ or oxetane.

6. The compound of claim 5,
wherein $R_{10}$ is C(O)—$CH_3$, C(O)—$CH_2CH_3$, C(O)—$CH_2CH_2CH_3$, C(O)—CH($CH_3$)$_2$, C(O)—$CH_2$CH($CH_3$)$_2$, C(O)-t-Bu, C(O)—$CH_2OCH_3$, C(O)—$CH_2CF_3$, C(O)—$CH_2Cl$, C(O)—$CH_2F$, C(O)—$CH_2CH_2OCH_3$, C(O)—$CH_2CH_2CF_3$, C(O)—$CH_2CH_2Cl$, C(O)—$CH_2CH_2F$,

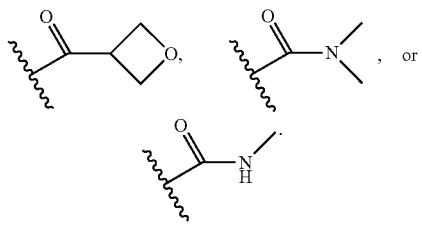

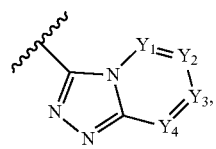

7. The compound of claim 1, wherein B has the structure:

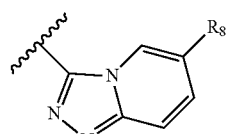

wherein
$Y_1$, $Y_2$, $Y_3$ and $Y_4$ are each independently $CR_8$ or N,
wherein each $R_8$ is independently H, halogen, $C_1$-$C_4$ alkyl, $C_1$-$C_4$ cycloalkyl, O($C_1$-$C_4$ alkyl), CN, $CF_3$, C(O)OH, C(O)—$NH_2$, C(O)—N($CH_3$)$_2$, C(O)—$NHCH_3$, or NHC(O)—N($CH_3$)$_2$.

8. The compound of claim 7, wherein B has the structure:

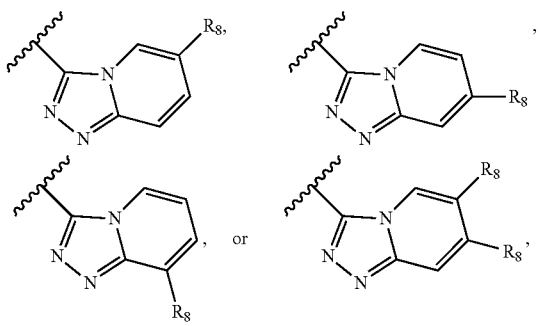

wherein each $R_8$ is independently H, halogen, $C_1$-$C_4$ alkyl, $C_1$-$C_4$ cycloalkyl, O($C_1$-$C_4$ alkyl), CN, $CF_3$, C(O)OH, C(O)—$NH_2$, C(O)—N($CH_3$)$_2$, C(O)—$NHCH_3$, or NHC(O)—N($CH_3$)$_2$.

9. The compound of claim 8, wherein B has the structure:

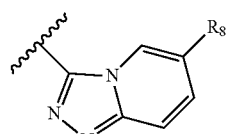

wherein each $R_8$ is independently H, halogen, $C_1$-$C_4$ alkyl, $C_1$-$C_4$ cycloalkyl, O($C_1$-$C_4$ alkyl), CN, $CF_3$, C(O)OH, C(O)—$NH_2$, C(O)—N($CH_3$)$_2$, C(O)—$NHCH_3$, or NHC(O)—N($CH_3$)$_2$.

10. The compound of claim 8,
wherein each $R_8$ is independently H, Cl, Br, F, $OCH_3$, $OCH_2CH_3$, $CF_3$, CN, $CH_3$, $CH_3CH_3$, C(O) OH, C(O)—$NH_2$, C(O)—N($CH_3$)$_2$, C(O)—$NHCH_3$, NHC(O)—$NHCH_3$, NHC(O)—N($CH_3$)$_2$, $SO_2$—$NHCH_3$ or $SO_2$—N($CH_3$)$_2$.

11. The compound of claim 9,
wherein $R_8$ is H, Cl, Br, F, $OCH_3$, $OCH_2CH_3$, $CF_3$, CN, $CH_3$, $CH_3CH_3$, C(O)OH, C(O)—$NH_2$, C(O)—N($CH_3$)$_2$, C(O)—$NHCH_3$, NHC(O)—$NHCH_3$, NHC(O)—N($CH_3$)$_2$, $SO_2$—$NHCH_3$ or $SO_2$—N($CH_3$)$_2$.

12. The compound of claim 1, wherein B has the structure:

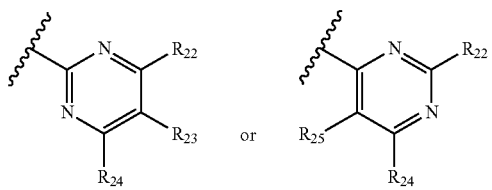

wherein $R_{21}$, $R_{22}$, $R_{23}$, $R_{24}$, and $R_{25}$ are each independently
H, halogen CN, $CF_3$, OH, $NH_2$, $C_1$-$C_{10}$ alkyl, $C_3$-$C_6$ cycloalkyl, O($C_1$-$C_{10}$ alkyl), C(O)$NH_2$, C(O)NH($C_1$-$C_{10}$ alkyl), C(O)N($C_1$-$C_4$ alkyl)$_2$, C(O)OH, C(O)O($C_1$-$C_{10}$ alkyl), C(O)($C_1$-$C_{10}$ alkyl), C(O)NH($SO_2$)—($C_1$-$C_{10}$ alkyl), C(O)NH($SO_2$)—($C_3$-$C_6$ cycloalkyl), C(O)NH($SO_2$)-(aryl), O($SO_2$)—$NH_2$, NHC(O)—NH($C_1$-$C_{10}$ alkyl), NHC(O)—N($C_1$-$C_4$ alkyl)$_2$, $SO_2$—($C_1$-$C_{10}$ alkyl).

13. The compound of claim 12, wherein B has the structure:

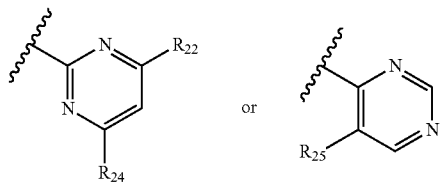

wherein $R_{21}$, $R_{22}$, $R_{24}$ and $R_{25}$ are each independently
H, halogen, OH, $NH_2$, $C_1$-$C_4$ alkyl, $C_3$-$C_6$ cycloalkyl, O($C_1$-$C_4$ alkyl), C(O)$NH_2$, C(O)NH($C_1$-$C_4$ alkyl), C(O)N($C_1$-$C_4$ alkyl)$_2$, C(O)OH, C(O)O($C_1$-$C_4$ alkyl), C(O)($C_1$-$C_4$ alkyl), C(O)NH(SO$_2$)—($C_1$-$C_4$ alkyl), C(O)NH(SO$_2$)—($C_3$-$C_6$ cycloalkyl), C(O)NH(SO$_2$)-(aryl), or O(SO$_2$)—$NH_2$, SO$_2$—($C_1$-$C_4$ alkyl).

14. The compound of claim 12, wherein B has the structure:

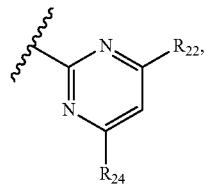

wherein $R_{22}$ and $R_{24}$ are each independently
H, halogen, OH, $NH_2$, $C_1$-$C_4$ alkyl, $C_3$-$C_6$ cycloalkyl, O($C_1$-$C_4$ alkyl), C(O)$NH_2$, C(O)NH($C_1$-$C_4$ alkyl), C(O)N($C_1$-$C_4$ alkyl)$_2$, C(O)OH, C(O)O($C_1$-$C_4$ alkyl), C(O) ($C_1$-$C_4$ alkyl), C(O)NH(SO$_2$)—($C_1$-$C_4$ alkyl), C(O)NH(SO$_2$)—($C_3$-$C_6$ cycloalkyl), C(O)NH(SO$_2$)-(aryl), or O(SO$_2$)—$NH_2$, SO$_2$—($C_1$-$C_4$ alkyl).

15. The compound of claim 13, wherein $R_{21}$, $R_{22}$, $R_{24}$ and $R_{25}$ are each independently H, F, Cl, CF$_3$, CH$_3$, OCH$_3$, OH, SO$_2$—CH$_3$, C(O)NH$_2$, C(O)OH, C(O)OCH$_3$,

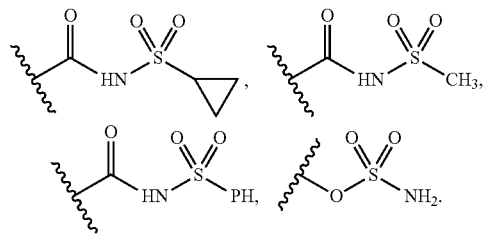

16. The compound of claim 14, wherein $R_{22}$ and $R_{24}$ are each independently H, F, Cl, CF$_3$, CH$_3$, OCH$_3$, OH, SO$_2$—CH$_3$, C(O)NH$_2$, C(O)OH, C(O)OCH$_3$,

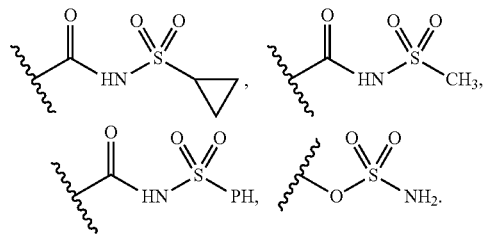

17. The compound of claim 12, wherein B has the structure

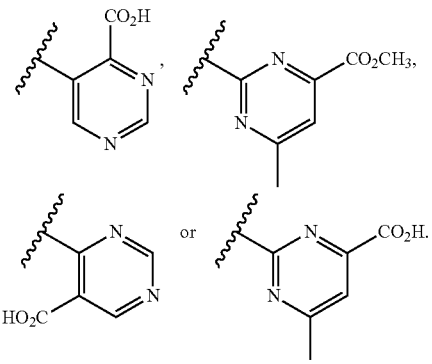

18. A pharmaceutical composition comprising the compound of claim 1 and a pharmaceutically acceptable carrier.

19. A method for treating a disease characterized by excessive lipofuscin accumulation in the retina in a mammal afflicted therewith comprising administering to the mammal an effective amount of the compound of claim 1.

20. The method of claim 19, wherein the disease characterized by excessive lipofuscin accumulation in the retina is Age-Related Macular Degeneration, dry (atrophic) Age-Related Macular Degeneration, Stargardt Disease, Best disease, adult vitelliform maculopathy or Stargardt-like macular dystrophy.

21. A compound having the structure:

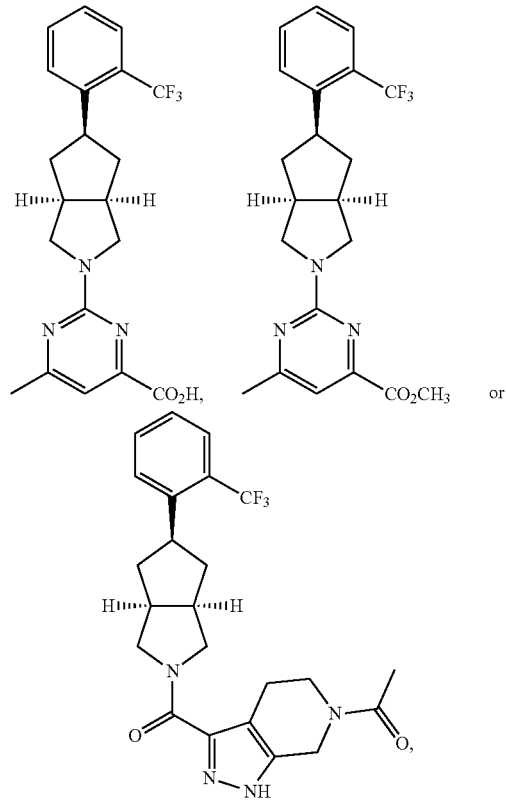

or a pharmaceutically acceptable salt thereof.

22. A pharmaceutical composition comprising the compound of claim 21 and a pharmaceutically acceptable carrier.

23. A method for treating a disease characterized by excessive lipofuscin accumulation in the retina in a mammal afflicted therewith comprising administering to the mammal an effective amount of the compound of claim 21.

24. The method of claim 23, wherein the disease characterized by excessive lipofuscin accumulation in the retina is Age-Related Macular Degeneration, dry (atrophic) Age-Related Macular Degeneration, Stargardt Disease, Best disease, adult vitelliform maculopathy or Stargardt-like macular dystrophy.

25. The method of claim 23, wherein the disease characterized by excessive lipofuscin accumulation in the retina is Age-Related Macular Degeneration or dry (atrophic) Age-Related Macular Degeneration.

26. A compound having the structure:

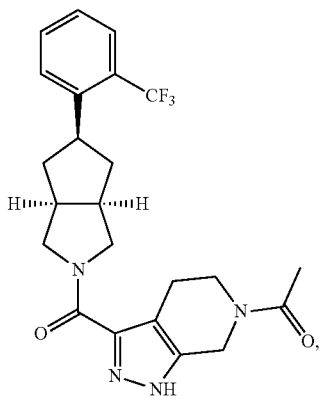 [SMILES: CC(=O)N1CCc2c(C(=O)N3C[C@H]4C[C@@H](c5ccccc5C(F)(F)F)C[C@H]4C3)n[nH]c2C1]

or a pharmaceutically acceptable salt thereof.

27. A compound having the structure:

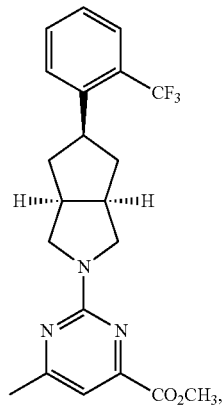 [SMILES: COC(=O)c1cc(C)nc(N2C[C@H]3C[C@@H](c4ccccc4C(F)(F)F)C[C@H]3C2)n1]

or a pharmaceutically acceptable salt thereof.

28. A compound having the structure:

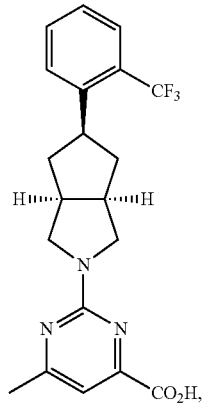 [SMILES: Cc1cc(C(=O)O)nc(N2C[C@H]3C[C@@H](c4ccccc4C(F)(F)F)C[C@H]3C2)n1]

or a pharmaceutically acceptable salt thereof.

* * * * *

UNITED STATES PATENT AND TRADEMARK OFFICE
CERTIFICATE OF CORRECTION

PATENT NO. : 9,926,271 B2  
APPLICATION NO. : 15/457821  
DATED : March 27, 2018  
INVENTOR(S) : Konstantin Petrukhin et al.

Page 1 of 1

It is certified that error appears in the above-identified patent and that said Letters Patent is hereby corrected as shown below:

In the Specification

In Column 1, the cross-reference to related applications of the first paragraph should be revised to read:

This application is a continuation of U.S. Ser. No. 14/775,540, filed Sep. 11, 2015, now allowed, which is a § 371 national stage of PCT International Application No. PCT/US2014/026818, filed Mar. 13, 2014, claiming the benefit of U.S. Provisional Application No. 61/785,288, filed Mar. 14, 2013, the contents of each of which are hereby incorporated by reference in their entirety.

Signed and Sealed this  
Fourteenth Day of May, 2019

Andrei Iancu  
*Director of the United States Patent and Trademark Office*